(12) United States Patent
Choi et al.

(10) Patent No.: US 10,870,647 B2
(45) Date of Patent: Dec. 22, 2020

(54) IMIDAZOPYRIDINE DERIVATIVE, METHOD FOR PREPARING SAME, AND PHARMACEUTICAL COMPOSITION CONTAINING SAME AS ACTIVE INGREDIENT FOR PREVENTING OR TREATING CANCER

(71) Applicant: DAEGU-GYEONGBUK MEDICAL INNOVATION FOUNDATION, Daegu (KR)

(72) Inventors: Hwan Geun Choi, Seoul (KR); Jung Beom Son, Daegu (KR); Shinae Kim, Daegu (KR); Seungyeon Lee, Daegu (KR); Eunhwa Ko, Daegu (KR); Joongheui Cho, Daegu (KR); Seock Yong Kang, Seoul (KR); So Young Kim, Daegu (KR); Jin-Hee Park, Daegu (KR); Yi Kyung Ko, Daegu (KR); Hee Yoon Ryu, Daegu (KR); Nam Doo Kim, Daegu (KR); Hyunkyoung Kim, Daegu (KR); Younho Lee, Incheon (KR); Sun-Hwa Lee, Daegu (KR); Dayea Kim, Daegu (KR); Sun Joo Lee, Daegu (KR); Seongho Hong, Busan (KR); Sang Hyun Min, Daegu (KR); Sungwoo Lee, Daegu (KR); Dong Kyu Choi, Yeongcheon-si (KR); Jae Hyun Bae, Daegu (KR); Eunmi Hong, Yongin-si (KR); Tae-Ho Jang, Gyeongsan-si (KR); Jaeyoung Song, Daegu (KR); Sangbum Kim, Jeollabuk-do (KR); Suk Kyoon Yoon, Seoul (KR)

(73) Assignee: DAEGU-GYEONGBUK MEDICAL INNOVATION FOUNDATION, Daegu (KR)

( * ) Notice: Subject to any disclaimer, the term of this patent is extended or adjusted under 35 U.S.C. 154(b) by 0 days.

(21) Appl. No.: 16/311,654

(22) PCT Filed: Jun. 20, 2017

(86) PCT No.: PCT/KR2017/006487
§ 371 (c)(1),
(2) Date: May 1, 2019

(87) PCT Pub. No.: WO2017/222285
PCT Pub. Date: Dec. 28, 2017

(65) Prior Publication Data
US 2019/0315738 A1 Oct. 17, 2019

(30) Foreign Application Priority Data

Jun. 20, 2016 (KR) .................. 10-2016-0076666

(51) Int. Cl.
C07D 471/04 (2006.01)
A23L 29/00 (2016.01)
C07D 519/00 (2006.01)

(52) U.S. Cl.
CPC .......... *C07D 471/04* (2013.01); *A23L 29/045* (2016.08); *C07D 519/00* (2013.01)

(58) Field of Classification Search
CPC .................................................. C07D 471/04
See application file for complete search history.

(56) References Cited

FOREIGN PATENT DOCUMENTS

| KR | 10-1436303 B1 | 9/2014 | |
|---|---|---|---|
| WO | WO 2005/060969 A1 | 7/2005 | |
| WO | WO 2007/075869 A2 | 7/2007 | |
| WO | WO 2013/101281 A1 | 7/2013 | |
| WO | WO 2013/162727 A1 | 10/2013 | |
| WO | WO-2017222287 A1 * | 12/2017 | .......... C07D 519/00 |

OTHER PUBLICATIONS

Taniguchi et al. "Inhibition of Src Kinase Blocks High Glucose-Induced EGFR Transactivation and Collagen Synthesis in Mesangial Cells and Prevents Diabetic Nephropathy in Mice" *Diabetes* 62:3874-3886 (2013).

* cited by examiner

*Primary Examiner* — John S Kenyon
(74) *Attorney, Agent, or Firm* — Klarquist Sparkman, LLP

(57) ABSTRACT

The present invention relates to a novel imidazopyridine derivative, a method for preparing the same, and a pharmaceutical composition containing the same as an active ingredient for preventing or treating cancer. The novel imidazopyridine derivative according to the present invention, a stereoisomer thereof and a pharmaceutically acceptable salt thereof can effectively inhibit cancer-related kinases, are excellent in inhibiting proliferation of cancer cells in a cancer cell line, and effectively inhibit proliferation of cancer cells (cancer cell apoptosis) in a cancer cell heterograft model, and thus can be useful as a pharmaceutical composition containing the same as an active ingredient for preventing or treating cancer.

Also, the novel imidazopyridine derivative according to the present invention, the stereoisomer thereof, and the pharmaceutically acceptable salt thereof can effectively inhibit Src and Fyn, thereby being useful as a pharmaceutical composition for preventing or treating the Src and Fyn related diseases, and in particular, have been confirmed to be useful in diabetic nephropathy in animal model experiments. Therefore, the compound of the present invention can be effective as a pharmaceutical composition containing the same as an active ingredient for preventing or treating diabetic nephropathy.

21 Claims, 9 Drawing Sheets
Specification includes a Sequence Listing.

IMIDAZOPYRIDINE DERIVATIVE, METHOD FOR PREPARING SAME, AND PHARMACEUTICAL COMPOSITION CONTAINING SAME AS ACTIVE INGREDIENT FOR PREVENTING OR TREATING CANCER

CROSS REFERENCE TO RELATED APPLICATIONS

This is the U.S. National Stage of International Application No. PCT/KR2017/006487, filed Jun. 20, 2017, which in turn claims the benefit of Korean Application No. 10-2016-0076666, filed Jun. 20, 2016, both of which applications are herein incorporated in their entirety.

BACKGROUND OF THE INVENTION

1. Field of the Invention

The present invention relates to a novel imidazopyridine derivative, a method for preparing the same, and a pharmaceutical composition containing the same as an active ingredient for preventing or treating cancer.

2. Description of the Related Art

Chronic myeloid leukemia (CML) is a kind of blood cancer which is developed by chromosome aberration in hematopoietic stem cells existing in bone marrow. That is, Bcr (breakpoint cluster region) gene on chromosome 22 and Abl (V-abl Abelson murine leukemia viral oncogene homolog) gene on chromosome 9 are crossed and inverted to form the Bcr-Abl tyrosine fusion tumor gene. The tyrosine kinase which is produced by the Bcr-Abl gene continues its activity to activate intracellular cell division related signal transduction system, resulting in hyperproliferation of leukocytes, and at the same time inhibits apoptosis related signal transduction, resulting in leukemia. P210-Bcr-Abl is known as a direct tumor factor causing chronic myeloid leukemia (CML).

Gleevec has an excellent therapeutic effect and safety, so that it has been widely used as the primary standard therapy for the treatment of chronic myeloid leukemia (CML). However, many of CML patients who had been treated with Gleevec display resistance, and recently, the variable species showing resistance have been confirmed. Gleevec resistance is caused by a point mutation that occurs at the active site of Bcr-Abl tyrosine kinase. For example, such mutations as T315I in which the 315$^{th}$ threonine is replaced with isoleucine and T253H in which the 253$^{rd}$ tyrosine is replaced with histidine are most frequent. Among the Gleevec resistant point mutations, T315I-Bcr-Abl is the most dominant.

The proliferation of cells having point mutations is not regulated by Gleevec anymore. The therapeutic effect is not any better even with increasing the dose of Gleevec.

The second generation anticancer agents that can treat Gleevec resistance are nilotinib (Tasigna) and dasatinib (Sprycel). However, their ability to inhibit the T315I-Bcr-Abl mutant is very weak. Since the activity of the existing second generation anticancer agents to inhibit mutant species is very weak, continuous study is still requested and also the development of a novel next generation anticancer agent capable of preventing or treating Gleevec resistance is highly requested as well.

In the meantime, RET (rearranged during transfection) is one of the receptor tyrosine kinases belonging to cadherin. RET tyrosine kinase has a transmembrane region in the center, a tyrosine kinase region in the carboxyl terminus, and an extracellular region in the amino terminus. Three types of proteins are present due to the difference of splicing in the carboxyl terminus.

RET forms a dimer mediated by the ligand/GFR complex, by which its tyrosine is phosphorylated, resulting in the activation of RET. When an abnormality occurs in RET gene (point mutation, chromosomal translocation, chromosome inversion, or gene amplification), it is involved in carcinogenesis. For example, in the case of thyroid cancer, a point mutation in RET gene is observed and thereby the expression of RET tyrosine kinase involved in carcinogenesis is confirmed. In the case of thyroid papillary carcinoma, RET gene is fused with CCDC6 gene (coiled-coildomain containing 6) or NCOA4 gene (nuclear receptor coactivator 4) by such a mutation in RET gene as chromosomal inversion or chromosomal translocation to express the fusion type tyrosine kinase RET/PTC which induces cancer. In the case of non small cell lung cancer, RET is fused with K1F5B gene (kinesin family protein 5B), one of the constituent molecules of the protein complex involved in microtubule transport in cells, or CCDC6 gene, and as a result, non small cell lung cancer is developed by the tyrosine kinase activity of the fusion type tyrosine kinase KIF5B-RET or CCDC6-RET.

Therefore, a compound having the activity of inhibiting RET tyrosine kinase is very useful for the prevention or treatment of cancer. It was reported that such multi-kinase inhibitors as Sorafenib, Sunitinib, XL184, Vandetanib and Ponatinib were able to inhibit cell proliferation in the cell line expressing KIF5B-RET (J Clin Oncol 30, 2012, suppl; Abstract no: 7510).

A fibroblast growth factor receptor (FGFR) tyrosine kinase is composed of approximately 800 amino acids and is a type 5 receptor tyrosine kinase having three kinds of immunoglobulin (Ig)-like domains (D1, D2 and D3). FGFR has largely 4 kinds of sub-types: FGFR1, FGFR2, FGFR3 and FGFR4.

Fibroblast growth factor (FGF) and its receptor (FGFR) are a part of unique and diverse signal transduction systems playing an important role in various physiological processes including embryogenesis and various aspects of adult pathophysiology. It is known that FGF stimulates broad cell functions including migration, proliferation, differentiation and survival by binding with FGFR.

The over-expression or mutation of FGFR can cause cancer (for example, bladder cancer, breast cancer, cervical cancer, colorectal cancer, endometrial cancer, stomach cancer, head and neck cancer, kidney cancer, liver cancer, lung cancer, ovarian cancer, and prostate cancer), hematopoietic malignant tumor (for example, multiple myeloma, chronic lymphocytic lymphoma, adult T-cell leukemia, acute myelogenous leukemia, non-Hodgkin's lymphoma, myeloproliferative neoplasm, and Waldenstrom's macroglubulinemia), glioblastoma, melanoma and rhabdoid tumor. FGFR gene fusion occurs in various types of cancer, and activation of FGFR signal transduction is known to promote cancer cell proliferation. Thus, efforts have been made to develop drugs targeting FGFR for the purpose of treating cancer.

In particular, numbers of in vivo and in vitro studies have been performed to identify FGFR1-FGFR 4 as important cancer targeting agents. However, effective drug development has not been achieved at a desired level so far, and thus continuous efforts are requested.

The present inventors tried to develop a drug to treat cancer or tumor that can overcome T315I resistance and inhibit Ret or FGFR efficiently. In the course of our study, the present inventors confirmed from the experiment with K562 (wild type Bcr-Abl) cell line that the compound of the present invention can overcome T315I resistance and inhibit Ret and FGFR efficiently and further inhibit the proliferation of cancer cells in a xenograft model efficiently. Thus, the present inventors confirmed that a pharmaceutical composition comprising the compound of the present invention as an active ingredient can be effectively used for the prevention or treatment of cancer, leading to the completion of the present invention.

The present inventors also confirmed that the compound of the present invention had an excellent activity to inhibit Src/Fyn enzyme involved in metabolic disease including diabetic nephropathy in addition to cancer. The representative disease involved in Src/Fyn enzyme is diabetic nephropathy (DN), which is one of major complications of diabetes along with retinopathy and neuropathy.

Most of the recent studies on diabetic nephropathy are focused on glomerular sclerosis due to proliferation and hypertrophy of mesangium or fibrosis caused by extracellular matrix accumulation of renal tubular epilepsy.

More recently, it has been suggested that the extracellular domain of nephrin can form a slit membrane and the tyrosine residue of the intracellular domain can be phosphorylated by Fyn belonging to src-kinase family to be involved in signal transduction in podocytes.

Previous studies are focused and progressed on the idea that Nck (non-catalytic region of tyrosine kinase adaptor protein 1) or PI3K (Phosphoinositide 3-kinase) having SH2 (Src homology 2) domain recognizes the phosphorylated region of nephrin so that it plays an important role in keeping the structure of podocytes by regulating actin cytoskeleton mediated by the recognition above. However, studies about the signal transduction and its regulators in podocytes via nephrin phosphorylation are still insufficient.

From the continued study, the present inventors confirmed that the compound of the present invention was very useful as a novel therapeutic agent for diabetic nephropathy and further the present inventors evaluated the pharmaceutical effect of the compound of the present invention by using urinary obstruction and diabetic-induced mouse models. As a result, to our surprise, the compound of the present invention was confirmed to be effective in preventing or treating diabetic nephropathy, leading to the completion of the present invention.

INCORPORATION OF ELECTRONIC SEQUENCE LISTING

The Sequence Listing is submitted as an ASCII text file named "7037-101847-01 Sequence listing", created on Sep. 16, 2020, 2 KB, which is incorporated by reference herein.

SUMMARY OF THE INVENTION

It is an object of the present invention to provide a compound useful as an active ingredient of a pharmaceutical composition for the prevention or treatment of cancer.

It is another object of the present invention to provide a preparation method of the compound above.

It is further an object of the present invention to provide a pharmaceutical composition comprising the compound above as an active ingredient for the prevention or treatment of cancer.

It is also an object of the present invention to provide a health functional food composition comprising the compound above as an active ingredient for preventing or ameliorating cancer.

It is also an object of the present invention to provide a compound useful as an active ingredient of a pharmaceutical composition for the prevention or treatment of diabetic nephropathy.

It is also an object of the present invention to provide a pharmaceutical composition comprising the compound above as an active ingredient for the prevention or treatment of diabetic nephropathy.

It is also an object of the present invention to provide a health functional food composition comprising the compound above as an active ingredient for preventing or ameliorating diabetic nephropathy.

To achieve the above objects, the present invention provides a compound represented by formula 1 below, an optical isomer thereof or a pharmaceutically acceptable salt thereof.

[Formula 1]

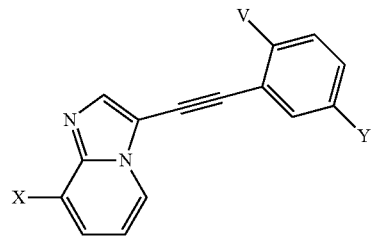

In formula 1,

V is hydrogen, halogen, or substituted or nonsubstituted $C_{1-5}$ straight or branched alkyl, wherein, the substituted alkyl can be substituted with one or more substituents selected from the group consisting of hydroxyl, halogen, nitro, and —CN;

X is —NHR$^1$,

R$^1$ is nonsubstituted or substituted $C_{6-10}$ aryl or nonsubstituted or substituted 5~10 membered heteroaryl containing one or more heteroatoms selected from the group consisting of N, O and S, wherein, the substituted aryl or the substituted heteroaryl can be substituted with nonsubstituted $C_{1-10}$ straight or branched alkyl, or $C_{1-10}$ straight or branched alkyl substituted with one or more substituents selected from the group consisting of halogen, methoxy and dimethylamine, or halogen, or amino, or 5~10 membered heterocycloalkyl containing one or more heteroatoms selected from the group consisting of N, O and S, or the substituted aryl or the substituted heteroaryl is fused with $C_{3-10}$ ring or 5~10 membered ring containing one or more heteroatoms selected from the group consisting of N, O and S to form a fused ring; and Y is —(C═O)NHR$^2$, —NH(C═O)R$^2$, —NH(C═O)NHR$^2$ or

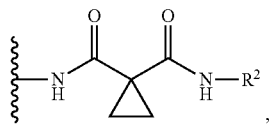

, $R^2$ is nonsubstituted or substituted $C_{6-10}$ aryl or nonsubstituted or substituted 5~10 membered heteroaryl containing one or more heteroatoms selected from the group consisting of N, O and S, wherein, the substituted aryl or the substituted heteroaryl can be substituted with one or more substituents selected from the group consisting of halogen, —$CH_2$—$R^3$, $C_{1-10}$ straight or branched alkyl substituted or nonsubstituted with halogen, $C_{1-2}$ alkoxy substituted or nonsubstituted with halogen, $C_{6-10}$ cycloalkyl substituted or nonsubstituted with halogen, substituted or nonsubstituted 5~10 membered heterocycloalkyl containing one or more heteroatoms selected from the group consisting of N, O and S, nonsubstituted or substituted 5~10 membered heteroaryl containing one or more heteroatoms selected from the group consisting of N, O and S, and nonsubstituted or substituted amino, wherein, the substituted heteroaryl, the substituted heterocycloalkyl, and the substituted amino can be substituted with substituted or nonsubstituted $C_{1-3}$ straight or branched alkyl, wherein, the substituted $C_{1-3}$ straight or branched alkyl can be substituted with dimethyl amino, $R^3$ is 5~10 membered heterocycloalkyl containing one or more heteroatoms selected from the group consisting of N, O and S, the heterocycloalkyl can be substituted or nonsubstituted with one or more substituents selected from the group consisting of methyl, ethyl, dimethyl amino, and halogen.

The present invention also provides a preparation method of the compound represented by formula 1 comprising the following steps, as shown in reaction formula 1 below:

preparing the compound represented by formula 4 by reacting the compound represented by formula 2 with the compound represented by formula 3 (step 1);

preparing the compound represented by formula 6 by reacting the compound represented by formula 4 prepared in step 1 above with the compound represented by formula 5 (step 2);

preparing the compound represented by formula 7 from the compound represented by formula 6 prepared in step 2 above (step 3); and preparing the compound represented by formula 1 by reacting the compound represented by formula 7 prepared in step 3 above with the compound represented by formula 8 (step 4).

[Reaction Formula 1]

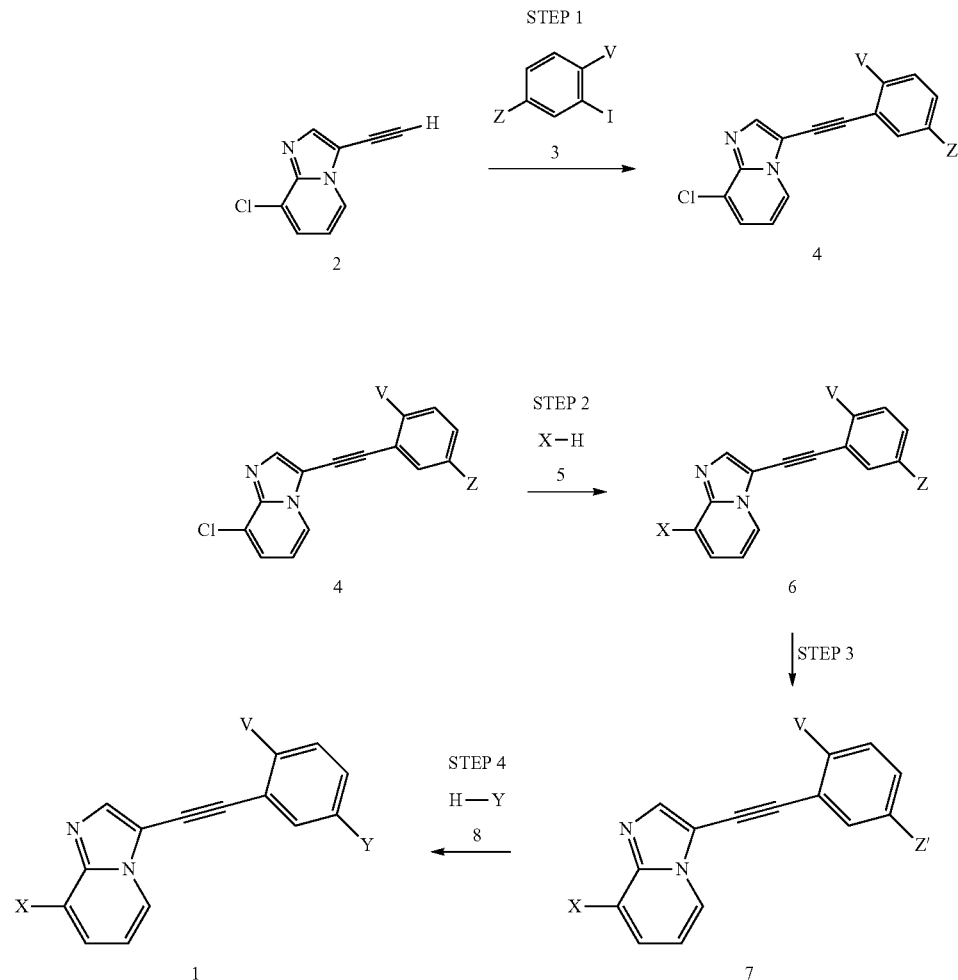

In reaction formula 1,
V, X and Y are as defined in formula 1; and
Z' is —NH² when Z is —NO² and Z' is

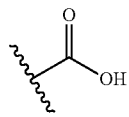

when Z is

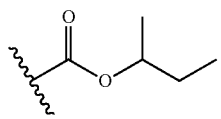

In addition, the present invention provides a pharmaceutical composition comprising the compound represented by formula 1, the optical isomer thereof or the pharmaceutically acceptable salt thereof as an active ingredient for the prevention or treatment of Ret (Rearranged during transfection), ABL1 (E255K)-phosphorylated, ABL1 (F317I)-nonphosphorylated, ABL1 (F317I)-phosphorylated, ABL1 (F317L)-nonphosphorylated, ABL1 (F317L)-phosphorylated, ABL1 (H396P)-nonphosphorylated, ABL1 (H396P)-phosphorylated, ABL1 (M351T)-phosphorylated, ABL1 (Q252H)-nonphosphorylated, ABL1 (Q252H)-phosphorylated, ABL1 (T315I)-nonphosphorylated, ABL1 (T315I)-phosphorylated, ABL1 (Y253F)-phosphorylated, ABL1-nonphosphorylated, ABL1-phosphorylated, ABL2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR (E746-A750del), EGFR (G719C), EGFR (G719S), EGFR (L747-E749del, A750P), EGFR (L747-S752del, P753S), EGFR (L747-T751del,Sins), EGFR (L858R), EGFR (L858R,T790M), EGFR (L861Q), EGFR (S752-I759del), EGFR (T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3 (G697C), FGFR4, FGR, FLT1, FLT3, FLT3 (D835H), FLT3 (D835V), FLT3 (D835Y), FLT3 (ITD), FLT3 (ITD,D835V), FLT3 (ITD,F691L), FLT3 (K663Q), FLT3 (N841I), FLT3 (R834Q), FLT4, FRK, FYN, GAK, GCN2 (Kin.Dom.2, S808G), HCK, HIPK4, HPK1, IKK-alpha, IKK-beta, IRAK1, IRAK4, ITK, JAK1 (JH1 domain-catalytic), JAK2 (JH1 domain-catalytic), JAK3 (JH1domain-catalytic), JNK1, JNK2, JNK3, KIT, KIT (A829P), KIT (D816H), KIT (D816V), KIT (L576P), KIT (V559D), KIT (V559D,T670I), KIT (V559D,V654A), LCK, LIMK1, LIMK2, LOK, LRRK2, LRRK2 (G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1 (*P. falciparum*), PFTAIRE2, PFTK1, PKAC-alpha, PKAC-beta, PYK2, RAF1, RET, RET (M918T), RET (V804L), RET (V804M), RIPK1, RIPK2, RIPK4, ROCK2, RPS6KA4 (Kin.Dom.1-N-terminal), RSK2 (Kin.Dom.1-N-terminal), RSK3 (Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or FGFR (Fibroblast growth factor receptor) related diseases.

The present invention also provides a pharmaceutical composition comprising the compound represented by formula 1 above, the optical isomer thereof or the pharmaceutically acceptable salt thereof as an active ingredient for the prevention or treatment of cancer.

The present invention also provides a health functional food composition comprising the compound represented by formula 1 above, the optical isomer thereof or the pharmaceutically acceptable salt thereof as an active ingredient for preventing or ameliorating cancer.

The present invention also provides a pharmaceutical composition comprising the compound represented by formula 1 above, the optical isomer thereof or the pharmaceutically acceptable salt thereof as an active ingredient for the prevention or treatment of diabetic nephropathy.

In addition, the present invention provides a health functional food composition comprising the compound represented by formula 1 above, the optical isomer thereof or the pharmaceutically acceptable salt thereof as an active ingredient for preventing or ameliorating diabetic nephropathy.

Advantageous Effect

The novel imidazopyridine derivative according to the present invention, a stereoisomer thereof and a pharmaceutically acceptable salt thereof can effectively inhibit cancer-related kinases, are excellent in inhibiting proliferation of cancer cells in a cancer cell line, and effectively inhibit proliferation of cancer cells (cancer cell apoptosis) in a cancer cell heterograft model, and thus can be useful as a pharmaceutical composition containing the same as an active ingredient for preventing or treating cancer.

Also, the novel imidazopyridine derivative according to the present invention, the stereoisomer thereof, and the pharmaceutically acceptable salt thereof can effectively inhibit Src and Fyn, thereby being useful as a pharmaceutical composition for preventing or treating the Src and Fyn related diseases, and in particular, have been confirmed to be useful in diabetic nephropathy in animal model experiments. Therefore, the compound of the present invention can be effective as a pharmaceutical composition containing the same as an active ingredient for preventing or treating diabetic nephropathy.

DESCRIPTION OF THE PREFERRED EMBODIMENTS

Figure 1:
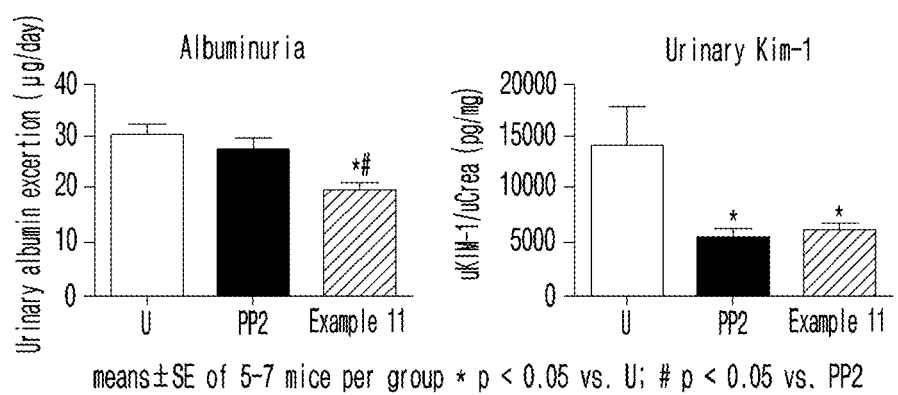
FIG. 1 presents graphs illustrating the proteinuria and urinary KIM-1 according to the treatment of three different compounds which were the compound of the present invention, PP2 and DMSO/Tween 20/DW, measured to evaluate renal damage in a UUO induced mouse model.

Hereinafter, the present invention is described in detail.

The following description is provided in order to help the understanding of the invention, and the present invention is not limited thereto.

The present invention provides a compound represented by formula 1 below, an optical isomer thereof or a pharmaceutically acceptable salt thereof.

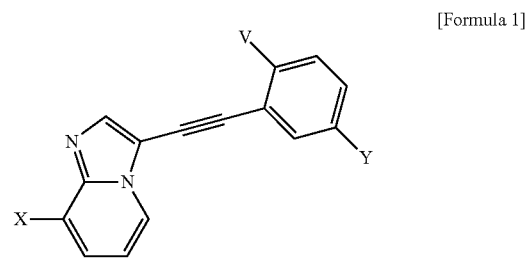

[Formula 1]

In formula 1,

V is hydrogen, halogen, or substituted or nonsubstituted $C_{1-5}$ straight or branched alkyl, wherein, the substituted alkyl can be substituted with one or more substituents selected from the group consisting of hydroxyl, halogen, nitro, and —CN;

X is —NHR$^1$,

R$^1$ is nonsubstituted or substituted $C_{6-10}$ aryl or nonsubstituted or substituted 5-membered heteroaryl containing one or more heteroatoms selected from the group consisting of N, O and S, wherein, the substituted aryl or the substituted heteroaryl can be substituted with nonsubstituted $C_{1-10}$ straight or branched alkyl, or $C_{1-10}$ straight or branched alkyl substituted with one or more substituents selected from the group consisting of halogen, methoxy and dimethylamine, or halogen, or amino, or 5~10 membered heterocycloalkyl containing one or more heteroatoms selected from the group consisting of N, O and S, or the substituted aryl or the substituted heteroaryl is fused with $C_{3-10}$ ring or 5~10 membered ring containing one or more heteroatoms selected from the group consisting of N, O and S to form a fused ring; and Y is —(C=O)NHR$^2$, —NH(C=O)R$^2$, —NH(C=O)NHR$^2$ or

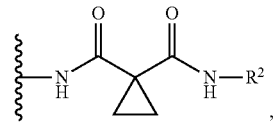

R$^2$ is nonsubstituted or substituted $C_{6-10}$ aryl or nonsubstituted or substituted 5~10 membered heteroaryl containing one or more heteroatoms selected from the group consisting of N, O and S, wherein, the substituted aryl or the substituted heteroaryl can be substituted with one or more substituents selected from the group consisting of halogen, —CH$_2$—R$^3$, $C_{1-10}$ straight or branched alkyl substituted or nonsubstituted with halogen, $C_{1-2}$ alkoxy substituted or nonsubstituted with halogen, $C_{6-10}$ cycloalkyl substituted or nonsubstituted with halogen, substituted or nonsubstituted 5~10 membered heterocycloalkyl containing one or more heteroatoms selected from the group consisting of N, O and S, nonsubstituted or substituted 5~10 membered heteroaryl containing one or more heteroatoms selected from the group consisting of N, O and S, and nonsubstituted or substituted amino, wherein, the substituted heteroaryl, the substituted heterocycloalkyl, and the substituted amino can be substituted with substituted or nonsubstituted $C_{1-3}$ straight or branched alkyl, wherein, the substituted $C_{1-3}$ straight or branched alkyl can be substituted with dimethyl amino, $R^3$ is 5~10 membered heterocycloalkyl containing one or more heteroatoms selected from the group consisting of N, O and S, the heterocycloalkyl can be substituted or nonsubstituted with one or more substituents selected from the group consisting of methyl, ethyl, dimethyl amino, and halogen.

Preferably, $R^2$ is nonsubstituted or substituted $C_{6-10}$ aryl or nonsubstituted or substituted 5~10 membered heteroaryl containing one or more heteroatoms selected from the group consisting of N, O and S, wherein, the substituted aryl or the substituted heteroaryl can be substituted with one or more substituents selected from the group consisting of halogen, —$CH_2$—$R^3$, $C_{1-10}$ straight or branched alkyl substituted or nonsubstituted with halogen, $C_{1-2}$ alkoxy substituted or nonsubstituted with halogen, $C_{6-10}$ cycloalkyl substituted or nonsubstituted with halogen, substituted or nonsubstituted 5~10 membered heterocycloalkyl containing one or more heteroatoms selected from the group consisting of N, O and S, nonsubstituted or substituted 5~10 membered heteroaryl containing one or more heteroatoms selected from the group consisting of N, O and S, and nonsubstituted or substituted amino, wherein, the substituted heteroaryl, the substituted heterocycloalkyl, and the substituted amino can be substituted with substituted or nonsubstituted $C_{1-3}$ straight or branched alkyl, wherein, the substituted $C_{1-3}$ straight or branched alkyl can be substituted with dimethyl amino.

More preferably,

X is

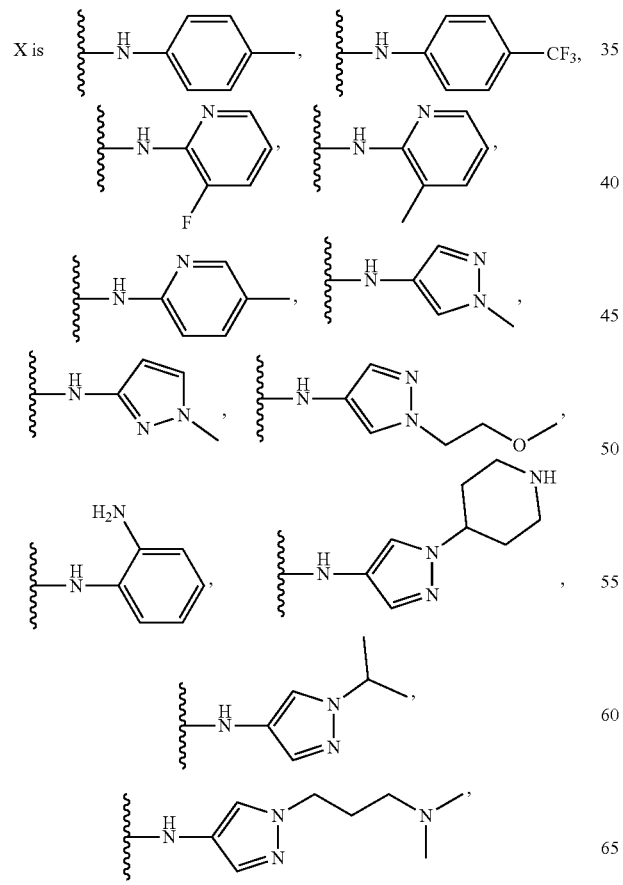

Y is

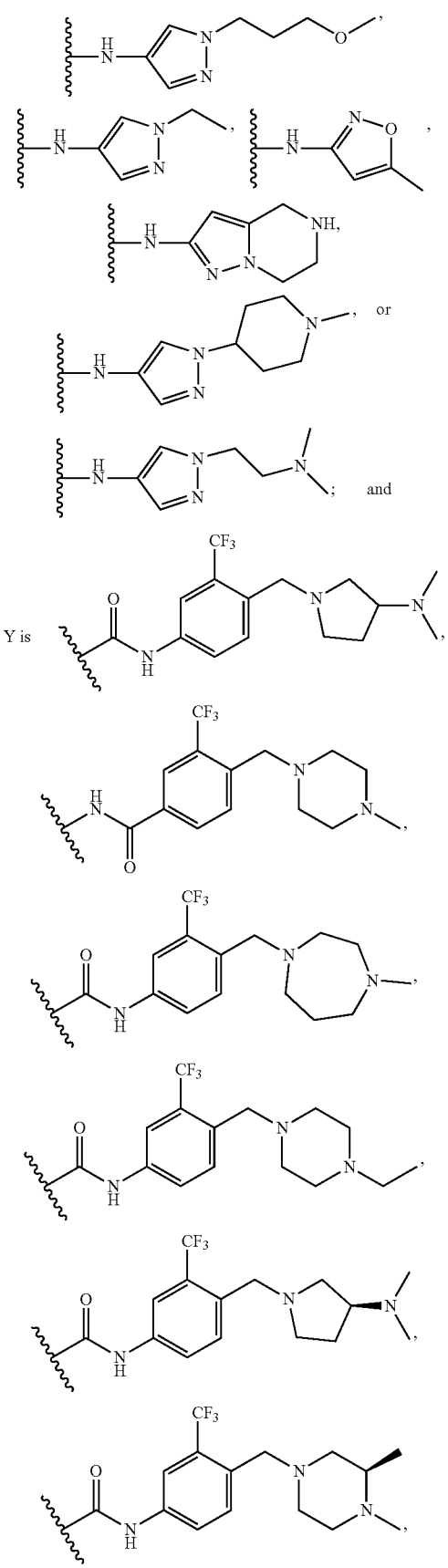

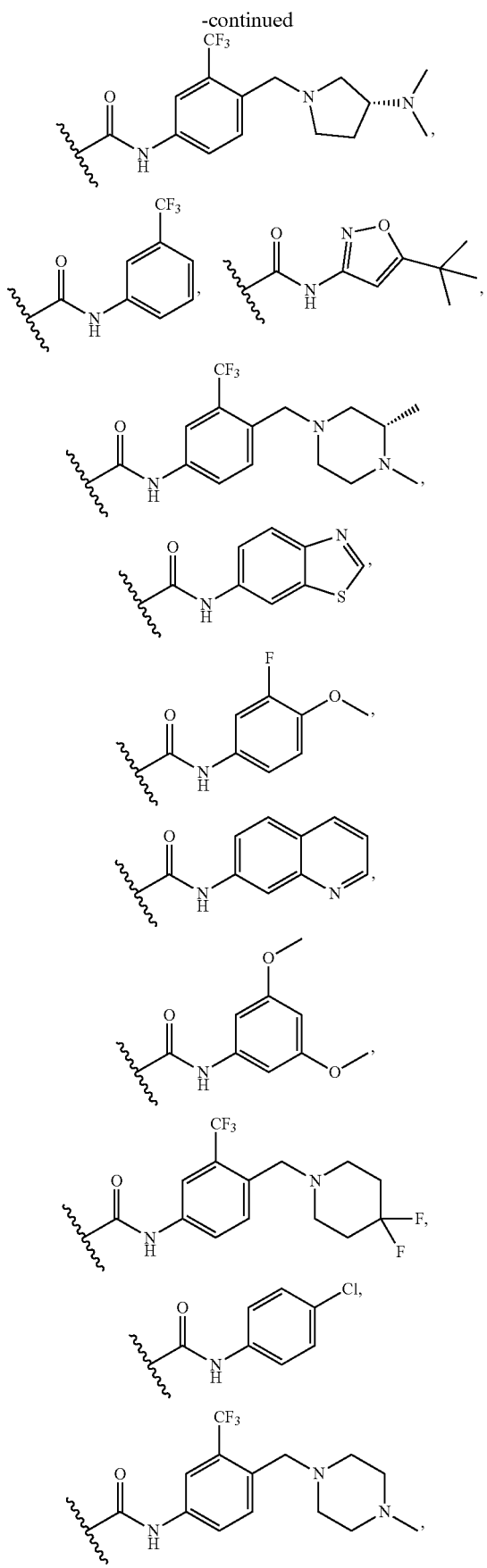
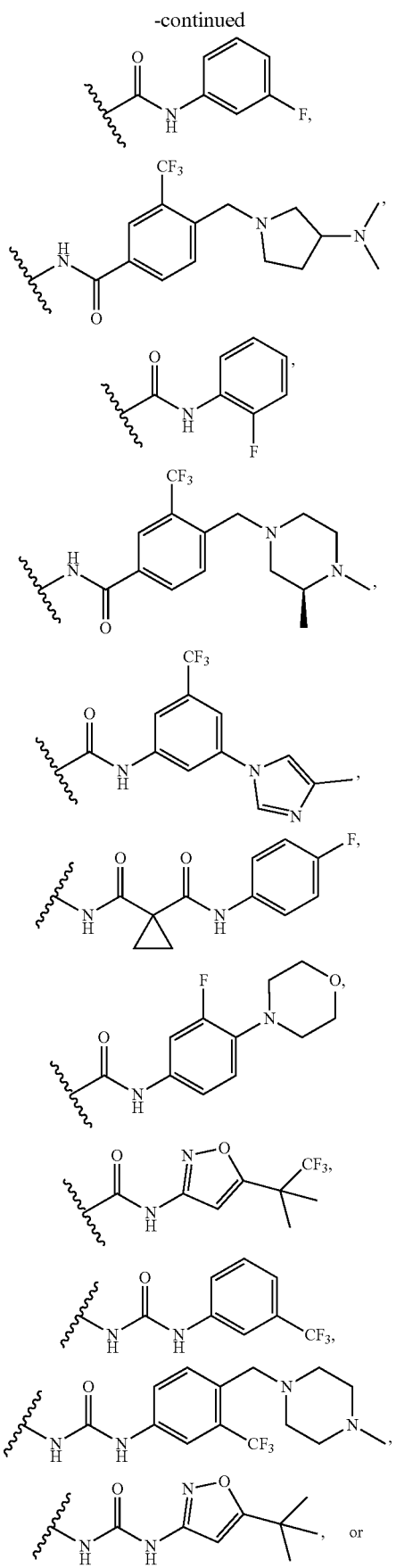

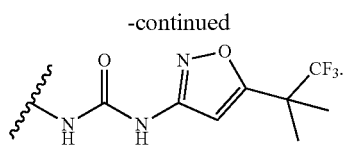

Most preferably, preferable examples of the compound represented by formula 1 according to the present invention include the following compounds.

(1) 4-methyl-3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;
(2) N-(2-fluorophenyl)-4-methyl-3-((8-((1-methyl-1H-pyrazol-4-yl)amino)imidazo[1,2-a]pyridin-3-yl)ethynyl)benzamide;
(3) N-(3,5-dimethoxyphenyl)-4-methyl-3-((8-((1-methyl-1H-pyrazol-4-yl)amino)imidazo[1,2-a]pyridin-3-yl)ethynyl)benzamide;
(4) N-(3-fluoro-4-methoxyphenyl)-4-methyl-3-((8-((1-methyl-1H-pyrazol-4-yl)amino)imidazo[1,2-a]pyridin-3-yl)ethynyl)benzamide;
(5) 3-((8-((2-aminophenyl)amino)imidazo[1,2-a]pyridin-3-yl)ethynyl)-4-methyl-N-(4-((4-methylpiperazin-1-yl)methyl)-3-(trifluoromethyl)phenyl)benzamide;
(6) N-(3-fluorophenyl)-4-methyl-3-((8-((1-methyl-1H-pyrazol-4-yl)amino)imidazo[1,2-a]pyridin-3-yl)ethynyl)benzamide;
(7) N-(4-chlorophenyl)-4-methyl-3-((8-((1-methyl-1H-pyrazol-4-yl)amino)imidazo[1,2-a]pyridin-3-yl)ethynyl)benzamide;
(8) N-(4-((4-ethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;
(9) 4-methyl-3-((8-((1-methyl-1H-pyrazol-3-yl)amino)imidazo[1,2-a]pyridin-3-yl)ethynyl)-N-(4-((4-methylpiperazin-1-yl)methyl)-3-(trifluoromethyl)phenyl)benzamide;
(10) N-(4-((4-ethylpiperazin-1-yl)methyl)-3-(trifluoromethyl)phenyl)-4-methyl-3-((8-((1-methyl-1H-pyrazol-3-yl)amino)imidazo[1,2-a]pyridin-3-yl)ethynyl)benzamide;
(11) 4-methyl-3-((8-((1-(piperidin-4-yl)-1H-pyrazol-4-yl)amino)imidazo[1,2-a]pyridin-3-yl)ethynyl)-N-(3-(trifluoromethyl)phenyl)benzamide;
(12) 4-methyl-N-(3-(4-methyl-1H-imidazol-1-yl)-5-(trifluoromethyl)phenyl)-3-((8-((1-methyl-1H-pyrazol-4-yl)amino)imidazo[1,2-a]pyridin-3-yl)ethynyl)benzamide;
(13) 4-methyl-3-((8-((1-methyl-1H-pyrazol-4-yl)amino)imidazo[1,2-a]pyridin-3-yl)ethynyl)-N-(3-(trifluoromethyl)phenyl)benzamide;
(14) 3-((8-((1-isopropyl-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;
(15) N-(4-((4-ethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;
(16) 3-((8-((3-fluoropyridin-2-yl)amino)imidazo[1,2-a]pyridin-3-yl)ethynyl)-4-methyl-N-(4-((4-methylpiperazin-1-yl)methyl)-3-(trifluoromethyl)phenyl)benzamide;
(17) N-(4-((4-ethylpiperazin-1-yl)methyl)-3-(trifluoromethyl)phenyl)-3-((8-((3-fluoropyridin-2-yl)amino)imidazo[1,2-a]pyridin-3-yl)ethynyl)-4-methylbenzamide;
(18) 4-methyl-N-(4-((4-methylpiperazin-1-yl)methyl)-3-(trifluoromethyl)phenyl)-3-((8-((3-methylpyridin-2-yl)amino)imidazo[1,2-a]pyridin-3-yl)ethynyl)benzamide;
(19) 4-methyl-N-(4-((4-methylpiperazin-1-yl)methyl)-3-(trifluoromethyl)phenyl)-3-((8-((4-(trifluoromethyl)phenyl)amino)imidazo[1,2-a]pyridin-3-yl)ethynyl)benzamide;
(20) 4-methyl-N-(4-((4-methylpiperazin-1-yl)methyl)-3-(trifluoromethyl)phenyl)-3-((8-((5-methylpyridin-2-yl)amino)imidazol[1,2-a]pyridin-3-yl)ethynyl)benzamide;
(21) N-(4-((4-ethylpiperazin-1-yl)methyl)-3-(trifluoromethyl)phenyl)-4-methyl-3-((8-((5-methylpyridin-2-yl)amino)imidazol[1,2-a]pyridin-3-yl)ethynyl)benzamide;
(22) 3-((8-((1-ethyl-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;
(23) 3-((8-((1-ethyl-1H-pyrazol-4-yl)amino)imidazo[1,2-a]pyridin-3-yl)ethynyl)-N-(4-((4-ethylpiperazin-1-yl)methyl)-3-(trifluoromethyl)phenyl)-4-methylbenzamide;
(24) 4-methyl-N-(4-((4-methylpiperazin-1-yl)methyl)-3-(trifluoromethyl)phenyl)-3-((8-(p-toylamino)imidazo[1,2-a]pyridin-3-yl)ethynyl)benzamide;
(25) N-(4-((4-ethylpiperazin-1-yl)methyl)-3-(trifluoromethyl)phenyl)-4-methyl-3-((8-(p-toylamino)imidazo[1,2-a]pyridin-3-yl)ethynyl)benzamide;
(26) 3-((8-((1-(3-(dimethylamino)propyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;
(27) 3-((8-((1-(3-(dimethylamino)propyl)-1H-pyrazol-4-yl)amino)imidazo[1,2-a]pyridin-3-yl)ethynyl)-4-methyl-N-(3-(trifluoromethyl)phenyl)benzamide;
(28) 4-methyl-3-((8-((5-methylisoxazol-3-yl)amino)imidazo[1,2-a]pyridin-3-yl)ethynyl)-N-(4-((4-methylpiperazin-1-yl)methyl)-3-(trifluoromethyl)phenyl)benzamide;
(29) (R)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;
(30) N-(4-((3-(dimethylamino)pyrrolidin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;
(31) (R)—N-(4-((3,4-dimethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;
(32) N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;
(33) 3-((8-((1-(3-(dimethylamino)propyl)-1H-pyrazol-4-yl)amino)imidazo[1,2-a]pyridin-3-yl)ethynyl)-N-(4-((4-ethylpiperazin-1-yl)methyl)-3-(trifluoromethyl)phenyl)-4-methylbenzamide;
(34) (R)-3-((8-((1-(3-(dimethylamino)propyl)-1H-pyrazol-4-yl)amino)imidazo[1,2-a]pyridin-3-yl)ethynyl)-N-(4-((3,4-dimethylpiperazin-1-yl)methyl)-3-(trifluoromethyl)phenyl)-4-methylbenzamide;
(35) 3-((8-((1-(3-(dimethylamino)propyl)-1H-pyrazol-4-yl)amino)imidazo[1,2-a]pyridin-3-yl)ethynyl)-N-(4-((3-(dimethylamino)pyrrolidin-1-yl)methyl)-3-(trifluoromethyl)phenyl)-4-methylbenzamide;
(36) 3-((8-((1-(3-(dimethylamino)propyl)-1H-pyrazol-4-yl)amino)imidazo[1,2-a]pyridin-3-yl)ethynyl)-N-(4-((3-(dimethylamino)pyrrolidin-1-yl)methyl)-3-(trifluoromethyl)phenyl)-4-methylbenzamide;
(37) N-(benzo[d]thiazol-6-yl)-4-methyl-3-((8-((1-methyl-1H-pyrazol-4-yl)amino)imidazo[1,2-a]pyridin-3-yl)ethynyl)benzamide;

(38) 3-((8-((1-isopropyl-1H-pyrazol-4-yl)amino)imidazo[1,2-a]pyridin-3-yl)ethynyl)-4-methyl-N-(4-((4-methyl-1,4-diazepin-1-yl)methyl)-3-(trifluoromethyl)phenyl)benzamide;

(39) 3-((8-((1-(3-(dimethylamino)propyl)-1H-pyrazol-4-yl)amino)imidazo[1,2-a]pyridin-3-yl)ethynyl)-4-methyl-N-(4-((4-methyl-1,4-diazepin-1-yl)methyl)-3-(trifluoromethyl)phenyl)benzamide;

(40) (R)—N-(4-((3,4-dimethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;

(41) N-(4-((3-(dimethylamino)pyrrolidin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;

(42) (R)—N-(4-((3,4-dimethylpiperazin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide;

(43) N-(4-((3-(dimethylamino)pyrrolidin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide;

(44) (S)—N-(4-((3,4-dimethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;

(45) N-(4-((3-(dimethylamino)pyrrolidin-1-yl)methyl)-3-(trifluoromethyl)phenyl)-4-methyl-3-((8-((5-methylisoxazol-3-yl)amino)imidazo[1,2-a]pyridin-3-yl)ethynyl)benzamide;

(46) (S)—N-(4-((3,4-dimethylpiperazin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide;

(47) (S)—N-(4-((3,4-dimethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(48) (S)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;

(49) (S)-3-((8-((1-(3-(dimethylamino)propyl)-1H-pyrazol-4-yl)amino)imidazo[1,2-a]pyridin-3-yl)ethynyl)-N-(4-((3,4-dimethylpiperazin-1-yl)methyl)-3-(trifluoromethyl)phenyl)-4-methylbenzamide;

(50) (R)—N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(51) (S)—N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(52) N-(4-((4,4-difluoropiperidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(53) (R)—N-(4-((3-(dimethylamino)pyrrolidin-1-yl)methyl)-3-(trifluoromethyl)phenyl)-3-((8-((1-ethyl-1H-pyrazol-4-yl)amino)imidazo[1,2-a]pyridin-3-yl)ethynyl)-4-methylbenzamide;

(54) (S)—N-(4-((3-(dimethylamino)pyrrolidin-1-yl)methyl)-3-(trifluoromethyl)phenyl)-3-((8-((1-ethyl-1H-pyrazol-4-yl)amino)imidazo[1,2-a]pyridin-3-yl)ethynyl)-4-methylbenzamide;

(55) N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(56) 3-((8-((1-ethyl-1H-pyrazol-4-yl)amino)imidazo[1,2-a]pyridin-3-yl)ethynyl)-N-(3-fluoro-4-morpholinophenyl)-4-methylbenzamide;

(57) 3-((8-((1-(2-methoxyethyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;

(58) 3-((8-((1-(2-methoxyethyl)-1H-pyrazol-4-yl)amino)imidazo[1,2-a]pyridin-3-yl)ethynyl)-4-methyl-N-(5-(1,1,1-trifluoro-2-methylpropan-2-yl)isoxazol-3-yl)benzamide;

(59) N-(5-(tert-butyl)isoxazol-3-yl)-3-((8-((1-(2-methoxyethyl)-1H-pyrazol-4-yl)amino)imidazo[1,2-a]pyridin-3-yl)ethynyl)-4-methylbenzamide;

(60) 3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;

(61) 4-fluoro-3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;

(62) N-(4-chloro-3-(trifluoromethyl)phenyl)-4-methyl-3-((8-((1-methyl-1H-pyrazol-4-yl)amino)imidazo[1,2-a]ethynyl)benzamide;

(63) N-(4-chloro-3-(trifluoromethyl)phenyl)-4-methyl-3-((8-((1-(piperidin-4-yl)-1H-pyrazol-4-yl)amino)imidazo[1,2-a]pyridin-3-yl)ethynyl)benzamide;

(64) 3-((8-(6-(2-hydroxypropan-2-yl)pyridin-2-yl)amino-imidazo[1,2-a]pyridin-3-yl)ethynyl)-4-methyl-N-(4-((4-methylpiperazin-1-yl)methyl)-3-(trifluoromethyl)phenyl)benzamide;

(65) 3-((8-(1-(3-methoxypropyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;

(66) 4-methyl-N-(4-((4-methylpiperazin-1-yl)methyl)-3-(trifluoromethyl)phenyl)-3-((8-((4,5,6,7-tetrahydropyrazolo[1,5-a]pyrazin-2-yl)amino)imidazo[1,2-a]pyridin-3-yl)ethynyl)benzamide;

(67) 4-methyl-3-((8-((4,5,6,7-tetrahydropyrazolo[1,5-a]pyrazin-2-yl)amino)imidazo[1,2-a]pyridin-3-yl)ethynyl)-N-(3-(trifluoromethyl)phenyl)benzamide;

(68) N-(5-(tert-butyl)isoxazol-3-yl)-4-methyl-3-((8-((4,5,6,7-tetrahydropyrazolo[1,5-a]pyrazin-2-yl)amino)imidazo[1,2-a]pyridin-3-yl)ethynyl)benzamide;

(69) N-(4-((4-ethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;

(70) 3-((8-(1-(2-methoxyethyl)-1H-pyrazol-4-yl)amino)imidazo[1,2-a]pyridin-3-yl)ethynyl)-4-methyl-N-((trifluoromethyl)phenyl)benzamide;

(71) 3-((8-(1-(2-methoxyethyl)-1H-pyrazol-4-yl)amino)imidazo[1,2-a]pyridin-3-yl)ethynyl)-4-methyl-N-((4-methyl-1H-imidazol-1-yl)-5-(trifluoromethyl)phenyl)benzamide;

(72) 4-methyl-3-((8-((1-(1-methylpiperidin-4-yl)-1H-pyrazol-4-yl)amino)imidazo[1,2-a]pyridin-3-yl)-N-(3-(trifluoromethyl)phenyl)benzamide;

(73) 3-((8-(2-(dimethylamino)ethyl)-1H-pyrazol-4-yl)amino)imidazo[1,2-a]pyridin-3-yl)-ethynyl)-N-((4-ethylpiperazin-1-yl)methyl)-3-(trifluoromethyl)phenyl)-4-methylbenzamide;

(74) 3-((8-(2-(dimethylamino)ethyl)-1H-pyrazol-4-yl)amino)imidazo[1,2-a]pyridin-3-yl)N-(3-(trifluoromethyl)phenyl)benzamide;

(75) 3-((8-(2-(dimethylamino)ethyl)-1H-pyrazol-4-yl) amino)imidazo[1,2-a]pyridin-3-yl)N-(3-(4-methyl-1H-imidazol-1-yl)-5-(trifluoromethyl)phenyl)benzamide;
(76) (3-(4-methyl-1H-imidazol-1-yl)-5-(trifluoromethyl) phenyl)-3-((8-((1-(1-methylpiperidin-4-yl)-1H-pyrazol-4-yl)amino)imidazo[1,2-a]pyridin-3-yl)ethynyl)benzamide;
(77) N-(3-((8-((1-isopropyl-1H-pyrazol-4-yl)amino)imidazo[1,2-a]pyridin-3-yl)ethynyl)-4-methylphenyl)-4-((4-methylpiperazin-1-yl)methyl)-3-(trifluoromethyl)benzamide;
(78) N-(4-fluorophenyl)-N-(3-((8-((1-isopropyl-1H-pyrazol-4-yl)amino)imidazo[1,2-a]pyridin-3-yl)ethynyl)-4-methylphenyl)cyclopropan-1,1-dicarboxamide;
(79) N-(4-fluorophenyl)-N-(4-methyl-3-((8-((1-methyl-1H-pyrazol-4-yl)amino)imidazo[1,2-a]pyridin-3-yl)ethynyl) phenyl)cyclopropan-1,1-dicarboxamide;
(80) N-(4-methyl-3-((8-((1-methyl-1H-pyrazol-4-yl)amino) imidazo[1,2-a]pyridin-3-yl)ethynyl)phenyl)-4-((4-methylpiperazin-1-yl)methyl)-3-(trifluoromethyl)benzamide;
(81) (R)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;
(82) 1-(3-((8-((1-isopropyl-1H-pyrazol-4-yl)amino)imidazo [1,2-a]pyridin-3-yl)ethynyl)-4-methylphenyl)-3-(4-((4-methylpiperazin-1-yl)methyl)-3-(trifluoromethyl)phenyl) urea;
(83) 1-(3-((8-((1-isopropyl-1H-pyrazol-4-yl)amino)imidazo [1,2-a]pyridin-3-yl)ethynyl)-4-methylphenyl)-3-(3-(trifluoromethyl)phenyl)urea;
(84) 1-(5-(tert-butyl)isoxazol-3-yl)-3-(3-((8-((1-isopropyl-1H-pyrazol-4-yl)amino)imidazo[1,2-a]pyridin-3-yl)ethynyl)-4-methylphenyl)urea; and
(85) 1-(3-((8-((1-isopropyl-1H-pyrazol-4-yl)amino)imidazo [1,2-a]pyridin-3-yl)ethynyl)-4-methylphenyl)-3-(5-(1,1,1-trifluoro-2-methylpropan-2-yl)isoxazol-3-yl)urea.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexan-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, an optical isomer, or a hydrate possibly produced from the same.

The present invention also provides a preparation method of the compound represented by formula 1 comprising the following steps, as shown in reaction formula 1 below:

preparing the compound represented by formula 4 by reacting the compound represented by formula 2 with the compound represented by formula 3 (step 1);

preparing the compound represented by formula 6 by reacting the compound represented by formula 4 prepared in step 1 above with the compound represented by formula 5 (step 2);

preparing the compound represented by formula 7 from the compound represented by formula 6 prepared in step 2 above (step 3); and preparing the compound represented by formula 1 by reacting the compound represented by formula 7 prepared in step 3 above with the compound represented by formula 8 (step 4).

[Reaction Formula 1]

STEP 1

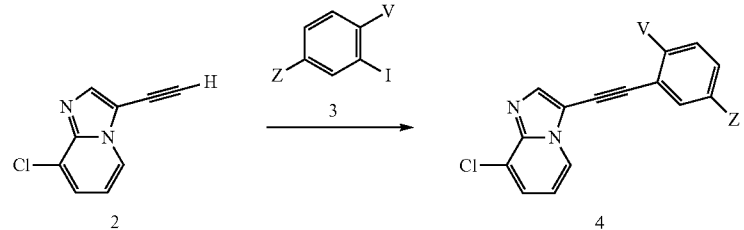

-continued

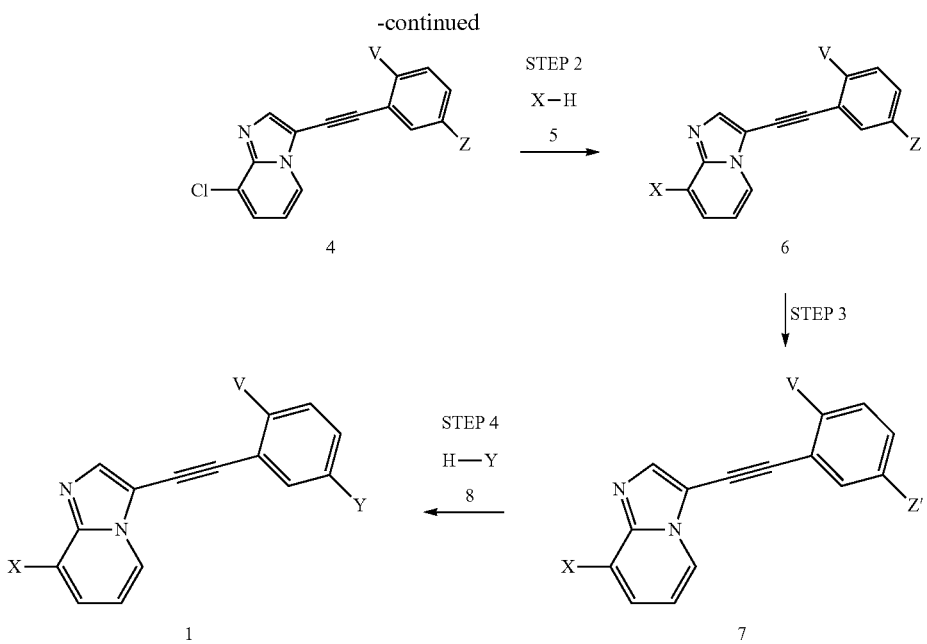

In reaction formula 1,
V, X and Y are as defined in formula 1; and
Z' is —NH² when Z is —NO² and Z' is

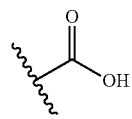

when Z is

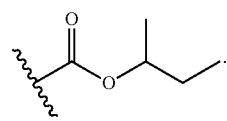 [SMILES: *C(=O)OC(C)CC]

Hereinafter, the preparation method of the compound represented by formula 1 of the present invention is described in more detail, step by step.

In the preparation method of the compound represented by formula 1 of the present invention, step 1 is to prepare the compound represented by formula 4 by reacting the compound represented by formula 2 with the compound represented by formula 3.

At this time, a usable solvent in this step is exemplified by dimethylformamide (DMF), H₂O, methanol, ethanol, tetrahydrofuran (THF), mehtylene chloride, toluene and acetonitrile, among which dimethylformamide (DMF) is more preferred.

In the step above, the reaction temperature is preferably 80 to 120° C., and the reaction time is not particularly limited but it is preferable that the reaction is carried out for 0.5~30 hours.

In the preparation method of the compound represented by formula 1 according to the present invention, step 2 is to prepare the compound represented by formula 6 by reacting the compound represented by formula 4 prepared in step 1 above with the compound represented by formula 5.

At this time, a usable solvent in this step is exemplified by dimethylformamide (DMF), H₂O, methanol, ethanol, tetrahydrofuran (THF), mehtylene chloride, toluene and acetonitrile, and t-butanol (t-BuOH) is more preferred.

In the step above, the reaction temperature is preferably 80 to 120° C., and the reaction time is not particularly limited but it is preferable that the reaction is carried out for 0.5~30 hours.

In the preparation method of the compound represented by formula 1 according to the present invention, step 3 is to prepare the compound represented by formula 7 from the compound represented by formula 6 prepared in step 2 above.

At this time, a usable solvent in this step is exemplified by dimethylformamide (DMF), H₂O, methanol, ethanol, tetrahydrofuran (THF), mehtylene chloride, toluene and acetonitrile, and a mixture of tetrahydrofuran, methanol and H₂O is more preferred.

In the step above, the reaction temperature is preferably 40 to 80° C., and the reaction time is not particularly limited but it is preferable that the reaction is carried out for 0.5~10 hours.

In the preparation method of the compound represented by formula 1 according to the present invention, step 4 is to prepare the compound represented by formula 1 by reacting the compound represented by formula 7 prepared in step 3 above with the compound represented by formula 8.

At this time, a usable solvent in this step is exemplified by dimethylformamide (DMF), H₂O, methanol, ethanol, tetrahydrofuran (THF), mehtylene chloride, toluene and acetonitrile, among which dimethylformamide (DMF) is more preferred.

In the step above, the reaction temperature is preferably 40 to 80° C., and the reaction time is not particularly limited but it is preferable that the reaction is carried out for 0.5~20 hours.

In the preparation method of the compound represented by formula 1 according to the present invention, each step described above can be accomplished by the method for preparing the compounds of examples of the present invention described below. The preparation method above includes any possible changes or modifications of experimental methods or conditions made by those in the art.

In addition, the present invention provides a pharmaceutical composition comprising the compound represented by formula 1, the optical isomer thereof or the pharmaceutically acceptable salt thereof as an active ingredient for the prevention or treatment of Ret (Rearranged during transfection), ABL1 (E255K)-phosphorylated, ABL1 (F317I)-nonphosphorylated, ABL1 (F317I)-phosphorylated, ABL1 (F317L)-nonphosphorylated, ABL1 (F317L)-phosphorylated, ABL1 (H396P)-nonphosphorylated, ABL1 (H396P)-phosphorylated, ABL1 (M351T)-phosphorylated, ABL1 (Q252H)-nonphosphorylated, ABL1 (Q252H)-phosphorylated, ABL1 (T315I)-nonphosphorylated, ABL1 (T315I)-phosphorylated, ABL1 (Y253F)-phosphorylated, ABL1-nonphosphorylated, ABL1-phosphorylated, ABL2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR (E746-A750del), EGFR (G719C), EGFR (G719S), EGFR (L747-E749del, A750P), EGFR (L747-S752del, P753S), EGFR (L747-T751del,Sins), EGFR (L858R), EGFR (L858R,T790M), EGFR (L861Q), EGFR(S752-I759del), EGFR (T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3 (G697C), FGFR4, FGR, FLT1, FLT3, FLT3 (D835H), FLT3 (D835V), FLT3 (D835Y), FLT3 (ITD), FLT3 (ITD,D835V), FLT3 (ITD,F691L), FLT3 (K663Q), FLT3 (N841I), FLT3 (R834Q), FLT4, FRK, FYN, GAK, GCN2 (Kin.Dom.2,S808G), HCK, HIPK4, HPK1, IKK-alpha, IKK-beta, IRAK1, IRAK4, ITK, JAK1 (JH1domain-catalytic), JAK2 (JH1domain-catalytic), JAK3 (JH1domain-catalytic), JNK1, JNK2, JNK3, KIT, KIT (A829P), KIT (D816H), KIT (D816V), KIT (L576P), KIT (V559D), KIT (V559D,T670I), KIT (V559D,V654A), LCK, LIMK1, LIMK2, LOK, LRRK2, LRRK2 (G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1 (*P. falciparum*), PFTAIRE2, PFTK1, PKAC-alpha, PKAC-beta, PYK2, RAF1, RET, RET (M918T), RET (V804L), RET (V804M), RIPK1, RIPK2, RIPK4, ROCK2, RPS6KA4 (Kin.Dom.1-N-terminal), RSK2 (Kin.Dom.1-N-terminal), RSK3 (Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or FGFR (Fibroblast growth factor receptor) related diseases include, but not limited thereto, all diseases caused by abnormal activity of the enzyme such as abnormality, modification, and over-expression. In particular, an example of the enzyme related diseases above is cancer. When cancer is developed by abnormal activity of Ret or FGFR involved in cancer cell proliferation, the compound of the present invention, the optical isomer thereof and the pharmaceutically acceptable salt thereof can efficiently inhibit the activity of the enzymes above at nanomol units, indicating that the compound of the present invention, the optical isomer thereof and the pharmaceutically acceptable salt thereof can be effectively used for the prevention or treatment of the mentioned enzyme related diseases.

Among the enzymes mentioned above, the Src and Fyn related disease is exemplified by diabetic nephropathy, but not always limited thereto. Any disease that can be efficiently treated by inhibiting Src and Fyn by the method informed by those in the art can be included in the criteria of the present invention.

In particular, the compound of the present invention was proved by experiments to be an effective compound to treat cancer and diabetic nephropathy. Since the compound displays an efficient effect on the diseases related to the enzymes listed above and thereby can be used as a drug, which is well understood by those in the art, the compound above is included in the present invention.

The present invention also provides a pharmaceutical composition comprising the compound represented by formula 1 above, the optical isomer thereof or the pharmaceutically acceptable salt thereof as an active ingredient for the prevention or treatment of cancer.

Herein, the compound of the present invention is characterized by preventing or treating cancer by inhibiting the enzymes mentioned above. At this time, the cancer can be one or more cancers selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblastic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamous cell carcinoma of lung, skin cancer, anal cancer, rhabdomyosarcoma, laryngeal cancer, pleural cancer, and thymus cancer.

The present invention also provides a health functional food composition comprising the compound represented by formula 1 above, the optical isomer thereof or the pharmaceutically acceptable salt thereof as an active ingredient for preventing or ameliorating cancer.

Herein, the compound of the present invention is characterized by preventing or ameliorating cancer by inhibiting Ret (Rearranged during transfection), ABL1 (E255K)-phosphorylated, ABL1 (F317I)-nonphosphorylated, ABL1 (F317I)-phosphorylated, ABL1 (F317L)-nonphosphorylated, ABL1 (F317L)-phosphorylated, ABL1 (H396P)-nonphosphorylated, ABL1 (H396P)-phosphorylated, ABL1 (M351T)-phosphorylated, ABL1 (Q252H)-nonphosphorylated, ABL1 (Q252H)-phosphorylated, ABL1 (T315I)-nonphosphorylated, ABL1 (T315I)-phosphorylated, ABL1 (Y253F)-phosphorylated, ABL1-nonphosphorylated, ABL1-phosphorylated, ABL2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR (E746-A750del), EGFR (G719C), EGFR (G719S), EGFR (L747-E749del, A750P), EGFR (L747-S752del, P753S), EGFR (L747-T751del, Sins), EGFR (L858R), EGFR (L858R,T790M), EGFR (L861Q), EGFR(S752-I759del), EGFR (T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3 (G697C), FGFR4, FGR, FLT1, FLT3, FLT3 (D835H), FLT3 (D835V), FLT3 (D835Y), FLT3 (ITD), FLT3 (ITD,D835V), FLT3 (ITD,F691L), FLT3 (K663Q), FLT3 (N841I), FLT3 (R834Q), FLT4, FRK, FYN, GAK, GCN2 (Kin.Dom.2,S808G), HCK, HIPK4, HPK1, IKK-alpha, IKK-beta, IRAK1, IRAK4, ITK, JAK1 (JH1domain-catalytic), JAK2 (JH1domain-catalytic), JAK3 (JH1domain-catalytic), JNK1, JNK2, JNK3, KIT, KIT (A829P), KIT (D816H), KIT (D816V), KIT (L576P), KIT (V559D), KIT (V559D,T670I), KIT (V559D,V654A), LCK, LIMK1, LIMK2, LOK, LRRK2, LRRK2 (G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1 (*P. falciparum*), PFTAIRE2, PFTK1, PKAC-alpha, PKAC-beta, PYK2, RAF1, RET, RET (M918T), RET (V804L), RET (V804M), RIPK1, RIPK2, RIPK4, ROCK2, RPS6KA4 (Kin.Dom.1-N-terminal), RSK2 (Kin.Dom.1-N-terminal), RSK3 (Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or FGFR (Fibroblast growth factor receptor). At this time, the cancer can be one or more cancers selected from the group consisting of colon cancer, liver cancer, stomach cancer, breast cancer, colon cancer, bone cancer, pancreatic cancer, head and neck cancer, uterine cancer, ovarian cancer, rectal cancer, esophageal cancer, small bowel cancer, anal cancer, colon cancer, fallopian tube carcinoma, endometrial carcinoma, cervical carcinoma, vaginal carcinoma, vulvar carcinoma, Hodgkin's disease, prostate cancer, bladder cancer, kidney cancer, ureter cancer, kidney cell carcinoma, kidney pelvic carcinoma, central nervous system tumor and leukemia.

The present invention also provides a pharmaceutical composition comprising the compound represented by formula 1 above, the optical isomer thereof or the pharmaceutically acceptable salt thereof as an active ingredient for the prevention or treatment of diabetic nephropathy.

Herein, diabetic nephropathy is understood as the common nephrosis caused by diabetes. In this invention, the compound of the present invention was confirmed to be used as a drug to treat Src and Fyn related diseases in a diabetic nephropathy animal model. Therefore, the compound of the present invention is provided as an active ingredient of a drug to treat diabetic nephropathy.

The compound of the present invention can be used as a pharmaceutical composition for the prevention and/or treatment of diabetic microalbuminuria characterized by decreasing albuminuria in the early microalbuminuria stage of diabetic nephropathy and reducing the ratio of albumin-creatinine, but not always limited thereto. Therefore, the compound of the present invention is provided as a pharmaceutical composition for the prevention or treatment of disease that can be confirmed to be prevented or treated by the composition from the experiment with the enzyme activity inhibition animal model of the present invention.

In addition, the present invention provides a health functional food composition comprising the compound represented by formula 1 above, the optical isomer thereof or the pharmaceutically acceptable salt thereof as an active ingredient for preventing or ameliorating diabetic nephropathy.

The compound represented by formula 1 according to the present invention can be prepared for oral or parenteral administration by mixing with generally used diluents or excipients such as fillers, extenders, binders, wetting agents, disintegrating agents and surfactants.

Solid formulations for oral administration are tablets, pills, powders, granules, capsules and troches. These solid formulations are prepared by mixing one or more the compounds of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the compound of the present invention can vary depending on the patient's age, weight, gender, administration form, health condition and disease severity, which is generally about 0.001-100 mg/kg/day, and preferably 0.01-35 mg/kg/day. Based on an adult patient weighing 70 kg, the dosage is generally 0.07-7000 mg/day, and preferably 0.7-2500 mg/day. The compound of the present invention can be administered once or several times a day at a predetermined time interval according to the judgment of a doctor or a pharmacist.

In addition, the present invention provides a treatment method of cancer comprising the step of administering a therapeutically effective dose of the compound of the present invention above, the optical isomer thereof or the pharmaceutically acceptable salt thereof to a subject having cancer.

At this time, the said cancer includes all the cancers mentioned above.

The therapeutically effective dose means the amount of the compound above, the optical isomer or the pharmaceutically acceptable salt thereof that can ameliorate symptoms or conditions of a subject when administered in vivo. The amount can vary depending on the weight, age, gender, condition, and family history of the subject to be administered. The treatment method in the present invention, therefore, can set different doses according to different conditions depending on the subject.

The "effective dose" above indicates the amount that is efficient in treating proliferative, inflammatory, infectious, neurological or cardiovascular disorder or in treating cancer. In another preferred embodiment of the present invention, the "effective dose" means the amount at least it can inhibit the proliferation of cancer.

The present invention also provides a treatment method of diabetic nephropathy comprising the step of administering a therapeutically effective dose of the compound of the present invention above, the optical isomer thereof or the pharmaceutically acceptable salt thereof to a subject having diabetic nephropathy.

The therapeutically effective dose means the amount of the compound above, the optical isomer or the pharmaceutically acceptable salt thereof that can ameliorate symptoms or conditions of a subject when administered in vivo. The amount can vary depending on the weight, age, gender, condition, and family history of the subject to be administered. The treatment method in the present invention, therefore, can set different doses according to different conditions depending on the subject.

The "effective dose" above indicates the amount that is efficient in treating proliferative, inflammatory, infectious, neurological or cardiovascular disorder or in treating diabetic nephropathy. In another preferred embodiment of the present invention, the "effective dose" means the amount at least it can inhibit the proliferation of cancer.

The compound and the composition of the present invention can be administered at an effective dose by a random administration pathway for the treatment of a disease. The required dose can be determined according to the species, age, and general condition of a subject, severity of infection, a specific agent being used and its mode of administration, etc. The compound of the present invention can be frequently formulated in a dose unit form for ease of administration and uniformity. The term "dose unit form" means a physically independent unit of formulation which is appropriate for the treatment of a target subject, as used herein. However, it is well understood that the total daily dose of the compound and the composition of the present invention can be determined by a doctor within the scope of sound medical judgment. A required dose for a target subject or an organism is determined by various factors including the followings.

The term "subject" herein indicates an animal, for example a mammal, and a human.

The pharmaceutical composition of the present invention can be administered orally, rectally, parenterally, intracavally, intravaginally, intraperitoneally, topically (as powders, ointments, lotions, ointments, or drops) to human and other animals, depending on the severity of the infection to be treated. In a preferred embodiment of the present invention, the compound of the present invention can be administered orally or parenterally at the dose of approximately 0.01 mg/kg-50 mg/kg in order to obtain a desired therapeutic effect, more precisely approximately 1 mg/kg-25 mg/subject body weight kg/day can be administered at least once a day within a daily dose.

Liquid formulation for oral administration includes pharmaceutically acceptable emulsions, microemulsions, solutions, suspensions, syrups and elixirs, but not always limited thereto. In addition to the active compound, the liquid formulation can additionally include inert diluents of the following examples commonly used in the art: water or other solvents, solubilizing agents and emulsifying agents such as ethyl alcohol, isopropyl alcohol, ethyl carbonate, ethyl acetate, benzyl alcohol, benzyl benzoate, propylene glycol, 1,3-butylene glycol, dimethyl formamide, oil (for example, cotton seed oil, peanut oil, corn oil, bacteria oil, olive oil, caster oil, and sesame oil), glycerol, tetrahydrofuryl alcohol, polyethylene glycol, fatty acid ester of sorbitan, and mixtures thereof. In addition to the inert diluents, the formulation for oral administration can also include adjuvants such as wetting agents, emulsifying and suspending agents, sweetening agents, flavoring agents, and flavoring agents.

Injectable preparations, for example, sterile injectable aqueous or lipid productive suspensions can be formulated by using proper dispersing or wetting agents and suspending agents according to the well known art. The sterile injectable preparations can also be sterile injectable solutions, suspensions or emulsions in a non-toxic parenterally acceptable diluent or solvent, for example 1,3-butanediol solution. Among usable vehicles and solvents, water, Ringer's solution, USP and isotonic sodium chloride solution can be selected. A sterilized fixed oil has been used conventionally as a solvent or a dispersion medium. A random blend fixed oil including synthetic mono- or diglyceride can be used for this purpose. In addition, fatty acids such as oleic acid can be used for the preparation of injectable preparations.

The injectable formulations can be sterilized by filtering using a bacteria-fixed filter or incorporating a germicide as a sterilized solid composition form that can be dissolved or dispersed in sterilized water or other sterilized injectable media.

To obtain a continued effect of the compound of the present invention, slow absorption of the compound from subcutaneous or intramuscular injection is often desired. This slow absorption can be achieved by using a liquid suspension of crystalline or amorphous material having poor water solubility. The absorption rate of a compound depends on the dissolution rate affected by the crystal size and the crystal form. Alternatively, delayed absorption of the parenterally administered compound can be achieved by dissolving or suspending the compound in an oil vehicle. The injectable depot formulation can be prepared by forming a microencapsule matrix of the compound in a biodegradable polymer such as polylactide-polyglycolide. According to the ratio of the compound to the polymer and the characteristics of the particular polymer used herein, the discharge rate of the compound can be regulated. Examples of other biodegradable polymers include poly (orthoester) and poly (anhydride). The injectable depot formulation can also be prepared by entrapping the compound in liposome or microemulsion compatible with body tissues.

The composition for rectal or vaginal administration is, for example, a suppository which can be prepared by mixing the compound of the present invention with a suitable non-irritating excipient or a carrier such as cocoa butter, polyethylene glycol or suppository wax. This suppository is a solid at a solid ambient temperature, but is a liquid at body temperature and therefore melts in the rectum or vagina to release the active compound.

Solid formulations for oral administration include capsules, tablets, pills, powders, and granules. In such solid formulations for oral administration, the active compound is mixed with the followings: at least one inert, pharmaceutically acceptable excipient or carrier such as sodium citrate or dicalcium phosphate and/or a) fillers or extenders such as starch, lactose, sucrose, glucose, mannitol and silicic acid, b) binders such as carboxymethylcellulose, alginate, gelatin, polyvinylpyrrolidinone, sucrose and acacia, c) humectant such as glycerol, d) disintegrating agent such as agar-agar, calcium carbonate, potato or tapioca starch, alginic acid, any silicate and sodium carbonate, e) solution retarders such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the administration formulations can also contain buffering agents.

Solid compositions of a similar type can also be employed as fillers in soft and hard-filled gelatin capsules using excipients such as lactose or milk sugar as well as high molecular polyethylene glycol. Solid formulations such as tablets, dragees, capsules, tablets, and granules can be prepared by mixing with coating materials and shells such as enteric coating materials and other coating materials well known in the field of pharmaceutical formulation technology. The composition can contain an opacifying agent. The composition of the present invention can be a composition that releases only the active ingredient(s), for example, in a particular part of the intestinal tract in a delayed manner. A usable embedding composition is exemplified by a polymeric substance and wax. Solid compositions of a similar type can also be employed as fillers in soft and hard-filled gelatin capsules using excipients such as lactose or milk sugar as well as high molecular polyethylene glycol.

The active compound can also be in a microencapsulated form with one or more excipients as described above. Solid formulations such as tablets, dragees, capsules, tablets, and granules can be prepared by mixing with coating materials and shells such as enteric coating materials and other coating materials well known in the field of pharmaceutical formulation technology. In such solid formulations, the active compound can be mixed with one or more inert diluents such as sucrose, lactose and starch. Such administration formulations can also contain additional substances other than inert diluents, such as tabletting lubricants and other tabletting aids such as magnesium stearate and microcrystalline cellulose. In the case of capsules, tablets and pills, the administration formulations can also contain buffering agents. The composition can contain an opacifying agent. The composition of the present invention can be a composition that releases only the active ingredient(s), for example, in a particular part of the intestinal tract in a delayed manner. A usable embedding composition is exemplified by a polymeric substance and wax.

The formulations for topical or transdermal administration of the present invention include ointments, pastes, creams, lotions, gels, powders, solutions, sprays, inhalants or patches. The active ingredient is mixed with a pharmaceutically acceptable carrier and any necessary preservative or buffer under the sterile condition. Ophthalmic formulations, ear drops, and eye drops are also contemplated as being within the scope of the present invention. The present invention additionally includes transdermal patches which had advantage of providing controlled cleavage of the compound to the body. Such administration formulations can be prepared by dissolving or dispersing the compound in a proper medium. An absorption enhancer can also be used to increase the flow of the compound across the skin. The absorption rate can be controlled by providing a rate controlling membrane or by dispersing the compound in a polymer matrix or gel.

In a preferred embodiment of the present invention, the compound of the present invention or the pharmaceutical composition comprising the same can be administered with an anticancer agent. In the present invention, the term "anticancer agent" refers to any agent that is administered to a subject with cancer for the purpose of cancer treatment. Combination therapy includes administration of the therapeutic agents concurrently or sequentially. Alternatively, the therapeutic agent can be combined into one composition to be administered to a subject.

In a preferred embodiment of the present invention, the compound of the present invention is co-treated with other therapeutic agents. The compound of the present invention can be administered alone or treated together with cytotoxic drugs, radiation therapy, and immunotherapy.

Additional agents can be administered separately from the combination therapy provided as a part of a multiple dose regimen. Alternatively, the agents can be a part of a single dosage form mixed with the compound of the present invention. If administered as a part of a combination therapy, the two therapeutic agents can be administered simultaneously, sequentially, or intermittently. The combination therapy can be used for any of symptoms described herein. In a preferred embodiment of the present invention, the combination therapy is performed to treat a proliferative disorder (for example, cancer) of a subject.

In another aspect of the present invention, the present invention relates to inhibit cancer in a biological sample or a subject. The method comprises administering the compound represented by formula 1 or the composition comprising the said compound, or contacting the biological sample with the said compound. The term "biological sample" herein includes in vivo, in vitro and ex vivo materials, and also includes cell cultures or extracts thereof; biopsied materials obtained from a mammal or extracts thereof; and blood, saliva, urine, feces, semen, tears, or other body fluids or extracts thereof.

The compound of the present invention, the optical isomer thereof or the pharmaceutically acceptable salt thereof has been confirmed through experiments to be efficient in preventing or treating cancer.

To evaluate the inhibitory activity of the compound of the present invention on enzymes, the experiment was performed as described in Experimental Example 1. As a result, it was confirmed that the compound of the present invention had inhibitory activity against Ret (Rearranged during transfection), ABL1 (E255K)-phosphorylated, ABL1 (F317I)-nonphosphorylated, ABL1 (F317I)-phosphorylated, ABL1 (F317L)-nonphosphorylated, ABL1 (F317L)-phosphorylated, ABL1 (H396P)-nonphosphorylated, ABL1 (H396P)-phosphorylated, ABL1 (M351T)-phosphorylated, ABL1 (Q252H)-nonphosphorylated, ABL1 (Q252H)-phosphorylated, ABL1 (T315I)-nonphosphorylated, ABL1 (T315I)-phosphorylated, ABL1 (Y253F)-phosphorylated, ABL1-nonphosphorylated, ABL1-phosphorylated, ABL2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR (E746-A750del), EGFR (G719C), EGFR (G719S), EGFR (L747-E749del, A750P), EGFR (L747-S752del, P753S), EGFR (L747-T751del,Sins), EGFR (L858R), EGFR (L858R,T790M), EGFR (L861Q), EGFR (S752-I759del), EGFR (T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3 (G697C), FGFR4, FGR, FLT1, FLT3, FLT3 (D835H), FLT3 (D835V), FLT3 (D835Y), FLT3 (ITD), FLT3 (ITD,D835V), FLT3 (ITD,F691L), FLT3 (K663Q), FLT3 (N841I), FLT3 (R834Q), FLT4, FRK, FYN, GAK, GCN2 (Kin.Dom.2, S808G), HCK, HIPK4, HPK1, IKK-alpha, IKK-beta, IRAK1, IRAK4, ITK, JAK1 (JH1 domain-catalytic), JAK2 (JH1 domain-catalytic), JAK3 (JH1domain-catalytic), JNK1, JNK2, JNK3, KIT, KIT (A829P), KIT (D816H), KIT (D816V), KIT (L576P), KIT (V559D), KIT (V559D,T670I), KIT (V559D,V654A), LCK, LIMK1, LIMK2, LOK, LRRK2, LRRK2 (G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1 (*P. falciparum*), PFTAIRE2, PFTK1, PKAC-alpha, PKAC-beta, PYK2, RAF1, RET, RET (M918T), RET (V804L), RET (V804M), RIPK1, RIPK2, RIPK4, ROCK2, RPS6KA4 (Kin.Dom.1-N-terminal), RSK2 (Kin.Dom.1-N-terminal), RSK3 (Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or FGFR (Fibroblast growth factor receptor), more precisely the compound demonstrated excellent enzyme inhibitory activity at nanomol level. Thus, the compound of the present invention can be effectively used for the prevention or treatment of not only the diseases related with the enzymes listed above but also cancers induced therefrom such as colon cancer, liver cancer, stomach cancer, breast cancer, colon cancer, bone cancer, pancreatic cancer, head and neck cancer, uterine cancer, ovarian cancer, rectal cancer, esophageal cancer, small bowel cancer, anal cancer, colon cancer, fallopian tube carcinoma, endometrial carcinoma, cervical carcinoma, vaginal carcinoma, vulvar carcinoma, Hodgkin's disease, prostate cancer, bladder cancer, kidney cancer, ureter cancer, kidney cell carcinoma, kidney pelvic carcinoma, central nervous system tumor, leukemia, or distal metastatic cancers of solid tumors (see Experimental Example 1).

The cancer cell proliferation inhibition activity of the compound of the present invention was investigated with various cancer cell lines as shown in Experimental Example 2. As a result, the cancer cell proliferation inhibition effect of the compound was surprisingly excellent and thus the compound of the present invention was confirmed to be useful for the prevention or treatment of cancer.

In addition, the present inventors performed experiments with urinary obstruction or diabetic animal models as illustrated in Experimental Example 3 to evaluate the effect of the compound of the present invention. As a result, it was confirmed that the compound of the present invention was able to ameliorate the conditions of the test animals and the compound had a similar or superior pharmaceutical effect to the drugs of the clinical stage used as the control. Thus, the present invention provides the compound of the present invention as a drug for the prevention or treatment of diabetic nephropathy.

Practical and presently preferred embodiments of the present invention are illustrative as shown in the following Examples.

However, it will be appreciated that those skilled in the art, on consideration of this disclosure, may make modifications and improvements within the spirit and scope of the present invention.

In the following examples, the HPLC conditions for the structural analysis of the prepared compounds are as follows.

Condition A
Device name: Shimadzu
Column: YMC-pack pro C18, 150×4.6 mm I.D., 5 um, 40° C.
Moving phase: 5%→100% acetonitrile/H$_2$O+0.1% TFA,
Analysis time: 9 minutes, flow rate: 1 ml/min
UV detector: 254 nm
Condition B
Device name: Shimadzu
Column: YMC-pack pro C18, 150×4.6 mm I.D., 5 um, 40° C.
Moving phase: 30%→100% acetonitrile/H$_2$O+0.1% TFA,
Analysis time: 9 minutes, flow rate: 1 ml/min
UV detector: 254 nm
Condition C
Device name: Thermo Scientific
Column: YMC Triart C18, 100×2 mm I.D., 1.9 um, 40° C.
Moving phase: 5%→100% acetonitrile/H$_2$O+0.1% TFA,
Analysis time: 4.5 minutes, flow rate: 0.5 ml/min
UV detector: 254 nm
Hereinafter, the method for preparing the compounds of the present invention is described in detail.

<Preparative Example 1> Preparation of sec-butyl 3-((8-chloroimidazo[1,2-a]pyridin-3-yl)ethynyl)-4-methylbenzoate

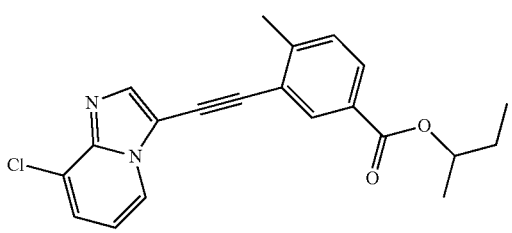 [SMILES: CCC(C)OC(=O)c1ccc(C)c(C#Cc2cnc3c(Cl)cccn23)c1]

Step 1. Preparation of 8-chloroimidazo[1,2-a]pyridine 3-chloropyridin-2-amine (1.5 g, 11.7 mmol) was dissolved in ethanol (1.5 ml), to which p-toluene sulfonic acid (11.1 g, 58.3 mmol) and chloroacetaldehyde dimethylacetal (1.5 ml, 13.2 mmol) were added, followed by reaction in a microwave reactor at 15° C. for 1 hour. The reaction mixture was cooled down and then washed with distilled water. As a result, a target compound was obtained as a brown solid (1.5 g, 84% yield).
MS m/z: 153[M+H]

Step 2. Preparation of 8-chloro-3-iodoimidazo[1,2-a]pyridine

The compound prepared in step 1 above (40 g, 262 mmol) was dissolved in DMF (150 ml), to which N-iodo-succinimide (70.8 g, 315 mmol) was added, followed by stirring for 1 hour. The reaction mixture was washed with water. As a result, a target compound 8-chloro-3-iodoimidazo[1,2-a]pyridine (71.5 g, 98%) was obtained as a brown solid.
MS m/z: 279[M+H]

Step 3. Preparation of 8-chloro-3-((trimethylsilyl)ethynyl)imidazo[1,2-a]pyridine Ethyltrimethylsilane (23.7 ml, 171 mmol), Pd(PPh$_3$)$_4$ (9.89 g, 8.56 mmol), CuI (3.26 g, 17.1 mmol) and DIPEA (50.7 ml, 291 mmol) were added to MeCN solution (150 ml) containing the compound prepared in step 2 above (71.5 g, 257 mmol), followed by stirring at 80° C. for 1 hour. The reaction mixture was cooled down to room temperature and then diluted with ethyl acetate. Then, the reaction mixture was washed with water. The organic layer was dried over MgSO$_4$, filtered and concentrated. The obtained residue was purified by silica gel chromatography (0-100% hexane: dichloromethane (3:1)/dichloromethane). As a result, a target compound was obtained as a brown solid (25 g, 59% yield).
MS m/z: 249[M+H]

Step 4. Preparation of 8-chloro-3-ethynylimidazo[1,2-a]pyridine

The compound prepared in step 3 (25 g, 100 mmol) was dissolved in THF (200 ml), to which K$_2$CO$_3$ (69.4 g, 502 mmol) was added. Methanol (200 ml) was added to the reaction mixture, followed by stirring at room temperature for 10 minutes. The reaction mixture was filtered with celite and then concentrated. The obtained residue was washed with water. As a result, a target compound was obtained as a brown solid (17 g, 96% yield).
MS m/z: 177[M+H]

Step 5. Preparation of sec-butyl 3-((8-chloroimidazo[1,2-a]pyridin-3-yl)ethynyl)-4-methylbenzoate Sec-butyl 3-iodo-4-methylbenzoate (3.6 g, 11.3 mmol), DIPEA (3.35 ml, 19.3 mmol), CuI (0.216 g, 1.13 mmol) and Pd(PPh$_3$)$_4$ (0.65 g, 0.566 mmol) were added to DMF solution (40 ml) containing the compound prepared in step 4 above (2 g, 11.3 mmol), followed by stirring at 100° C. for 15 hours. The reaction mixture was cooled down to room temperature and filtered with celite, followed by concentration. The obtained residue was diluted with ethyl acetate, followed by washing with water and brine. The organic layer was dried over MgSO$_4$, filtered and concentrated. The obtained residue was purified by silica gel chromatography. As a result, a target compound was obtained as a yellow solid (3 g, 72% yield).
MS m/z: 367[M+H]

The compounds 1~85 of the present invention were prepared by combining the compound prepared in Preparative Example 1 and the compounds prepared in Preparative Examples 2~14.

<Preparative Example 2> Preparation of (R)-4-((3,4-dimethylpiperazin-1-yl)methyl)-3-(trifluoromethyl)aniline

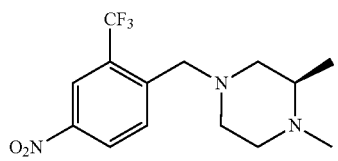 [SMILES: C[C@@H]1CN(Cc2ccc([N+](=O)[O-])cc2C(F)(F)F)CCN1C]

Step 1. Preparation of (R)-1,2-dimethyl-4-(4-nitro-2-(trifluoromethyl)benzyl)piperazine (R)-1,2-dimethylpiperazine (200 mg, 1.76 mmol) (synthesized according to the method described in PCT No. WO 2009061879) was dissolved in acetonitrile (10 ml), to which 1-(bromomethyl)-4-nitro-2-(trifluoromethyl)benzene (500 mg, 1.76 mmol) (synthesized according to the method described in PCT No. WO 2011093684) and $K_2CO_3$ (365 mg, 2.64 mmol) were added. The reaction mixture was stirred at room temperature for 3 hours. The reaction mixture was filtered and concentrated, followed by purification with silica gel chromatography (0-10% MeOH/$CH_2Cl_2$). As a result, a target compound was obtained (395 mg, 71% yield).

$^1$H NMR (400 MHz, CDCl$_3$) δ 8.50 (d, 1H), 8.37 (dd, 1H), 8.09 (d, 1H), 3.72 (s, 2H), 2.82-2.79 (m, 1H), 2.73-2.69 (m, 1H), 2.65-2.61 (m, 1H), 2.44-2.36 (m, 2H), 2.32 (s, 3H), 2.25-2.18 (m, 1H), 2.05 (t, 1H), 1.05 (d, 3H); MS m/z: 318[M+H]

Step 2. Preparation of (R)-4-((3,4-dimethylpiperazin-1-yl)methyl)-3-(trifluoromethyl)aniline (R)-1,2-dimethyl-4-(4-nitro-2-(trifluoromethyl)benzyl)piperazine (267 mg, 0.841 mmol) was dissolved in methanol (5 ml), to which Pd/C (27 mg, 0.252 mmol) was added.

The reaction mixture was filtered with celite and then concentrated. The obtained residue was purified by silica gel chromatography (0-10% MeOH/$CH_2Cl_2$). As a result, a target compound was obtained (200 mg, 83% yield).

$^1$H NMR (400 MHz, CDCl$_3$) δ 7.47 (d, 1H), 6.91 (d, 1H), 6.79 (dd, 1H), 3.76 (br s, 2H), 3.50 (s, 2H), 2.74-2.69 (m, 2H), 2.67-2.63 (m, 1H), 2.34-2.33 (m, 5H), 2.14-2.10 (m, 1H), 1.90 (t, 1H), 1.69-1.64 (m, 1H), 1.01 (d, 3H); MS m/z: 288[M+H]

<Preparative Example 3> Preparation of (S)-4-((3,4-dimethylpiperazin-1-yl)methyl)-3-(trifluoromethyl)aniline

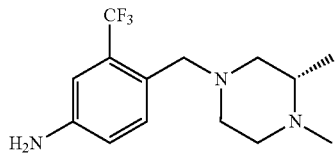

A target compound was prepared by performing steps 1 and 2 of Preparative Example 2 except that (S)-1,2-dimethylpiperazine was used instead of (R)-1,2-dimethylpiperazine in step 1 of Preparative Example 2.

$^1$H NMR (400 MHz, CDCl$_3$) δ 7.47 (d, 1H), 6.91 (d, 1H), 6.79 (dd, 1H), 3.75 (br s, 2H), 3.50 (s, 2H), 2.76-2.63 (m, 3H), 2.33-2.25 (m, 5H), 2.13-2.11 (m, 1H), 1.89 (t, 1H), 1.01 (d, 3H); MS m/z: 288[M+H]

<Preparative Example 4> Preparation of 1-(4-amino-2-(trifluoromethyl)benzyl)-N,N-dimethylpyrrolidin-3-amine

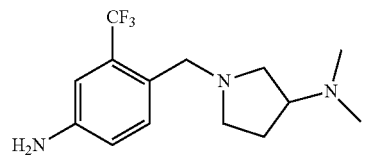 [SMILES: CN(C)C1CCN(Cc2ccc(N)cc2C(F)(F)F)C1]

A target compound was prepared by performing steps 1 and 2 of Preparative Example 2 except that N,N-dimethylpyrrolidin-3-amine was used instead of (R)-1,2-dimethylpiperazine in step 1 of Preparative Example 2.

$^1$H NMR (400 MHz, CDCl$_3$) δ 7.47 (d, 1H), 6.91 (d, 1H), 6.79 (dd, 1H), 3.75 (s, 2H), 3.63 (q, 2H), 2.75 (m, 2H), 2.71-2.64 (m, 1H), 2.57-2.51 (m, 1H), 2.42-2.32 (m, 1H), 2.19 (s, 6H), 2.04-1.92 (m, 1H), 1.75-1.66 (m, 1H); MS m/z: 288[M+H]

<Preparative Example 5> Preparation of 4-((4-methyl-1,4-diazepin-1-yl)methyl)-3-(trifluoromethyl)aniline

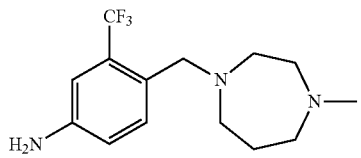 [SMILES: CN1CCCN(Cc2ccc(N)cc2C(F)(F)F)CC1]

A target compound was prepared by performing steps 1 and 2 of Preparative Example 2 except that 1-methyl-1,4-diazepine was used instead of (R)-1,2-dimethylpiperazine in step 1 of Preparative Example 2.

MS m/z: 288[M+H]

<Preparative Example 6> Preparation of (R)-1-(4-amino-2-(trifluoromethyl)benzyl)-N,N-dimethylpyrrolidin-3-amine

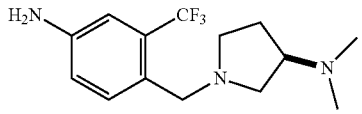 [SMILES: CN(C)[C@@H]1CCN(Cc2ccc(N)cc2C(F)(F)F)C1]

A target compound was prepared by performing steps 1 and 2 of Preparative Example 2 except that (R)—N,N-dimethylpyrrolidin-3-amine was used instead of (R)-1,2-dimethylpiperazine in step 1 of Preparative Example 2.

$^1$H NMR (400 MHz, CDCl$_3$) δ 7.46 (d, 1H), 6.91 (d, 1H), 6.79 (d, 1H), 3.75 (s, 2H), 3.64 (q, 2H), 2.83-2.71 (m, 2H), 2.68 (q, 1H), 2.56 (q, 1H), 2.40 (t, 1H), 2.21 (s, 6H), 2.01-1.74 (m, 1H), 1.75-1.70 (m, 1H); MS m/z 288 [M+H]

<Preparative Example 7> Preparation of (S)-1-(4-amino-2-(trifluoromethyl)benzyl)-N,N-dimethylpyrrolidin-3-amine

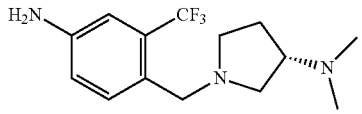 [SMILES: CN(C)[C@H]1CCN(Cc2ccc(N)cc2C(F)(F)F)C1]

A target compound was prepared by performing steps 1 and 2 of Preparative Example 2 except that (S)—N,N-dimethylpyrrolidin-3-amine was used instead of (R)-1,2-dimethylpiperazine in step 1 of Preparative Example 2.

$^1$H NMR (400 MHz, CDCl$_3$) δ 7.47 (d, 1H), 6.92 (s, 1H), 6.80 (d, 1H), 3.76 (s, 2H), 3.64 (q, 2H), 2.84-2.72 (m, 2H), 2.69 (q, 1H), 2.56 (q, 1H), 2.40 (t, 1H), 2.21 (s, 6H), 2.06-1.89 (m, 1H), 1.78-1.65 (m, 1H); MS m/z 288 [M+H]

<Preparative Example 8> Preparation of 4-((4,4-difluoropiperidin-1-yl)methyl)-3-(trifluoromethyl)aniline

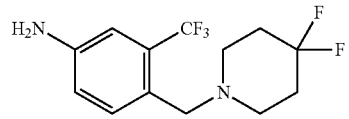 [SMILES: Nc1ccc(CN2CCC(F)(F)CC2)c(C(F)(F)F)c1]

A target compound was prepared by performing steps 1 and 2 of Preparative Example 2 except that 4,4-difluoropiperidine was used instead of (R)-1,2-dimethylpiperazine in step 1 of Preparative Example 2.
MS m/z: 295[M+H]

<Preparative Example 9> Preparation of 4-((4-methylpiperazin-1-yl)methyl)-3-(trifluoromethyl)benzoic Acid

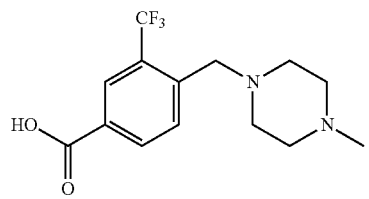 [SMILES: CN1CCN(Cc2ccc(C(=O)O)cc2C(F)(F)F)CC1]

4-(Bromomethyl)-3-(trifluoromethyl)benzoic acid (1 g, 3.53 mmol) was dissolved in acetonitrile (35 ml), to which 1-methylpiperazine (389 mg, 3.89 mmol) and $K_2CO_3$ (732 mg, 5.30 mmol) were added, followed by stirring at 100° C. for 15 hours. The reaction mixture was cooled down to room temperature and then concentrated. Distilled water (30 ml) was added to the reaction mixture, followed by extraction with EtOAc. The water layer was separated, which was saturated with NaCl. PH of the mixture was adjusted to 3 by using 6 N HCl, followed by extraction with 1-BuOH. The organic layer was concentrated. The obtained residue was added with EtOAc. The precipitated solid compound was filtered and dried in vacuo. As a result, a target compound was obtained (400 mg, 37.5% yield).
MS m/z: 303[M+H]

<Preparative Example 10> Preparation of 4-((3-(dimethylamino)pyrrolidin-1-yl)methyl)-3-(trifluoromethyl)benzoic Acid

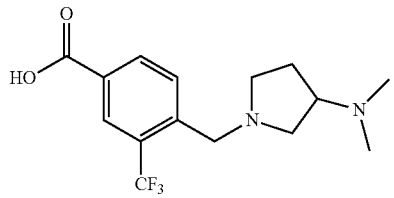 [SMILES: CN(C)C1CCN(Cc2ccc(C(=O)O)cc2C(F)(F)F)C1]

A target compound was prepared by the same manner as described in Preparative Example 9 except that N,N-dimethylpyrrolidin-3-amine was used instead of 1-methylpiperazine in Preparative Example 9.
MS m/z: 317[M+H]

<Preparative Example 11> Preparation of (R)-4-((3,4-dimethylpiperazin-1-yl)methyl)-3-(trifluoromethyl)benzoic Acid

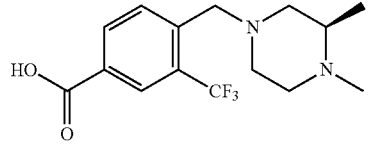 [SMILES: C[C@@H]1CN(Cc2ccc(C(=O)O)cc2C(F)(F)F)CCN1C]

A target compound was prepared by the same manner as described in Preparative Example 9 except that (R)-1,2-dimethylpiperazine was used instead of 1-methylpiperazine in Preparative Example 9.
MS m/z: 317[M+H]

<Preparative Example 12> Preparation of 4-nitrophenyl (4-((4-methylpiperazin-1-yl)methyl)-3-(trifluoromethyl)phenyl)carbamate

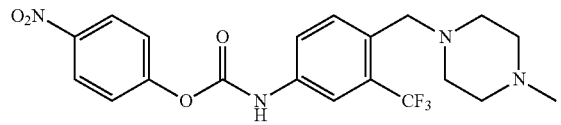 [SMILES: CN1CCN(Cc2ccc(NC(=O)Oc3ccc([N+](=O)[O-])cc3)cc2C(F)(F)F)CC1]

Pyridine (163 ul, 2.01 mmol) and 4-nitrophenyl chloroformate (Combi-Blocks, Cat #OT-0341, CAS [7693-46-1]) (369 mg, 1.83 mmol) were added to the mixed solution comprising 4-((4-methylpiperazin-1-yl)methyl)-3-(trifluoromethyl)aniline (AK Scientific Co., Cat #AK-83227, CAS [694499-26-8]) (500 mg, 1.83 mmol) and $CH_2Cl_2$ (10 ml), followed by stirring at room temperature for 3 hours. The reaction mixture was concentrated. The obtained residue was treated with diethyl ether. As a result, a target compound was obtained as a brown solid (611 mg, 76% yield).
MS m/z: 439[M+H]

<Preparative Example 13> Preparation of 4-nitrophenyl (5-(tert-butyl)isoxazol-3-yl)carbamate

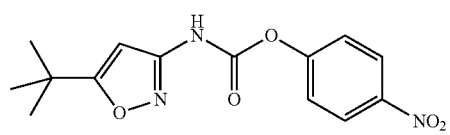 [SMILES: CC(C)(C)c1cc(NC(=O)Oc2ccc([N+](=O)[O-])cc2)no1]

A target compound was prepared by the same manner as described in Preparative Example 12 except that 5-(tert-butyl)isoxazol-3-amine was used instead of 4-((4-methylpiperazin-1-yl)methyl)-3-(trifluoromethyl)aniline in Preparative Example 12.
MS m/z: 306[M+H]

<Preparative Example 14> Preparation of 4-nitrophenyl (5-(1,1,1-trifluoro-2-methylpropan-2-yl)isoxazol-3-yl)carbamate

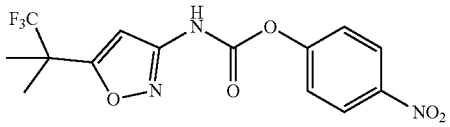 [SMILES: CC(C)(c1cc(NC(=O)Oc2ccc([N+](=O)[O-])cc2)no1)C(F)(F)F]

A target compound was prepared by the same manner as described in Preparative Example 12 except that 5-(1,1,1-trifluoro-2-methyltropan-2-yl)isoxazol-3-amine was used instead of 4-((4-methylpiperazin-1-yl)methyl)-3-(trifluoromethyl)aniline in Preparative Example 12.

MS m/z: 360[M+H]

Hereinafter, referring to Preparative Examples 1-14, the compounds of Examples 1-85 prepared in the present invention are described by the chemical names and the chemical formulas. And NMR, ESI-MS and HPLC data are presented to demonstrate that the compounds were prepared.

<Example 1> Preparation of 4-methyl-3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide

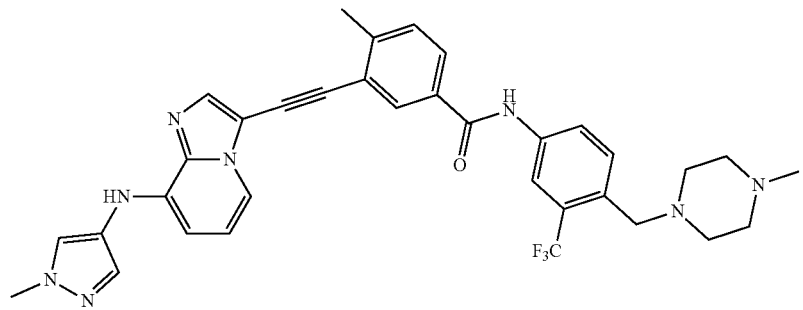

The compound of Example 1 was prepared by the same manner as described in Example 24 except that 1-methyl-1H-pyrazol-4-amine was used instead of p-toluidine used in step 1 of Example 24 and 4-((methylpiperazin-1-yl)methyl)-3-(trifluoromethyl)aniline was used in step 3 by the same manner as in Example 24 to give a final target compound.

$^1$H NMR (400 MHz, DMSO-$d_6$) δ 10.56 (s, 1H), 8.23 (br s, 3H), 8.07 (d, 1H), 7.98 (s, 1H), 7.94 (m, 2H), 7.82 (s, 1H), 7.71 (d, 1H), 7.55 (d, 1H), 7.52 (s, 1H), 6.97 (t, 1H), 6.59 (d, 1H), 3.83 (s, 3H), 3.57 (s, 2H), 2.60 (s, 3H), 2.39 (m, 8H), 2.17 (s, 3H); 627[M+H]; HPLC $t_R$ 3.87 min (method B)

<Example 2> Preparation of N-(2-fluorophenyl)-4-methyl-3-((8-((1-methyl-1H-pyrazol-4-yl)amino)imidazo[1,2-a]pyridin-3-yl)ethynyl)benzamide

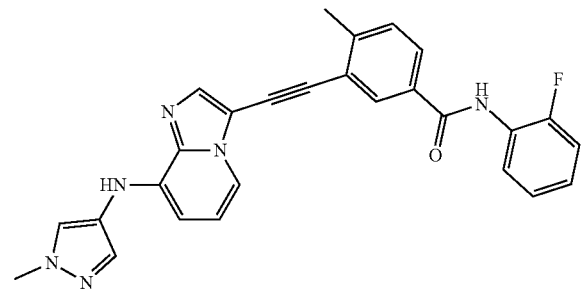 [SMILES: Cc1ccc(C(=O)Nc2ccccc2F)cc1C#Cc1cnc2c(Nc3cnn(C)c3)cccn12]

The compound of Example 2 was prepared by the same manner as described in Example 24 except that 1-methyl-1H-pyrazol-4-amine was used instead of p-toluidine used in step 1 of Example 24 and 2-fluorobenzeneamine was used in step 3 by the same manner as in Example 24 to give a final target compound.

$^1$H NMR (400 MHz, DMSO-$d_6$) δ 10.22 (s, 1H), 8.24 (m, 2H), 7.98 (s, 1H), 7.94 (d, 1H), 7.92 (d, 1H), 7.82 (s, 1H), 7.61 (t, 1H), 7.53 (d, 1H), 7.51 (s, 1H), 7.34-7.21 (m, 3H), 6.97 (t, 1H), 6.59 (d, 1H), 3.35 (s, 3H), 2.60 (s, 3H); 465[M+H]; HPLC $t_R$ 2.71 min (method C)

<Example 3> Preparation of N-(3,5-dimethoxyphenyl)-4-methyl-3-((8-((1-methyl-1H-pyrazol-4-yl)amino)imidazo[1,2-a]pyridin-3-yl)ethynyl)benzamide

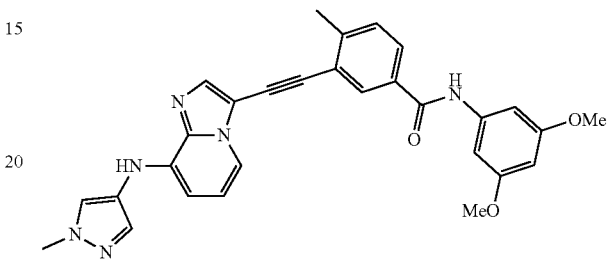

The compound of Example 3 was prepared by the same manner as described in Example 24 except that 1-methyl-1H-pyrazol-4-amine was used instead of p-toluidine used in step 1 of Example 24 and 3,5-dimethoxybenzeneamine was used instead of 4-((methylpiperazin-1-yl)methyl)-3-(trifluoromethyl)aniline in step 3 of Example 24 to give a final target compound.

$^1$H NMR (400 MHz, DMSO-$d_6$) δ 10.23 (s, 1H), 8.25 (s, 1H), 8.21 (s, 1H), 7.98 (s, 1H), 7.95 (d, 1H), 7.89 (d, 1H), 7.82 (s, 1H), 7.53 (d, 1H), 7.52 (s, 1H), 7.10 (s, 2H), 6.97 (t, 1H), 6.59 (d, 1H), 6.27 (s, 1H), 3.83 (s, 3H), 3.74 (s, 6H), 2.60 (s, 3H); 507[M+H]; HPLC $t_R$ 6.48 min (method A)

<Example 4> Preparation of N-(3-fluoro-4-methoxyphenyl)-4-methyl-3-((8-((1-methyl-1H-pyrazol-4-yl)amino)imidazo[1,2-a]pyridin-3-yl)ethynyl)benzamide

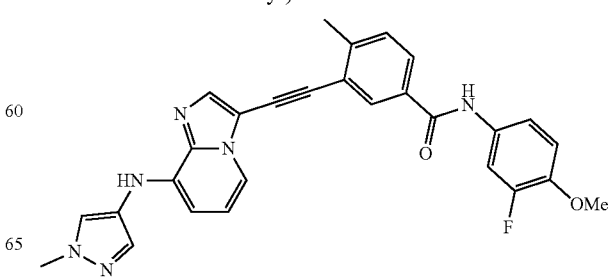

The compound of Example 4 was prepared by the same manner as described in Example 24 except that 1-methyl-1H-pyrazol-4-amine was used instead of p-toluidine used in step 1 of Example 24 and 3-fluoro-4methoxybenzeneamine was used instead of 4-((methylpiperazin-1-yl)methyl)-3-(trifluoromethyl)aniline in step 3 of Example 24 to give a final target compound.

$^1$H NMR (400 MHz, DMSO-d$_6$) δ 10.32 (s, 1H), 8.23 (s, 1H), 8.20 (s, 1H), 7.97 (s, 1H), 7.92 (dd, 1H), 7.82 (s, 1H), 7.75 (d, 1H), 7.17 (t, 1H), 6.97 (t, 1H), 6.59 (d, 1H), 3.83 (s, 6H), 2.59 (s, 3H); 495[M+H]; HPLC t$_R$ 6.42 min (method B)

<Example 5> Preparation of 3-((8-((2-aminophenyl)amino)imidazo[1,2-a]pyridin-3-yl)ethynyl)-4-methyl-N-(4-((4-methylpiperazin-1-yl)methyl)-3-(trifluoromethyl)phenyl)benzamide

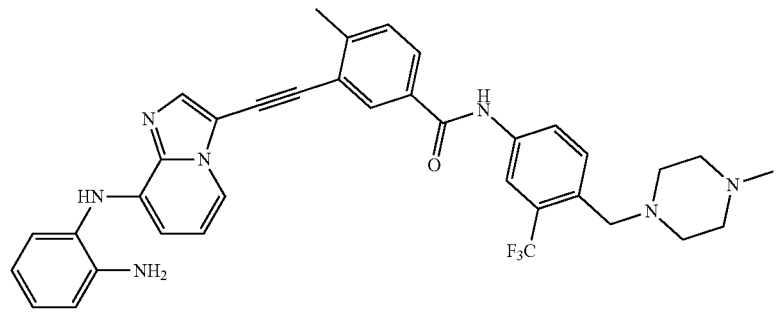 [SMILES: Cc1ccc(C(=O)Nc2ccc(CN3CCN(C)CC3)c(C(F)(F)F)c2)cc1C#Cc1cnc2c(Nc3ccccc3N)cccn12]

Step 1: Preparation of 4-methyl-N-(4-((4-methylpiperazin-1-nyl)methyl)-3-(trifluoromethyl)phenyl)-3-((8-((2-nitrophenyl)amino)imidazo[1,2-a]pyridin-3-nyl)ethynyl)benzamide A target compound was prepared by the same manner as described in Example 24 except that 2-nitroaniline was used instead of p-toluidine in Example 24.

MS m/z: 668[M+H]

Step 2: Preparation of 3-((8-((2-aminophenyl)amino)imidazo[1,2-a]pyridin-3-nyl)ethynyl)-4-methyl-N-(4-((4-methylpiperazin-1-nyl)methyl)-3-(trifluoromethyl)phenyl)benzamide The compound prepared in step 1 above (40 mg) was dissolved in ethyl acetate, to which tin chloride (SnCl$_2$) was added. The reaction mixture was stirred at 50° C. for 12 hours. The reaction mixture was cooled down to room temperature, and then washed with a saturated sodium bicarbonate (NaHCO$_3$) solution. The organic layer was dried over anhydrous Na$_2$SO$_4$, followed by filtering and concentration. The concentrated material was purified by prep-TLC. As a result, a target compound was obtained (1.7 mg).

MS m/z: 638[M+H]

<Example 6> Preparation of N-(3-fluorophenyl)-4-methyl-3-((8-((1-methyl-1H-pyrazol-4-yl)amino)imidazo[1,2-a]pyridin-3-yl)ethynyl)benzamide

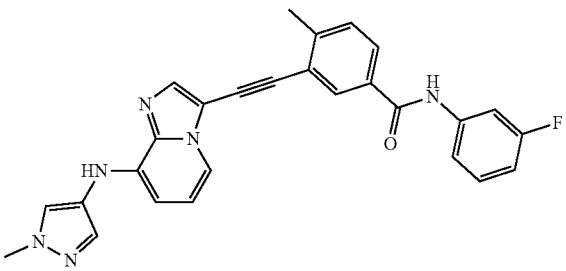 [SMILES: Cc1ccc(C(=O)Nc2cccc(F)c2)cc1C#Cc1cnc2c(Nc3cnn(C)c3)cccn12]

The compound of Example 6 was prepared by the same manner as described in Example 24 except that 1-methyl-1H-pyrazol-4-amine was used instead of p-toluidine used in step 1 of Example 24 and 3-fluorobenzeneamine was used instead of 4-((methylpiperazin-1-yl)methyl)-3-(trifluoromethyl)aniline in step 3 of Example 24 to give a final target compound.

$^1$H NMR (400 MHz, MeOH-d$_4$) δ 8.19 (s, 1H), 7.99 (d, 1H), 7.93 (s, 1H), 7.91 (m, 1H), 7.87 (s, 1H), 7.71 (s, 1H), 7.69 (m, 1H), 7.56 (s, 1H), 7.41 (t, 2H), 7.35 (m, 1H), 7.02 (t, 1H), 6.89 (t, 1H), 6.67 (d, 1H), 3.94 (s, 3H), 2.67 (s, 3H); 465[M+H]; HPLC t$_R$ 6.58 min (method A)

<Example 7> Preparation of N-(4-chlorophenyl)-4-methyl-3-((8-((1-methyl-1H-pyrazol-4-yl)amino)imidazo[1,2-a]pyridin-3-yl)ethynyl)benzamide

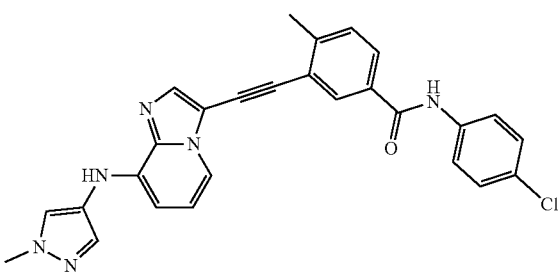 [SMILES: Cc1ccc(C(=O)Nc2ccc(Cl)cc2)cc1C#Cc1cnc2c(Nc3cnn(C)c3)cccn12]

The compound of Example 7 was prepared by the same manner as described in Example 24 except that 1-methyl-1H-pyrazol-4-amine was used instead of p-toluidine used in step 1 of Example 24 and 4-chlorobenzeneamine was used instead of 4-((methylpiperazin-1-yl)methyl)-3-(trifluoromethyl)aniline in step 3 of Example 24 to give a final target compound.

¹H NMR (400 MHz, CDCl₃) δ 8.01 (s, 1H), 7.83 (s, 1H), 7.81 (d, 1H), 7.75 (d, 1H), 7.64 (d, 2H), 7.53 (s, 1H), 7.43 (s, 1H), 7.41 (d, 2H), 7.36 (d, 2H), 6.84 (t, 1H), 6.58 (s, 1H), 6.49 (d, 1H), 3.93 (s, 3H), 2.63 (s, 3H); 481[M+H]; HPLC t$_R$ 6.82 min (method A)

<Example 8> Preparation of N-(4-((4-ethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

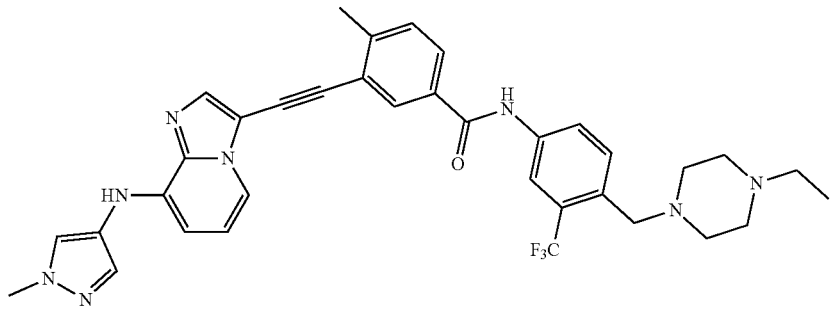 [SMILES: CCN1CCN(Cc2ccc(NC(=O)c3ccc(C)c(C#Cc4cnc5c(Nc6cnn(C)c6)cccn45)c3)cc2C(F)(F)F)CC1]

The compound of Example 8 was prepared by the same manner as described in Example 24 except that 1-methyl-1H-pyrazol-4-amine was used instead of p-toluidine used in step 1 of Example 24 and 4-((4-ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

¹H NMR (400 MHz, DMSO-d₆) δ 10.61 (s, 1H), 9.30 (br s, 1H), 8.24 (m, 3H), 8.12 (d, 1H), 8.03 (s, 1H), 7.97 (d, 1H), 7.93 (d, 1H), 7.83 (s, 1H), 7.73 (d, 1H), 7.56 (d, 1H), 7.52 (s, 1H), 7.01 (t, 1H), 6.63 (d, 1H), 3.83 (S, 3H), 3.69 (s, 2H), 3.47 (d, 2H), 3.14 (q, 2H), 2.95 (m, 4H), 2.61 (s, 3H), 2.37 (m, 2H), 1.20 (t, 3H); 641[M+H]; HPLC t$_R$ 2.36 min (method C)

<Example 9> Preparation of 4-methyl-3-((8-((1-methyl-1H-pyrazol-3-yl)amino)imidazo[1,2-a]pyridin-3-yl)ethynyl)-N-(4-((4-methylpiperazin-1-yl)methyl)-3-(trifluoromethyl)phenyl)benzamide The compound of Example 9 was prepared by the same manner as described in Example 24 except that 1-methyl-1H-pyrazol-4-amine was used instead of p-toluidine used in step 1 of Example 24 to give a final target compound.
626 [M+H]; HPLC t$_R$ 5.26 min (method A)

<Example 10> Preparation of N-(4-((4-ethylpiperazin-1-yl)methyl)-3-(trifluoromethyl)phenyl)-4-methyl-3-((8-((1-methyl-1H-pyrazol-3-yl)amino)imidazo[1,2-a]pyridin-3-yl)ethynyl)benzamide

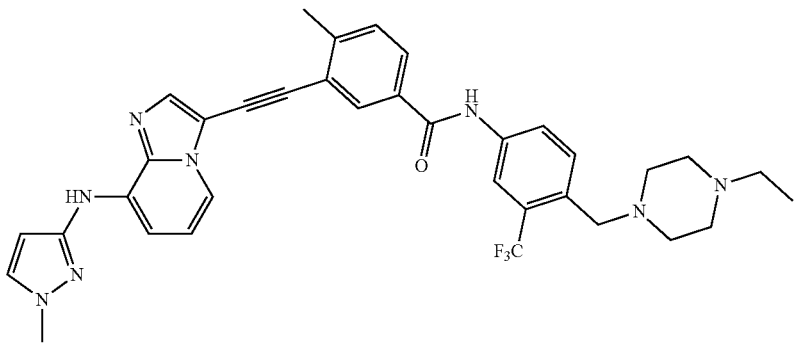 [SMILES: CCN1CCN(Cc2ccc(NC(=O)c3ccc(C)c(C#Cc4cnc5c(Nc6ccn(C)n6)cccn45)c3)cc2C(F)(F)F)CC1]

The compound of Example 10 was prepared by the same manner as described in Example 24 except that 1-methyl-1H-pyrazol-3-amine was used instead of p-toluidine used in step 1 of Example 24 and 4-((4-ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, DMSO-$d_6$) δ 10.61 (s, 1H), 9.30 (br Ss, 1H), 8.94 (s, 1H), 8.24 (d, 2H), 8.12 (d, 1H), 8.04 (m, 2H), 7.93 (br d, 2H), 7.73 (d, 1H), 7.56 (d, 1H), 7.55 (s, 1H), 7.11 (t, 1H), 6.11 (s, 1H), 3.79 (s, 3H), 3.69 (s, 2H), 3.47 (d, 2H), 3.14 (m, 2H), 2.96 (m, 4H), 2.61 (s, 3H), 2.38 (m, 2H), 1.20 (t, 3H); 641[M+H]; HPLC $t_R$ 5.32 min (method A)

<Example 11> Preparation of 4-methyl-3-((8-((1-(piperidin-4-yl)-1H-pyrazol-4-yl)amino)imidazo[1,2-a]pyridin-3-yl)ethynyl)-N-(3-(trifluoromethyl)phenyl)benzamide

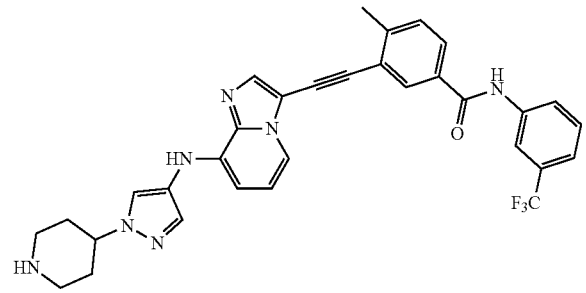 [SMILES: Cc1ccc(C(=O)Nc2cccc(C(F)(F)F)c2)cc1C#Cc1cnc2c(Nc3cnn(C4CCNCC4)c3)cccn12]

Step 1. Preparation of tert-butyl 4-(4-(4-((3-((2-methyl-5-((3-(trifluoromethyl)phenyl)carbamoyl)phenyl)ethynyl)imidazo[1,2-a]pyridin-8-nyl)amino)-1H-pyrazol-1-nyl)piperidin-1-carboxylate A target compound was prepared (46.5 mg) by the same manner as described in Example 24 except that tert-butyl 4-(4-amino-1-H-pyrazol-1-nyl)piperidin-1-carboxylate and 3-(trifluoromethyl)aniline were used instead of p-toluidine and 4-((4-methylpiperazin-1-yl)methyl)-3-(trifluoromethyl)aniline.
MS m/z: 684[M+H]

Step 2. Preparation of 4-methyl-3-((8-((1-(piperidin-4-nyl)-1H-pyrazol-4-nyl)amino)imidazo[1,2-a]pyridin-3-nyl)ethynyl)-N-(3-(trifluoromethyl)phenyl)benzamide The compound prepared in step 1 above (46 mg) was dissolved in dichloromethane, to which TFA (2 ml) was added. The reaction mixture was stirred at room temperature for 30 minutes. The reaction solvent was concentrated under reduced pressure. HPLC was performed to give a target compound as a solid (30 mg, 82%).

$^1$H NMR (400 MHz, DMSO-$d_6$) δ 10.63 (s, 1H), 8.74 (br s, 1 h), 8.47 (br s, 1H), 8.33 (s, 1H), 8.25 (s, 2H), 8.08 (d, 1H), 8.03 (s, 1H), 7.99 (d, 1H), 7.94 (dd, 1H), 7.91 (s, 1H), 7.62 (m, 3H), 7.63 (d, 1H), 7.47 (d, 1H), 7.01 (t, 1H), 6.66 (d, 1H), 4.46 (m, 1H), 3.43 (br d, 2H), 3.09 (br q, 2H), 2.61 (s, 3H), 2.23-2.08 (m, 4H); MS m/z: 584[M+H]; HPLC $t_R$ 5.6 min (method A)

<Example 12> Preparation of 4-methyl-N-(3-(4-methyl-1H-imidazol-1-yl)-5-(trifluoromethyl)phenyl)-3-((8-((1-methyl-1H-pyrazol-4-yl)amino)imidazo[1,2-a]pyridin-3-yl)ethynyl)benzamide

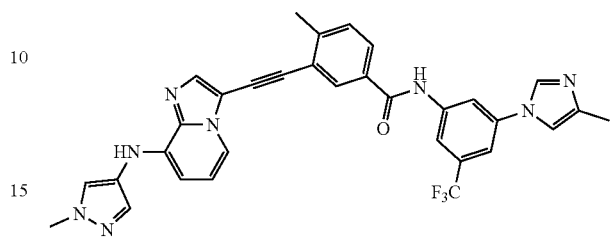

The compound of Example 12 was prepared by the same manner as described in Example 24 except that 1-methyl-1H-pyrazol-4-amine was used instead of p-toluidine used in step 1 of Example 24 and 3-(trifluoromethyl)-5-(4-methyl-1H-imidazol-1-yl)benzeneamine was used instead of 4-((methylpiperazin-1-yl)methyl)-3-(trifluoromethyl)aniline in step 3 of Example 24 to give a final target compound.

$^1$H NMR (400 MHz, DMSO-$d_6$) δ 10.22 (s, 1H), 8.24 (m, 2H), 7.98 (s, 1H), 7.94 (d, 1H), 7.92 (d, 1H), 7.82 (s, 1H), 7.61 (t, 1H), 7.53 (d, 1H), 7.51 (s, 1H), 7.34-7.21 (m, 3H), 6.97 (t, 1H), 6.59 (d, 1H), 3.35 (s, 3H), 2.60 (s, 3H); 465[M+H]; HPLC $t_R$ 5.85 min (method A)

<Example 13> Preparation of 4-methyl-3-((8-((1-methyl-1H-pyrazol-4-yl)amino)imidazo[1,2-a]pyridin-3-yl)ethynyl)-N-(3-(trifluoromethyl)phenyl)benzamide

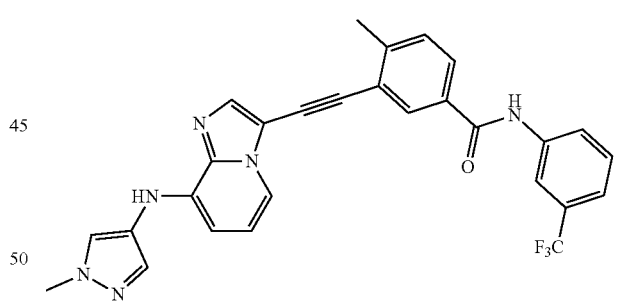

The compound of Example 13 was prepared by the same manner as described in Example 24 except that 1-methyl-1H-pyrazol-4-amine was used instead of p-toluidine used in step 1 of Example 24 and 3-trifluoromethyl-benzeneamine was used instead of 4-((methylpiperazin-1-yl)methyl)-3-(trifluoromethyl)aniline in step 3 of Example 24 to give a final target compound.

$^1$H NMR (400 MHz, DMSO-$d_6$) δ 10.58 (s, 1H), 8.25 (s, 1H), 8.24 (s, 1H), 8.20 (s, 1H), 8.07 (d, 1H), 7.97 (s, 1H), 7.94 (d, 1H), 7.92 (d, 1H), 7.81 (s, 1H), 7.60 (t, 1H), 7.55 (d, 1H), 7.51 (s, 1H), 7.45 (d, 1H), 6.96 (t, 1H), 6.58 (d, 1H), 3.82 (s, 3H), 2.71 (s, 3H); 515[M+H]; HPLC $t_R$ 6.99 min (method A)

<Example 14> Preparation of 3-((8-((1-isopropyl-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide

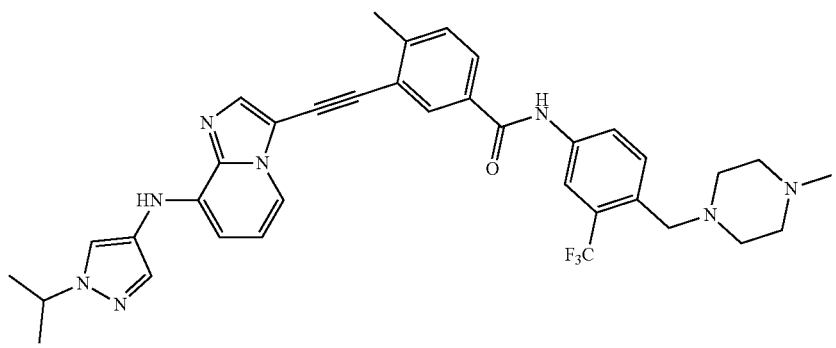 [SMILES: Cc1ccc(C(=O)Nc2ccc(CN3CCN(C)CC3)c(C(F)(F)F)c2)cc1C#Cc1cnc2c(Nc3cnn(C(C)C)c3)cccn12]

The compound of Example 14 was prepared by the same manner as described in Example 24 except that 1-isopropyl-1H-pyrazol-4-amine was used instead of p-toluidine used in step 1 of Example 24 to give a final target compound.

$^1$H NMR (400 MHz, Methanol-d$_4$) δ 8.23 (d, 1H), 8.18 (d, 1H), 8.07-8.00 (m, 2H), 7.98 (s, 1H), 7.93 (dd, 1H), 7.84 (d, 1H), 7.80 (d, 1H), 7.59 (d, 1H), 7.53 (d, 1H), 7.09 (dd, 1H), 6.75 (d, 1H), 4.57 (septet, 1H), 3.80 (s, 2H), 3.57 (d, 2H), 3.24 (dd, 2H), 3.18-3.02 (m, 4H), 2.68 (s, 3H), 2.49 (t, 2H), 1.55 (d, 6H), 1.37 (t, 3H); 655[M+H]; HPLC t$_R$ 5.43 min (method A)

<Example 15> Preparation of N-(4-((4-ethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide

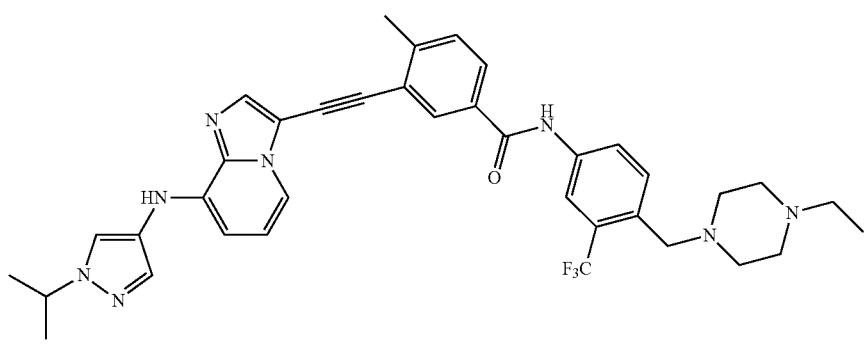 [SMILES: CCN1CCN(Cc2ccc(NC(=O)c3ccc(C)c(C#Cc4cnc5c(Nc6cnn(C(C)C)c6)cccn45)c3)cc2C(F)(F)F)CC1]

The compound of Example 15 was prepared by the same manner as described in Example 24 except that 1-isopropyl-1H-pyrazol-4-amine was used instead of p-toluidine used in step 1 of Example 24 and 4-((4-ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.23 (d, 1H), 8.18 (d, 1H), 8.07-8.00 (m, 2H), 7.98 (s, 1H), 7.93 (dd, 1H), 7.84 (d, 1H), 7.80 (d, 1H), 7.59 (d, 1H), 7.53 (d, 1H), 7.09 (dd, 1H), 6.75 (d, 1H), 4.57 (septet, 1H), 3.80 (s, 2H), 3.57 (d, 2H), 3.24 (dd, 2H), 3.18-3.02 (m, 4H), 2.68 (s, 3H), 2.49 (t, 2H), 1.55 (d, 6H), 1.37 (t, 3H); 670[M+H]; HPLC t$_R$ 5.48 min (method A)

<Example 16> Preparation of 3-((8-((3-fluoropyridin-2-yl)amino)imidazo[1,2-a]pyridin-3-yl)ethynyl)-4-methyl-N-(4-((4-methylpiperazin-1-yl)methyl)-3-(trifluoromethyl)phenyl)benzamide

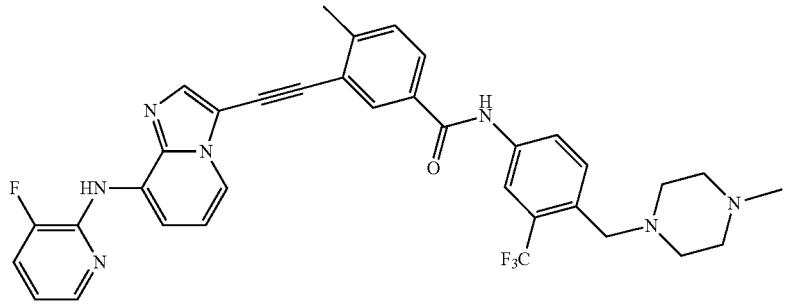 [SMILES: Cc1ccc(C(=O)Nc2ccc(CN3CCN(C)CC3)c(C(F)(F)F)c2)cc1C#Cc1cnc2c(Nc3ncccc3F)cccn12]

The compound of Example 16 was prepared by the same manner as described in Example 24 except that 3-fluoropyridin-2-amine was used instead of p-toluidine used in step 1 of Example 24 to give a final target compound.

$^1$H NMR (400 MHz, Methanol-d$_4$) δ 8.44 (d, 1H), 8.18-8.09 (m, 2H), 8.06 (d, 1H), 8.01 (d, 1H), 7.92 (dd, 1H), 7.85 (s, 1H), 7.81 (dd, 1H), 7.68 (d, 1H), 7.51-7.44 (m, 1H), 7.41 (d, 1H), 7.09 (dd, 1H), 6.86 (ddd, 1H), 3.68 (s, 2H), 3.44-3.34 (m, 3H), 3.13-3.01 (m, 3H), 2.95 (d, 2H), 2.82 (s, 3H), 2.57 (s, 3H), 2.37 (t, 2H); 642[M+H]; HPLC t$_R$ 5.81 min (method A)

<Example 17> Preparation of N-(4-((4-ethylpiperazin-1-yl)methyl)-3-(trifluoromethyl)phenyl)-3-((8-((3-fluoropyridin-2-yl)amino)imidazo[1,2-a]pyridin-3-yl)ethynyl)-4-methylbenzamide The compound of Example 17 was prepared by the same manner as described in Example 24 except that 3-fluoropyridin-2-amine was used instead of p-toluidine used in step 1 of Example 24 and 4-((4-ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.44 (dd, 1H), 8.13 (dd, 1H), 8.11 (d, 1H), 8.06 (d, 1H), 8.01 (d, 1H), 7.97-7.88 (m, 1H), 7.85 (s, 1H), 7.81 (dd, 1H), 7.68 (d, 1H), 7.46 (ddd, 1H), 7.41 (d, 1H), 7.09 (dd, 1H), 6.91-6.82 (m, 1H), 3.68 (s, 2H), 3.45 (d, 2H), 3.13 (q, 2H), 3.07-2.88 (m, 4H), 2.57 (s, 3H), 2.37 (t, 2H), 1.25 (t, 4H); 656[M+H]; HPLC t$_R$ 5.89 min (method A)

<Example 18> Preparation of 4-methyl-N-(4-((4-methylpiperazin-1-yl)methyl)-3-(trifluoromethyl)phenyl)-3-((8-((3-methylpyridin-2-yl)amino)imidazo[1,2-a]pyridin-3-yl)ethynyl)benzamide

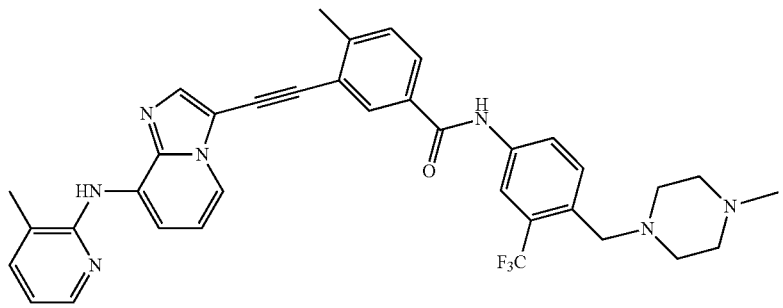 [SMILES: Cc1ccc(C(=O)Nc2ccc(CN3CCN(C)CC3)c(C(F)(F)F)c2)cc1C#Cc1cnc2c(Nc3ncccc3C)cccn12]

The compound of Example 18 was prepared by the same manner as described in Example 24 except that 3-methylpyridin-2-amine was used instead of p-toluidine used in step 1 of Example 24 to give a final target compound.

$^1$H NMR (400 MHz, Methanol-$d_4$) δ 8.26 (d, 1H), 8.12 (d, 1H), 8.09-8.02 (m, 2H), 7.96-7.89 (m, 2H), 7.86 (s, 1H), 7.82 (dd, 1H), 7.68 (d, 1H), 7.63 (d, 1H), 7.42 (d, 1H), 7.12 (dd, 1H), 6.86 (dd, 1H), 3.68 (s, 2H), 3.44-3.33 (m, 2H), 3.12-3.00 (m, 2H), 2.95 (d, 2H), 2.82 (s, 3H), 2.57 (s, 3H), 2.37 (s, 3H), 2.40-2.34 (m, 2H); 639[M+H]; HPLC $t_R$ 5.08 min (method A)

<Example 19> Preparation of 4-methyl-N-(4-((4-methylpiperazin-1-yl)methyl)-3-(trifluoromethyl)phenyl)-3-((8-((4-(trifluoromethyl)phenyl)amino)imidazo[1,2-a]pyridin-3-yl)ethynyl)benzamide

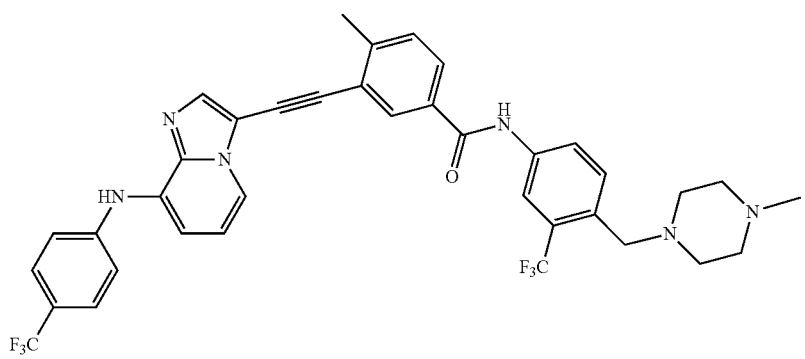 [SMILES: Cc1ccc(C(=O)Nc2ccc(CN3CCN(C)CC3)c(C(F)(F)F)c2)cc1C#Cc1cnc2c(Nc3ccc(C(F)(F)F)cc3)cccn12]

The compound of Example 19 was prepared by the same manner as described in Example 24 except that 4-(trifluoromethyl)benzeneamine was used instead of p-toluidine used in step 1 of Example 24 to give a final target compound.

$^1$H NMR (400 MHz, Methanol-$d_4$) δ 8.51 (d, 1H), 8.36 (br s, 1H), 8.28-8.26 (m, 1H), 8.19-8.15 (m, 1H), 8.04-8.00 (m, 1H), 7.97 (dd, 1H), 7.79 (s, 1H), 7.77-7.76 (m, 1H), 7.63 (d, 2H), 7.55-7.48 (m, 2H), 7.31 (d, 2H), 3.80-3.79 (m, 2H), 3.55-3.36 (m, 2H), 3.21-3.13 (m, 2H), 3.11-3.04 (m, 2H), 2.92 (s, 3H), 2.68 (s, 3H), 2.55-2.48 (m, 2H); 691[M+H]; HPLC $t_R$ 6.16 min (method A)

<Example 20> Preparation of 4-methyl-N-(4-((4-methylpiperazin-1-yl)methyl)-3-(trifluoromethyl)phenyl)-3-((8-((5-methylpyridin-2-yl)amino)imidazo[1,2-a]pyridin-3-yl)ethynyl)benzamide

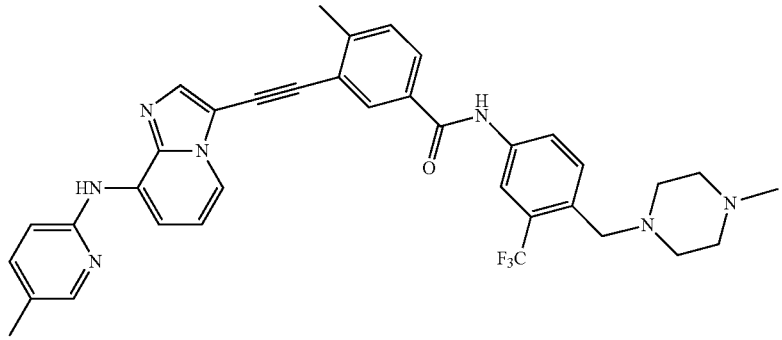

The compound of Example 20 was prepared by the same manner as described in Example 24 except that 5-methylidyne-2-amine was used instead of p-toluidine used in step 1 of Example 24 to give a final target compound.

$^1$H NMR (400 MHz, Methanol-d$_4$) δ 8.61 (dd, 1H), 8.26 (d, 1H), 8.18 (d, 1H), 8.11 (s, 1H), 8.04 (dd, 1H), 7.97 (dd, 2H), 7.94-7.91 (m, H), 7.80 (d, 1H), 7.68 (dd, 1H), 7.55 (d, 1H), 7.37 (dd, 1H), 7.25 (d, 1H), 3.80 (s, 2H), 3.61-3.41 (m, 2H), 3.28-3.17 (m, 2H), 3.12-2.99 (m, 2H), 2.94 (s, 3H), 2.70 (s, 3H), 2.65-2.40 (m, 2H), 2.36 (s, 3H); 638[M+H]; HPLC t$_R$ 5.10 min (method A)

<Example 21> Preparation of N-(4-((4-ethylpiperazin-1-yl)methyl)-3-(trifluoromethyl)phenyl)-4-methyl-3-((8-((5-methylpyridin-2-yl)amino)imidazo[1,2-a]pyridin-3-yl)ethynyl)benzamide

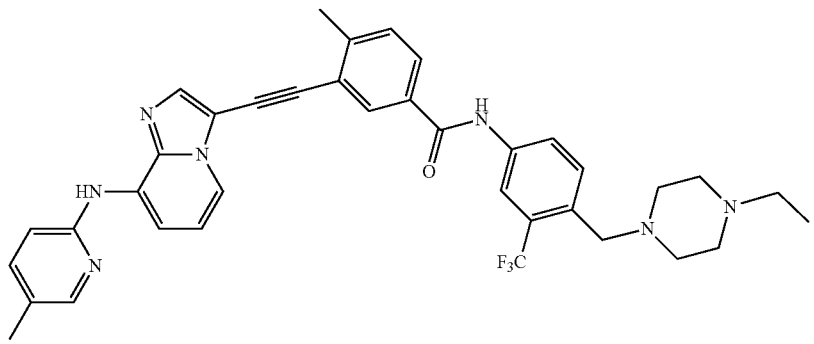 [SMILES: CCN1CCN(Cc2ccc(NC(=O)c3ccc(C)c(C#Cc4cnc5c(Nc6ccc(C)cn6)cccn45)c3)cc2C(F)(F)F)CC1]

The compound of Example 21 was prepared by the same manner as described in Example 24 except that 5-methylidyne-2-amine was used instead of p-toluidine used in step 1 of Example 24 and 4-((4-ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.59 (dd, 1H), 8.26 (d, 1H), 8.18 (d, 1H), 8.10 (s, 1H), 8.05 (dd, 1H), 8.00-7.91 (m, 3H), 7.81 (d, 1H), 7.69 (dd, 1H), 7.56 (d, 1H), 7.36 (dd, 1H), 7.24 (d, 1H), 3.81 (s, 2H), 3.65-3.53 (m, 2H), 3.25 (q, 2H), 3.20-3.01 (m, 4H), 2.70 (s, 3H), 2.60-2.41 (m, 2H), 2.36 (s, 3H), 1.38 (t, 3H); 652[M+H]; HPLC t$_R$ 5.14 min (method A)

<Example 22> Preparation of 3-((8-((1-ethyl-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide

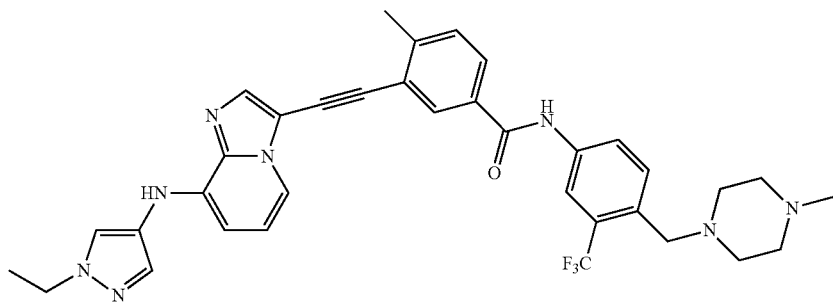 [SMILES: CCn1cc(Nc2cccn3c(C#Cc4cc(C(=O)Nc5ccc(CN6CCN(C)CC6)c(C(F)(F)F)c5)ccc4C)cnc23)cn1]

The compound of Example 22 was prepared by the same manner as described in Example 24 except that 1-ethyl-1H-pyrazol-4-amine was used instead of p-toluidine used in step 1 of Example 24 to give a final target compound.

$^1$H NMR (400 MHz, Methanol-$d_4$) δ 8.26 (d, 1H), 8.25 (s, 1H), 8.20 (dd, 1H), 8.17 (d, 1H), 8.04 (dd, 1H), 7.98 (dd, 1H), 7.85 (d, 1H), 7.80 (d, 1H), 7.59 (d, 1H), 7.56 (d, 1H), 7.30 (dd, 1H), 7.03 (dd, 1H), 4.24 (q, 2H), 3.80 (s, 2H), 3.60-3.40 (m, 2H), 3.26-3.14 (m, 2H), 3.14-2.97 (m, 2H), 2.94 (s, 3H), 2.69 (s, 3H), 2.50 (s, 2H), 1.52 (t, 3H); 641[M+H]; HPLC $t_R$ 5.28 min (method A)

<Example 23> Preparation of 3-((8-((1-ethyl-1H-pyrazol-4-yl)amino)imidazo[1,2-a]pyridin-3-yl)ethynyl)-N-(4-((4-ethylpiperazin-1-yl)methyl)-3-(trifluoromethyl)phenyl)-4-methylbenzamide

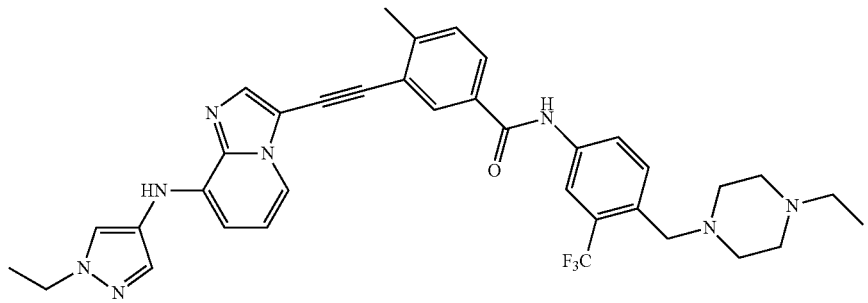 [SMILES: CCN1CCN(Cc2ccc(NC(=O)c3ccc(C)c(C#Cc4cnc5c(Nc6cnn(CC)c6)cccn45)c3)cc2C(F)(F)F)CC1]

The compound of Example 23 was prepared by the same manner as described in Example 24 except that 1-ethyl-1H-pyrazol-4-amine was used instead of p-toluidine used in step 1 of Example 24 and 4-((4-ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.26 (d, 1H), 8.23 (s, 1H), 8.22-8.15 (m, 2H), 8.07-8.00 (m, 1H), 7.97 (dd, 1H), 7.85 (d, 1H), 7.80 (d, 1H), 7.59 (d, 1H), 7.55 (d, J=8.1 Hz, 1H), 7.29 (dd, 1H), 7.01 (dd, 1H), 4.24 (q, 2H), 3.80 (s, 2H), 3.65-3.51 (m, 2H), 3.24 (q, 2H), 3.18-3.01 (m, 4H), 2.69 (s, 3H), 2.61-2.40 (m, 2H), 1.52 (t, 3H), 1.37 (t, 3H); 655[M+H]; HPLC $t_R$ 5.33 min (method A)

<Example 24> Preparation of 4-methyl-N-(4-((4-methylpiperazin-1-yl)methyl)-3-(trifluoromethyl)phenyl)-3-((8-(p-toylamino)imidazo[1,2-a]pyridin-3-yl)ethynyl)benzamide

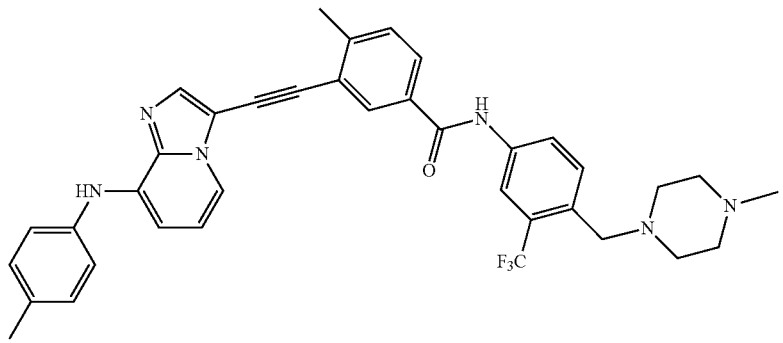 [SMILES: Cc1ccc(Nc2cccn3c(C#Cc4cc(C(=O)Nc5ccc(CN6CCN(C)CC6)c(C(F)(F)F)c5)ccc4C)cnc23)cc1]

Step 1. Preparation of sec-butyl 4-methyl-3-((8-(p-toylamino)imidazo[1,2-a]pyridin-3-yl)ethynyl)benzoate P-toluidine (158 mg, 1.47 mmol), XPhos Pd G2 (97 mg, 0.12 mmol), and $Cs_2CO_3$ (1.20 g, 3.68 mmol) were added to t-butanol (7.5 ml) solution containing the compound prepared in Preparative Example 1 (450 mg, 1.23 mmol), followed by stirring at 100° C. for 15 hours. The reaction mixture was filtered with celite without cooling, followed by concentration. The obtained residue was purified by silica gel chromatography (40-50% ethyl acetate/hexane). As a result, a target compound was obtained (63 mg, 12% yield).
MS m/z: 438[M+H]

Step 2. Preparation of 4-methyl-3-((8-(p-toylamino)imidazo[1,2-a]pyridin-3-yl)ethynyl)benzoic Acid The compound prepared in step 1 above (63 mg, 0.14 mmol) was dissolved in 2 ml of tetrahydrofuran:methanol:water (2:1:1, v/v/v) mixture, to which LiOH. $H_2O$ (30 mg, 0.72 mmol) was added, followed by stirring at 60° C. for 4 hours. The reaction mixture was cooled down to room temperature, to which 1 N HCl solution was slowly added to adjust the pH of the mixture to 4. The produced solid was filtered and dried in vacuo. As a result, a target compound was obtained (51 mg, 93% yield).
MS m/z: 382[M+H]

Step 3. Preparation of 4-methyl-N-(4-((4-methylpiperazin-1-yl)methyl)-3-(trifluoromethyl)phenyl)-3-((8-(p-toylamino)imidazo[1,2-a]pyridin-3-yl)ethynyl)benzamide The compound prepared in step 2 above (25 mg, 0.07 mmol) was dissolved in DMF (1 ml), to which 4-((4-methylpiperazin-1-yl)methyl)-3-(trifluoromethyl)aniline (36 mg, 0.13 mmol) (AK Scientific Co., Cat #AK-83227, CAS [694499-26-8]), EDC (25 mg, 0.13 mmol) and DMAP (16 mg, 0.13 mmol) were added, followed by stirring at 60° C. for 15 hours. The reaction mixture was cooled down to room temperature. The reaction mixture was diluted with ethyl acetate, which was washed with saturated sodium bicarbonate solution, water and brine. The organic layer was dried over $MgSO_4$, filtered and then concentrated. The obtained residue was purified by preparative HPLC (0.1% TFA in water/acetonitrile). As a result, a target compound was obtained (21 mg, 42.5% yield).
$^1$H NMR (400 MHz, Methanol-$d_4$) δ 8.29 (td, 3H), 8.18 (d, 1H), 8.04 (dd, 1H), 7.98 (dd, 1H), 7.80 (d, 1H), 7.56 (d, 1H), 7.43-7.30 (m, 2H), 7.26 (d, 2H), 7.23-7.16 (m, 2H), 3.80 (s, 2H), 3.56-3.43 (m, 2H), 3.24-3.13 (m, 2H), 3.13-2.98 (m, 2H), 2.93 (s, 3H), 2.70 (s, 3H), 2.64-2.42 (m, 2H), 2.37 (s, 3H); MS m/z: 638[M+H]; HPLC $t_R$ 5.89 min (method A)

<Example 25> Preparation of N-(4-((4-ethylpiperazin-1-yl)methyl)-3-(trifluoromethyl)phenyl)-4-methyl-3-((8-(p-toylamino)imidazo[1,2-a]pyridin-3-yl)ethynyl)benzamide

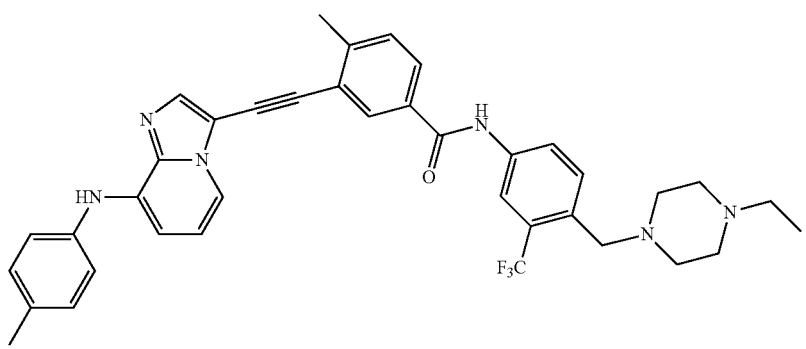 [SMILES: CCN1CCN(Cc2ccc(NC(=O)c3ccc(C)c(C#Cc4cnc5c(Nc6ccc(C)cc6)cccn45)c3)cc2C(F)(F)F)CC1]

The compound of Example 25 was prepared by the same manner as described in Example 24 except that 4-((4-ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.32-8.25 (m, 3H), 8.18 (d, 1H), 8.01 (ddd, 2H), 7.81 (d, 1H), 7.56 (d, 1H), 7.41-7.30 (m, 2H), 7.28-7.17 (m, 4H), 3.80 (s, 2H), 3.59-3.54 (m, 2H), 3.25 (q, 2H), 3.18-3.02 (m, 4H), 2.70 (s, 3H), 2.53-2.48 (m, 2H), 2.37 (s, 3H), 1.37 (t, 3H); 652[M+H]; HPLC t$_R$ 5.94 min (method A)

<Example 26> Preparation of 3-((8-((1-(3-(dimethylamino)propyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide

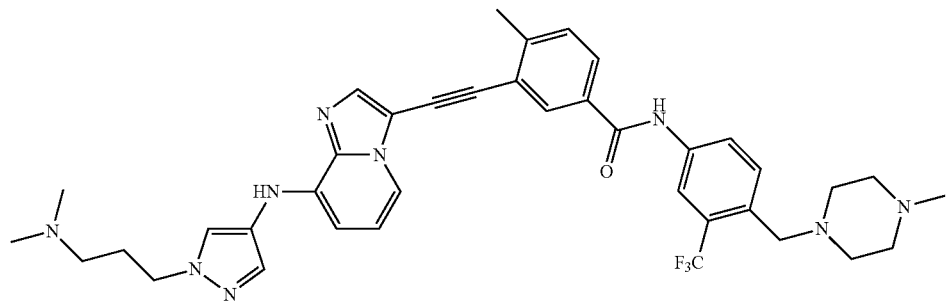

The compound of Example 26 was prepared by the same manner as described in Example 24 except that 1-(3-(dimethylamino)propyl)-1H-pyrazol-4-amine was used instead of p-toluidine used in step 1 of Example 24 to give a final target compound.

$^1$H NMR (400 MHz, Methanol-d$^4$) δ 8.24 (s, 1H), 8.19-8.12 (m, 2H), 8.01 (d, 1H), 7.97-7.91 (m, 1H), 7.88 (s, 1H), 7.78 (d, 1H), 7.65 (s, 1H), 7.53 (d, 1H), 7.24 (t, 1H), 6.99 (d, 1H), 4.32 (t, 1H), 3.78 (s, 1H), 3.48-3.46 (m, 1H), 3.23-3.17 (m, 1H), 3.09-3.02 (m, 2H), 2.92 (s, 9H), 2.67 (s, 3H), 2.57-2.50 (m, 2H), 2.39-2.27 (m, 2H); 698 [M+H]; HPLC t$_R$ 4.69 min (method A)

<Example 27> Preparation of 3-((8-((1-(3-(dimethylamino)propyl)-1H-pyrazol-4-yl)amino)imidazo[1,2-a]pyridin-3-yl)ethynyl)-4-methyl-N-(3-(trifluoromethyl)phenyl)benzamide

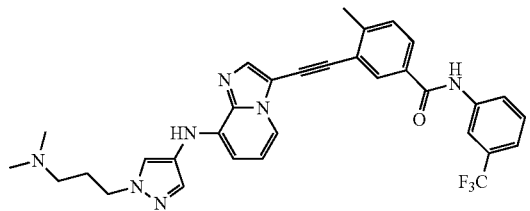 [SMILES: Cc1ccc(C(=O)Nc2cccc(C(F)(F)F)c2)cc1C#Cc1cnc2c(Nc3cnn(CCCN(C)C)c3)cccn12]

The compound of Example 27 was prepared by the same manner as described in Example 24 except that 1-(3-(dimethylamino)propyl)-1H-pyrazol-4-amine was used instead of p-toluidine used in step 1 of Example 24 and 3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, MeOH-d$_4$) δ 8.24 (d, 1H), 8.19 (s, 1H), 8.16-8.14 (m, 2H), 7.95 (d, 2H), 7.87 (s, 1H), 7.65 (s, 1H), 7.57 (t, 1H), 7.53 (d, 1H), 7.45 (d, 1H), 7.23 (t, 1H), 6.97 (d, 1H), 4.31 (t, 2H), 3.25-3.17 (m, 2H), 2.92 (s, 6H), 2.67 (s, 3H), 2.32 (quint, 2H); 586[M+H]; HPLC t$_R$ 5.61 min (method A)

<Example 28> Preparation of 4-methyl-3-((8-((5-methylisoxazol-3-yl)amino)imidazo[1,2-a]pyridin-3-yl)ethynyl)-N-(4-((4-methylpiperazin-1-yl)methyl)-3-(trifluoromethyl)phenyl)benzamide

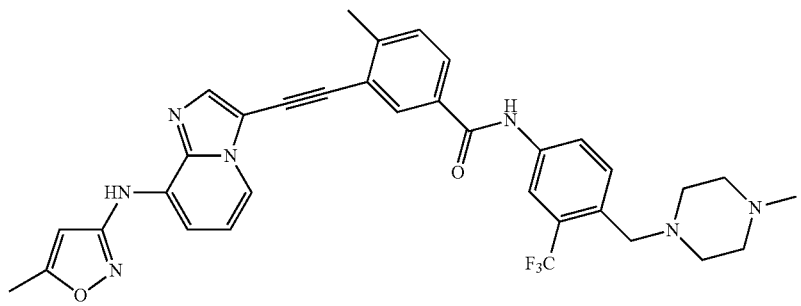

The compound of Example 28 was prepared by the same manner as described in Example 24 except that 5-methyl-isoxazol-3-amine was used instead of p-toluidine used in step 1 of Example 24 to give a final target compound.

$^1$H NMR (400 MHz, MeOH-$d_4$) δ 8.25 (d, 1H), 8.16 (dd, 3H), 8.08 (d, 1H), 8.00 (d, 1H), 7.94-7.89 (m, 1H), 7.76 (d, 1H), 7.48 (d, 1H), 7.37-7.30 (m, 1H), 6.05 (s, 1H), 3.78 (s, 2H), 3.54-3.37 (m, 2H), 3.35 (s, 2H), 3.28-3.15 (m, 2H), 3.0-2.95 (m, 1H), 2.91 (s, 3H), 2.86 (s, 1H), 2.70-2.63 (m, 5H), 2.51 (d, 9H), 2.38 (s, 3H); 628 [M+H]; HPLC $t_R$ 5.76 min (method A)

<Example 29> Preparation of (R)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide

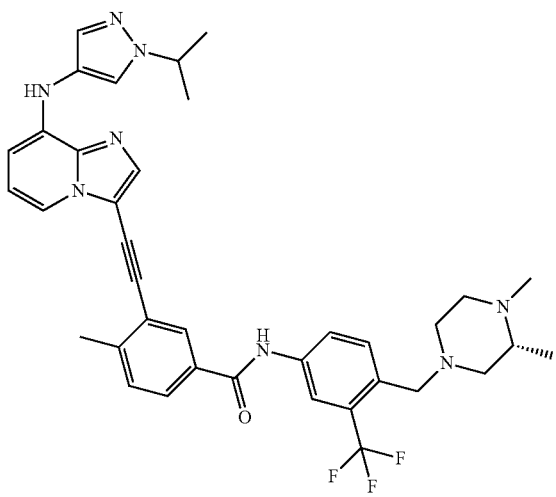 [SMILES: Cc1ccc(C(=O)Nc2ccc(CN3CCN(C)[C@H](C)C3)c(C(F)(F)F)c2)cc1C#Cc1cnc2c(Nc3cnn(C(C)C)c3)cccn12]

The compound of Example 29 was prepared by the same manner as described in Example 24 except that 1-isopropyl-1H-pyrazol-4-amine was used instead of p-toluidine used in step 1 of Example 24 and 3-(trifluoromethyl)-4-(((R)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.30 (s, 1H), 8.24 (s, 1H), 8.20 (d, 1H), 8.16 (s, 1H), 8.00-7.96 (d, 1H), 7.95-7.94 (m, 1H), 7.85 (s, 1H), 7.77 (d, 1H), 7.58 (s, 1H), 7.54-7.50 (m, 1H), 7.36-7.28 (m, 1H), 7.08-7.01 (m, 1H), 4.59-4.52 (t, 1H), 3.76 (s, 2H), 3.56-3.44 (m, 1H), 3.28-3.18 (m, 1H), 3.10-2.95 (m, 2H), 2.92 (s, 3H), 2.67-2.66 (m, 3H), 2.57-2.45 (m, 1H), 2.37-2.20 (m, 1H), 1.54 (d, 6H), 1.37 (d, 3H); 669[M+H]; HPLC tR 5.52 min (method A)

<Example 30> Preparation of N-(4-((3-(dimethylamino)pyrrolidin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide

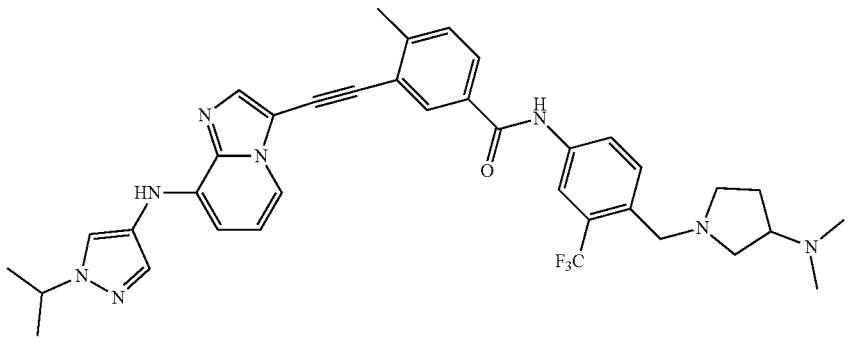 [SMILES: Cc1ccc(C(=O)Nc2ccc(CN3CCC(N(C)C)C3)c(C(F)(F)F)c2)cc1C#Cc1cnc2c(Nc3cnn(C(C)C)c3)cccn12]

The compound of Example 30 was prepared by the same manner as described in Example 24 except that 1-isopropyl-1H-pyrazol-4-amine was used instead of p-toluidine used in step 1 of Example 24 and 1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.37 (s, 1H), 8.32 (s, 1H), 8.30-8.21 (m, 2H), 8.13 (d, 1H), 7.98 (d, 1H), 7.86 (s, 1H), 7.83-7.81 (m, 1H), 7.58 (s, 1H), 7.55 (d, 1H), 7.40 (t, 1H), 7.14 (d, 1H), 4.60-4.53 (m, 1H), 4.47-4.46 (m, 1H), 4.15-4.12 (m, 1H), 3.79-3.62 (m, 2H), 3.57-3.48 (m, 1H), 3.01-2.87 (m, 6H), 2.68 (s, 3H), 2.57-2.56 (m, 1H), 2.38-2.28 (m, 1H), 1.54 (d, 6H); 669[M+H]; HPLC $t_R$ 5.03 min (method C)

<Example 31> Preparation of (R)—N-(4-((3,4-dimethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

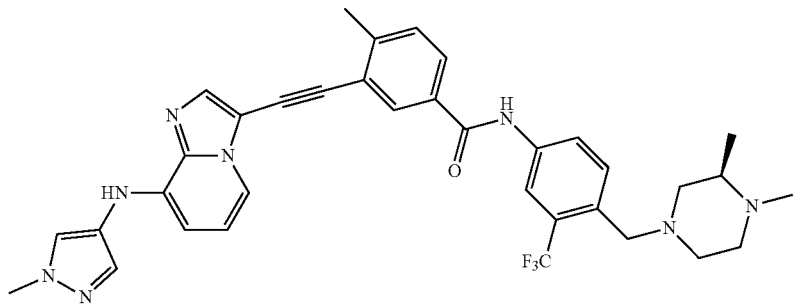

The compound of Example 31 was prepared by the same manner as described in Example 24 except that 1-methyl-1H-pyrazol-4-amine was used instead of p-toluidine used in step 1 of Example 24 and 3-(trifluoromethyl)-4-(((R)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.38 (s, 1H), 8.25 (m, 2H), 8.17 (s, 1H), 8.01-7.96 (m, 2H), 7.79-7.76 (m, 2H), 7.58-7.49 (m, 2H), 7.41 (t, 2H), 7.18 (d, 1H), 3.94 (s, 3H), 3.80-3.79 (m, 2H), 3.52-3.49 (m, 1H), 3.39-3.35 (m, 1H), 3.26-3.23 (m, 1H), 3.10-2.95 (m, 2H), 2.92 (s, 3H), 2.66 (d, 3H), 2.60-2.52 (m, 1H), 2.49-2.35 (m, 1H), 1.37 (d, 3H); 641[M+H]; HPLC $t_R$ 5.26 min (method A)

<Example 32> Preparation of N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

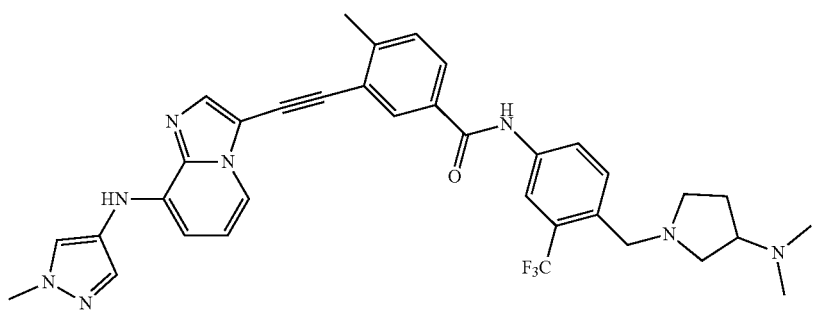

The compound of Example 32 was prepared by the same manner as described in Example 24 except that 1-methyl-1H-pyrazol-4-amine was used instead of p-toluidine used in step 1 of Example 24 and 1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.36 (s, 1H), 8.31 (s, 1H), 8.28-8.24 (m, 2H), 8.12 (d, 1H), 7.99 (dd, 2H), 7.78 (d, 2H), 7.58-7.49 (m, 2H), 7.44-7.38 (m, 1H), 7.18 (d, 1H), 4.42-4.37 (m, 2H), 4.13-4.08 (m, 1H), 3.94 (s, 3H), 3.72-3.56 (m, 2H), 3.49-3.48 (m, 2H), 2.94 (s, 6H), 2.68 (s, 3H), 2.55-2.52 (m, 1H), 2.33-2.28 (m, 1H); 641[M+H]; HPLC $t_R$ 4.80 min (method A)

<Example 33> Preparation of 3-((8-((1-(3-(dimethylamino)propyl)-1H-pyrazol-4-yl)amino)imidazo[1,2-a]pyridin-3-yl)ethynyl)-N-(4-((4-ethylpiperazin-1-yl)methyl)-3-(trifluoromethyl)phenyl)-4-methylbenzamide

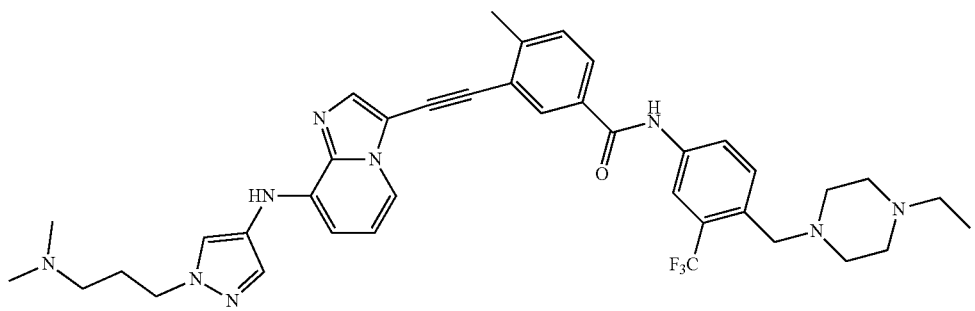 [SMILES: CCN1CCN(Cc2ccc(NC(=O)c3ccc(C)c(C#Cc4cnc5c(Nc6cnn(CCCN(C)C)c6)cccn45)c3)cc2C(F)(F)F)CC1]

The compound of Example 33 was prepared by the same manner as described in Example 24 except that 1-(3-(dimethylamino)propyl)-1H-pyrazol-4-amine was used instead of p-toluidine used in step 1 of Example 24 and 4-((ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, MeOH-$d_4$) δ 8.24 (d, 1H), 8.23-8.13 (m, 3H), 8.01 (d, 1H), 7.95 (dd, 1H), 7.87 (s, 1H), 7.78 (d, 1H), 7.64 (s, 1H), 7.53 (d, 1H), 7.30-7.24 (m, 1H), 7.06-7.00 (m, 1H), 4.31 (t, 2H), 3.79 (s, 2H), 3.59-3.48 (m, 2H), 3.26-3.18 (m, 4H), 3.15-3.00 (m, 4H), 2.92 (s, 6H), 2.67 (s, 3H), 2.59-2.41 (m, 2H), 2.39-2.27 (m, 2H), 1.35 (t, 3H); 712[M+H]; HPLC $t_R$ 4.80 min (method A)

<Example 34> Preparation of (R)-3-((8-((1-(3-(dimethylamino)propyl)-1H-pyrazol-4-yl)amino)imidazo[1,2-a]pyridin-3-yl)ethynyl)-N-(4-((3,4-dimethylpiperazin-1-yl)methyl)-3-(trifluoromethyl)phenyl)-4-methylbenzamide

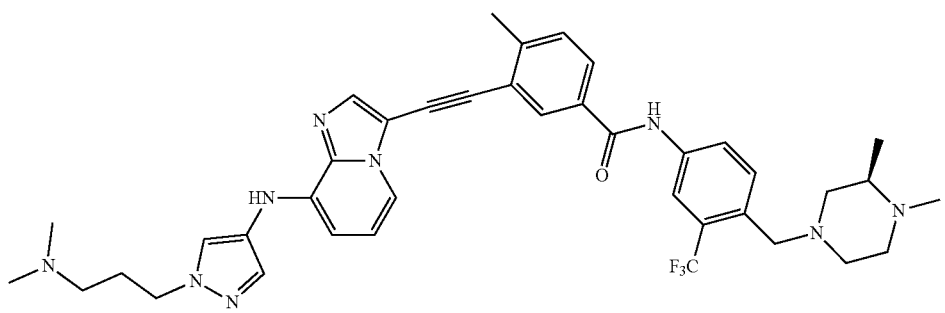

The compound of Example 34 was prepared by the same manner as described in Example 24 except that 1-(3-(dimethylamino)propyl)-1H-pyrazol-4-amine was used instead of p-toluidine used in step 1 of Example 24 and 3-(trifluoromethyl)-4-(((R)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.35-8.32 (m, 1H), 8.28-8.21 (m, 2H), 8.17 (s, 1H), 8.01 (d, 1H), 7.97 (dd, 1H), 7.89 (s, 1H), 7.78 (d, 1H), 7.65 (s, 1H), 7.54 (d, 1H), 7.40-7.34 (m, 1H), 7.18-7.13 (m, 1H), 4.32 (t, 3H), 3.78 (s, 3H), 3.51-3.48 (m, 1H), 3.45-3.35 (m, 1H), 3.24-3.18 (m, 2H), 3.12-2.96 (m, 2H), 2.92 (s, 9H), 2.67 (s, 3H), 2.63-2.45 (m, 2H), 2.39-2.29 (m, 2H), 1.37 (d, 3H); 712[M+H]; HPLC $t_R$ 4.83 min (method A)

<Example 35> Preparation of 3-((8-((1-(3-(dimethylamino)propyl)-1H-pyrazol-4-yl)amino)imidazo[1,2-a]pyridin-3-yl)ethynyl)-N-(4-((3-(dimethylamino)pyrrolidin-1-yl)methyl)-3-(trifluoromethyl)phenyl)-4-methylbenzamide

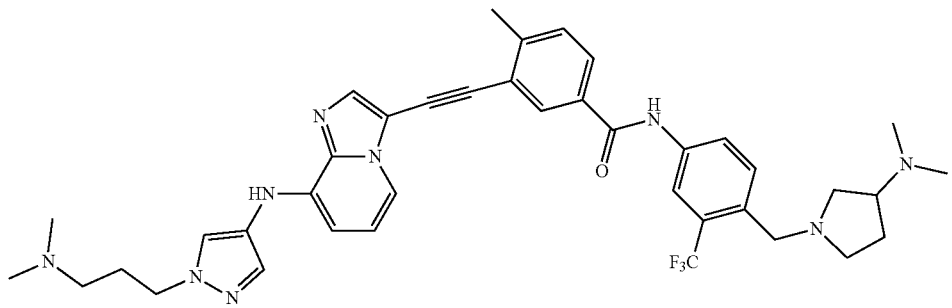

The compound of Example 35 was prepared by the same manner as described in Example 24 except that 1-(3-(dimethylamino)propyl)-1H-pyrazol-4-amine was used instead of p-toluidine used in step 1 of Example 24 and 1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.32 (s, 2H), 8.27 (s, 1H), 8.24 (d, 1H), 8.13 (d, 1H), 7.98 (d, 1H), 7.89 (s, 1H), 7.84 (d, 1H), 7.65 (s, 1H), 7.54 (d, 1H), 7.36 (t, 1H), 7.14 (d, 1H), 4.48-4.40 (m, 2H), 4.32 (t, 2H), 4.19-4.07 (m, 1H), 3.73-3.61 (m, 2H), 3.55-3.52 (m, 2H), 3.23-3.19 (m, 2H), 2.95 (s, 6H), 2.92 (s, 6H), 2.68 (s, 3H), 2.61-2.53 (m, 2H), 2.37-2.30 (m, 2H); 712[M+H]; HPLC $t_R$ 4.42 min (method A)

<Example 36> Preparation of 4-methyl-3-((8-((1-methyl-1H-pyrazol-4-yl)amino)imidazo[1,2-a]pyridin-3-yl)ethynyl)-N-(quinolin-7-yl)benzamide

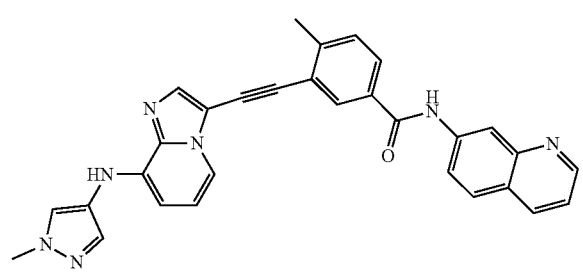 [SMILES: Cc1ccc(C(=O)Nc2ccc3cccnc3c2)cc1C#Cc1cnc2c(Nc3cnn(C)c3)cccn12]

The compound of Example 36 was prepared by the same manner as described in Example 24 except that 1-methyl-1H-pyrazol-4-amine was used instead of p-toluidine used in step 1 of Example 24 and quinolin-7-amine was used instead of 4-((methylpiperazin-1-yl)methyl)-3-(trifluoromethyl)aniline in step 3 of Example 24 to give a final target compound.

$^1$H NMR (400 MHz, MeOH-$d_4$) δ 9.17 (s, 1H), 9.09-9.07 (m, 2H), 8.36 (s, 1H), 8.34-8.30 (m, 2H), 8.24 (d, 1H), 8.10 (dd, 1H), 8.03 (dd, 1H), 7.96-7.93 (m, 1H), 7.78 (s, 1H), 7.56-7.54 (m, 2H), 7.41-7.37 (m, 1H), 7.14 (d, 1H), 3.93 (s, 3H), 2.67 (s, 3H); 498 [M+H]; HPLC $t_R$ 4.83 min (method A)

<Example 37> Preparation of N-(benzo[d]thiazol-6-yl)-4-methyl-3-((8-((1-methyl-1H-pyrazol-4-yl)amino)imidazo[1,2-a]pyridin-3-yl)ethynyl)benzamide

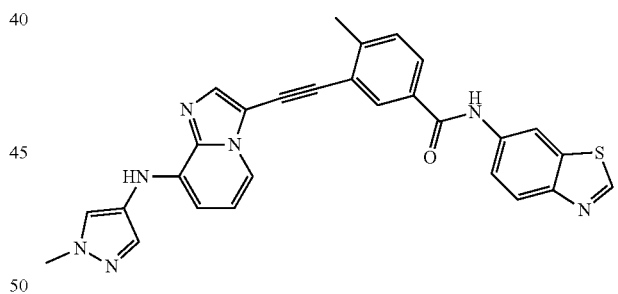

The compound of Example 37 was prepared by the same manner as described in Example 24 except that 1-methyl-1H-pyrazol-4-amine was used instead of p-toluidine used in step 1 of Example 24 and benzo[d]thiazol-6-amine was used instead of 4-((methylpiperazin-1-yl)methyl)-3-(trifluoromethyl)aniline in step 3 of Example 24 to give a final target compound.

$^1$H NMR (400 MHz, MeOH-$d_4$) δ 9.19 (s, 1H), 8.64 (d, 1H), 8.32 (s, 1H), 8.27 (d, 1H), 8.24 (d, 1H), 8.05 (d, 1H), 7.99 (dd, 1H), 7.82-7.76 (m, 2H), 7.56-7.53 (m, 2H), 7.37-7.33 (m, 1H), 7.10 (d, 1H), 3.94 (s, 3H), 2.67 (s, 3H); 504[M+H]; HPLC $t_R$ 5.93 min (method A)

<Example 38> Preparation of 3-((8-((1-isopropyl-1H-pyrazol-4-yl)amino)imidazo[1,2-a]pyridin-3-yl)ethynyl)-4-methyl-N-(4-((4-methyl-1,4-diazepin-1-yl)methyl)-3-(trifluoromethyl)phenyl)benzamide

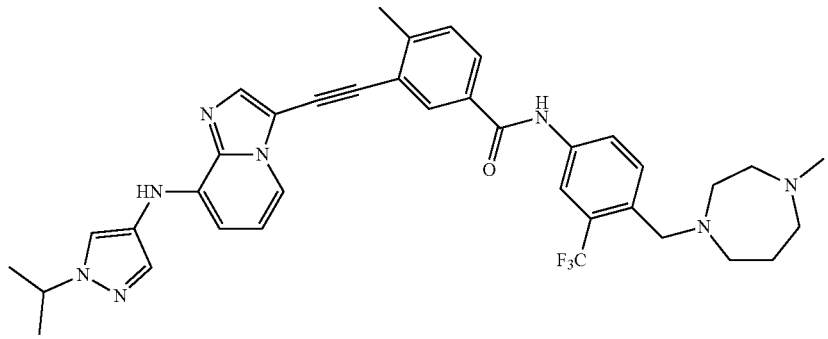 [SMILES: Cc1ccc(C(=O)Nc2ccc(CN3CCCN(C)CC3)c(C(F)(F)F)c2)cc1C#Cc1cnc2c(Nc3cnn(C(C)C)c3)cccn12]

The compound of Example 38 was prepared by the same manner as described in Example 24 except that 1-isopropyl-1H-pyrazol-4-amine was used instead of p-toluidine used in step 1 of Example 24 and 3-(trifluoromethyl)-4((4-methyl-1-diazepin-1-yl)methyl)benzeneamine was used instead of 4-((methylpiperazin-1-yl)methyl)-3-(trifluoromethyl)aniline in step 3 of Example 24 to give a final target compound.

1H NMR (400 MHz, Methanol-d4) δ 8.33-8.32 (m, 1H), 8.26 (d, 2H), 8.24-8.21 (m, 1H), 8.10-8.08 (m, 1H), 7.97 (dd, 1H), 7.88-7.86 (m, 2H), 7.58 (s, 1H), 7.54 (d, 1H), 7.38-7.34 (m, 1H), 7.09 (d, 1H), 4.56 (hept, 1H), 4.30-4.19 (m, 2H), 3.60-3.53 (m, 2H), 3.53-3.45 (m, 2H), 3.40-3.32 (m, 2H), 3.12-3.13 (m, 2H), 2.96 (s, 3H), 2.67 (s, 3H), 2.21-2.20 (m, 2H), 1.55 (s, 3H), 1.53 (s, 3H); 669[M+H]; HPLC tR 5.15 min (method A)

<Example 39> Preparation of 3-((8-((1-(3-(dimethylamino)propyl)-1H-pyrazol-4-yl)amino)imidazo[1,2-a]pyridin-3-yl)ethynyl)-4-methyl-N-(4-((4-methyl-1,4-diazepin-1-yl)methyl)-3-(trifluoromethyl)phenyl)benzamide

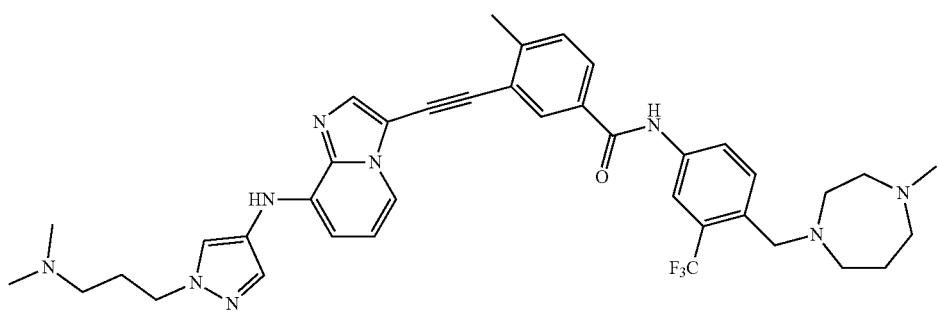

The compound of Example 39 was prepared by the same manner as described in Example 24 except that 1-(3-(dimethylamino)propyl)-1H-pyrazol-4-amine was used instead of p-toluidine used in step 1 of Example 24 and 3-(trifluoromethyl)-4((4-methyl-1-diazepin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.23 (d, 1H), 8.19 (d, 1H), 8.15-8.09 (m, 1H), 8.05 (dd, 1H), 7.94 (dd, 1H), 7.91-7.83 (m, 3H), 7.64 (d, 1H), 7.52 (d, 1H), 7.20 (dd, 1H), 6.93 (d, 1H), 4.31 (t, 2H), 4.02 (s, 1H), 3.48 (dd, 2H), 3.25-3.16 (m, 3H), 3.07 (d, 2H), 2.94 (d, 5H), 2.92 (s, 6H), 2.67 (s, 3H), 2.33 (dt, 3H), 2.14 (dd, 3H); 712[M+H]; HPLC $t_R$ 2.16 min (method C)

<Example 40> Preparation of (R)—N-(4-((3,4-dimethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide

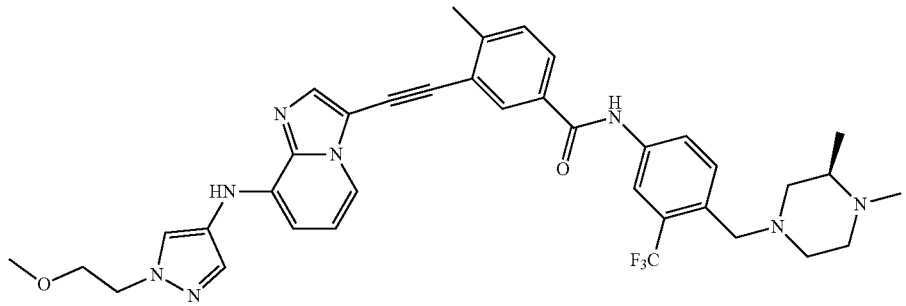

The compound of Example 40 was prepared by the same manner as described in Example 24 except that 1-((2-methoxy)ethyl)-1H-pyrazol-4-amine was used instead of p-toluidine used in step 1 of Example 24 and 3-(trifluoromethyl)-4-(((R)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.37-8.30 (m, 1H), 8.28-8.19 (m, 2H), 8.16 (d, 1H), 7.99 (ddd, 2H), 7.83 (d, 1H), 7.77 (d, 1H), 7.59 (d, 1H), 7.53 (d, 1H), 7.42-7.32 (m, 1H), 7.19-7.01 (m, 1H), 4.34 (t, 2H), 3.84-3.70 (m, 4H), 3.55-3.45 (m, 1H), 3.36 (s, 3H), 3.32-3.18 (m, 2H), 3.12-2.97 (m, 2H), 2.92 (s, 3H), 2.67 (s, 3H), 2.59-2.43 (m, 1H), 2.42-2.17 (m, 1H), 1.37 (d, 3H); 685[M+H]; HPLC $t_R$ 5.36 min (method A)

<Example 41> Preparation of N-(4-((3-(dimethylamino)pyrrolidin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide

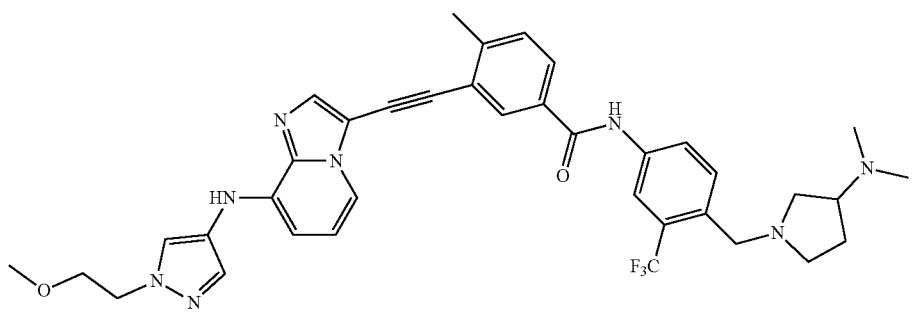

The compound of Example 41 was prepared by the same manner as described in Example 24 except that 1-((2-methoxy)ethyl)-1H-pyrazol-4-amine was used instead of p-toluidine used in step 1 of Example 24 and 1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.31 (s, 2H), 8.28-8.25 (m, 1H), 8.21 (dd, 1H), 8.12 (d, 1H), 7.98 (dt, 1H), 7.84 (s, 2H), 7.60 (d, 1H), 7.54 (t, 1H), 7.35 (t, 1H), 7.10 (d, 1H), 4.52-4.37 (m, 2H), 4.35 (t, 2H), 4.12 (s, 1H), 3.79 (t, 2H), 3.75-3.38 (m, 3H), 3.37 (s, 3H), 3.29-3.06 (m, 1H), 3.03-2.90 (m, 6H), 2.68 (d, 3H), 2.55 (s, 1H), 2.31 (s, 1H); 685[M+H]; HPLC $t_R$ 4.85 min (method A)

<Example 42> Preparation of (R)—N-(4-((3,4-dimethylpiperazin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide

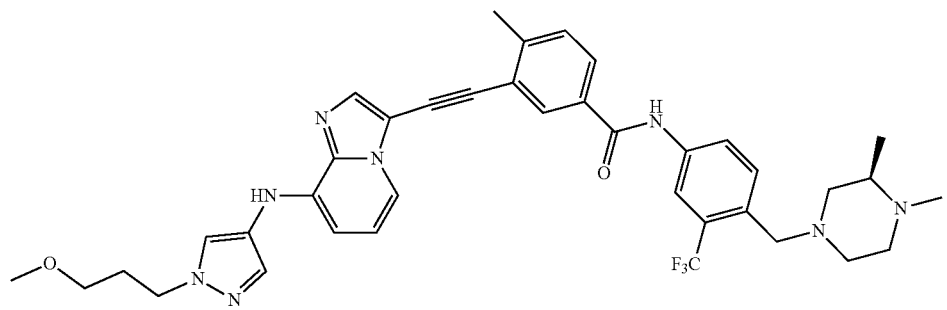

The compound of Example 42 was prepared by the same manner as described in Example 24 except that 1-((3-methoxy)propyl)-1H-pyrazol-4-amine was used instead of p-toluidine used in step 1 of Example 24 and 3-(trifluoromethyl)-4-(((R)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.
$^1$H NMR (400 MHz, Methanol-d$_4$) δ 8.35 (s, 1H), 8.29-8.22 (m, 2H), 8.22-8.15 (m, 1H), 8.07-8.01 (m, 1H), 7.98 (dd, 1H), 7.86-7.82 (m, 1H), 7.79 (d, 1H), 7.61 (d, 1H), 7.55 (d, 1H), 7.42-7.33 (m, 1H), 7.17-7.09 (m, 1H), 4.35 (t, 2H), 3.86-3.74 (m, 4H), 3.57-3.46 (m, 1H), 3.37 (s, 3H), 3.30-3.20 (m, 2H), 3.15-2.97 (m, 2H), 2.94 (s, 3H), 2.69 (s, 3H), 2.64-2.44 (m, 1H), 2.44-2.21 (m, 1H), 1.39 (d, 3H); 699 [M+H]; HPLC t$_R$ 2.49 min (method C)

<Example 43> Preparation of N-(4-((3-(dimethylamino)pyrrolidin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide

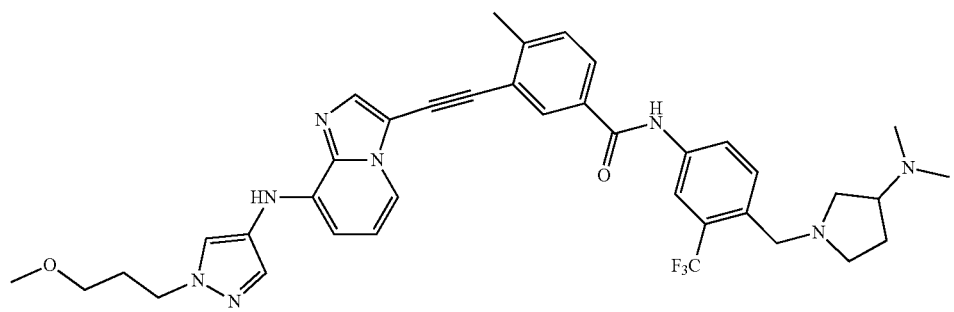

The compound of Example 43 was prepared by the same manner as described in Example 24 except that 1-((3-methoxy)propyl)-1H-pyrazol-4-amine was used instead of p-toluidine used in step 1 of Example 24 and 1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.34-8.23 (m, 3H), 8.20 (d, 1H), 8.11 (d, 1H), 7.96 (dd, 1H), 7.86-7.74 (m, 2H), 7.58 (s, 1H), 7.53 (t, 1H), 7.33 (tt, 1H), 7.07 (t, 1H), 4.43-4.30 (m, 1H), 4.26 (t, 2H), 4.16-3.96 (m, 1H), 3.69-3.43 (m, 4H), 3.39 (t, 2H), 3.34 (s, 3H), 3.26-3.02 (m, 1H), 2.94 (s, 6H), 2.67 (d, 3H), 2.61-2.39 (m, 1H), 2.38-2.18 (m, 1H), 2.12 (quint, 2H); 699[M+H]; HPLC t$_R$ 4.95 min (method A)

<Example 44> Preparation of (S)—N-(4-((3,4-dimethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide

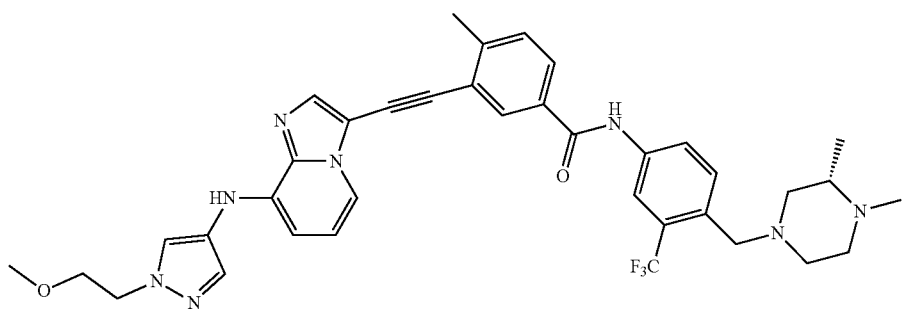

The compound of Example 44 was prepared by the same manner as described in Example 24 except that 1-((2-methoxy)ethyl)-1H-pyrazol-4-amine was used instead of p-toluidine used in step 1 of Example 24 and 3-(trifluoromethyl)-4-(((S)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.36-8.30 (m, 1H), 8.28-8.19 (m, 2H), 8.19-8.12 (m, 1H), 8.04-7.93 (m, 2H), 7.84-7.80 (m, 1H), 7.77 (d, 1H), 7.63-7.58 (m, 1H), 7.52 (t, 1H), 7.42-7.33 (m, 1H), 7.12 (dd, 1H), 4.26 (t, 2H), 3.77 (s, 2H), 3.59-3.44 (m, 1H), 3.39 (t, 2H), 3.34 (s, 3H), 3.29-3.19 (m, 2H), 3.14-2.97 (m, 2H), 2.92 (s, 3H), 2.74-2.62 (m, 3H), 2.62-2.45 (m, 1H), 2.44-2.25 (m, 1H), 2.12 (quint, 2H), 1.37 (d, 3H); 685[M+H]; HPLC t$_R$ 5.43 min (method A)

<Example 45> Preparation of N-(4-((3-(dimethylamino)pyrrolidin-1-yl)methyl)-3-(trifluoromethyl)phenyl)-4-methyl-3-((8-((5-methylisoxazol-3-yl)amino)imidazo[1,2-a]pyridin-3-yl)ethynyl)benzamide

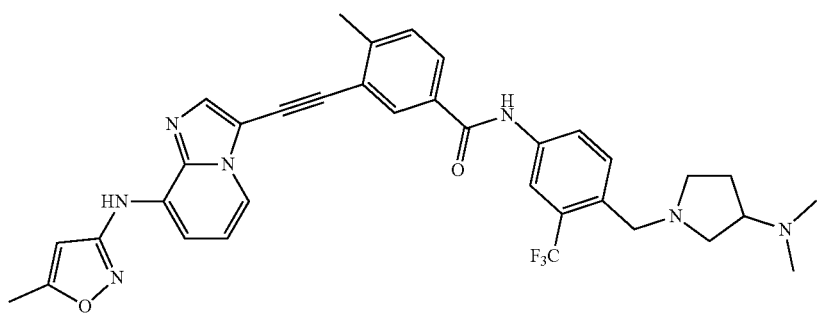

The compound of Example 45 was prepared by the same manner as described in Example 24 except that 5-methylisoxazol-3-amine was used instead of p-toluidine used in step 1 of Example 24 and 1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.31-8.20 (m, 4H), 8.13-8.07 (m, 2H), 8.05 (d, 1H), 7.98-7.90 (m, 1H), 7.81 (d, 1H), 7.56-7.44 (m, 1H), 7.30 (t, 1H), 4.35-4.14 (m, 1H), 4.14-3.96 (m, 1H), 3.79-3.61 (m, 1H), 3.58-3.43 (m, 1H), 3.43-3.35 (m, 1H), 3.28-3.16 (m, 1H), 3.12-2.98 (m, 1H), 2.93 (s, 6H), 2.67 (s, 3H), 2.56-2.45 (m, 1H), 2.42 (s, 3H), 2.33-2.14 (m, 1H); 642[M+H]; HPLC t$_R$ 2.52 min (method C)

<Example 46> Preparation of (S)—N-(4-((3,4-dimethylpiperazin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide

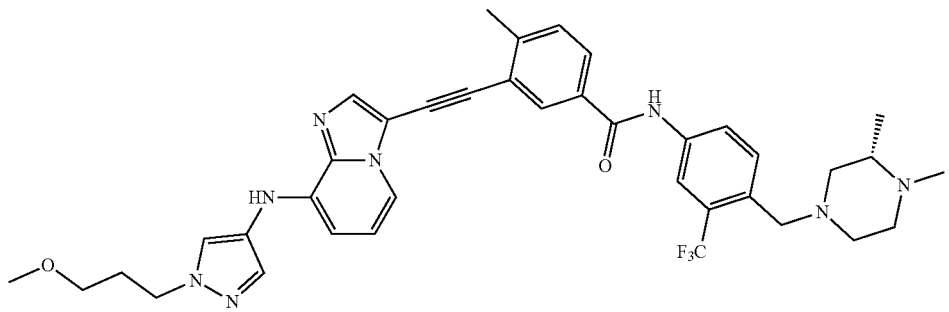

The compound of Example 46 was prepared by the same manner as described in Example 24 except that 1-((3-methoxy)propyl)-1H-pyrazol-4-amine was used instead of p-toluidine used in step 1 of Example 24 and 3-(trifluoromethyl)-4-(((S)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.41-8.29 (m, 1H), 8.29-8.20 (m, 2H), 8.16 (s, 1H), 8.01 (d, 1H), 7.97 (dd, 1H), 7.82 (s, 1H), 7.77 (d, 1H), 7.59 (s, 1H), 7.56-7.49 (m, 1H), 7.43-7.30 (m, 1H), 7.12 (d, 1H), 4.27 (t, 2H), 3.77 (s, 2H), 3.56-3.45 (m, 1H), 3.39 (t, 2H), 3.34 (s, 3H), 3.30-3.18 (m, 2H), 3.02 (d, 2H), 2.92 (s, 3H), 2.67 (s, 3H), 2.62-2.41 (m, 1H), 2.41-2.19 (m, 1H), 2.13 (quintet, 2H), 1.37 (d, 3H); 699 [M+H]; HPLC t$_R$ 2.52 min (method C)

<Example 47> Preparation of (S)—N-(4-((3,4-dimethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

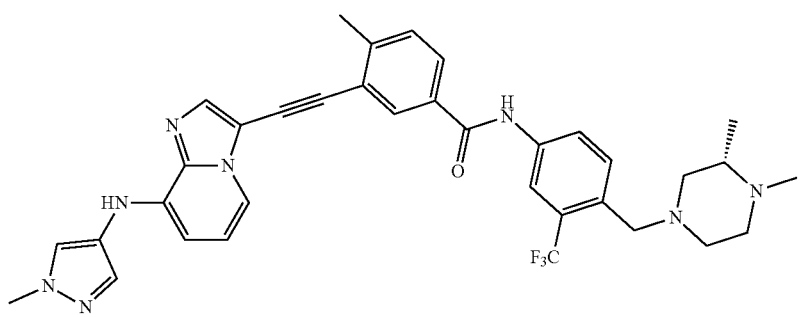

The compound of Example 47 was prepared by the same manner as described in Example 24 except that 1-methyl-1H-pyrazol-4-amine was used instead of p-toluidine used in step 1 of Example 24 and 3-(trifluoromethyl)-4-(((S)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.36-8.31 (m, 1H), 8.28-8.18 (m, 2H), 8.16 (d, 1H), 8.05-7.90 (m, 2H), 7.77 (dd, 2H), 7.56 (dd, 1H), 7.53-7.44 (m, 1H), 7.38 (dd, 1H), 7.18-7.08 (m, 1H), 3.95-3.88 (m, 3H), 3.78 (s, 2H), 3.50 (t, 1H), 3.38 (s, 1H), 3.25 (t, 1H), 3.03 (s, 3H), 2.92 (s, 3H), 2.69-2.60 (m, 3H), 2.39 (s, 1H), 1.37 (d, 3H); 641[M+H]; HPLC t$_R$ 2.46 min (method C)

<Example 48> Preparation of (S)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide

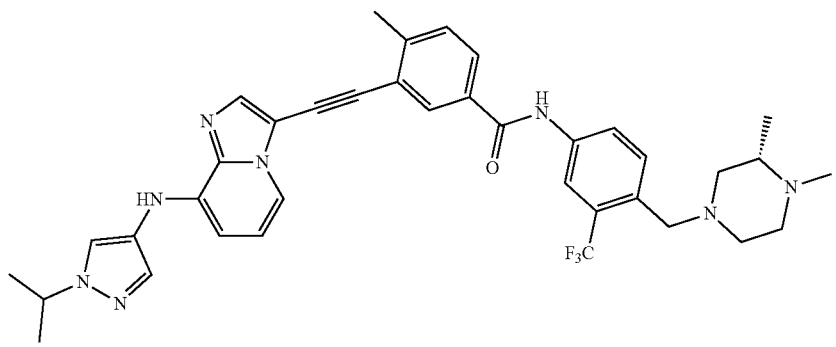 [SMILES: Cc1ccc(C(=O)Nc2ccc(CN3CCN(C)[C@@H](C)C3)c(C(F)(F)F)c2)cc1C#Cc1cnc2c(Nc3cnn(C(C)C)c3)cccn12]

The compound of Example 48 was prepared by the same manner as described in Example 24 except that 1-isopropyl-1H-pyrazol-4-amine was used instead of p-toluidine used in step 1 of Example 24 and 3-(trifluoromethyl)-4-(((S)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.30 (d, 1H), 8.25 (d, 1H), 8.21 (dd, 1H), 8.16 (d, 1H), 8.01 (dd, 1H), 7.96 (dd, 1H), 7.85 (d, 1H), 7.77 (d, 1H), 7.58 (d, 1H), 7.53 (d, 1H), 7.38-7.27 (m, 1H), 7.07 (d, 1H), 4.56 (septet, 1H), 3.76 (s, 2H), 3.56-3.42 (m, 1H), 3.31-3.15 (m, 2H), 3.14-2.97 (m, 2H), 2.92 (s, 3H), 2.67 (s, 3H), 2.58-2.42 (m, 1H), 2.41-2.18 (m, 1H), 1.54 (d, 6H), 1.37 (d, 3H); 669[M+H]; HPLC $t_R$ 2.61 min (method C)

<Example 49> Preparation of (S)-3-((8-((1-(3-(dimethylamino)propyl)-1H-pyrazol-4-yl)amino)imidazo[1,2-a]pyridin-3-yl)ethynyl)-N-(4-((3,4-dimethylpiperazin-1-yl)methyl)-3-(trifluoromethyl)phenyl)-4-methylbenzamide

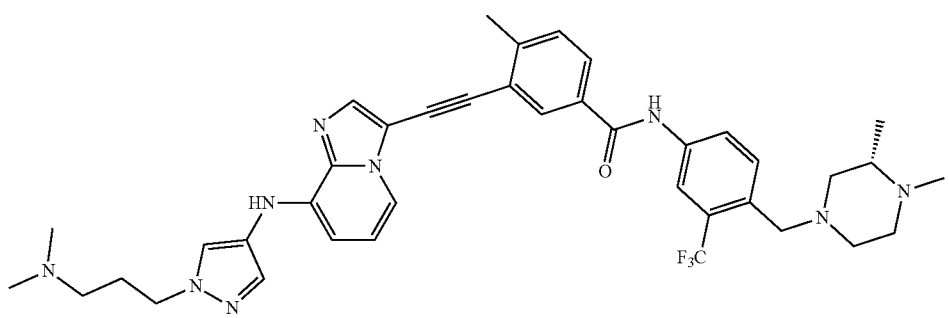

The compound of Example 49 was prepared by the same manner as described in Example 24 except that 1-(3-(dimethylamino)propyl)-1H-pyrazol-4-amine was used instead of p-toluidine used in step 1 of Example 24 and 3-(trifluoromethyl)-4-(((S)-3,4-dimethylpiperazin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.35-8.29 (m, 1H), 8.28-8.21 (m, 2H), 8.17 (d, 1H), 8.05-7.93 (m, 2H), 7.88 (s, 1H), 7.77 (d, 1H), 7.65 (s, 1H), 7.53 (d, 1H), 7.41-7.31 (m, 1H), 7.18-7.08 (m, 1H), 4.32 (t, 2H), 3.78 (s, 2H), 3.56-3.45 (m, 1H), 3.44-3.33 (m, 1H), 3.30-3.22 (m, 1H), 3.23-3.14 (m, 2H), 3.12-2.93 (m, 2H), 2.92 (s, 9H), 2.67 (s, 3H), 2.62-2.46 (m, 1H), 2.44-2.37 (m, 1H), 2.37-2.27 (m, 2H), 1.37 (d, 3H); 712[M+H]; HPLC $t_R$ 2.32 min (method C)

<Example 50> Preparation of (R)—N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

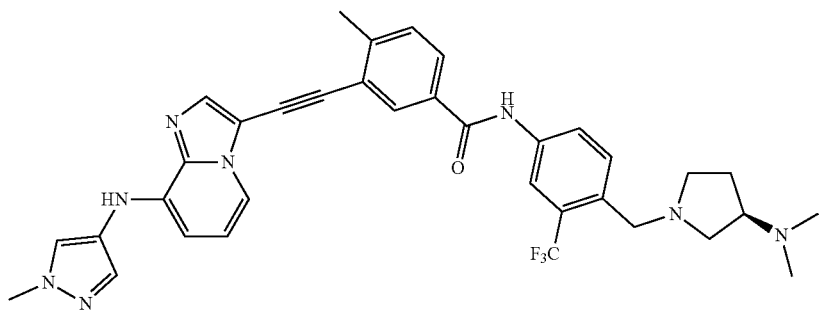

The compound of Example 50 was prepared by the same manner as described in Example 24 except that 1-methyl-1H-pyrazol-4-amine was used instead of p-toluidine used in step 1 of Example 24 and (R)-1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.35 (s, 1H), 8.34-8.31 (m, 1H), 8.29-8.19 (m, 2H), 8.13 (dd, 1H), 8.00-7.94 (m, 1H), 7.84 (d, 1H), 7.79 (s, 1H), 7.56 (s, 1H), 7.54-7.49 (m, 1H), 7.38 (t, 1H), 7.15 (d, 1H), 4.58-4.37 (m, 1H), 4.26-4.08 (m, 1H), 3.94 (s, 3H), 3.88-3.67 (m, 2H), 3.67-3.45 (m, 1H), 3.44-3.34 (m, 1H), 2.95 (s, 6H), 2.93-2.90 (m, 1H), 2.67 (s, 3H), 2.63-2.53 (m, 1H), 2.43-2.22 (m, 1H); 641[M+H]; HPLC t$_R$ 2.29 min (method C)

<Example 51> Preparation of (S)—N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

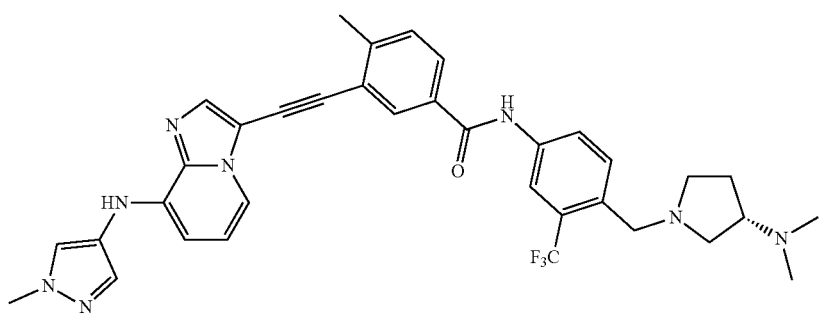

The compound of Example 51 was prepared by the same manner as described in Example 24 except that 1-methyl-1H-pyrazol-4-amine was used instead of p-toluidine used in step 1 of Example 24 and (S)-1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.35 (s, 1H), 8.28-8.17 (m, 3H), 8.16-8.03 (m, 1H), 7.97 (d, 1H), 7.84 (d, 1H), 7.79 (s, 1H), 7.56 (s, 1H), 7.54-7.48 (m, 1H), 7.38 (t, 1H), 7.14 (d, 1H), 4.59-4.35 (m, 2H), 4.23-4.01 (m, 3H), 3.94 (s, 3H), 3.86-3.66 (m, 1H), 3.65-3.43 (m, 1H), 2.95 (s, 6H), 2.68 (s, 3H), 2.58 (s, 1H), 2.34 (s, 1H); 641[M+H]; HPLC t$_R$ 2.27 min (method C)

<Example 52> Preparation of N-(4-((4,4-difluoropiperidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

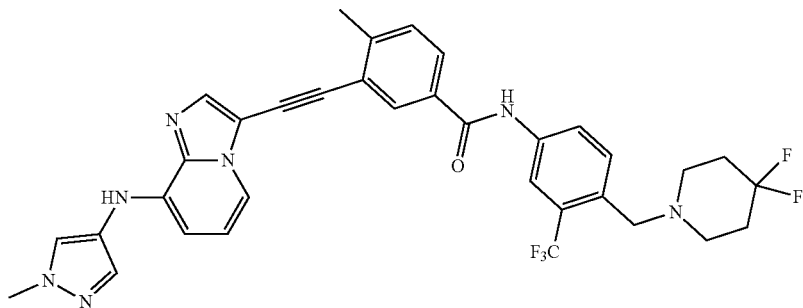 [SMILES: Cc1ccc(C(=O)Nc2ccc(CN3CCC(F)(F)CC3)c(C(F)(F)F)c2)cc1C#Cc1cnc2c(Nc3cnn(C)c3)cccn12]

The compound of Example 52 was prepared by the same manner as described in Example 24 except that 1-methyl-1H-pyrazol-4-amine was used instead of p-toluidine used in step 1 of Example 24 and 3-(trifluoromethyl)-4-((4,4-difluoropiperidin-1-yl)methyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.44-8.36 (m, 1H), 8.31-8.23 (m, 2H), 8.23-8.14 (m, 2H), 8.03-7.93 (m, 1H), 7.86 (d, 1H), 7.82-7.77 (m, 1H), 7.60-7.55 (m, 1H), 7.55-7.48 (m, 1H), 7.33 (t, 1H), 7.08 (d, 1H), 4.58 (s, 2H), 3.95 (s, 3H), 3.65-3.46 (m, 4H), 2.67 (s, 3H), 2.49-2.25 (m, 4H); 648[M+H]; HPLC $t_R$ 2.53 min (method C)

<Example 53> Preparation of (R)—N-(4-((3-(dimethylamino)pyrrolidin-1-yl)methyl)-3-(trifluoromethyl)phenyl)-3-((8-((1-ethyl-1H-pyrazol-4-yl)amino)imidazo[1,2-a]pyridin-3-yl)ethynyl)-4-methylbenzamide

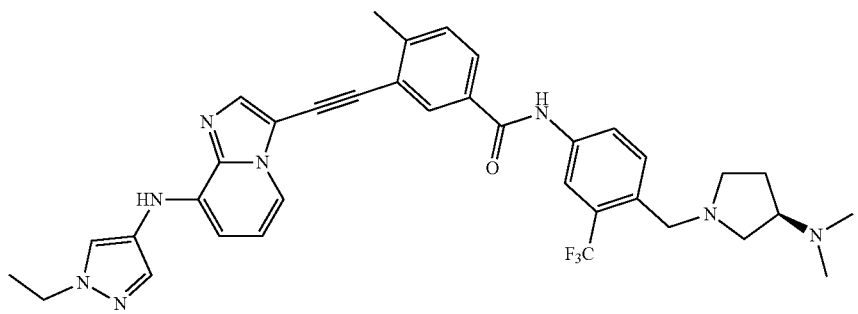 [SMILES: CCn1cc(Nc2cccn3c(C#Cc4cc(C(=O)Nc5ccc(CN6CC[C@@H](N(C)C)C6)c(C(F)(F)F)c5)ccc4C)cnc23)cn1]

The compound of Example 53 was prepared by the same manner as described in Example 24 except that 1-ethyl-1H-pyrazol-4-amine was used instead of p-toluidine used in step 1 of Example 24 and (R)-1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.33-8.32 (m, 1H), 8.31 (s, 1H), 8.28 (d, 1H), 8.26 (d, 1H), 8.22 (dd, 1H), 8.11 (dd, 1H), 7.97 (dd, 1H), 7.85-7.82 (m, 1H), 7.57 (s, 1H), 7.53 (d, 1H), 7.40-7.30 (m, 1H), 7.14-7.07 (m, 1H), 4.45-4.29 (m, 3H), 4.22 (q, 2H), 4.15-4.00 (m, 1H), 3.72-3.53 (m, 1H), 3.52-3.35 (m, 1H), 3.20-3.04 (m, 1H), 2.94 (s, 6H), 2.67 (s, 3H), 2.62-2.44 (m, 1H), 2.38-2.17 (m, 1H), 1.50 (t, 3H); 655 [M+H]; HPLC $t_R$ 2.34 min (method C)

<Example 54> Preparation of (S)—N-(4-((3-(dimethylamino)pyrrolidin-1-yl)methyl)-3-(trifluoromethyl)phenyl)-3-((8-((1-ethyl-1H-pyrazol-4-yl)amino)imidazo[1,2-a]pyridin-3-yl)ethynyl)-4-methylbenzamide

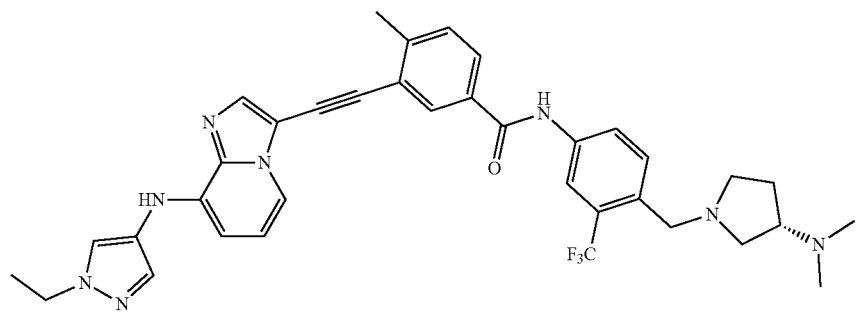 [SMILES: CCn1cc(Nc2cccn3c(C#Cc4cc(C(=O)Nc5ccc(CN6CC[C@H](N(C)C)C6)c(C(F)(F)F)c5)ccc4C)cnc23)cn1]

The compound of Example 54 was prepared by the same manner as described in Example 24 except that 1-ethyl-1H-pyrazol-4-amine was used instead of p-toluidine used in step 1 of Example 24 and (S)-1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-$d_4$) δ 8.34-8.28 (m, 2H), 8.26 (d, 1H), 8.21 (d, 1H), 8.11 (d, 1H), 7.97 (dd, 1H), 7.85-7.79 (m, 2H), 7.57 (s, 1H), 7.53 (d, 1H), 7.38-7.30 (m, 1H), 7.13-7.03 (m, 1H), 4.46-4.27 (m, 2H), 4.22 (q, 2H), 4.17-4.01 (m, 1H), 3.72-3.56 (m, 2H), 3.56-3.38 (m, 1H), 3.25-3.07 (m, 1H), 2.94 (s, 6H), 2.66 (s, 3H), 2.61-2.47 (m, 1H), 2.29 (dt, 1H), 1.50 (t, 3H); 655[M+H]; HPLC $t_R$ 2.34 min (method C)

<Example 55> Preparation of N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide

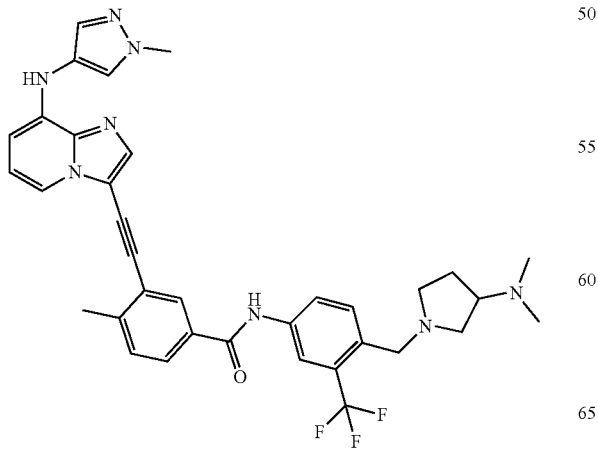

The compound of Example 55 was prepared by the same manner as described in Example 24 except that 1-ethyl-1H-pyrazol-4-amine was used instead of p-toluidine used in step 1 of Example 24 and 1-(4-amino-2-(trifluoromethyl)benzyl)-N,N-dimethylpyrrolidin-3-amine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 6 8.36 (s, 1H), 8.31 (s, 1H), 8.28-8.24 (m, 2H), 8.12 (d, 1H), 7.99 (dd, 2H), 7.78 (d, 2H), 7.58-7.49 (m, 2H), 7.44-7.38 (m, 1H), 7.18 (d, 1H), 4.42-4.37 (m, 2H), 4.13-4.08 (m, 1H), 3.94 (s, 3H), 3.72-3.56 (m, 2H), 3.49-3.48 (m, 2H), 2.94 (s, 6H), 2.68 (s, 3H), 2.55-2.52 (m, 1H), 2.33-2.28 (m, 1H); 641[M+H]; HPLC tR 4.80 min (method A)

<Example 56> Preparation of 3-((8-((1-ethyl-1H-pyrazol-4-yl)amino)imidazo[1,2-a]pyridin-3-yl)ethynyl)-N-(3-fluoro-4-morpholinophenyl)-4-methylbenzamide

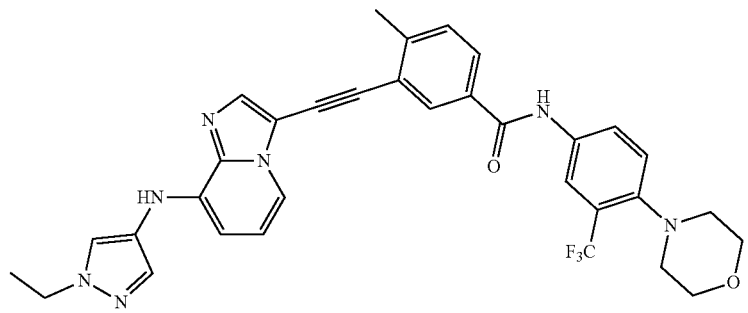 [SMILES: CCn1cc(Nc2cccn3c(C#Cc4cc(C(=O)Nc5ccc(N6CCOCC6)c(C(F)(F)F)c5)ccc4C)cnc23)cn1]

The compound of Example 56 was prepared by the same manner as described in Example 24 except that 1-ethyl-1H-pyrazol-4-amine was used instead of p-toluidine used in step 1 of Example 24 and 3-fluoro-4-morpholinobenzeneamine was used instead of 4-((methylpiperazin-1-yl)methyl)-3-(trifluoromethyl)aniline in step 3 of Example 24 to 5 give a final target compound.

$^1$H NMR (400 MHz, Methanol-d$_4$) δ 8.28 (s, 1H), 8.21 (d, 1H), 8.20 (s, 1H), 7.92 (dd, 1H), 7.83 (s, 1H), 7.61 (dd, 1H), 7.57 (s, 1H), 7.50 (d, 1H), 7.40 (dd, 1H), 7.33 (t, 1H), 7.10-7.01 (m, 2H), 4.22 (q, 2H), 3.90-3.79 (m, 4H), 3.12-3.02 (m, 4H), 2.65 (s, 3H), 1.50 (t, 3H); 564[M+H]; HPLC t$_R$ 2.74 min (method C)

<Example 57> Preparation of 3-((8-((1-(2-methoxyethyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide

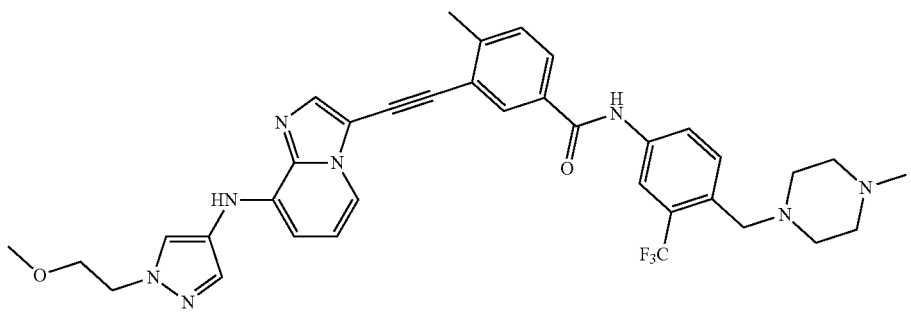

The compound of Example 57 was prepared by the same manner as described in Example 24 except that 1-((2-methoxy)ethyl)-1H-pyrazol-4-amine was used instead of p-toluidine used in step 1 of Example 24 to give a final target compound.

$^1$H NMR (400 MHz, Methanol-d$_4$) δ 8.30-8.29 (m, 1H), 8.25 (d, 1H), 8.22 (d, 1H), 8.16 (d, 1H), 8.01 (dd, 1H), 7.96 (dd, 1H), 7.82 (s, 1H), 7.78 (d, 1H), 7.59 (d, 1H), 7.53 (d, 1H), 7.38-7.31 (m, 1H), 7.09 (dd, 1H), 4.33 (t, 2H), 3.78 (t, 4H), 3.48 (d, 2H), 3.35 (s, 4H), 3.16 (d, 2H), 3.04 (d, 2H), 2.91 (s, 3H), 2.67 (s, 3H), 2.55 (d, 2H), 2.01 (s, 1H), 1.24 (t, 1H); 671[M+H]; HPLC t$_R$ 2.38 min (method C)

<Example 58> Preparation of 3-((8-((1-(2-methoxyethyl)-1H-pyrazol-4-yl)amino)imidazo[1,2-a]pyridin-3-yl)ethynyl)-4-methyl-N-(5-(1,1,1-trifluoro-2-methylpropan-2-yl)isoxazol-3-yl)benzamide

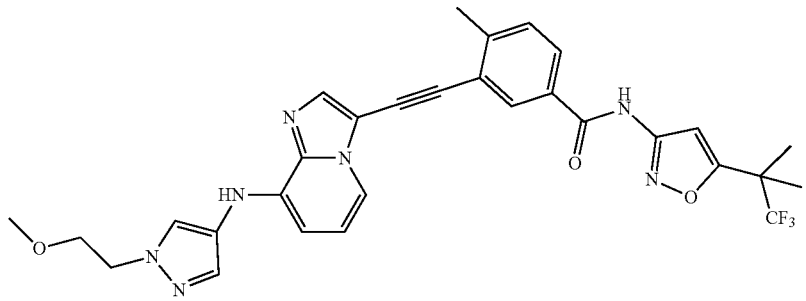 [SMILES: COCCn1cc(Nc2cccn3c(C#Cc4cc(C(=O)Nc5cc(C(C)(C)C(F)(F)F)on5)ccc4C)cnc23)cn1]

The compound of Example 58 was prepared by the same manner as described in Example 24 except that 1-((2-methoxy)ethyl)-1H-pyrazol-4-amine was used instead of p-toluidine used in step 1 of Example 24 and 5-(1,1,1-trifluoro-2-methylpropan-2-yl)isoxazol-3-amine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.22 (d, 1H), 8.04-8.02 (m, 1H), 7.96-7.91 (m, 2H), 7.80 (s, 1H), 7.58 (s, 1H), 7.51 (d, 1H), 7.07-7.04 (m, 2H), 6.75-6.73 (m, 1H), 4.32 (t, 2H), 3.77 (t, 2H), 3.36 (s, 3H), 2.66 (s, 3H), 1.63 (s, 6H); 592[M+H]; HPLC t$_R$ 2.81 min (method C)

<Example 59> Preparation of N-(5-(tert-butyl)isoxazol-3-yl)-3-((8-((1-(2-methoxyethyl)-1H-pyrazol-4-yl)amino)imidazo[1,2-a]pyridin-3-yl)ethynyl)-4-methylbenzamide

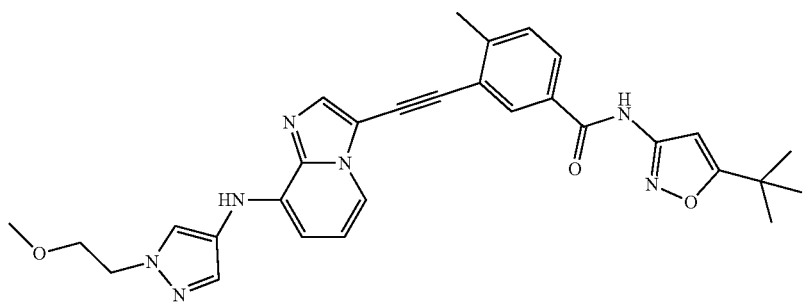 [SMILES: COCCn1cc(Nc2cccn3c(C#Cc4cc(C(=O)Nc5cc(C(C)(C)C)on5)ccc4C)cnc23)cn1]

The compound of Example 59 was prepared by the same manner as described in Example 24 except that 1-((2-methoxy)ethyl)-1H-pyrazol-4-amine was used instead of p-toluidine used in step 1 of Example 24 and 5-tert-butyl-isoxazol-3-amine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.24 (s, 2H), 8.20 (d, 1H), 7.95 (d, 1H), 7.82 (s, 1H), 7.58 (s, 1H), 7.52 (d, 1H), 7.30 (t, 1H), 7.03 (d, 1H), 6.70 (s, 1H), 4.33 (t, 2H), 3.78 (t, 2H), 3.36 (s, 3H), 2.66 (s, 3H), 1.38 (s, 9H); 538[M+H]; HPLC t$_R$ 2.77 min (method C)

<Example 60> Preparation of 3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide

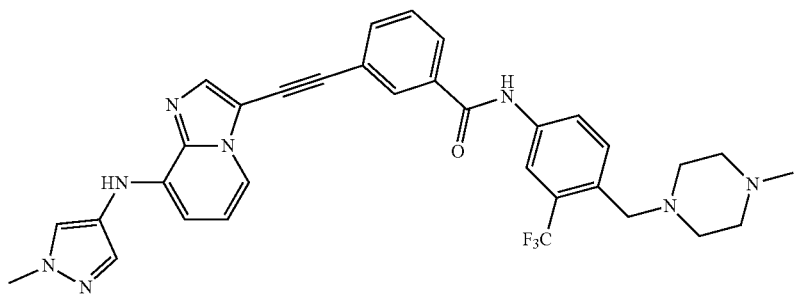

A target compound was prepared by the same manner as described in Example 24 except that sec-butyl 3-((8-chloroimidazo[1,2-a]pyridin-3-yl)ethynyl)benzoate was used instead of sec-butyl 3-((8-chloroimidazo[1,2-a]pyridin-3-yl)ethynyl)-4-methylbenzoate.

$^1$H NMR (400 MHz, Methanol-$d_4$) δ 8.26 (m, 3H), 8.17 (s, 1H), 8.09-7.99 (m, 2H), 7.91 (d, J=7.7 Hz, 1H), 7.79 (d, 2H), 7.65 (t, 1H), 7.55 (s, 1H), 7.35-7.25 (m, 1H), 7.12-7.01 (m, 1H), 3.94 (s, 3H), 3.79 (s, 2H), 3.50-3.45 (m, 2H), 3.25-3.15 (m, 2H), 3.10-2.96 (m, 2H), 2.92 (s, 3H), 2.58-2.42 (m, 2H); MS m/z: 613[M+H]; HPLC $t_R$ 2.31 min (method C)

<Example 61> Preparation of 4-fluoro-3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide

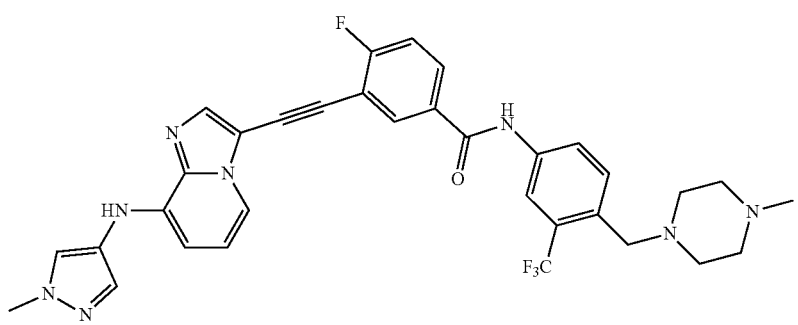

A target compound was prepared by the same manner as described in Example 24 except that sec-butyl 3-((8-chloroimidazo[1,2-a]pyridin-3-yl)ethynyl)-4-fluorobenzoate was used instead of sec-butyl 3-((8-chloroimidazo[1,2-a]pyridin-3-yl)ethynyl)-4-methylbenzoate.

$^1$H NMR (400 MHz, Methanol-$d_4$) δ 8.33 (dd, 2H), 8.19 (d, 1H), 8.15 (d, 1H), 8.13-8.09 (m, 1H), 8.00 (d, 1H), 7.81 (br s, 1H), 7.78 (d, 1H), 7.58 (br s, 1H), 7.44 (t, 1H), 7.33-7.29 (m, 1H), 7.06-7.02 (m, 1H), 3.93 (s, 3H), 3.79 (s, 2H), 3.50-3.35 (m, 2H), 3.25-3.11 (m, 2H), 3.08-2.95 (m, 2H), 2.91 (s, 3H), 2.73-2.45 (s, 2H); MS m/z: 631[M+H]; HPLC $t_R$ 2.36 min (method C)

<Example 62> Preparation of N-(4-chloro-3-(trifluoromethyl)phenyl)-4-methyl-3-((8-((1-methyl-1H-pyrazol-4-yl)amino)imidazo[1,2-a]ethynyl)benzamide

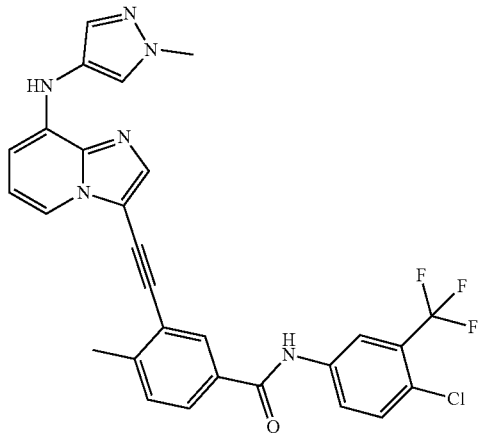 [SMILES: Cc1ccc(C(=O)Nc2ccc(Cl)c(C(F)(F)F)c2)cc1C#Cc1cnc2c(Nc3cnn(C)c3)cccn12]

The compound of Example 62 was prepared by the same manner as described in Example 24 except that 1-methyl-1H-pyrazol-4-amine was used instead of p-toluidine used in step 1 of Example 24 and 4-chloro-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.30 (s, 1H), 8.27 (d, 1H), 8.24-8.19 (m, 2H), 8.01-7.92 (m, 2H), 7.78 (s, 1H), 7.61-7.53 (m, 2H), 7.51 (d, 1H), 7.39-7.31 (m, 1H), 7.10 (d, 1H), 3.93 (s, 3H), 2.65 (s, 3H); 549[M+H]; HPLC $t_R$ 7.18 min (method A)

<Example 63> Preparation of N-(4-chloro-3-(trifluoromethyl)phenyl)-4-methyl-3-((8-((1-(piperidin-4-yl)-1H-pyrazol-4-yl)amino)imidazo[1,2-a]pyridin-3-yl)ethynyl)benzamide

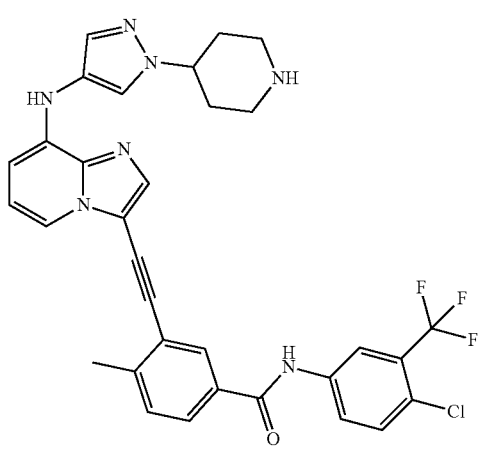 [SMILES: Cc1ccc(C(=O)Nc2ccc(Cl)c(C(F)(F)F)c2)cc1C#Cc1cnc2c(Nc3cnn(C4CCNCC4)c3)cccn12]

The compound of Example 63 was prepared by the same manner as described in Example 24 except that 1-(piperidin-4-yl)-1H-pyrazol-4-amine was used instead of p-toluidine used in step 1 of Example 24 and 4-chloro-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.28 (d, 1H), 8.21 (d, 1H), 8.10-8.02 (m, 2H), 7.98 (dd, 1H), 7.92 (dd, 1H), 7.86 (s, 1H), 7.64 (s, 1H), 7.59 (d, 1H), 7.50 (d, 1H), 7.18-7.09 (m, 1H), 6.88-6.80 (m, 1H), 4.60-4.51 (m, 1H), 3.59 (d, 2H), 3.23 (td, 2H), 2.65 (s, 3H), 2.40-2.25 (m, 4H); 619[M+H]; HPLC $t_R$ 2.65 min (method C)

<Example 64> Preparation of 3-((8-(6-(2-hydroxypropan-2-yl)pyridin-2-yl)aminoimidazo[1,2-a]pyridin-3-yl)ethynyl)-4-methyl-N-(4-((4-methylpiperazin-1-yl)methyl)-3-(trifluoromethyl)phenyl)benzamide

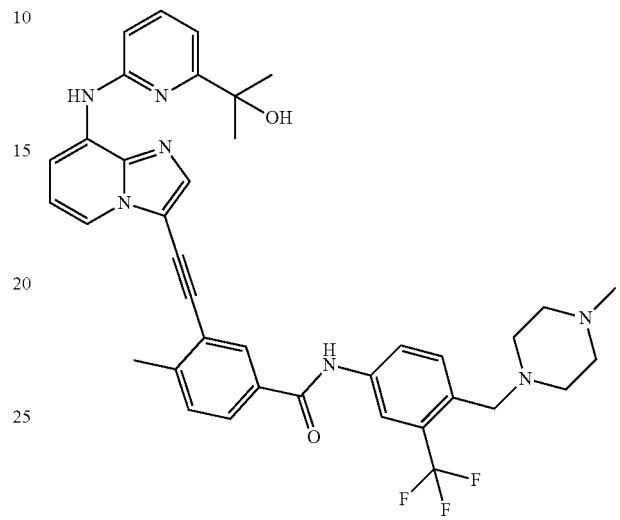

The compound of Example 64 was prepared by the same manner as described in Example 24 except that 2-(6-aminopyridin-2-yl)propan-2-ol was used instead of p-toluidine used in step 1 of Example 24 to give a final target compound.

$^1$H NMR (400 MHz, Methanol-d4) δ 8.50 (d, J=6.6 Hz, 1H), 8.26 (d, 1H), 8.19 (s, 1H), 8.17 (s, 1H), 8.01 (d, 1H), 7.96 (d, 1H), 7.91-7.84 (m, 1H), 7.81 (d, 1H), 7.78 (d, 1H), 7.53 (d, 1H), 7.46-7.40 (m, 2H), 7.18 (d, 1H), 7.06 (d, 1H), 3.80 (s, 2H), 3.52-3.35 (m, 2H), 3.18-2.96 (m, 2H), 2.91 (s, 3H), 2.89-2.71 (m, 2H), 2.65-2.40 (m, 2H), 1.62 (s, 6H); 682[M+H]; HPLC $t_R$ 5.25 min (method A)

<Example 65> Preparation of 3-((8-(1-(3-methoxypropyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide

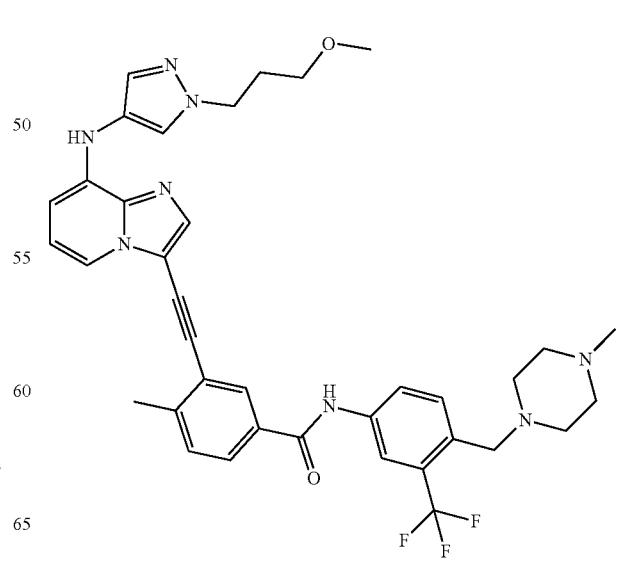

The compound of Example 65 was prepared by the same manner as described in Example 24 except that 1-(3-methoxypropyl)-1H-pyrazol-4-amine was used instead of p-toluidine used in step 1 of Example 24 to give a final target compound.

$^1$H NMR (400 MHz, Methanol-d$_4$) δ 8.24 (d, 1H), 8.19 (s, 1H), 8.18-8.12 (m, 2H), 8.01 (dd, 1H), 7.95 (dd, 1H), 7.81 (s, 1H), 7.78 (d, 1H), 7.58 (s, 1H), 7.53 (d, 1H), 7.28-7.22 (m, 1H), 6.97 (d, 1H), 4.26 (t, 2H), 3.78 (s, 2H), 3.55-3.44 (m, 2H), 3.39 (t, 2H), 3.34 (s, 3H), 3.25-3.12 (m, 2H), 3.10-2.97 (m, 2H), 2.91 (s, 3H), 2.67 (s, 3H), 2.56-2.40 (m, 2H), 2.18-2.07 (m, 2H); 685[M+H]; HPLC t$_R$ 2.42 min (method C)

<Example 66> Preparation of 4-methyl-N-(4-((4-methylpiperazin-1-yl)methyl)-3-(trifluoromethyl)phenyl)-3-((8-((4,5,6,7-tetrahydropyrazolo[1,5-a]pyrazin-2-yl)amino)imidazo[1,2-a]pyridin-3-yl)ethynyl)benzamide

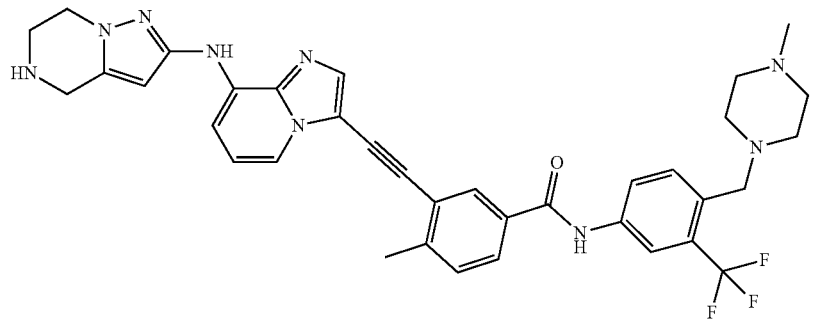 [SMILES: Cc1ccc(C(=O)Nc2ccc(CN3CCN(C)CC3)c(C(F)(F)F)c2)cc1C#Cc1cnc2c(Nc3cc4n(n3)CCNC4)cccn12]

The compound of Example 66 was prepared by the same manner as described in Example 24 except that 4,5,6,7-tetrahydropyrazolo[1,5-a]pyrazin-2-amine was used instead of p-toluidine used in step 1 of Example 24 to give a final target compound.

$^1$H NMR (400 MHz, DMSO-d$_6$) δ 10.62 (s, 1H), 9.43 (s, 2H), 9.21 (s, 1H), 8.24 (d, 2H), 8.12 (d, 1H), 8.07 (d, 1H), 8.04 (s, 1H), 7.95 (t, 2H), 7.72 (d, 1H), 7.56 (d, 1H), 7.12 (t, 1H), 6.17 (s, 1H), 4.42 (s, 2H), 4.25 (t, 2H), 3.47-3.35 (m, 4H), 3.10-3.00 (m, 2H), 2.92 (d, 2H), 2.81 (s, 3H), 2.62 (s, 3H), 2.40-2.30 (m, 4H); 668[M+H]; HPLC t$_R$2.15 min (method C)

<Example 67> Preparation of 4-methyl-3-((8-((4,5,6,7-tetrahydropyrazolo[1,5-a]pyrazin-2-yl)amino)imidazo[1,2-a]pyridin-3-yl)ethynyl)-N-(3-(trifluoromethyl)phenyl)benzamide

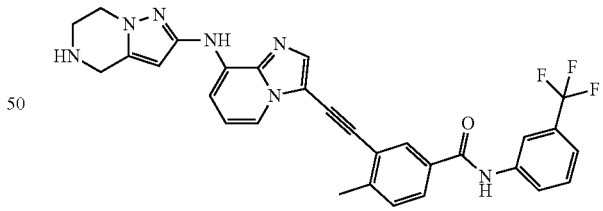

The compound of Example 67 was prepared by the same manner as described in Example 24 except that 4,5,6,7-tetrahydropyrazolo[1,5-a]pyrazin-2-amine was used instead of p-toluidine used in step 1 of Example 24 and 3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, Methanol-d$_4$) δ 8.24-8.17 (m, 3H), 8.11 (s, 1H), 8.08 (d, 1H), 7.98-7.92 (m, 2H), 7.57 (t, 1H), 7.52 (d, 1H), 7.45 (d, 1H), 7.28 (t, 1H), 6.11 (s, 1H), 4.53 (s, 2H), 4.38 (t, 2H), 3.83 (t, 2H), 2.66 (s, 3H); 556[M+H]; HPLC t$_R$ 2.49 min (method C)

<Example 68> Preparation of N-(5-(tert-butyl)isoxazol-3-yl)-4-methyl-3-((8-((4,5,6,7-tetrahydropyrazolo[1,5-a]pyrazin-2-yl)amino)imidazo[1,2-a]pyridin-3-yl)ethynyl)benzamide

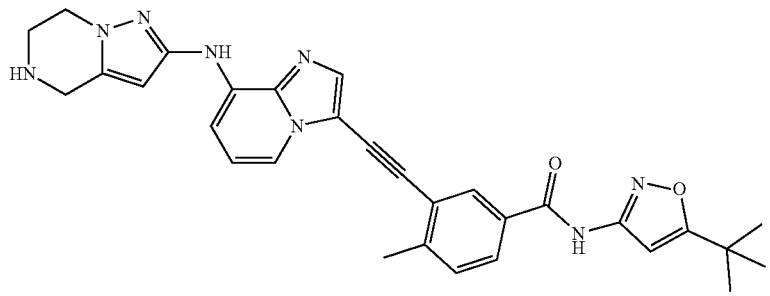 [SMILES: Cc1ccc(C(=O)Nc2cc(C(C)(C)C)on2)cc1C#Cc1cnc2c(Nc3cc4n(n3)CCNC4)cccn12]

The compound of Example 68 was prepared by the same manner as described in Example 24 except that 4,5,6,7-tetrahydropyrazolo[1,5-a]pyrazin-2-amine was used instead of p-toluidine used in step 1 of Example 24 and 5-tert-butylisoxazol-3-amine was used instead of 4-((methylpiperazin-1-yl)methyl)-3-(trifluoromethyl)aniline in step 3 of Example 24 to give a final target compound.
535[M+H]

<Example 69> Preparation of N-(4-((4-ethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide

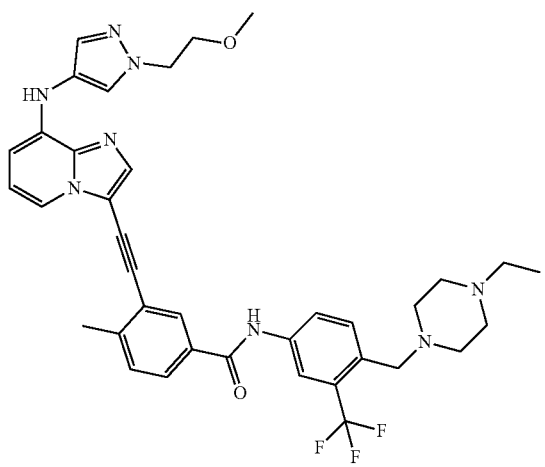 [SMILES: CCN1CCN(Cc2ccc(NC(=O)c3ccc(C)c(C#Cc4cnc5c(Nc6cnn(CCOC)c6)cccn45)c3)cc2C(F)(F)F)CC1]

The compound of Example 69 was prepared by the same manner as described in Example 24 except that 1-((2-methoxy)ethyl)-1H-pyrazol-4-amine was used instead of p-toluidine used in step 1 of Example 24 and 4-((ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.
$^1$H NMR (400 MHz, DMSO-d$_6$) δ 10.60 (s, 1H), 9.33 (br s, 1H), 8.25 (s, 2H), 8.12 (d, 1H), 7.99 (s, 1H), 7.94 (t, 2H), 7.85 (s, 1H), 7.73 (d, 1H), 7.58-7.54 (m, 2H), 6.99 (t, 1H), 6.60 (d, 1H), 4.24 (t, 2H), 3.80-3.65 (m, 6H), 3.25 (s, 3H), 3.18-3.09 (m, 2H), 3.05-2.88 (m, 2H), 2.71 (m, 2H), 2.61 (s, 3H), 2.43-2.30 (m, 2H), 1.21 (t, 3H); 685[M+H]; HPLC t$_R$ 5.29 min (method A)

<Example 70> Preparation of 3-((8-(1-(2-methoxyethyl)-1H-pyrazol-4-yl)amino)imidazo[1,2-a]pyridin-3-yl)ethynyl)-4-methyl-N-((trifluoromethyl)phenyl)benzamide

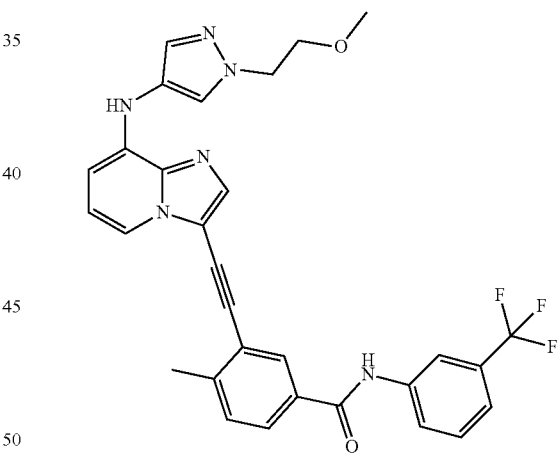

The compound of Example 70 was prepared by the same manner as described in Example 24 except that 1-((2-methoxy)ethyl)-1H-pyrazol-4-amine was used instead of p-toluidine used in step 1 of Example 24 and 3-(trifluoromethyl)benzeneamine was used instead of 4-((methylpiperazin-1-yl)methyl)-3-(trifluoromethyl)aniline in step 3 of Example 24 to give a final target compound.
$^1$H NMR (400 MHz, DMSO-d$_6$) δ 10.61 (s, 1H), 8.29-8.23 (m, 3H), 8.09 (d, 1H), 7.99 (s, 1H), 7.98-7.91 (m, 2H), 7.85 (s, 1H), 7.62 (t, 1H), 7.58-7.54 (m, 2H), 7.47 (d, 1H), 7.99 (t, 1H), 6.60 (d, 1H), 4.24 (t, 2H), 3.73-3.68 (m, 2H), 3.25 (s, 3H), 2.61 (s, 3H); 559[M+H]; HPLC t$_R$ 6.69 min (method A)

<Example 71> Preparation of 3-((8-(1-(2-methoxy-ethyl)-1H-pyrazol-4-yl)amino)imidazo[1,2-a]pyridin-3-yl)ethynyl)-4-methyl-N-((4-methyl-1H-imidazol-1-yl)-5-(trifluoromethyl)phenyl)benzamide

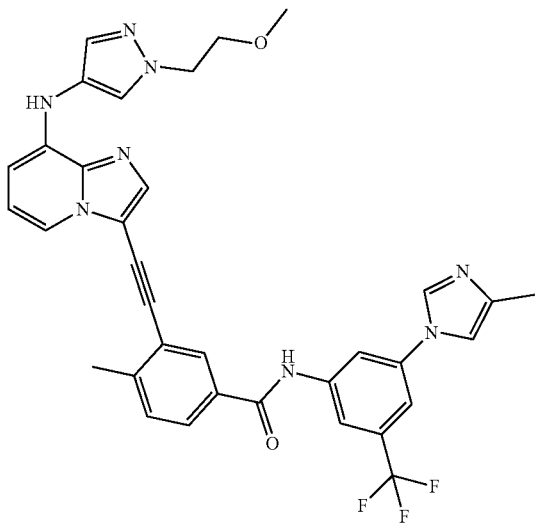 [SMILES: COCCn1cc(Nc2cccn3c(C#Cc4cc(C(=O)Nc5cc(-n6cnc(C)c6)cc(C(F)(F)F)c5)ccc4C)cnc23)cn1]

The compound of Example 71 was prepared by the same manner as described in Example 24 except that 1-((2-methoxy)ethyl)-1H-pyrazol-4-amine was used instead of p-toluidine used in step 1 of Example 24 and 3-(trifluoromethyl)-5-(4-methyl-1H-imidazol-1-yl)benzeneamine was used instead of 4-((methylpiperazin-1-yl)methyl)-3-(trifluoromethyl)aniline in step 3 of Example 24 to give a final target compound.

$^1$H NMR (400 MHz, DMSO-d$_6$) δ 10.89 (s, 1H), 9.27 (br s, 1H), 8.52 (s, 1H), 8.31-8.21 (m, 2H), 8.00 (s, 1H), 7.98-7.87 (m, 3H), 7.85 (s, 1H), 7.59 (d, 1H), 7.55 (s, 1H), 7.04-6.95 (m, 1H), 6.60 (d, 1H), 4.24 (t, 2H), 3.70 (t, 2H), 3.25 (s, 3H), 2.63 (s, 3H), 2.32 (s, 3H); 639[M+H]; HPLC t$_R$ 5.33 min (method A)

<Example 72> Preparation of 4-methyl-3-((8-((1-(1-methylpiperidin-4-yl)-1H-pyrazol-4-yl)amino)imidazo[1,2-a]pyridin-3-yl)-N-(3-(trifluoromethyl)phenyl)benzamide

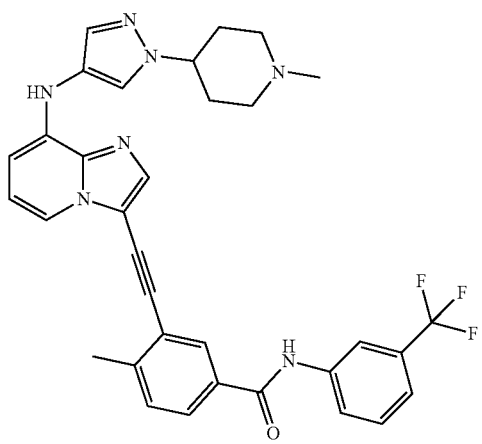 [SMILES: Cc1ccc(C(=O)Nc2cccc(C(F)(F)F)c2)cc1C#Cc1cnc2c(Nc3cnn(C4CCN(C)CC4)c3)cccn12]

The compound of Example 72 was prepared by the same manner as described in Example 24 except that 1-(1-methylpiperidin-4-yl)-1H-pyrazol-4-amine was used instead of p-toluidine used in step 1 of Example 24 and 3-(trifluoromethyl)-benzeneamine was used instead of 4-((methylpiperazin-1-yl)methyl)-3-(trifluoromethyl)aniline in step 3 of Example 24 to give a final target compound.

$^1$H NMR (400 MHz, DMSO-d$_6$) δ 10.62 (s, 1H), 9.53-9.45 (m, 1H), 8.31 (s, 1H), 8.26 (d, 2H), 8.09 (d, 1H), 8.01 (s, 1H), 7.98 (d, 1H), 7.96-7.92 (m, 1H), 7.68-7.59 (m, 2H), 7.56 (d, 1H), 7.47 (d, 1H), 7.00 (t, 1H), 6.64 (d, 1H), 4.47-4.37 (m, 1H), 4.35-4.01 (m, 2H), 3.21-3.10 (m, 2H), 2.89-2.82 (m, 3H), 2.61 (s, 3H), 2.35-2.25 (m, 2H), 2.23-2.11 (m, 2H); 598[M+H]; HPLC t$_R$ 5.69 min (method A)

<Example 73> Preparation of 3-((8-(2-(dimethylamino)ethyl)-1H-pyrazol-4-yl)amino)imidazo[1,2-a]pyridin-3-yl)-ethynyl)-N-((4-ethylpiperazin-1-yl)methyl)-3-(trifluoromethyl)phenyl)-4-methylbenzamide

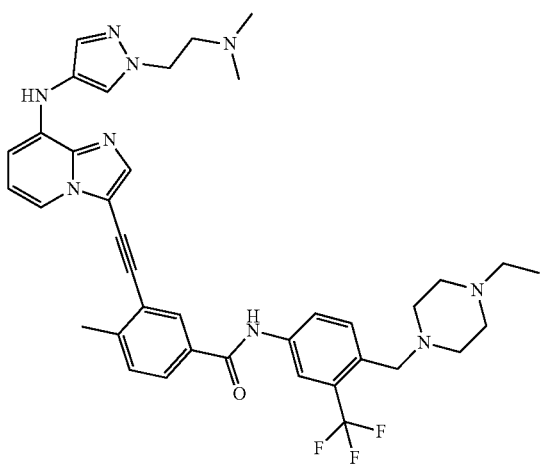 [SMILES: CCN1CCN(Cc2ccc(NC(=O)c3ccc(C)c(C#Cc4cnc5c(Nc6cnn(CCN(C)C)c6)cccn45)c3)cc2C(F)(F)F)CC1]

The compound of Example 73 was prepared by the same manner as described in Example 24 except that 1-(2-(dimethylamino)ethyl)-1H-pyrazol-4-amine was used instead of p-toluidine used in step 1 of Example 24 and 4-((ethylpiperazin-1-yl)methyl)-3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, DMSO) δ 10.61 (s, 1H), 9.53 (s, 1H), 9.39 (s, 1H), 8.43 (s, 1H), 8.24 (s, 2H), 8.13 (d, 1H), 8.00 (s, 1H), 7.98 (d, 1H), 7.94 (d, 1H), 7.73 (d, 1H), 7.68 (s, 1H), 7.56 (d, 1H), 7.04-6.97 (m, 1H), 6.67 (d, 1H), 4.52 (t, 2H), 3.71-3.66 (m, 2H), 3.67-3.55 (m, 2H), 3.02-2.88 (m, 4H), 2.82 (s, 6H), 2.61 (s, 2H), 2.43-2.34 (m, 2H), 2.08 (s, 3H), 1.21 (t, 3H); 698[M+H]; HPLC t$_R$ 5.17 min (method A)

<Example 74> Preparation of 3-((8-(2-(dimethyl-amino)ethyl)-1H-pyrazol-4-yl)amino)imidazo[1,2-a]pyridin-3-yl)N-(3-(trifluoromethyl)phenyl)benz-amide

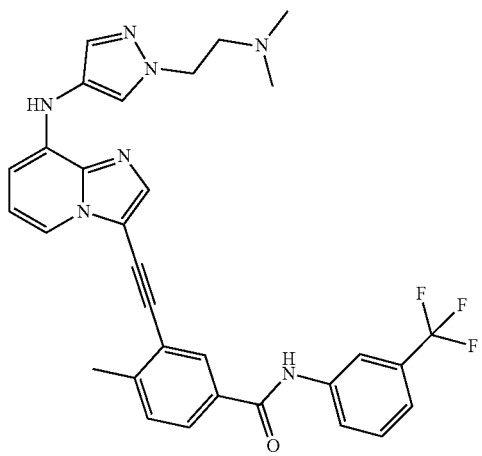 [SMILES: Cc1ccc(C(=O)Nc2cccc(C(F)(F)F)c2)cc1C#Cc1cnc2c(Nc3cnn(CCN(C)C)c3)cccn12]

The compound of Example 74 was prepared by the same manner as described in Example 24 except that 1-(2-(dimethylamino)ethyl)-1H-pyrazol-4-amine was used instead of p-toluidine used in step 1 of Example 24 and 3-(trifluoromethyl)benzeneamine was used instead of 4-((methylpiperazin-1-yl)methyl)-3-(trifluoromethyl)aniline in step 3 of Example 24 to give a final target compound.

$^1$H NMR (400 MHz, DMSO-$d_6$) δ 10.62 (s, 1H), 9.51 (s, 1H), 8.44 (s, 1H), 8.29-8.23 (m, 2H), 8.09 (d, 1H), 8.01 (s, 1H), 7.99 (d, 1H), 7.94 (dd, 1H), 7.68 (s, 1H), 7.62 (t, 1H), 7.56 (d, 1H), 7.47 (d, 1H), 7.04-6.98 (m, 1H), 6.67 (d, 1H), 4.52 (t, 2H), 3.62-3.57 (m, 2H), 2.82 (s, 6H), 2.61 (s, 3H); 572[M+H]; HPLC $t_R$ 5.92 min (method A)

<Example 75> Preparation of 3-((8-(2-(dimethyl-amino)ethyl)-1H-pyrazol-4-yl)amino)imidazo[1,2-a]pyridin-3-yl)N-(3-(4-methyl-1H-imidazol-1-yl)-5-(trifluoromethyl)phenyl)benzamide

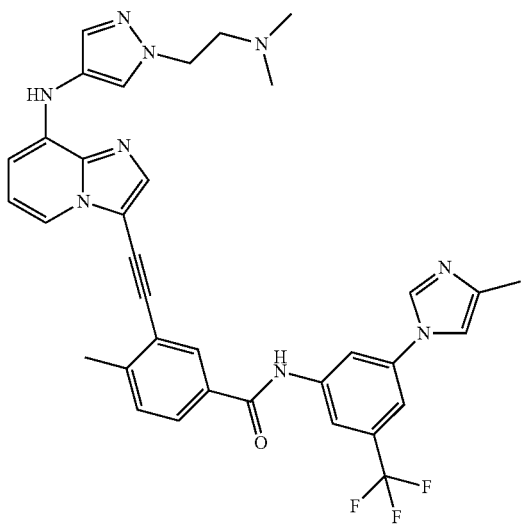 [SMILES: Cc1cn(-c2cc(NC(=O)c3ccc(C)c(C#Cc4cnc5c(Nc6cnn(CCN(C)C)c6)cccn45)c3)cc(C(F)(F)F)c2)cn1]

The compound of Example 75 was prepared by the same manner as described in Example 24 except that 1-(2-(dimethylamino)ethyl)-1H-pyrazol-4-amine was used instead of p-toluidine used in step 1 of Example 24 and 3-(trifluoromethyl)-5-(4-methyl-1H-imidazol-1-yl)benzeneamine was used instead of 4-((methylpiperazin-1-yl)methyl)-3-(trifluoromethyl)aniline in step 3 of Example 24 to give a final target compound.

$^1$H NMR (400 MHz, DMSO-$d_6$) δ 10.95 (s, 1H), 9.56 (s, 2H), 8.58 (s, 1H), 8.44 (s, 1H), 8.27 (d, 2H), 8.11-7.91 (m, 5H), 7.68 (s, 1H), 7.60 (d, 1H), 7.02 (t, 1H), 6.69 (d, 1H), 4.52 (t, 2H), 3.60-3.52 (m, 2H), 2.83 (s, 6H), 2.63 (s, 3H), 2.36 (s, 3H); 652[M+H]; HPLC $t_R$ 4.83 min (method A)

<Example 76> Preparation of (3-(4-methyl-1H-imidazol-1-yl)-5-(trifluoromethyl)phenyl)-3-((8-((1-(1-methylpiperidin-4-yl)-1H-pyrazol-4-yl)amino)imidazo[1,2-a]pyridin-3-yl)ethynyl)benzamide

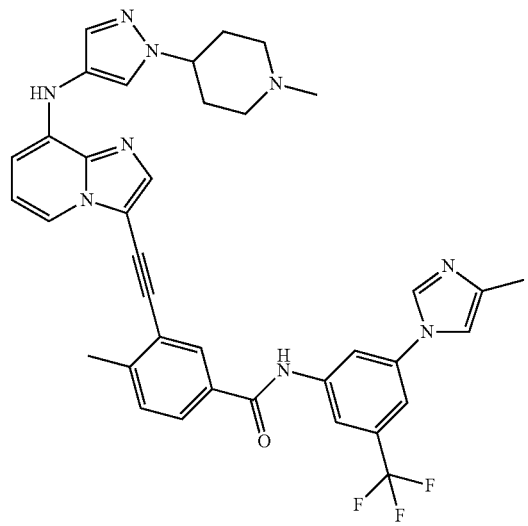 [SMILES: Cc1cn(-c2cc(NC(=O)c3ccc(C)c(C#Cc4cnc5c(Nc6cnn(C7CCN(C)CC7)c6)cccn45)c3)cc(C(F)(F)F)c2)cn1]

The compound of Example 76 was prepared by the same manner as described in Example 24 except that 1-(1-methylpiperidin-4-yl)-1H-pyrazol-4-amine was used instead of p-toluidine used in step 1 of Example 24 and 3-(trifluoromethyl)-5-(4-methyl-1H-imidazol-1-yl)benzeneamine was used instead of 4-((methylpiperazin-1-yl)methyl)-3-(trifluoromethyl)aniline in step 3 of Example 24 to give a final target compound.

$^1$H NMR (400 MHz, DMSO-$d_6$) δ 10.91 (s, 1H), 9.75-9.52 (m, 1H), 9.31 (s, 1H), 8.53 (s, 1H), 8.35-8.22 (m, 3H), 8.17-7.88 (m, 6H), 7.64-7.62 (m, 1H), 7.60 (d, 1H), 7.00 (t, 1H), 6.68-6.62 (m, 1H), 4.48-4.37 (m, 1H), 3.62-3.54 (m, 2H), 3.22-3.10 (m, 2H), 2.88-2.80 (m, 3H), 2.62 (s, 3H), 2.33 (s, 3H), 2.32-2.25 (m, 2H), 2.24-2.11 (m, 2H); 678[M+H]; HPLC $t_R$ 2.04 min (method C)

<Example 77> Preparation of N-(3-((8-((1-isopropyl-1H-pyrazol-4-yl)amino)imidazo[1,2-a]pyridin-3-yl)ethynyl)-4-methylphenyl)-4-((4-methylpiperazin-1-yl)methyl)-3-(trifluoromethyl)benzamide

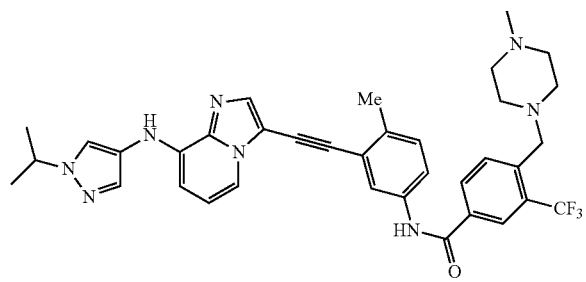 [SMILES: Cc1ccc(NC(=O)c2ccc(CN3CCN(C)CC3)c(C(F)(F)F)c2)cc1C#Cc1cnc2c(Nc3cnn(C(C)C)c3)cccn12]

Step 1. Preparation of 8-chloro-3-((2-methyl-5-nitrophenyl)ethynylimidazo[1,2-a]pyridine 8-Chloro-3-ethynylimidazo[1,2-a]pyridine (500 mg, 2.83 mmol) prepared in step 4 of Preparative Example 1, 2-iodo-1-methyl-4-nitrobenzene (745 mg, 2.83 mmol) (TCI Co., Cat #10706, CAS [7745-92-8]), Pd(PPh$_3$)$_4$ (164 mg, 0.142 mmol), DIPEA (0.84 ml, 4.81 mmol) and CuI (53.9 mg, 0.283 mmol) were dissolved in DMF (10 ml), followed by stirring at 100° C. for 15 hours. The reaction mixture was filtered with celite as it was without cooling and then concentrated. The obtained residue was recrystallized with ethyl acetate. As a result, a target compound was obtained (710 mg, 80% yield).

$^1$H NMR (400 MHz, Chloroform-d) δ 8.40 (d, 1H), 8.31 (dd, 1H), 8.13 (dd, 1H), 8.03 (s, 1H), 7.48-7.40 (m, 2H), 6.98 (t, 1H), 2.66 (s, 3H); MS m/z: 312[M+H]

Step 2. Preparation of N-(1-isopropyl-1H-pyrazol-4-yl)-3-((2-methyl-5-nitrophenyl)ethynyl)imidazo[1,2-a]pyridin-8-amine The mixed solution comprising the compound prepared in step 1 above (300 mg, 0.962 mmol), 1-isopropyl-1H-pyrazol-4-amine (133 mg, 1.059 mmol), Cs$_2$CO$_3$ (941 mg, 2.89 mmol) and t-BuOH (9 ml) was degassed using a nitrogen balloon, to which XPhos Pd G2 (76 mg, 0.096 mmol) was added. Then, the reaction mixture was loaded in a microwave reactor. The temperature of the reactor was raised to 160° C., which was maintained for 1 hour. The reaction mixture was filtered with celite and then concentrated. The obtained residue was purified by silica gel chromatography (40-50% ethyl acetate/hexane). As a result, a target compound was obtained (130 mg, 33.7% yield).

$^1$H NMR (400 MHz, Chloroform-d) δ 8.39 (d, 1H), 8.10 (dd, 1H), 7.86 (s, 1H), 7.80 (dd, 1H), 7.56 (s, 1H), 7.49 (s, 1H), 7.44 (d, 1H), 6.86 (t, 1H), 6.64 (s, 1H), 6.51 (dd, 1H), 4.51 (p, 1H), 2.66 (s, 3H), 1.55 (d, 6H); MS m/z: 401[M+H]

Step 3. Preparation of 3-((5-amino-2-methylphenyl)ethynyl)-N-(1-isopropyl-1H-pyrazol-4-yl)imidazo[1,2-a]pyridin-8-amine The compound prepared in step 2 above (71 mg, 0.177 mmol) was dissolved in methanol (1 ml) and THF (1 ml), to which Zn (116 mg, 1.773 mmol) and NH$_4$Cl (95 mg, 1.773 mmol) were added. The reaction mixture was stirred at room temperature for 1 hour, followed by filtering with celite and concentration. The obtained residue was purified by silica gel chromatography (40-50% ethyl acetate/hexane). As a result, a target compound was obtained (61 mg, 93% yield).
MS m/z: 371 [M+H]

Step 4. Preparation of N-(3-((8-((1-isopropyl-1H-pyrazol-4-yl)amino)imidazo[1,2-a]pyridin-3-yl)ethynyl)-4-methylphenyl)-4-((4-methylpiperazin-1-yl)methyl)-3-(trifluoromethyl)benzamide The compound prepared in step 3 above (14 mg, 0.046 mmol) and the compound prepared in Preparative Example 9 (17.2 mg, 0.046 mmol) were dissolved in DMF (1 ml), to which EDC (17.8 mg, 0.093 mmol) and DMAP (11.3 mg, 0.093 mmol) were added, followed by stirring at 60° C. for 15 hours. The reaction mixture was cooled down to room temperature and then concentrated. The obtained residue was purified by preparative HPLC (0.1% TFA in water/acetonitrile). As a result, a target compound was obtained (12 mg, 33% yield).

$^1$H NMR (400 MHz, Methanol-d$_4$) δ 8.34 (d, 2H), 8.23 (d, 2H), 8.16 (d, J=2.3 Hz, 1H), 8.02 (d, J=8.1 Hz, 1H), 7.88 (s, 1H), 7.65 (dd, J=8.3, 2.3 Hz, 1H), 7.60 (s, 1H), 7.46-7.34 (m, 2H), 7.15 (dd, J=8.0, 0.8 Hz, 1H), 4.57 (septet, 1H), 3.90 (s, 2H), 3.59-3.43 (m, 2H), 3.30-3.16 (m, 2H), 3.13-2.97 (m, 2H), 2.94 (s, 3H), 2.62-2.58 (m, 2H), 2.59 (s, 3H) 1.56 (d, J=6.7 Hz, 6H); MS m/z: 655[M+H]; HPLC tR 5.34 min (method A)

<Example 78> Preparation of N-(4-fluorophenyl)-N-(3-((8-((1-isopropyl-1H-pyrazol-4-yl)amino)imidazo[1,2-a]pyridin-3-yl)ethynyl)-4-methylphenyl)cyclopropan-1,1-dicarboxamide

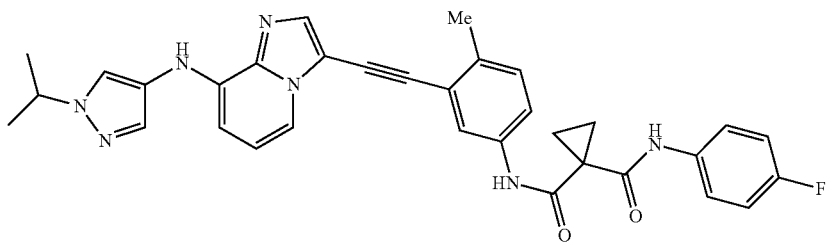 [SMILES: Cc1ccc(NC(=O)C2(C(=O)Nc3ccc(F)cc3)CC2)cc1C#Cc1cnc2c(Nc3cnn(C(C)C)c3)cccn12]

$^1$H NMR (400 MHz, Methanol-d$_4$) δ 8.22 (s, 1H), 8.10 (d, 1H), 7.87 (d, 1H), 7.78-7.70 (m, 1H), 7.49-7.41 (m, 3H), 7.39 (dd, 1H), 7.27 (dd, 1H), 7.21 (d, 1H), 7.05-6.91 (m, 3H), 4.46 (septet, 1H), 2.44 (s, 3H), 1.53 (s, 4H), 1.44 (d, 6H); 576[M+H]; HPLC tR 6.61 min (method A)

<Example 79> Preparation of N-(4-fluorophenyl)-N-(4-methyl-3-((8-((1-methyl-1H-pyrazol-4-yl)amino)imidazo[1,2-a]pyridin-3-yl)ethynyl)phenyl)cyclopropan-1,1-dicarboxamide

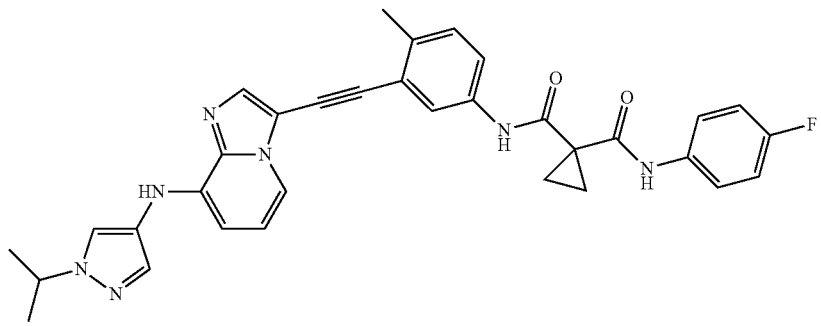 [SMILES: Cc1ccc(NC(=O)C2(C(=O)Nc3ccc(F)cc3)CC2)cc1C#Cc1cnc2c(Nc3cnn(C(C)C)c3)cccn12]

$^1$H NMR (400 MHz, Methanol-$d_4$) δ 8.31 (s, 1H), 8.22 (dd, 1H), 7.98 (d, 1H), 7.82-7.79 (m, 1H), 7.60-7.54 (m, 3H), 7.50 (dd, 1H), 7.40-7.29 (m, 2H), 7.15-7.05 (m, 3H), 3.96 (s, 3H), 2.56 (s, 3H), 1.65 (s, 4H); 548[M+H]; HPLC tR 6.37 min (method A)

<Example 80> Preparation of N-(4-methyl-3-((8-((1-methyl-1H-pyrazol-4-yl)amino)imidazo[1,2-a]pyridin-3-yl)ethynyl)phenyl)-4-((4-methylpiperazin-1-yl)methyl)-3-(trifluoromethyl)benzamide

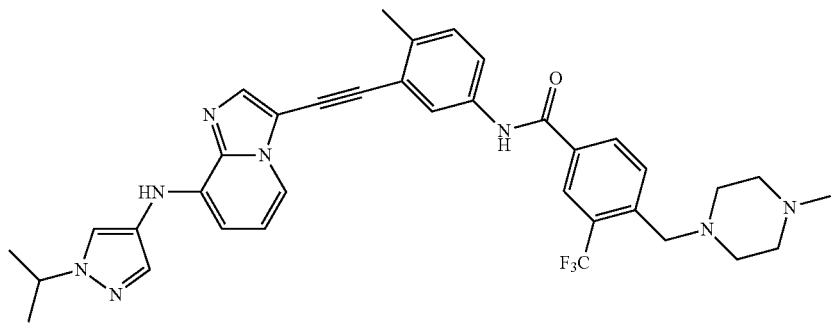 [SMILES: Cc1ccc(NC(=O)c2ccc(CN3CCN(C)CC3)c(C(F)(F)F)c2)cc1C#Cc1cnc2c(Nc3cnn(C(C)C)c3)cccn12]

$^1$H NMR (400 MHz, Methanol-$d_4$) δ 8.34-8.32 (m, 1H), 8.31 (s, 1H), 8.27-8.17 (m, 2H), 8.15 (d, 1H), 8.02 (d, J=8.2 Hz, 1H), 7.81 (d, 1H), 7.65 (dd, 1H), 7.57 (d, 1H), 7.44-7.30 (m, 2H), 7.11 (dd, 1H), 3.96 (s, 3H), 3.90 (s, 2H), 3.60-3.45 (m, 2H), 3.29-3.14 (m, 2H), 3.14-3.02 (m, 2H), 2.95 (s, 3H), 2.64-2.48 (m, 5H); 627[M+H]; HPLC tR 3.87 min (method B)

<Example 81> Preparation of (R)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide

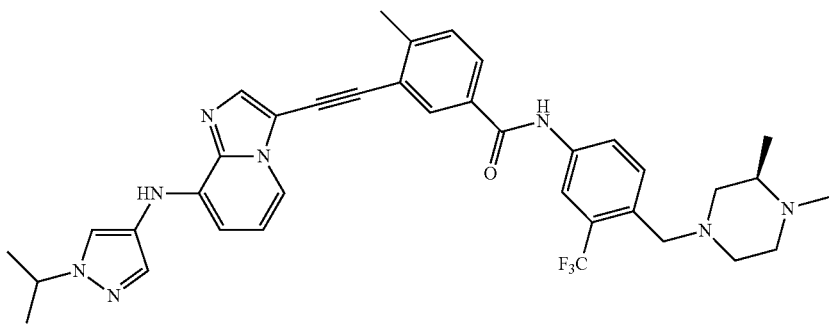 [SMILES: Cc1ccc(C(=O)Nc2ccc(CN3CCN(C)[C@H](C)C3)c(C(F)(F)F)c2)cc1C#Cc1cnc2c(Nc3cnn(C(C)C)c3)cccn12]

¹H NMR (400 MHz, Methanol-d₄) δ 8.30 (s, 1H), 8.24 (s, 1H), 8.20 (d, 1H), 8.16 (s, 1H), 8.00-7.96 (d, 1H), 7.95-7.94 (m, 1H), 7.85 (s, 1H), 7.77 (d, 1H), 7.58 (s, 1H), 7.54-7.50 (m, 1H), 7.36-7.28 (m, 1H), 7.08-7.01 (m, 1H), 4.59-4.52 (t, 1H), 3.76 (s, 2H), 3.56-3.44 (m, 1H), 3.28-3.18 (m, 1H), 3.10-2.95 (m, 2H), 2.92 (s, 3H), 2.67-2.66 (m, 3H), 2.57-2.45 (m, 1H), 2.37-2.20 (m, 1H), 1.54 (d, 6H), 1.37 (d, 3H); 669[M+H]; HPLC $t_R$ 5.52 min (method A)

<Example 82> Preparation of 1-(3-((8-((1-isopropyl-1H-pyrazol-4-yl)amino)imidazo[1,2-a]pyridin-3-yl)ethynyl)-4-methylphenyl)-3-(4-((4-methylpiperazin-1-yl)methyl)-3-(trifluoromethyl)phenyl)urea

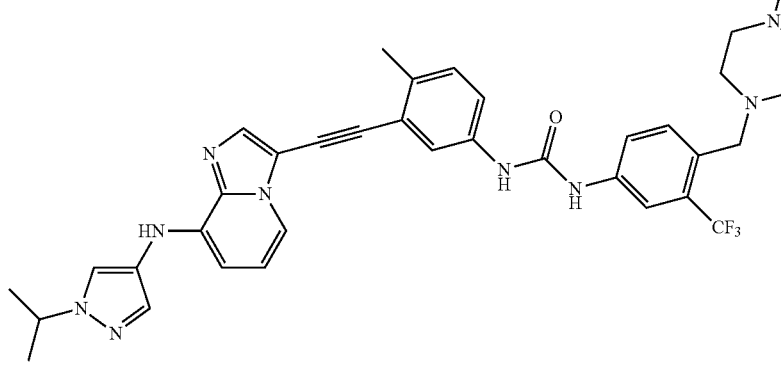

3-((5-Amino-2-methylphenyl)ethynyl)-N-(1-isopropyl-1H-pyrazol-4-yl)imidazo[1,2-a]pyridin-8-amine (30 mg, 0.08 mmol) prepared in step 3 of Example 77 and 4-nitrophenyl (4-((4-methylpiperazin-1-yl)methyl)-3-(trifluoromethyl)phenyl)carbamate (42.6 mg, 0.097 mmol) prepared in Preparative Example 12 were dissolved in pyridine (1 ml), followed by stirring at 60° C. for 2 hours. Then, the reaction mixture was concentrated. The obtained residue was purified by preparative HPLC (0.1% TFA in water/acetonitrile). As a result, a target compound was obtained (38 mg, 59.6% yield).

¹H NMR (400 MHz, Methanol-d₄) δ 8.27 (s, 1H), 8.21 (dd, 1H), 7.95-7.92 (m, 1H), 7.90 (d, 1H), 7.87 (d, 1H), 7.74-7.64 (m, 2H), 7.62-7.56 (m, 1H), 7.41-7.27 (m, 3H), 7.07 (d, 1H), 4.58 (septet, 1H), 3.76 (s, 2H), 3.60-3.38 (m, 2H), 3.28-2.96 (m, 4H), 2.93 (s, 3H), 2.56 (s, 3H), 2.53-2.35 (m, 2H), 1.56 (d, 6H); MS m/z: 670[M+H]; HPLC $t_R$ 5.33 min (method A)

<Example 83> Preparation of 1-(3-((8-((1-isopropyl-1H-pyrazol-4-yl)amino)imidazo[1,2-a]pyridin-3-yl)ethynyl)-4-methylphenyl)-3-(3-(trifluoromethyl)phenyl)urea

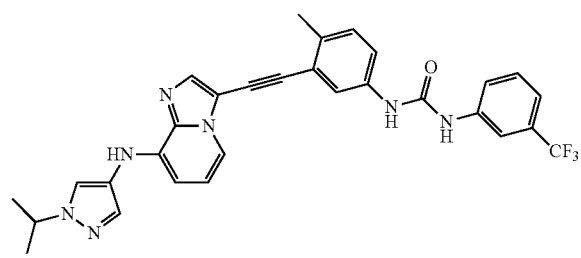 [SMILES: Cc1ccc(NC(=O)Nc2cccc(C(F)(F)F)c2)cc1C#Cc1cnc2c(Nc3cnn(C(C)C)c3)cccn12]

3-((5-Amino-2-methylphenyl)ethynyl)-N-(1-isopropyl-1H-pyrazol-4-yl)imidazo[1,2-a]pyridin-8-amine (26 mg, 0.07 mmol) prepared in step 3 of Example 77 and 1-isocyanato-3-(trifluoromethyl)benzene (13.8 mg, 0.07 mmol) were dissolved in CH₂Cl₂ (1 ml), followed by stirring at room temperature for 15 hours. Then, the reaction mixture was concentrated. The obtained residue was purified by preparative HPLC (0.1% TFA in water/acetonitrile). As a result, a target compound was obtained.

¹H NMR (400 MHz, Methanol-d₄) δ 8.31 (s, 1H), 8.22 (dd, 1H), 7.96 (s, 1H), 7.91 (d, 1H), 7.89-7.84 (m, 1H), 7.64-7.57 (m, 2H), 7.49 (t, 1H), 7.38 (dd, 1H), 7.35-7.25 (m, 3H), 7.11 (d, 1H), 4.57 (septet, 1H), 2.54 (s, 3H), 1.55 (d, 6H); MS m/z: 558[M+H]; HPLC tR 6.82 min (method A)

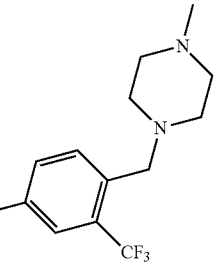

<Example 84> Preparation of 1-(5-(tert-butyl)isoxazol-3-yl)-3-(3-((8-((1-isopropyl-1H-pyrazol-4-yl)amino)imidazo[1,2-a]pyridin-3-yl)ethynyl)-4-methylphenyl)urea

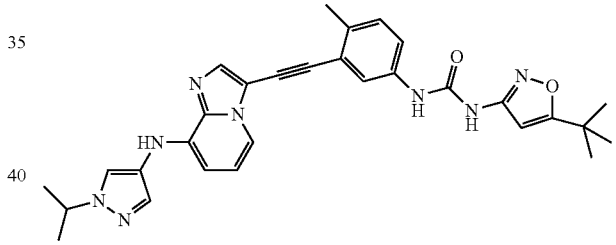

¹H NMR (400 MHz, Methanol-d₄) δ 8.20 (s, 1H), 8.17 (d, 1H), 7.89 (d, 1H), 7.87-7.86 (m, 1H), 7.61-7.56 (m, 1H), 7.40-7.24 (m, 3H), 6.99 (d, 1H), 6.40 (s, 1H), 4.58 (septet, 1H), 2.56 (s, 3H), 1.56 (d, 6H), 1.38 (s, 9H); 537[M+H]; HPLC $t_R$ 6.75 min (method A)

<Example 85> Preparation of 1-(3-((8-((1-isopropyl-1H-pyrazol-4-yl)amino)imidazo[1,2-a]pyridin-3-yl)ethynyl)-4-methylphenyl)-3-(5-(1,1,1-trifluoro-2-methylpropan-2-yl)isoxazol-3-yl)urea

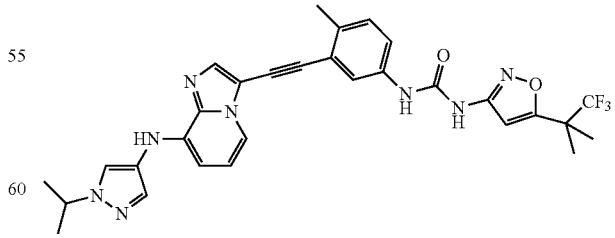

¹H NMR (400 MHz, Methanol-d₄) δ 8.05 (d, 1H), 8.03 (s, 1H), 7.83 (s, 2H), 7.56 (s, 1H), 7.35 (d, 1H), 7.28 (d, 1H), 7.15 (t, 1H), 6.84 (d, 1H), 6.78 (s, 1H), 4.58-4.51 (m, 1H), 1.59 (s, 6H), 1.53 (d, 6H); 591[M+H]; HPLC $t_R$ 2.90 min (method C)

The chemical structures of the compounds prepared in Examples 1-85 are shown in Table 1 below.
TABLE 1
| Example | Structure |
|---|---|
| 1 | 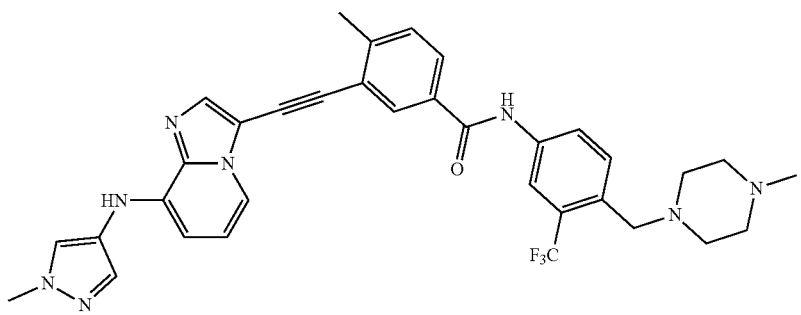 |
| 2 | 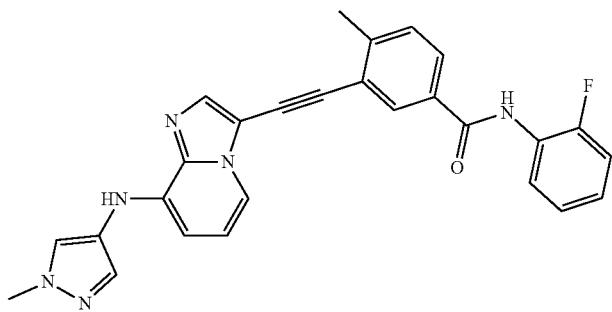 [SMILES: Cc1ccc(C(=O)Nc2ccccc2F)cc1C#Cc1cnc2c(Nc3cnn(C)c3)cccn12] |
| 3 | 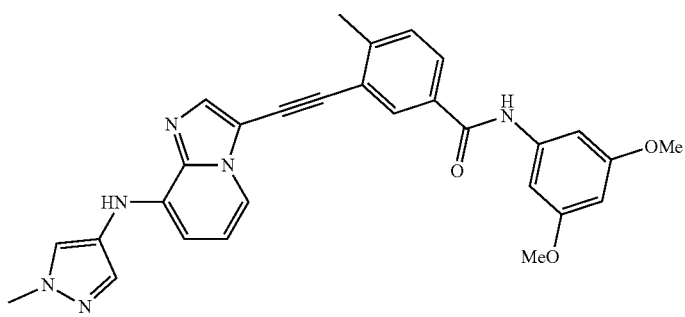 [SMILES: COc1cc(NC(=O)c2ccc(C)c(C#Cc3cnc4c(Nc5cnn(C)c5)cccn34)c2)cc(OC)c1] |
| 4 | 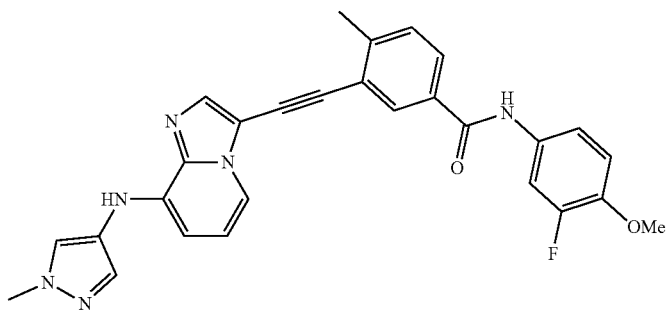 [SMILES: COc1ccc(NC(=O)c2ccc(C)c(C#Cc3cnc4c(Nc5cnn(C)c5)cccn34)c2)cc1F] |

TABLE 1-continued
| Example | Structure |
|---|---|
| 5 | 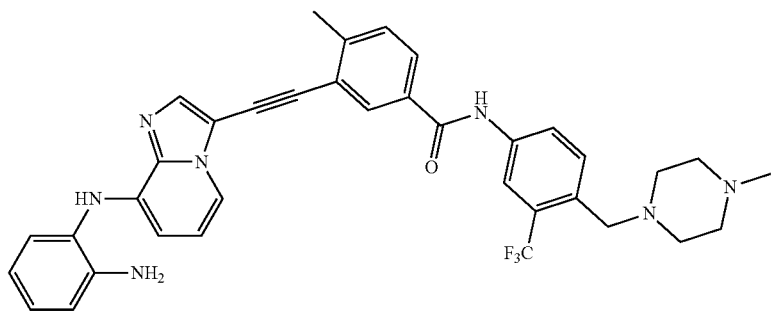 [SMILES: Cc1ccc(C(=O)Nc2ccc(CN3CCN(C)CC3)c(C(F)(F)F)c2)cc1C#Cc1cnc2c(Nc3ccccc3N)cccn12] |
| 6 | 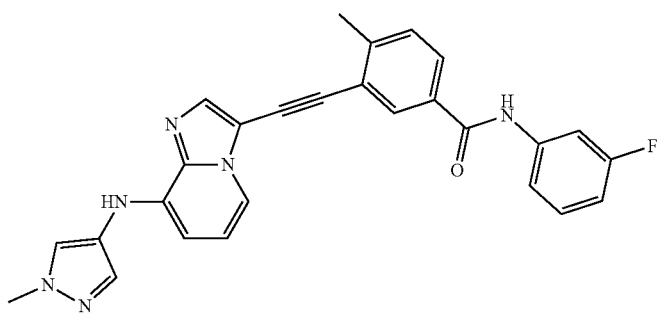 [SMILES: Cc1ccc(C(=O)Nc2cccc(F)c2)cc1C#Cc1cnc2c(Nc3cnn(C)c3)cccn12] |
| 7 | 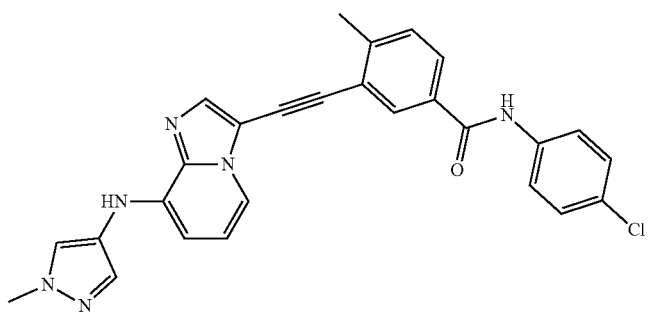 [SMILES: Cc1ccc(C(=O)Nc2ccc(Cl)cc2)cc1C#Cc1cnc2c(Nc3cnn(C)c3)cccn12] |
| 8 | 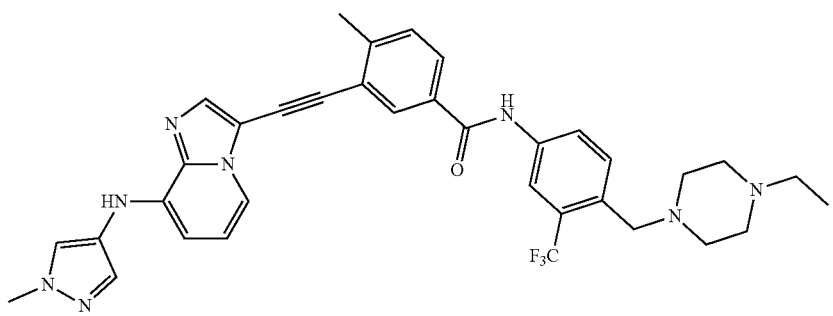 [SMILES: CCN1CCN(Cc2ccc(NC(=O)c3ccc(C)c(C#Cc4cnc5c(Nc6cnn(C)c6)cccn45)c3)cc2C(F)(F)F)CC1] |
| 9 | 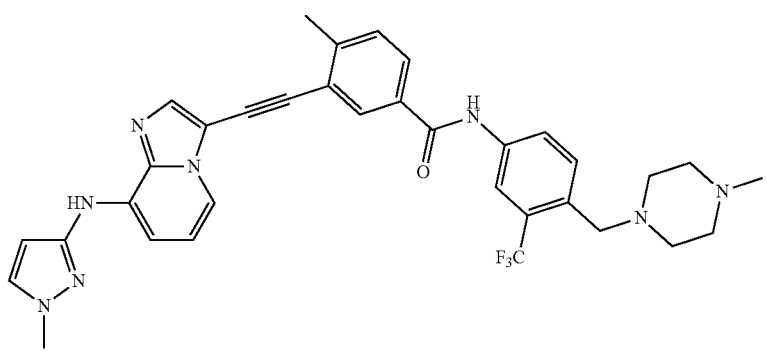 [SMILES: Cc1ccc(C(=O)Nc2ccc(CN3CCN(C)CC3)c(C(F)(F)F)c2)cc1C#Cc1cnc2c(Nc3ccn(C)n3)cccn12] |

TABLE 1-continued
| Example | Structure |
|---|---|
| 10 | 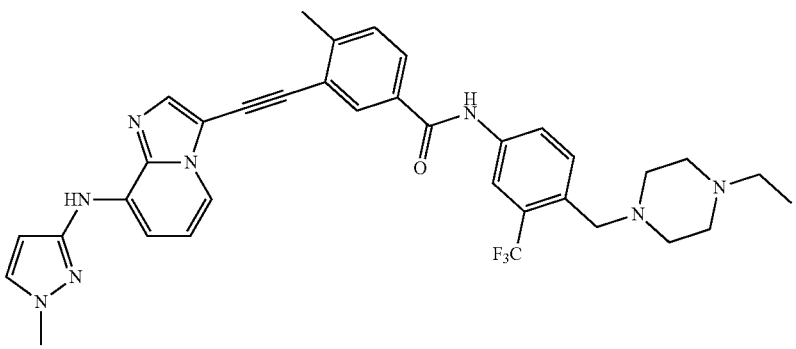 [SMILES: CCN1CCN(Cc2ccc(NC(=O)c3ccc(C)c(C#Cc4cnc5c(Nc6ccn(C)n6)cccn45)c3)cc2C(F)(F)F)CC1] |
| 11 | 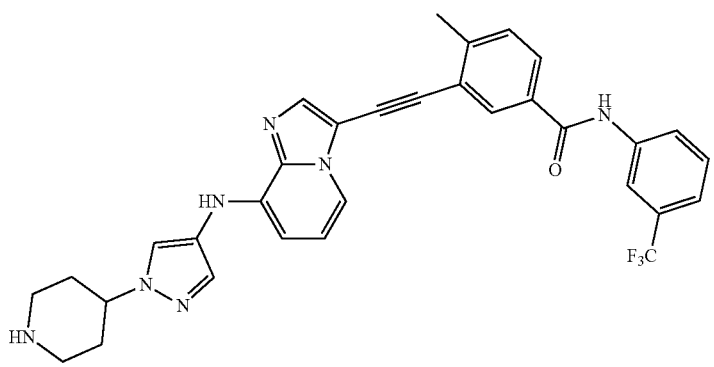 [SMILES: Cc1ccc(C(=O)Nc2cccc(C(F)(F)F)c2)cc1C#Cc1cnc2c(Nc3cnn(C4CCNCC4)c3)cccn12] |
| 12 | 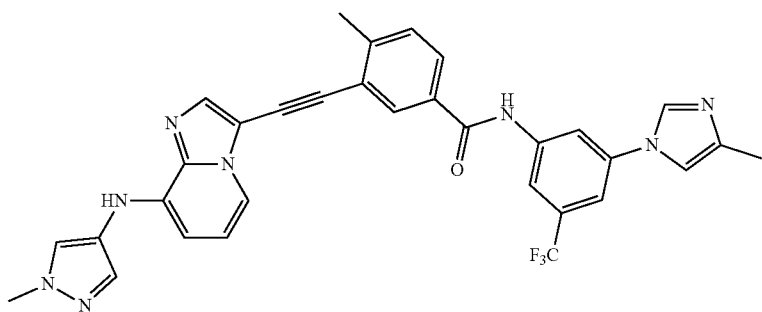 |
| 13 | 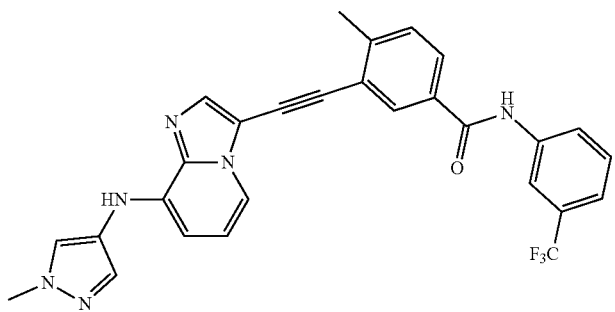 [SMILES: Cc1ccc(C(=O)Nc2cccc(C(F)(F)F)c2)cc1C#Cc1cnc2c(Nc3cnn(C)c3)cccn12] |

TABLE 1-continued
| Example | Structure |
|---|---|
| 14 | 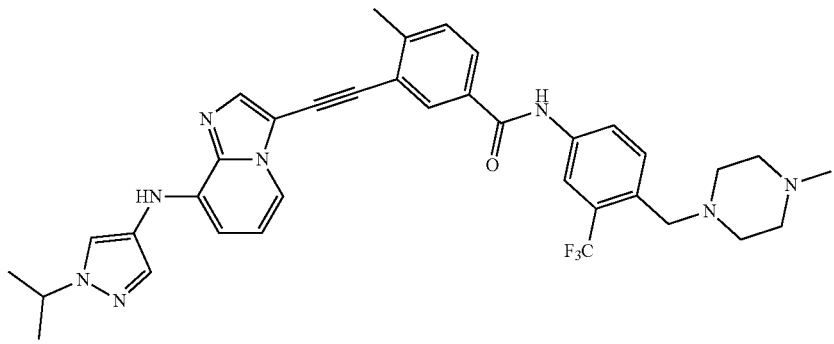 [SMILES: Cc1ccc(C(=O)Nc2ccc(CN3CCN(C)CC3)c(C(F)(F)F)c2)cc1C#Cc1cnc2c(Nc3cnn(C(C)C)c3)cccn12] |
| 15 | 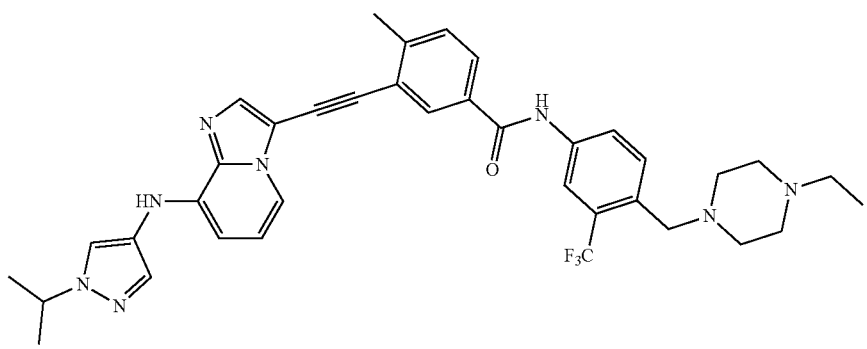 [SMILES: CCN1CCN(Cc2ccc(NC(=O)c3ccc(C)c(C#Cc4cnc5c(Nc6cnn(C(C)C)c6)cccn45)c3)cc2C(F)(F)F)CC1] |
| 16 | 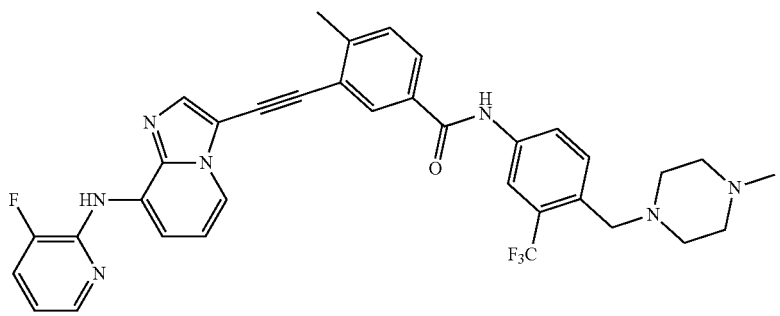 [SMILES: Cc1ccc(C(=O)Nc2ccc(CN3CCN(C)CC3)c(C(F)(F)F)c2)cc1C#Cc1cnc2c(Nc3ncccc3F)cccn12] |
| 17 | 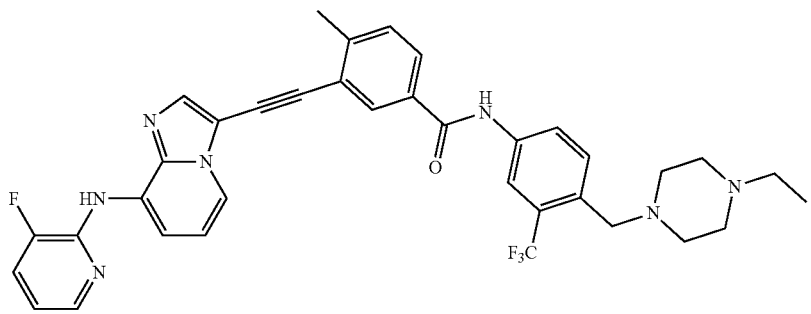 [SMILES: CCN1CCN(Cc2ccc(NC(=O)c3ccc(C)c(C#Cc4cnc5c(Nc6ncccc6F)cccn45)c3)cc2C(F)(F)F)CC1] |

TABLE 1-continued
Example Structure
18 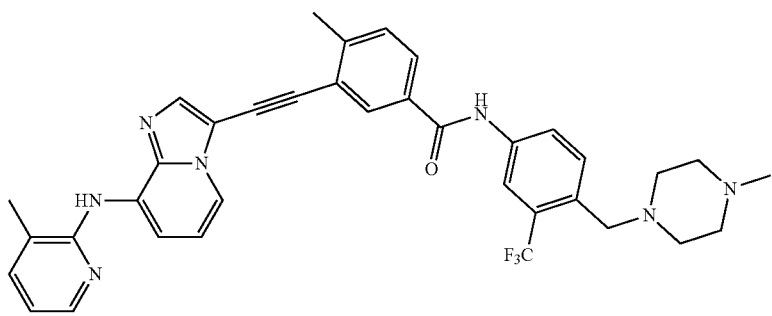 [SMILES: Cc1ccc(C(=O)Nc2ccc(CN3CCN(C)CC3)c(C(F)(F)F)c2)cc1C#Cc1cnc2c(Nc3ncccc3C)cccn12]
19 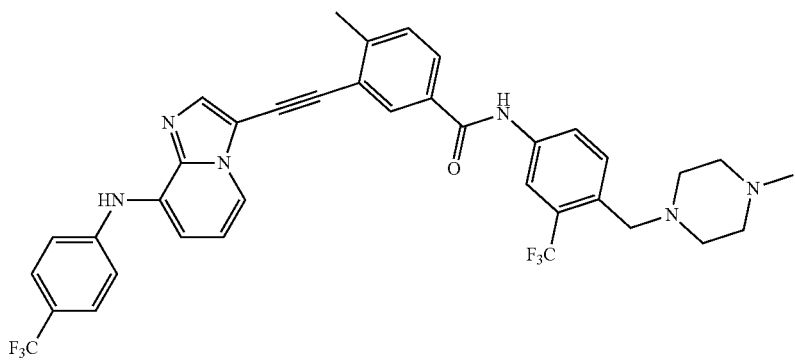 [SMILES: Cc1ccc(C(=O)Nc2ccc(CN3CCN(C)CC3)c(C(F)(F)F)c2)cc1C#Cc1cnc2c(Nc3ccc(C(F)(F)F)cc3)cccn12]
20 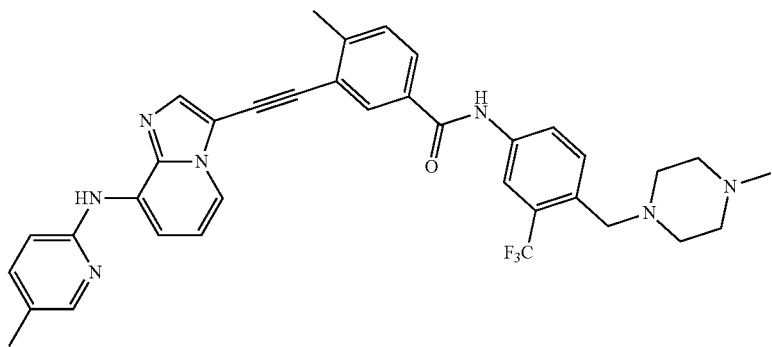 [SMILES: Cc1ccc(Nc2cccn3c(C#Cc4cc(C(=O)Nc5ccc(CN6CCN(C)CC6)c(C(F)(F)F)c5)ccc4C)cnc23)nc1]
21 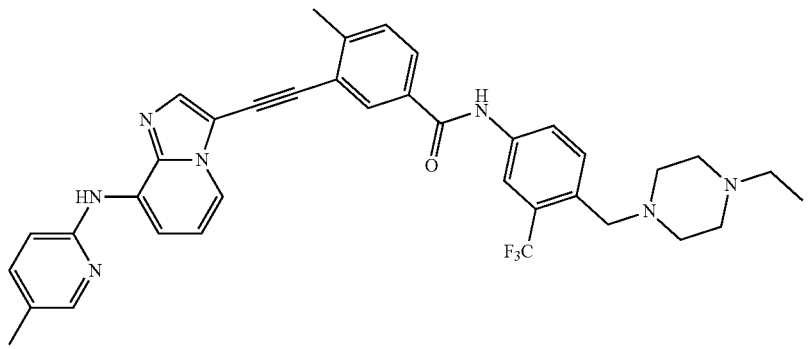 [SMILES: CCN1CCN(Cc2ccc(NC(=O)c3ccc(C)c(C#Cc4cnc5c(Nc6ccc(C)cn6)cccn45)c3)cc2C(F)(F)F)CC1]

TABLE 1-continued
| Example | Structure |
|---|---|
| 22 | 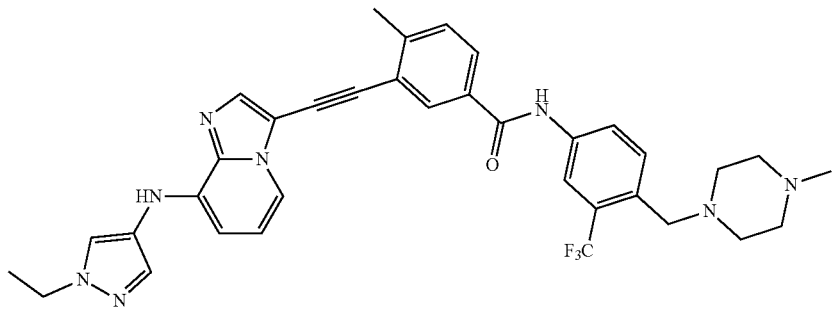 [SMILES: CCn1cc(Nc2cccn3c(C#Cc4cc(C(=O)Nc5ccc(CN6CCN(C)CC6)c(C(F)(F)F)c5)ccc4C)cnc23)cn1] |
| 23 | 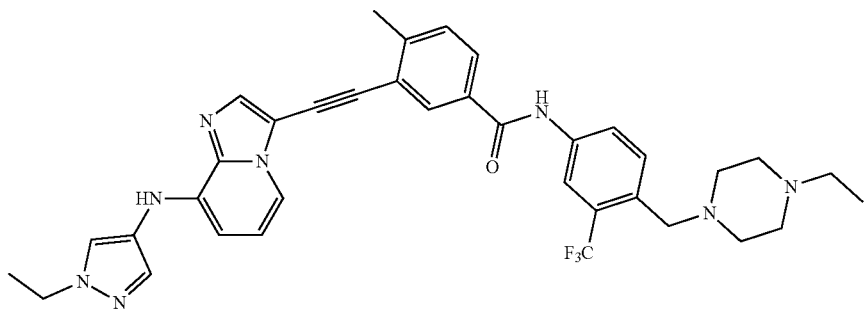 [SMILES: CCN1CCN(Cc2ccc(NC(=O)c3ccc(C)c(C#Cc4cnc5c(Nc6cnn(CC)c6)cccn45)c3)cc2C(F)(F)F)CC1] |
| 24 | 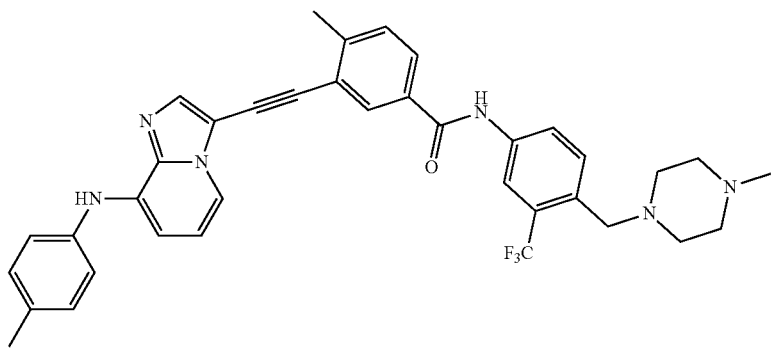 [SMILES: Cc1ccc(Nc2cccn3c(C#Cc4cc(C(=O)Nc5ccc(CN6CCN(C)CC6)c(C(F)(F)F)c5)ccc4C)cnc23)cc1] |
| 25 | 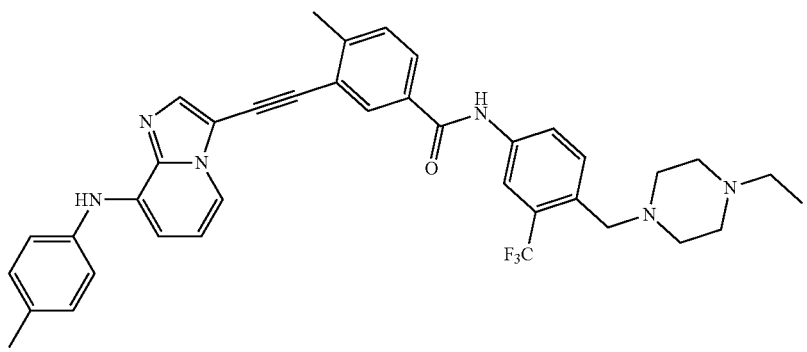 [SMILES: CCN1CCN(Cc2ccc(NC(=O)c3ccc(C)c(C#Cc4cnc5c(Nc6ccc(C)cc6)cccn45)c3)cc2C(F)(F)F)CC1] |

TABLE 1-continued
| Example | Structure |
|---|---|
| 26 | 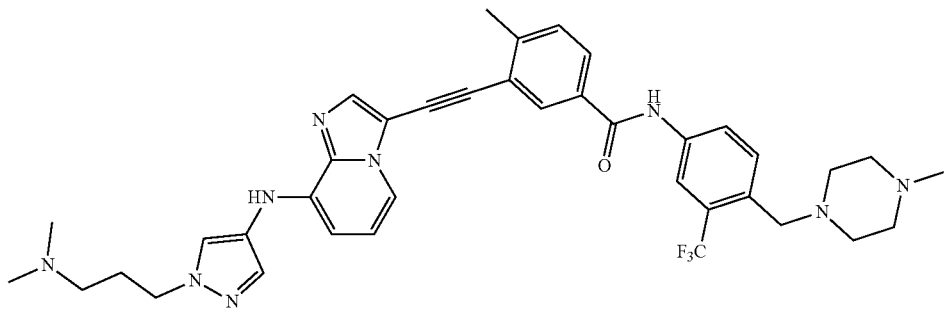 |
| 27 | 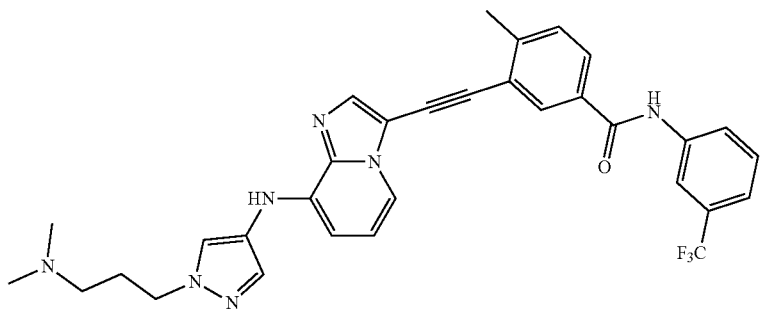 [SMILES: Cc1ccc(C(=O)Nc2cccc(C(F)(F)F)c2)cc1C#Cc1cnc2c(Nc3cnn(CCCN(C)C)c3)cccn12] |
| 28 | 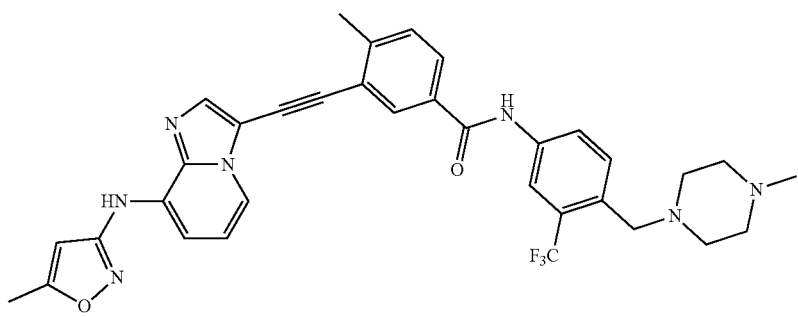 |
| 29 | 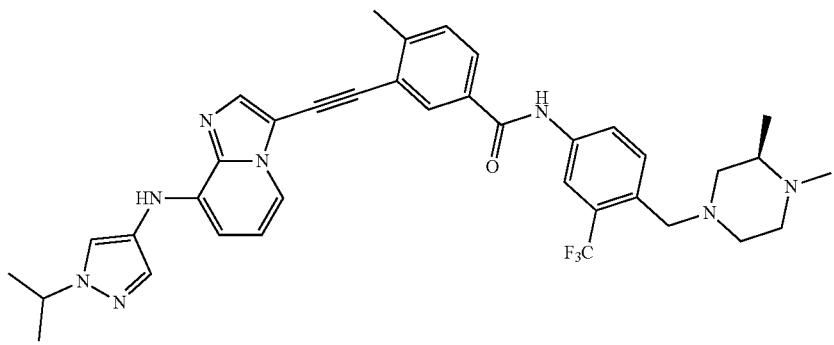 [SMILES: Cc1ccc(C(=O)Nc2ccc(CN3CCN(C)[C@H](C)C3)c(C(F)(F)F)c2)cc1C#Cc1cnc2c(Nc3cnn(C(C)C)c3)cccn12] |

TABLE 1-continued
| Example | Structure |
|---|---|
| 30 | 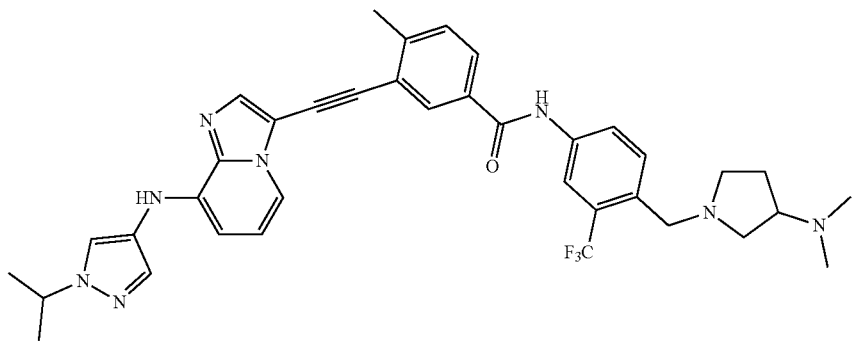 [SMILES: Cc1ccc(C(=O)Nc2ccc(CN3CCC(N(C)C)C3)c(C(F)(F)F)c2)cc1C#Cc1cnc2c(Nc3cnn(C(C)C)c3)cccn12] |
| 31 | 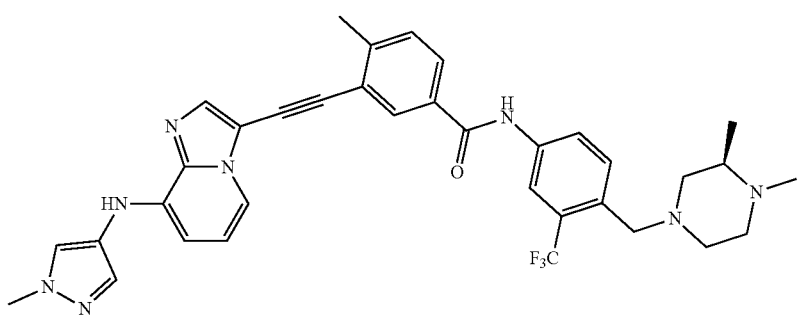 |
| 32 | 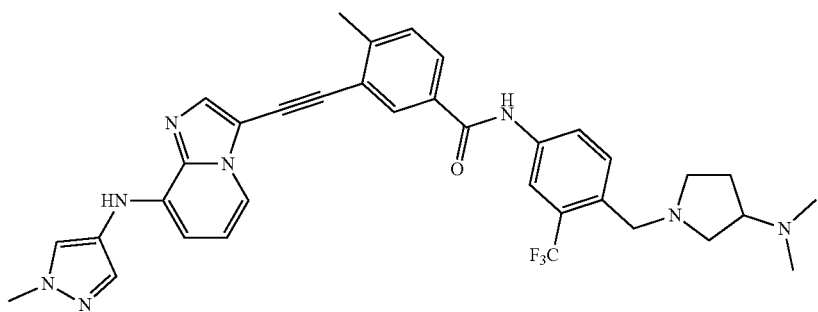 |
| 33 | 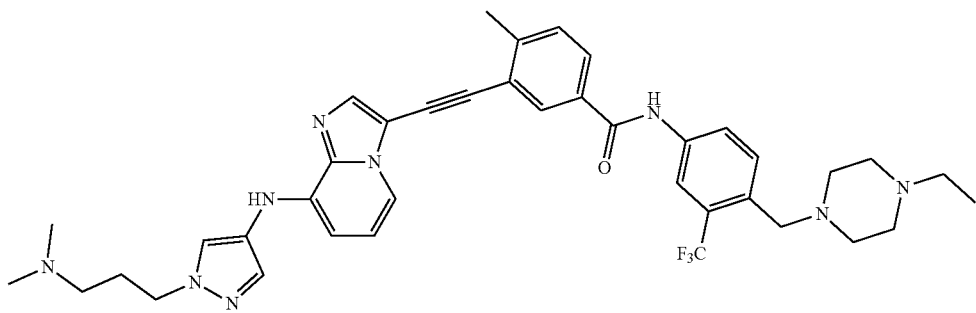 [SMILES: CCN1CCN(Cc2ccc(NC(=O)c3ccc(C)c(C#Cc4cnc5c(Nc6cnn(CCCN(C)C)c6)cccn45)c3)cc2C(F)(F)F)CC1] |
| 34 | 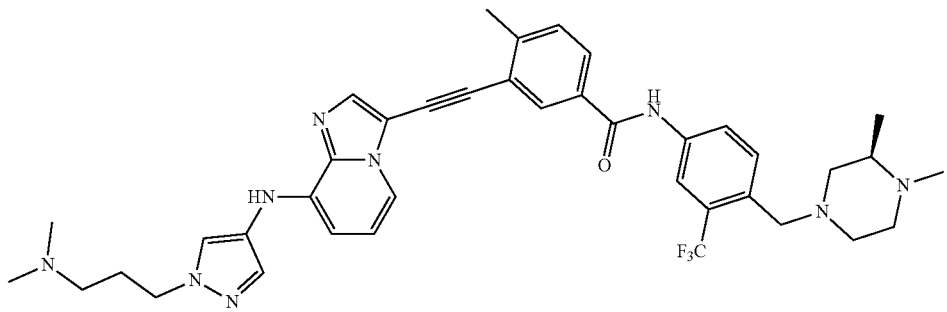 |

TABLE 1-continued
| Example | Structure |
|---|---|
| 35 | 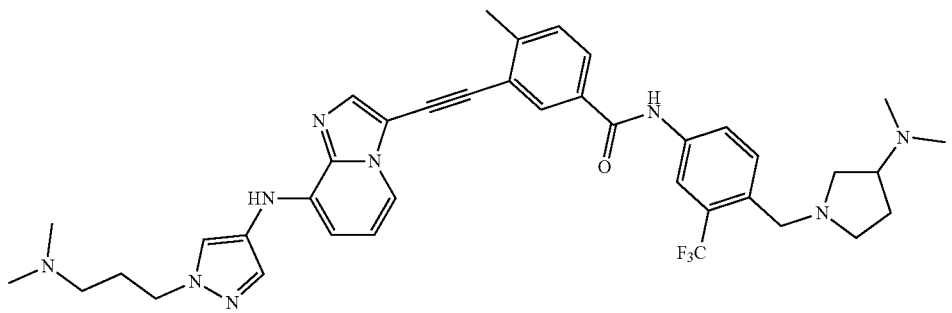 |
| 36 | 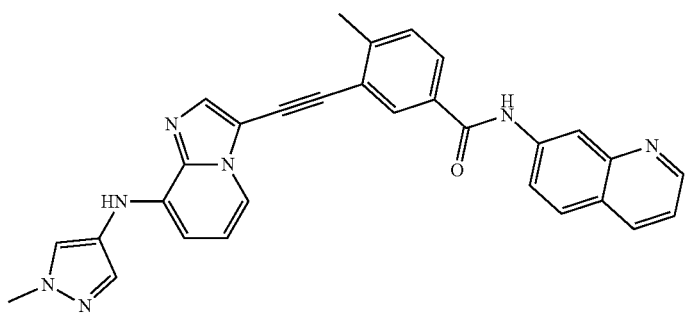 [SMILES: Cc1ccc(C(=O)Nc2ccc3cccnc3c2)cc1C#Cc1cnc2c(Nc3cnn(C)c3)cccn12] |
| 37 | 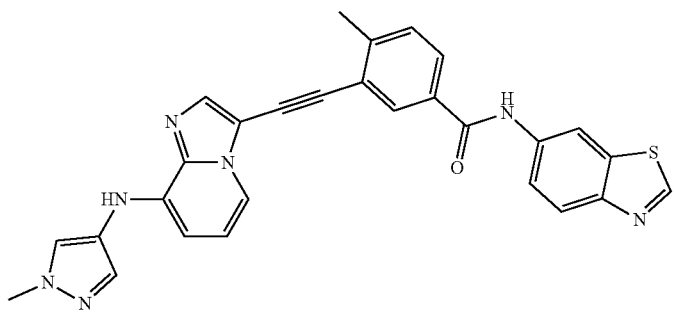 [SMILES: Cc1ccc(C(=O)Nc2ccc3ncsc3c2)cc1C#Cc1cnc2c(Nc3cnn(C)c3)cccn12] |
| 38 | 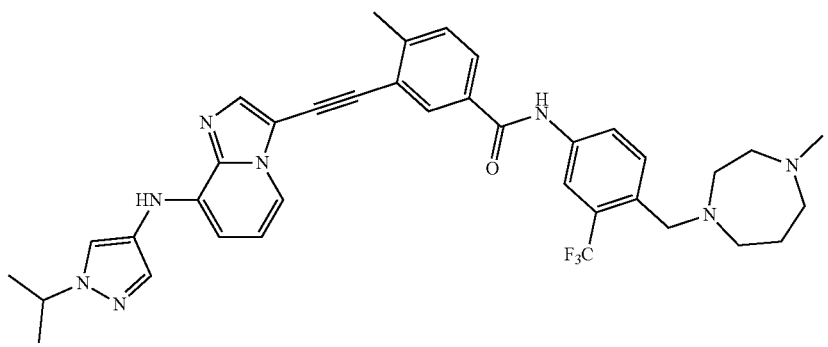 [SMILES: Cc1ccc(C(=O)Nc2ccc(CN3CCCN(C)CC3)c(C(F)(F)F)c2)cc1C#Cc1cnc2c(Nc3cnn(C(C)C)c3)cccn12] |
| 39 | 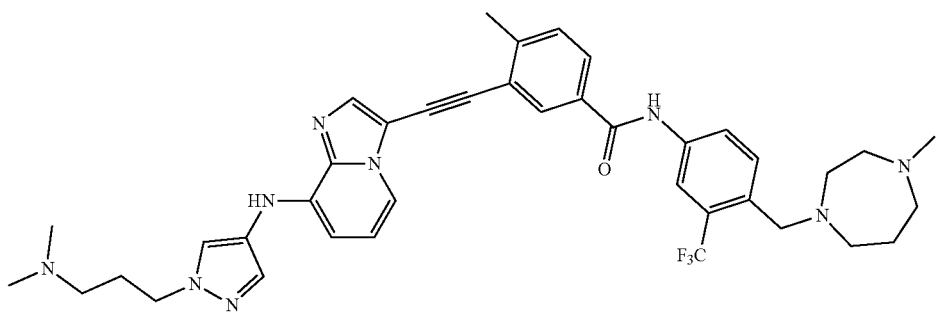 |

TABLE 1-continued
| Example | Structure |
|---|---|
| 40 | 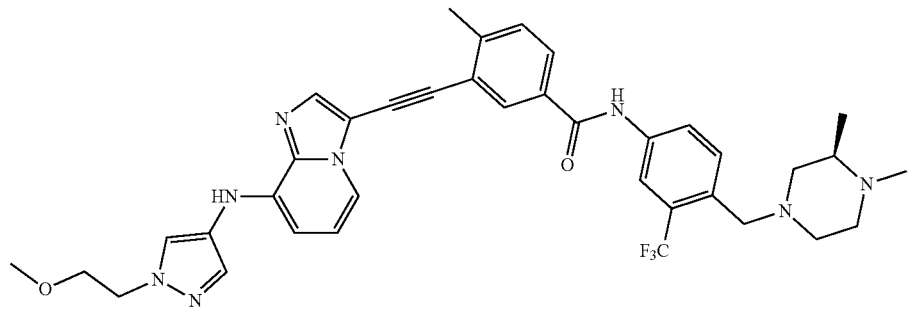 |
| 41 | 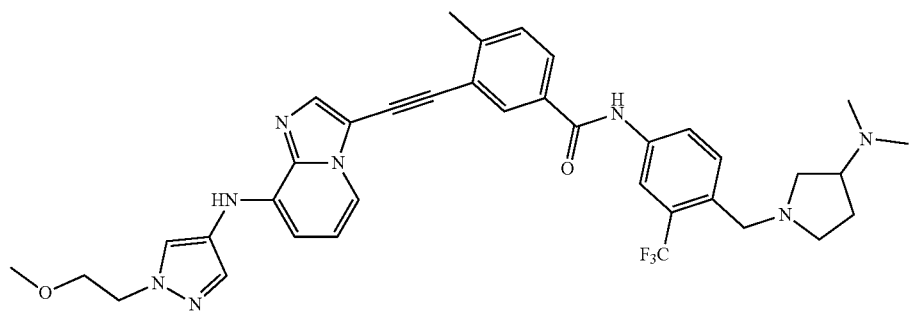 |
| 42 | 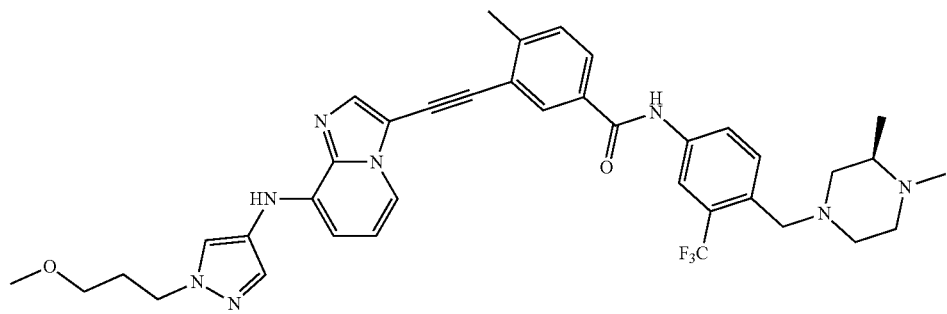 |
| 43 | 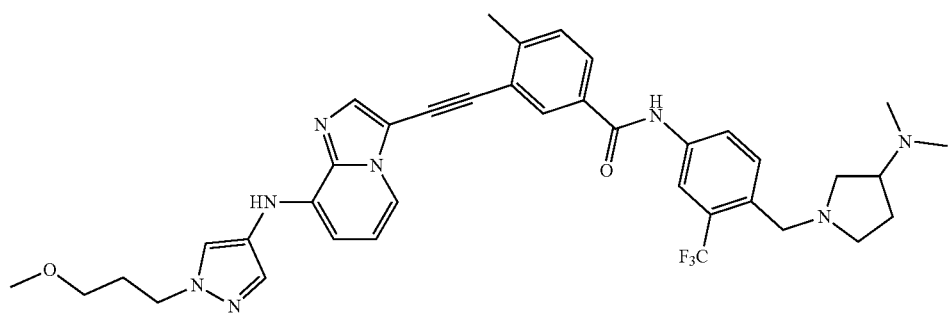 |
| 44 | 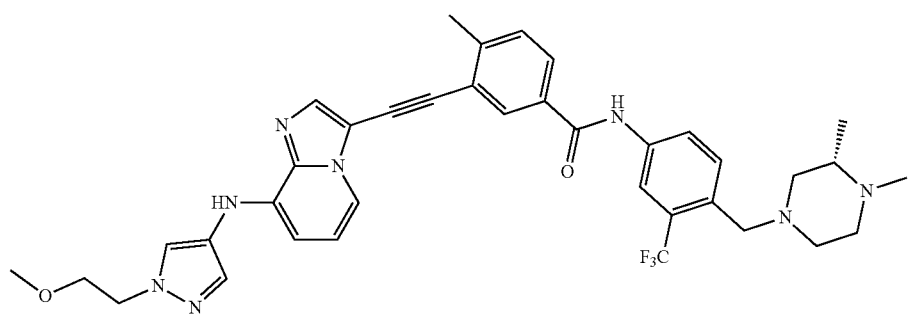 |

TABLE 1-continued
| Example | Structure |
|---|---|
| 45 | 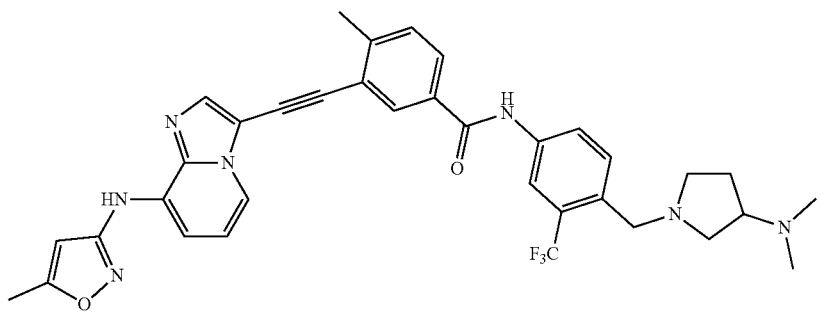 |
| 46 | 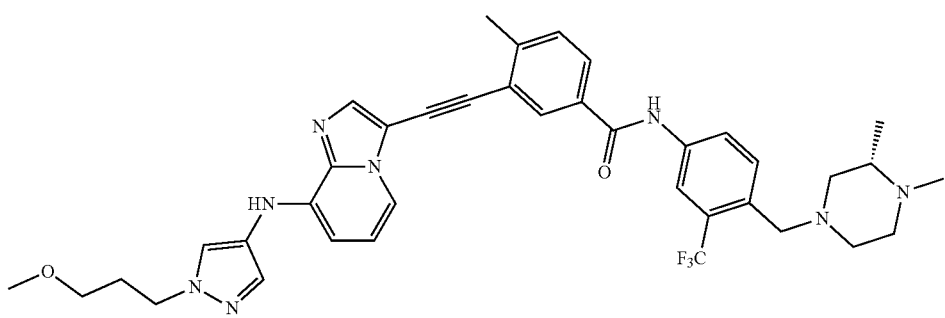 |
| 47 | 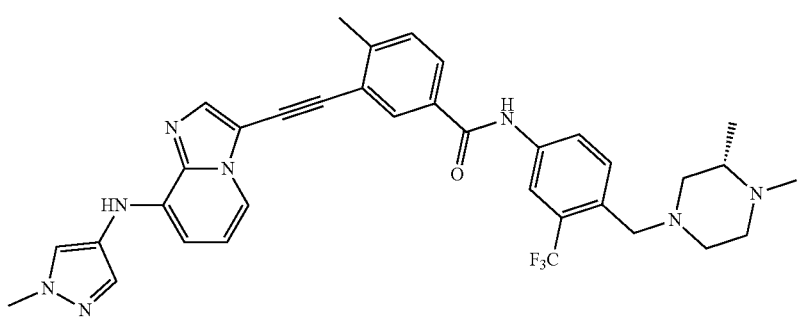 |
| 48 | 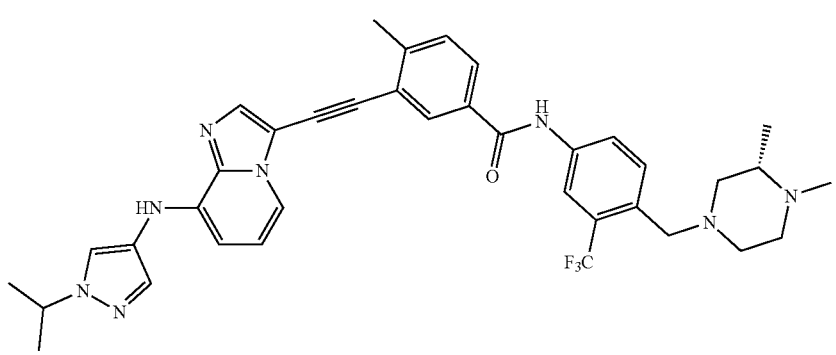 [SMILES: Cc1ccc(C(=O)Nc2ccc(CN3CCN(C)[C@@H](C)C3)c(C(F)(F)F)c2)cc1C#Cc1cnc2c(Nc3cnn(C(C)C)c3)cccn12] |
| 49 | 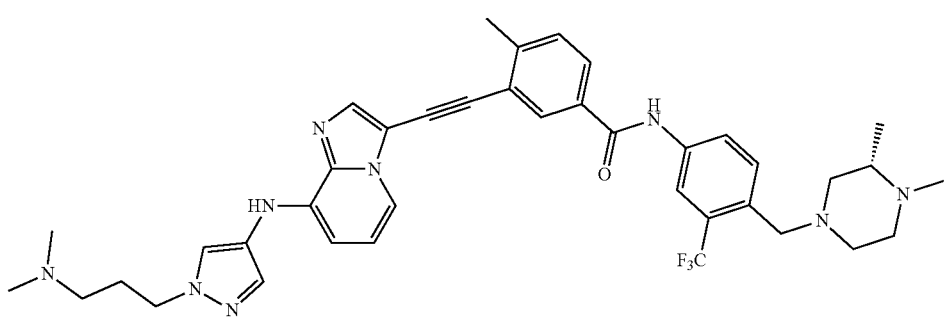 |

TABLE 1-continued
| Example | Structure |
|---|---|
| 50 | 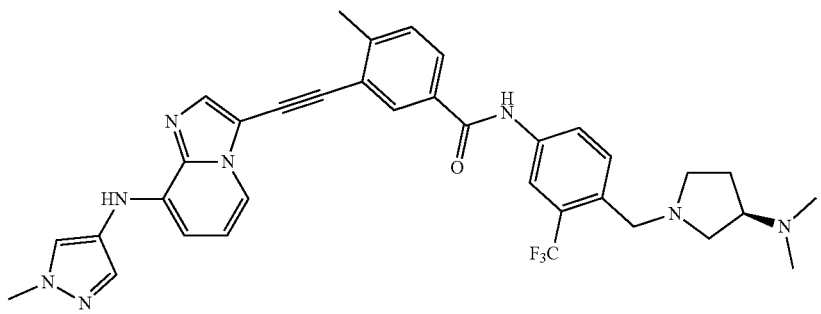 |
| 51 | 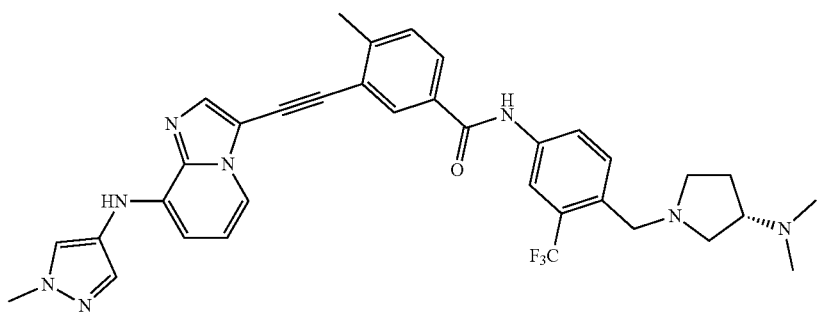 |
| 52 | 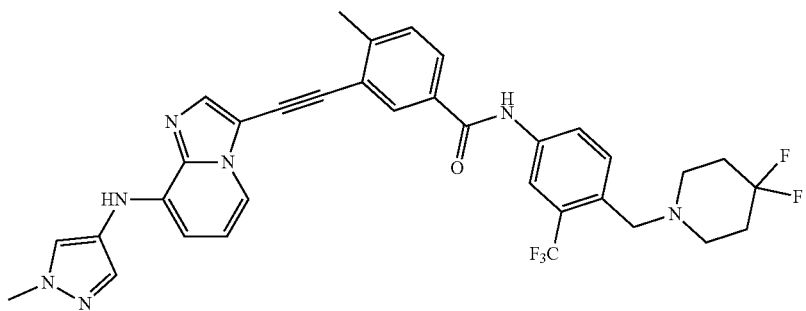 [SMILES: Cc1ccc(C(=O)Nc2ccc(CN3CCC(F)(F)CC3)c(C(F)(F)F)c2)cc1C#Cc1cnc2c(Nc3cnn(C)c3)cccn12] |
| 53 | 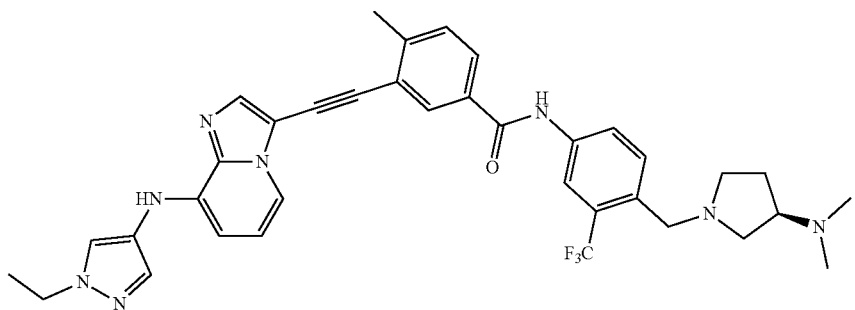 [SMILES: CCn1cc(Nc2cccn3c(C#Cc4cc(C(=O)Nc5ccc(CN6CC[C@@H](N(C)C)C6)c(C(F)(F)F)c5)ccc4C)cnc23)cn1] |
| 54 | 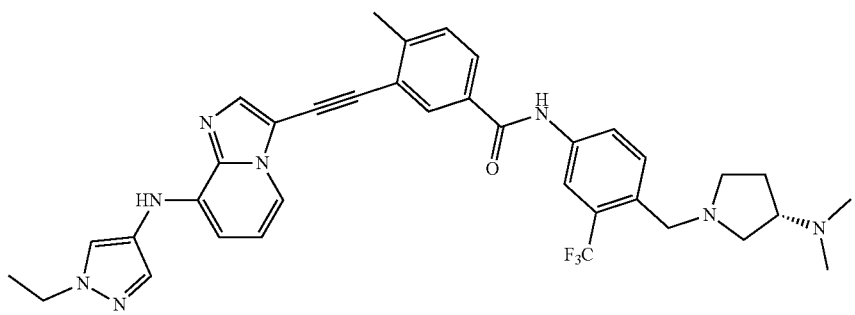 [SMILES: CCn1cc(Nc2cccn3c(C#Cc4cc(C(=O)Nc5ccc(CN6CC[C@H](N(C)C)C6)c(C(F)(F)F)c5)ccc4C)cnc23)cn1] |

TABLE 1-continued
| Example | Structure |
|---|---|
| 55 | 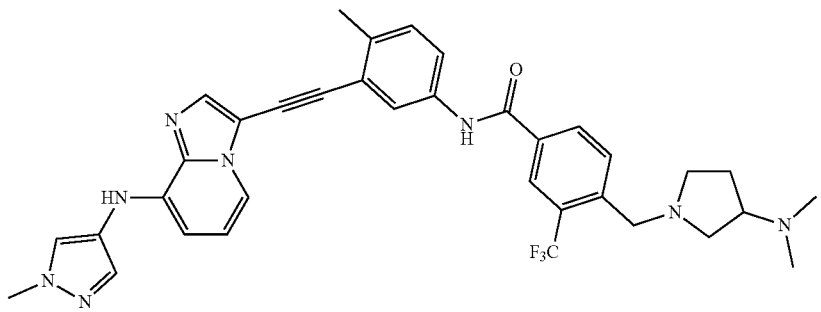 |
| 56 | 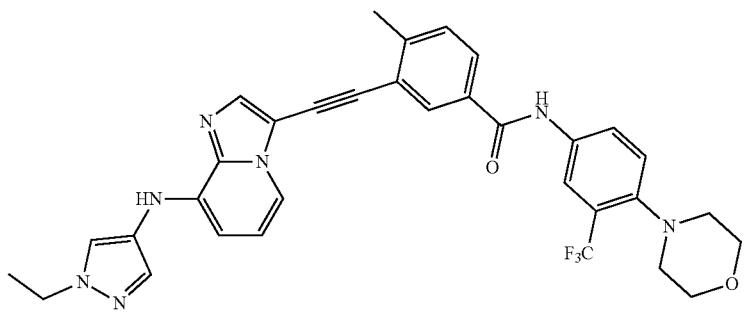 [SMILES: CCn1cc(Nc2cccn3c(C#Cc4cc(C(=O)Nc5ccc(N6CCOCC6)c(C(F)(F)F)c5)ccc4C)cnc23)cn1] |
| 57 | 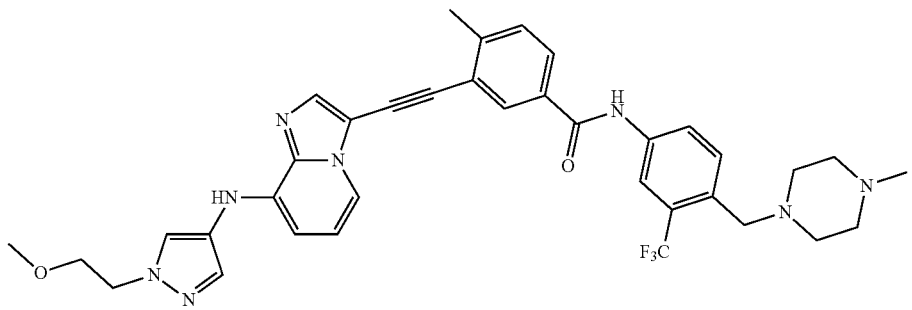 |
| 58 | 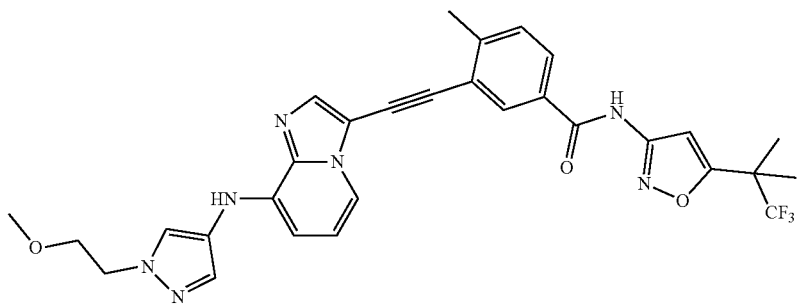 [SMILES: COCCn1cc(Nc2cccn3c(C#Cc4cc(C(=O)Nc5cc(C(C)(C)C(F)(F)F)on5)ccc4C)cnc23)cn1] |
| 59 | 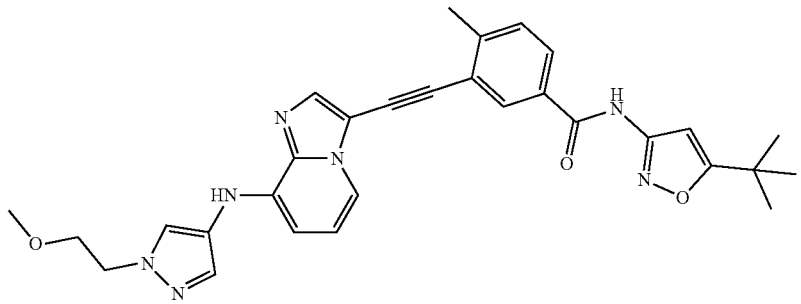 [SMILES: COCCn1cc(Nc2cccn3c(C#Cc4cc(C(=O)Nc5cc(C(C)(C)C)on5)ccc4C)cnc23)cn1] |

TABLE 1-continued
| Example | Structure |
|---|---|
| 60 | 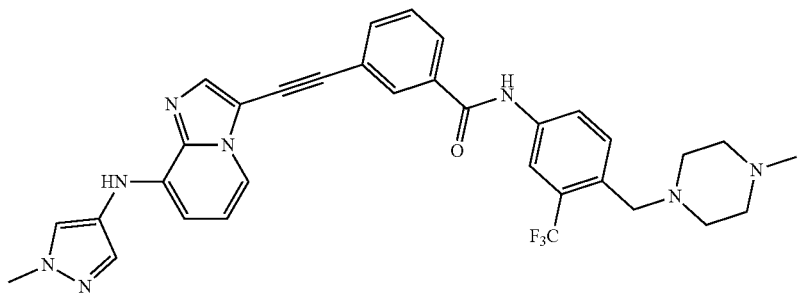 |
| 61 | 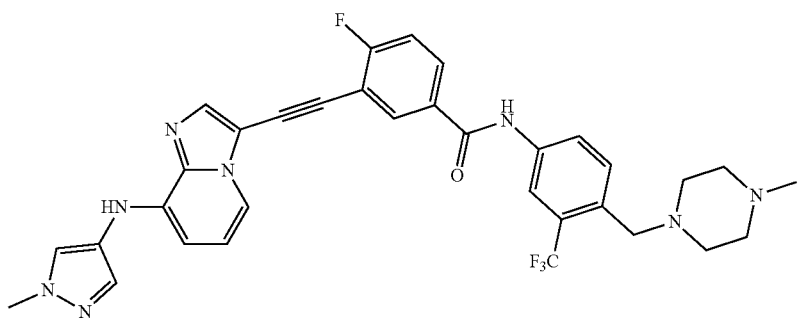 |
| 62 | 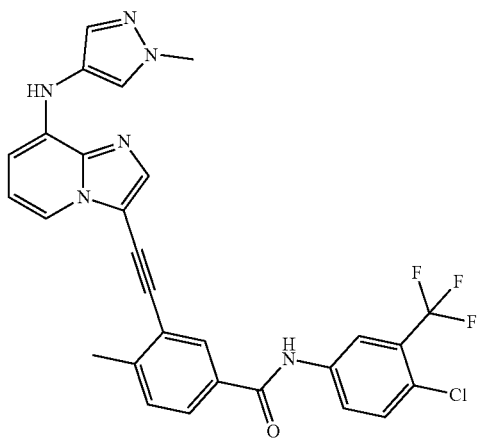 [SMILES: Cc1ccc(C(=O)Nc2ccc(Cl)c(C(F)(F)F)c2)cc1C#Cc1cnc2c(Nc3cnn(C)c3)cccn12] |
| 63 | 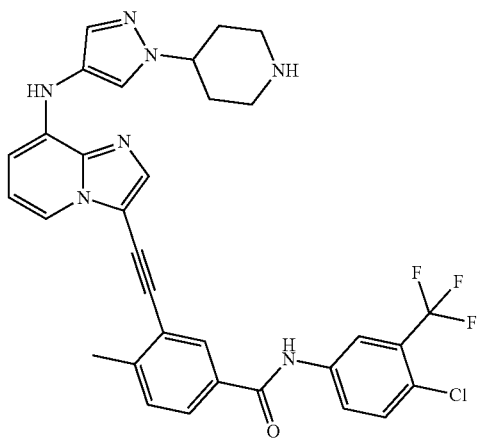 [SMILES: Cc1ccc(C(=O)Nc2ccc(Cl)c(C(F)(F)F)c2)cc1C#Cc1cnc2c(Nc3cnn(C4CCNCC4)c3)cccn12] |

TABLE 1-continued
| Example | Structure |
|---|---|
| 64 | 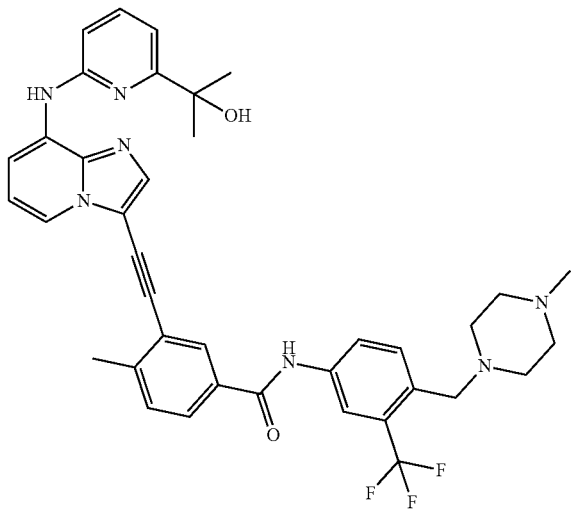 [SMILES: Cc1ccc(C(=O)Nc2ccc(CN3CCN(C)CC3)c(C(F)(F)F)c2)cc1C#Cc1cnc2c(Nc3cccc(C(C)(C)O)n3)cccn12] |
| 65 | 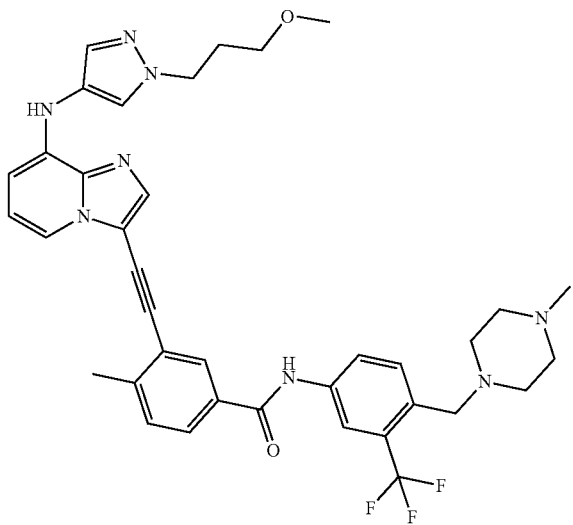 [SMILES: COCCCn1cc(Nc2cccn3c(C#Cc4cc(C(=O)Nc5ccc(CN6CCN(C)CC6)c(C(F)(F)F)c5)ccc4C)cnc23)cn1] |
| 66 | 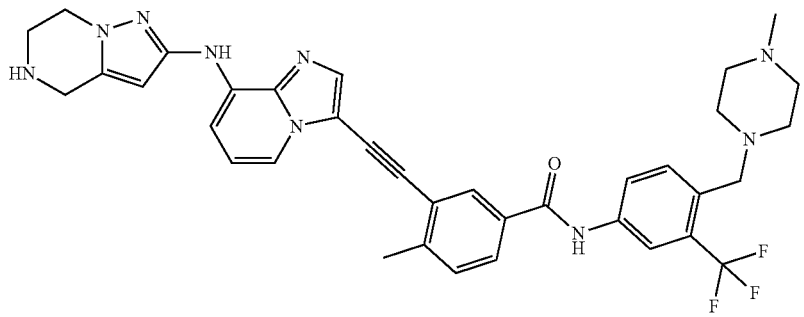 [SMILES: Cc1ccc(C(=O)Nc2ccc(CN3CCN(C)CC3)c(C(F)(F)F)c2)cc1C#Cc1cnc2c(Nc3cc4n(n3)CCNC4)cccn12] |

TABLE 1-continued
| Example | Structure |
|---|---|
| 67 | 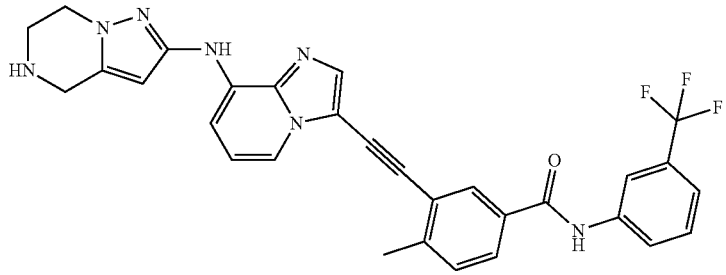 [SMILES: Cc1ccc(C(=O)Nc2cccc(C(F)(F)F)c2)cc1C#Cc1cnc2c(Nc3cc4n(n3)CCNC4)cccn12] |
| 68 | 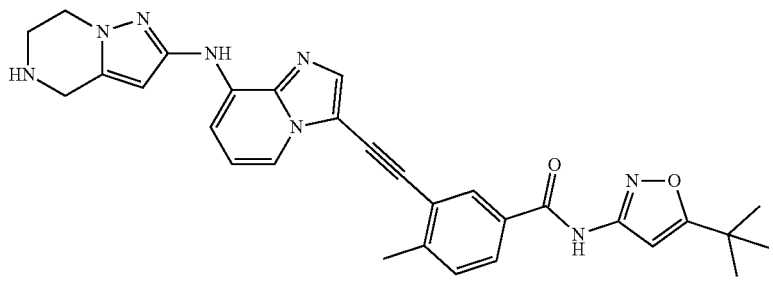 [SMILES: Cc1ccc(C(=O)Nc2cc(C(C)(C)C)on2)cc1C#Cc1cnc2c(Nc3cc4n(n3)CCNC4)cccn12] |
| 69 | 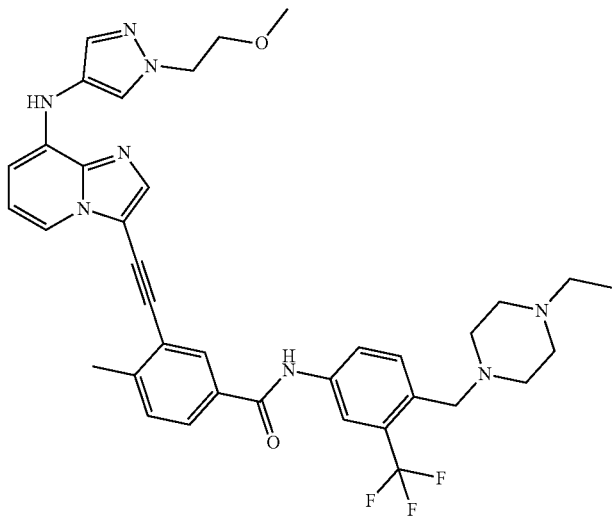 [SMILES: CCN1CCN(Cc2ccc(NC(=O)c3ccc(C)c(C#Cc4cnc5c(Nc6cnn(CCOC)c6)cccn45)c3)cc2C(F)(F)F)CC1] |
| 70 | 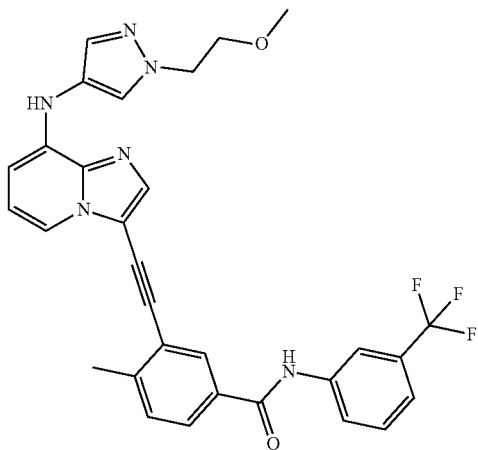 [SMILES: COCCn1cc(Nc2cccn3c(C#Cc4cc(C(=O)Nc5cccc(C(F)(F)F)c5)ccc4C)cnc23)cn1] |

TABLE 1-continued
Example Structure
71 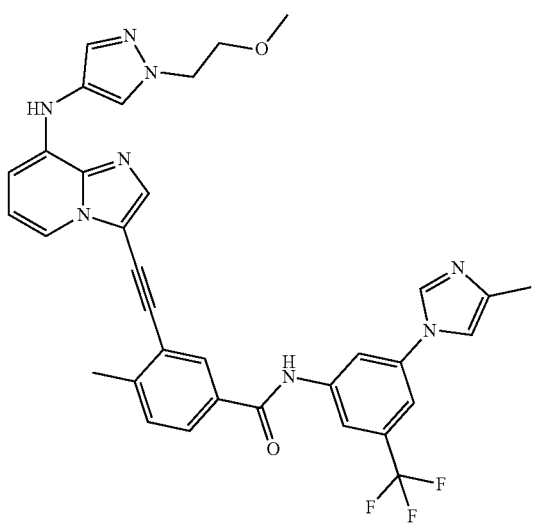 [SMILES: COCCn1cc(Nc2cccn3c(C#Cc4cc(C(=O)Nc5cc(-n6cnc(C)c6)cc(C(F)(F)F)c5)ccc4C)cnc23)cn1]
72 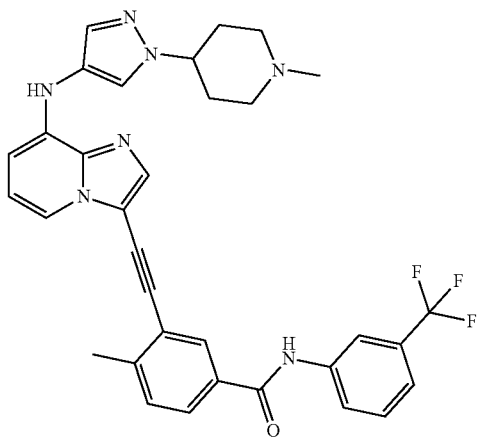 [SMILES: Cc1ccc(C(=O)Nc2cccc(C(F)(F)F)c2)cc1C#Cc1cnc2c(Nc3cnn(C4CCN(C)CC4)c3)cccn12]
73 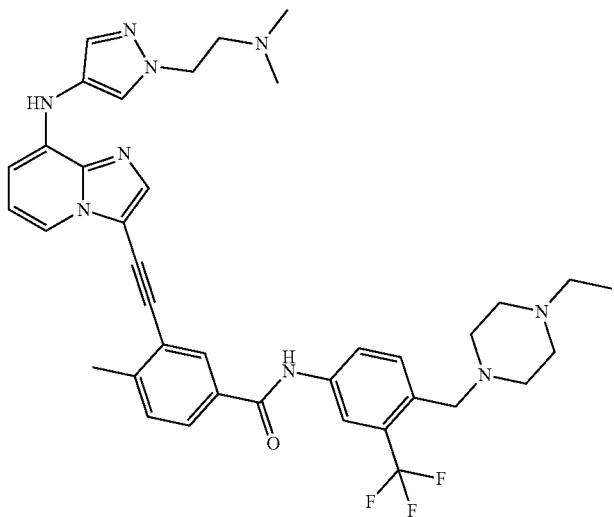 [SMILES: CCN1CCN(Cc2ccc(NC(=O)c3ccc(C)c(C#Cc4cnc5c(Nc6cnn(CCN(C)C)c6)cccn45)c3)cc2C(F)(F)F)CC1]

TABLE 1-continued
Example Structure
74 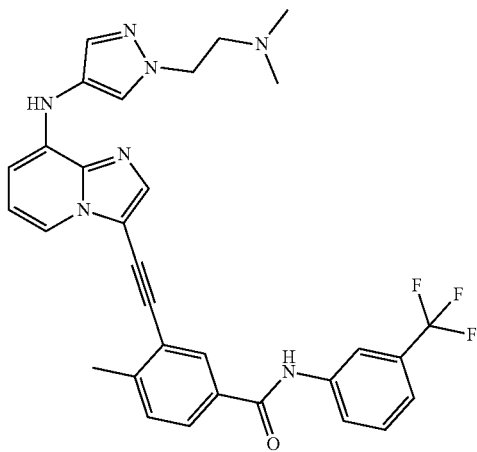 [SMILES: Cc1ccc(C(=O)Nc2cccc(C(F)(F)F)c2)cc1C#Cc1cnc2c(Nc3cnn(CCN(C)C)c3)cccn12]
75 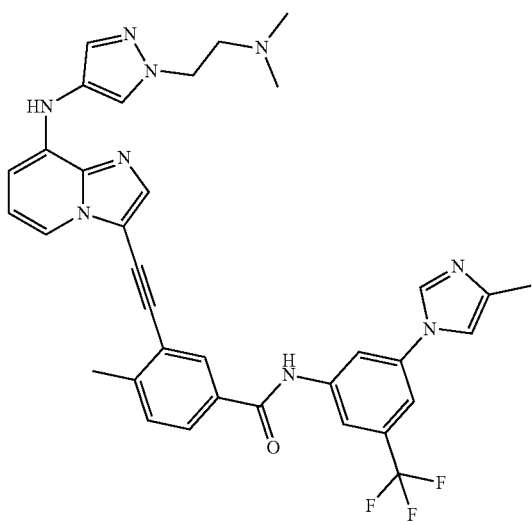 [SMILES: Cc1cn(-c2cc(NC(=O)c3ccc(C)c(C#Cc4cnc5c(Nc6cnn(CCN(C)C)c6)cccn45)c3)cc(C(F)(F)F)c2)cn1]
76 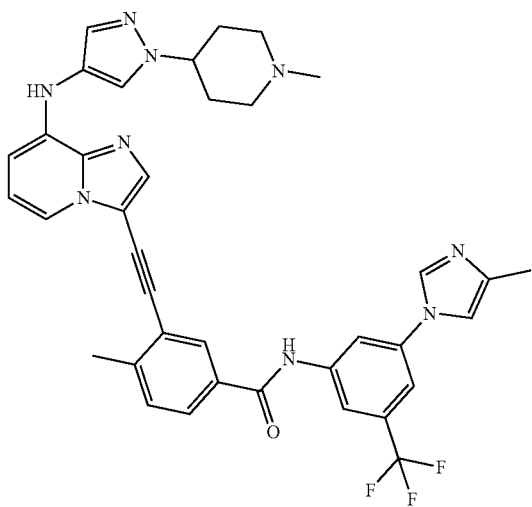 [SMILES: Cc1cn(-c2cc(NC(=O)c3ccc(C)c(C#Cc4cnc5c(Nc6cnn(C7CCN(C)CC7)c6)cccn45)c3)cc(C(F)(F)F)c2)cn1]

TABLE 1-continued
| Example | Structure |
|---|---|
| 77 | 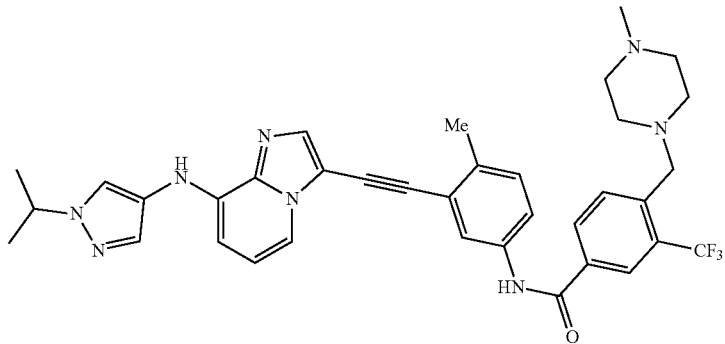 [SMILES: Cc1ccc(NC(=O)c2ccc(CN3CCN(C)CC3)c(C(F)(F)F)c2)cc1C#Cc1cnc2c(Nc3cnn(C(C)C)c3)cccn12] |
| 78 | 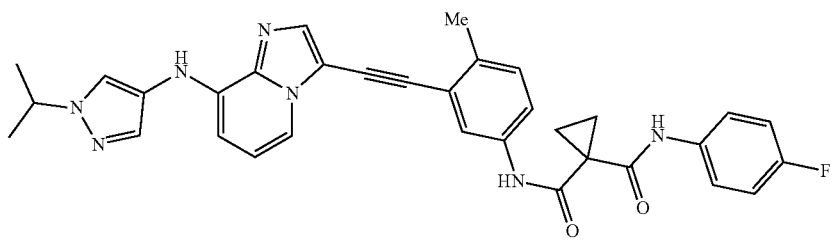 [SMILES: Cc1ccc(NC(=O)C2(C(=O)Nc3ccc(F)cc3)CC2)cc1C#Cc1cnc2c(Nc3cnn(C(C)C)c3)cccn12] |
| 79 | 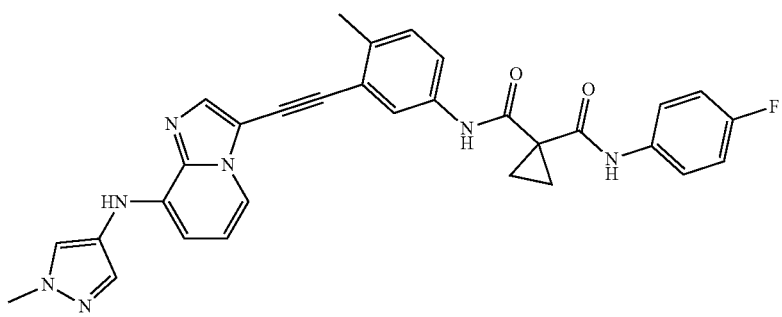 [SMILES: Cc1ccc(NC(=O)C2(C(=O)Nc3ccc(F)cc3)CC2)cc1C#Cc1cnc2c(Nc3cnn(C)c3)cccn12] |
| 80 | 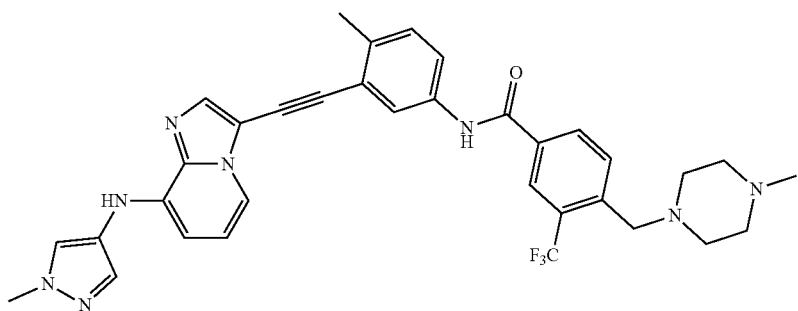 |
| 81 | 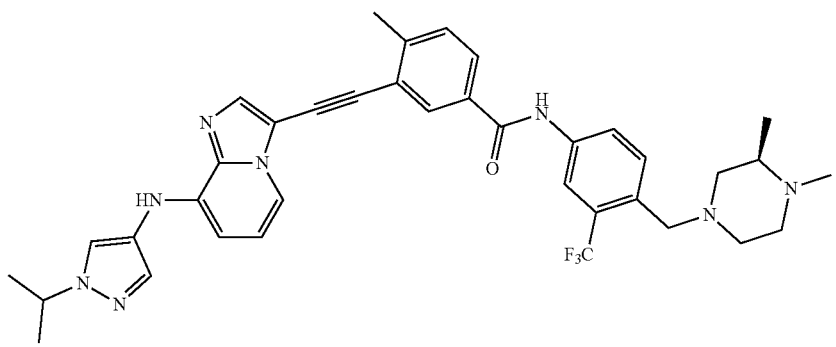 [SMILES: Cc1ccc(C(=O)Nc2ccc(CN3CCN(C)[C@H](C)C3)c(C(F)(F)F)c2)cc1C#Cc1cnc2c(Nc3cnn(C(C)C)c3)cccn12] |

TABLE 1-continued
Example Structure
82
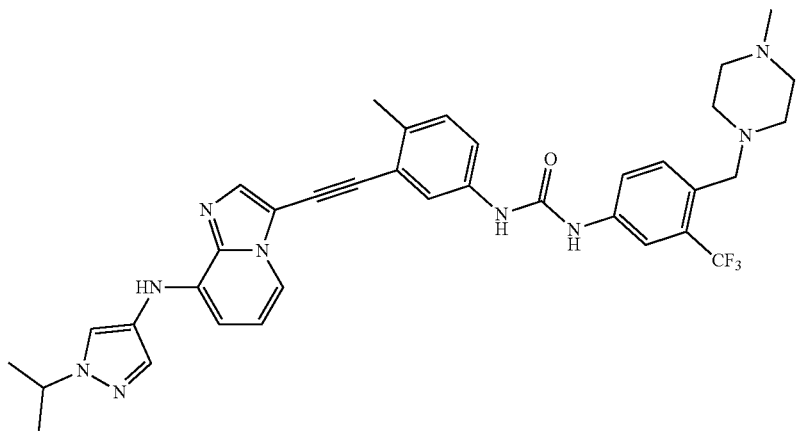 [SMILES: Cc1ccc(NC(=O)Nc2ccc(CN3CCN(C)CC3)c(C(F)(F)F)c2)cc1C#Cc1cnc2c(Nc3cnn(C(C)C)c3)cccn12]
83
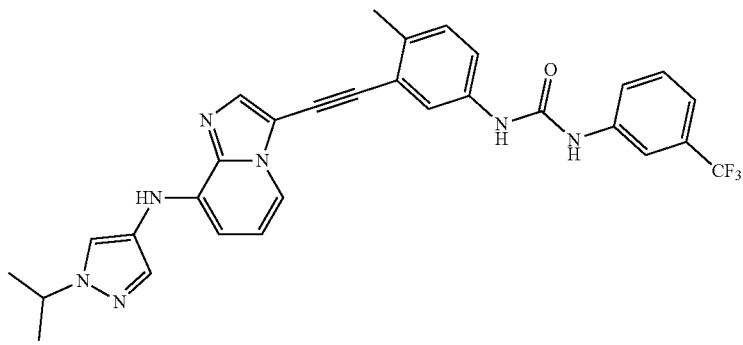 [SMILES: Cc1ccc(NC(=O)Nc2cccc(C(F)(F)F)c2)cc1C#Cc1cnc2c(Nc3cnn(C(C)C)c3)cccn12]
84
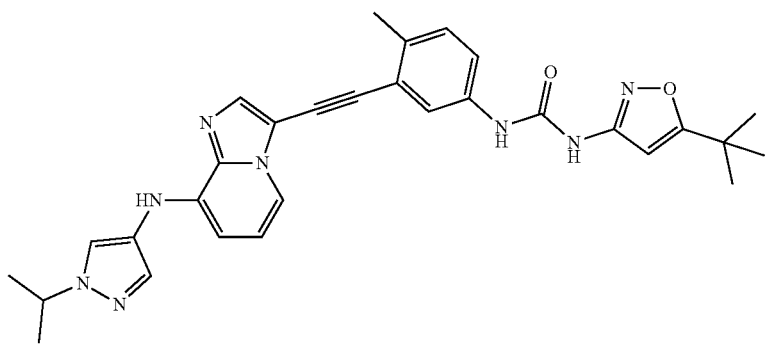 [SMILES: Cc1ccc(NC(=O)Nc2cc(C(C)(C)C)on2)cc1C#Cc1cnc2c(Nc3cnn(C(C)C)c3)cccn12]
85
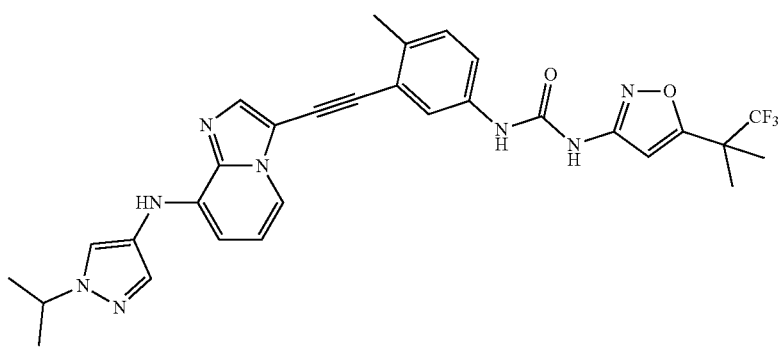 [SMILES: Cc1ccc(NC(=O)Nc2cc(C(C)(C)C(F)(F)F)on2)cc1C#Cc1cnc2c(Nc3cnn(C(C)C)c3)cccn12]

<Experimental Example 1> Evaluation of Enzyme Inhibitory Activity

Experimental Example 1-1

The following experiment was performed to evaluate the enzyme inhibitory activity of the compound of the present invention.

Particularly, the enzyme inhibitory activity of the compound of the present invention against BLK, CDK11, CHEK1, CSF1R, EPHB6, FGFR4, FGR, FLT3, FYN, GCN2 (Kin.Dom.2, S808G), HCK, JAK2 (JH1domain-catalytic), LCK, LOK, LYN, RET, RET (V804M), SRC and YES was investigated by Reaction Biology Co. The results are shown in Table 2 below.

Example 78 were selected and assigned to DiscoverX to measure the kinase selectivity. The experiment was performed by using scanMAX™ Kinase assay panel.

At this time, the concentration of the drug to be treated to the enzyme was adjusted to 1 uM in DMSO, and the control percentage (% control) was determined according to the following Equation 1. The results are shown in Table 3 below.

[Example Compound−Positive Control/Negative Control−Positive Control]×100 [Equation 1]

Herein, the positive control indicates the compound showing the % control of 0, while the negative control is DMSO which displays the percent control of 100. The enzyme selectivity of the compound of the present invention was judged to be active for the enzyme if the % control was <35 (i.e. less than 35%) for each enzyme.

TABLE 2

| enzyme(Kd, nM) | Example | | | | | | | | | | | |
|---|---|---|---|---|---|---|---|---|---|---|---|---|
| | 1 | 8 | 12 | 9 | 14 | 15 | 26 | 5 | 30 | 77 | 78 | 82 |
| BLK | | 5 | | | | | | | | | | |
| CDK11 | 140 | | | | | | | | | | | |
| CHEK1 | | | | | | | | | | | | |
| CSF1R | 34 | | | | | | | | | 440 | | |
| EPHB6 | | | | | | | | | | | 15 | |
| FGFR4 | 56 | 57 | 370 | 200 | 73 | 130 | 82 | | 190 | 94 | | |
| FGR | | 13 | | | | | | | | | | |
| FLT3 | | | | | | | | | | | | |
| FLT3(ITD) | | | | | | | | | | | | |
| FYN | | 52 | | | | | | | | | | |
| GCN2(Kin.Dom.2, S808G) | | | | | | | | | | | | |
| HCK | | 7.7 | | | | | | | | | | |
| JAK2(JH1domain-catalytic) | 220 | 270 | | | | | | | | 340 | | 2600 |
| LCK | | 6.4 | | | | | | | | | | |
| LOK | 7.3 | | | | | | | | | | 37 | |
| LYN | | 15 | | | | | | | | | | |
| RET | 10 | 7.5 | 25 | 22 | 12 | 16 | 7.9 | 4.6 | 9.3 | 9.3 | | 14 |
| RET(V804M) | 11 | 9.1 | 32 | 36 | 24 | 17 | 12 | 6 | 13 | 19 | | 29 |
| SRC | | 10 | | | | | | | | | | |
| YES | | 17 | | | | | | | | | | |

As shown in Table 2, it was confirmed that the compound of the present invention was able to inhibit FGFR4, RET and RET (V804M) significantly at the concentration of nanomol units.

The compound of the present invention inhibited FGFR4, RET and RET (V804M) significantly at the concentration of nanomol units, so that the compound of the present invention can be effectively used as an active ingredient of a pharmaceutical composition for the prevention or treatment of FGFR4, RET and RET (V804M) related diseases including cancer.

In the meantime, the excellent inhibitory activity against Src and Fyn of the compound of the present invention suggests that it can be effectively used for the treatment of Src and Fyn related diseases such as diabetic nephropathy. Therefore, the compound of the present invention can be effectively used as an active ingredient of a pharmaceutical composition for the prevention or treatment of diabetic nephropathy.

Experimental Example 1-2

The following experiment was performed to evaluate the inhibitory activity of the compound of the present invention on more enzymes.

Particularly, among the compounds of the present invention, the compounds of Example 1, Example 12 and

TABLE 3

| | Example 1 | Example 12 | Example 78 |
|---|---|---|---|
| | Concentration | | |
| DiscoveRx Gene Symbol (enzyme identification gene) | 1 uM | 1 uM | 1 uM |
| | Percent Control (%) | | |
| AAK1 | 64 | 85 | 100 |
| ABL1 (E255K)-phosphorylated | 0 | 8 | 84 |
| ABL1 (F317I)-nonphosphorylated | 1 | 10 | 36 |
| ABL1 (F317I)-phosphorylated | 3 | 28 | 72 |
| ABL1 (F317L)-nonphosphorylated | 9 | 3 | 16 |
| ABL1 (F317L)-phosphorylated | 2 | 6 | 85 |
| ABL1 (H396P)-nonphosphorylated | 1 | 0 | 4 |
| ABL1 (H396P)-phosphorylated | 0 | 10 | 64 |
| ABL1 (M351T)-phosphorylated | 1 | 11 | 59 |
| ABL1 (Q252H)-nonphosphorylated | 7 | 3 | 6 |
| ABL1 (Q252H)-phosphorylated | 0 | 14 | 91 |
| ABL1 (T315I)-nonphosphorylated | 1 | 15 | 100 |
| ABL1 (T315I)-phosphorylated | 1 | 15 | 100 |
| ABL1 (Y253F)-phosphorylated | 0 | 10 | 88 |
| ABL1-nonphosphorylated | 1 | 1 | 4 |
| ABL1-phosphorylated | 0 | 6 | 56 |
| ABL2 | 0 | 1 | 14 |
| ACVR1 | 100 | 100 | 100 |
| ACVR1B | 89 | 94 | 100 |

TABLE 3-continued

| DiscoveRx Gene Symbol (enzyme identification gene) | Example 1 | Example 12 | Example 78 |
|---|---|---|---|
| | 1 uM | 1 uM | 1 uM |
| | Percent Control (%) | | |
| ACVR2A | 95 | 100 | 100 |
| ACVR2B | 93 | 96 | 94 |
| ACVRL1 | 99 | 99 | 100 |
| ADCK3 | 100 | 93 | 100 |
| ADCK4 | 88 | 95 | 100 |
| AKT1 | 80 | 88 | 98 |
| AKT2 | 37 | 82 | 99 |
| AKT3 | 99 | 99 | 95 |
| ALK | 70 | 100 | 100 |
| ALK (C1156Y) | 76 | 100 | 100 |
| ALK (L1196M) | 29 | 100 | 100 |
| AMPK-alpha1 | 7 | 74 | 100 |
| AMPK-alpha2 | 4 | 79 | 100 |
| ANKK1 | 4 | 100 | 97 |
| ARK5 | 99 | 100 | 94 |
| ASK1 | 100 | 95 | 100 |
| ASK2 | 71 | 81 | 100 |
| AURKA | 72 | 100 | 100 |
| AURKB | 3 | 56 | 34 |
| AURKC | 1 | 48 | 88 |
| AXL | 2 | 48 | 93 |
| BIKE | 81 | 85 | 100 |
| BLK | 0 | 1 | 35 |
| BMPR1A | 77 | 60 | 94 |
| BMPR1B | 99 | 100 | 100 |
| BMPR2 | 82 | 100 | 84 |
| BMX | 3 | 9 | 96 |
| BRAF | 18 | 80 | 100 |
| BRAF (V600E) | 5 | 56 | 100 |
| BRK | 23 | 68 | 99 |
| BRSK1 | 100 | 83 | 100 |
| BRSK2 | 96 | 87 | 100 |
| BTK | 1 | 37 | 100 |
| BUB1 | 84 | 100 | 100 |
| CAMK1 | 35 | 73 | 100 |
| CAMK1B | 62 | 100 | 100 |
| CAMK1D | 65 | 82 | 98 |
| CAMK1G | 71 | 91 | 100 |
| CAMK2A | 82 | 96 | 100 |
| CAMK2B | 76 | 96 | 100 |
| CAMK2D | 82 | 78 | 100 |
| CAMK2G | 73 | 80 | 100 |
| CAMK4 | 99 | 87 | 100 |
| CAMKK1 | 23 | 81 | 100 |
| CAMKK2 | 32 | 77 | 100 |
| CASK | 74 | 90 | 100 |
| CDC2L1 | 20 | 80 | 100 |
| CDC2L2 | 28 | 72 | 100 |
| CDC2L5 | 5 | 27 | 100 |
| CDK11 | 0 | 19 | 100 |
| CDK2 | 29 | 85 | 95 |
| CDK3 | 62 | 89 | 86 |
| CDK4 | 83 | 100 | 100 |
| CDK4-cyclinD1 | 84 | 100 | 100 |
| CDK4-cyclinD3 | 78 | 100 | 100 |
| CDK5 | 30 | 89 | 100 |
| CDK7 | 4 | 66 | 82 |
| CDK8 | 4 | 31 | 100 |
| CDK9 | 72 | 88 | 100 |
| CDKL1 | 25 | 60 | 83 |
| CDKL2 | 0 | 55 | 94 |
| CDKL3 | 1 | 53 | 100 |
| CDKL5 | 94 | 100 | 92 |
| CHEK1 | 90 | 100 | 98 |
| CHEK2 | 34 | 84 | 91 |
| CIT | 0 | 0 | 100 |
| CLK1 | 25 | 82 | 79 |
| CLK2 | 64 | 91 | 100 |
| CLK3 | 48 | 100 | 100 |
| CLK4 | 10 | 100 | 100 |
| CSF1R | 0 | 0 | 2 |
| CSF1R-autoinhibited | 74 | 100 | 91 |
| CSK | 2 | 1 | 98 |
| CSNK1A1 | 67 | 76 | 85 |
| CSNK1A1L | 93 | 70 | 100 |
| CSNK1D | 91 | 79 | 92 |
| CSNK1E | 90 | 99 | 94 |
| CSNK1G1 | 73 | 95 | 100 |
| CSNK1G2 | 91 | 94 | 100 |
| CSNK1G3 | 100 | 84 | 100 |
| CSNK2A1 | 83 | 100 | 100 |
| CSNK2A2 | 56 | 98 | 100 |
| CTK | 22 | 74 | 90 |
| DAPK1 | 87 | 80 | 98 |
| DAPK2 | 82 | 97 | 100 |
| DAPK3 | 68 | 100 | 100 |
| DCAMKL1 | 54 | 91 | 95 |
| DCAMKL2 | 91 | 78 | 100 |
| DCAMKL3 | 98 | 88 | 100 |
| DDR1 | 0 | 7 | 1 |
| DDR2 | 0 | 7 | 3 |
| DLK | 29 | 100 | 100 |
| DMPK | 100 | 96 | 92 |
| DMPK2 | 100 | 92 | 100 |
| DRAK1 | 98 | 100 | 100 |
| DRAK2 | 90 | 95 | 100 |
| DYRK1A | 100 | 97 | 100 |
| DYRK1B | 93 | 100 | 99 |
| DYRK2 | 75 | 91 | 94 |
| EGFR | 3 | 28 | 85 |
| EGFR (E746-A750del) | 0 | 8 | 93 |
| EGFR (G719C) | 1 | 21 | 97 |
| EGFR (G719S) | 1 | 20 | 100 |
| EGFR (L747-E749del, A750P) | 3 | 5 | 100 |
| EGFR (L747-S752del, P753S) | 1 | 6 | 87 |
| EGFR (L747-T751del, Sins) | 2 | 6 | 100 |
| EGFR (L858R) | 0 | 47 | 84 |
| EGFR (L858R, T790M) | 17 | 69 | 84 |
| EGFR (L861Q) | 1 | 22 | 92 |
| EGFR (S752-I759del) | 7 | 8 | 100 |
| EGFR (T790M) | 10 | 75 | 100 |
| EIF2AK1 | 67 | 95 | 94 |
| EPHA1 | 2 | 8 | 69 |
| EPHA2 | 2 | 9 | 91 |
| EPHA3 | 19 | 27 | 76 |
| EPHA4 | 1 | 24 | 91 |
| EPHA5 | 1 | 31 | 100 |
| EPHA6 | 2 | 19 | 90 |
| EPHA7 | 5 | 69 | 100 |
| EPHA8 | 0 | 1 | 46 |
| EPHB1 | 0 | 15 | 90 |
| EPHB2 | 0 | 27 | 98 |
| EPHB3 | 47 | 100 | 100 |
| EPHB4 | 3 | 41 | 100 |
| EPHB6 | 1 | 0 | 0 |
| ERBB2 | 1 | 68 | 81 |
| ERBB3 | 86 | 98 | 99 |
| ERBB4 | 0 | 32 | 100 |
| ERK1 | 87 | 100 | 100 |
| ERK2 | 100 | 92 | 100 |
| ERK3 | 100 | 94 | 100 |
| ERK4 | 91 | 100 | 100 |
| ERK5 | 78 | 90 | 100 |
| ERK8 | 29 | 71 | 87 |
| ERN1 | 62 | 100 | 97 |
| FAK | 39 | 10 | 96 |
| FER | 1 | 40 | 100 |
| FES | 0 | 6 | 100 |
| FGFR1 | 0 | 6 | 100 |
| FGFR2 | 2 | 11 | 100 |
| FGFR3 | 3 | 33 | 100 |
| FGFR3 (G697C) | 3 | 34 | 96 |
| FGFR4 | 0 | 32 | 100 |
| FGR | 0 | 4 | 80 |
| FLT1 | 3 | 16 | 84 |
| FLT3 | 1 | 4 | 42 |

TABLE 3-continued

| DiscoveRx Gene Symbol (enzyme identification gene) | Example 1 | Example 12 | Example 78 |
|---|---|---|---|
| | Concentration | | |
| | 1 uM | 1 uM | 1 uM |
| | Percent Control (%) | | |
| FLT3 (D835H) | 1 | 10 | 95 |
| FLT3 (D835V) | 0 | 27 | 87 |
| FLT3 (D835Y) | 5 | 14 | 79 |
| FLT3 (ITD) | 1 | 4 | 71 |
| FLT3 (ITD, D835V) | 20 | 100 | 35 |
| FLT3 (ITD, F691L) | 2 | 45 | 31 |
| FLT3 (K663Q) | 2 | 1 | 74 |
| FLT3 (N841I) | 0 | 28 | 59 |
| FLT3 (R834Q) | 3 | 62 | 100 |
| FLT3-autoinhibited | 46 | 100 | 100 |
| FLT4 | 1 | 6 | 26 |
| FRK | 2 | 14 | 69 |
| FYN | 1 | 15 | 84 |
| GAK | 7 | 87 | 100 |
| GCN2 (Kin.Dom.2, S808G) | 0 | 76 | 89 |
| GRK1 | 65 | 85 | 99 |
| GRK2 | 84 | 100 | 96 |
| GRK3 | 82 | 100 | 97 |
| GRK4 | 100 | 100 | 100 |
| GRK7 | 81 | 100 | 92 |
| GSK3A | 76 | 100 | 100 |
| GSK3B | 79 | 85 | 96 |
| HASPIN | 80 | 100 | 85 |
| HCK | 0 | 1 | 71 |
| HIPK1 | 51 | 71 | 91 |
| HIPK2 | 61 | 100 | 100 |
| HIPK3 | 54 | 84 | 100 |
| HIPK4 | 2 | 66 | 84 |
| HPK1 | 1 | 5 | 78 |
| HUNK | 74 | 79 | 93 |
| ICK | 58 | 100 | 100 |
| IGF1R | 56 | 100 | 100 |
| IKK-alpha | 2 | 28 | 100 |
| IKK-beta | 3 | 39 | 100 |
| IKK-epsilon | 66 | 100 | 100 |
| INSR | 54 | 99 | 100 |
| INSRR | 47 | 95 | 93 |
| IRAK1 | 6 | 100 | 100 |
| IRAK3 | 84 | 72 | 87 |
| IRAK4 | 22 | 81 | 100 |
| ITK | 0 | 69 | 97 |
| JAK1 (JH1domain-catalytic) | 17 | 78 | 92 |
| JAK1 (JH2domain-pseudokinase) | 70 | 44 | 100 |
| JAK2 (JH1domain-catalytic) | 7 | 100 | 98 |
| JAK3 (JH1domain-catalytic) | 1 | 19 | 100 |
| JNK1 | 4 | 63 | 99 |
| JNK2 | 0 | 66 | 100 |
| JNK3 | 19 | 98 | 100 |
| KIT | 0 | 1 | 0 |
| KIT (A829P) | 4 | 29 | 21 |
| KIT (D816H) | 7 | 70 | 63 |
| KIT (D816V) | 3 | 7 | 61 |
| KIT (L576P) | 0 | 17 | 0 |
| KIT (V559D) | 0 | 1 | 0 |
| KIT (V559D, T670I) | 0 | 3 | 63 |
| KIT (V559D, V654A) | 1 | 11 | 10 |
| KIT-autoinhibited | 77 | 98 | 93 |
| LATS1 | 40 | 96 | 82 |
| LATS2 | 67 | 98 | 100 |
| LCK | 0 | 0 | 40 |
| LIMK1 | 4 | 38 | 100 |
| LIMK2 | 3 | 50 | 100 |
| LKB1 | 98 | 85 | 100 |
| LOK | 0 | 0 | 0 |
| LRRK2 | 10 | 100 | 95 |
| LRRK2 (G2019S) | 27 | 100 | 100 |
| LTK | 9 | 12 | 94 |
| LYN | 0 | 3 | 84 |
| LZK | 71 | 100 | 94 |
| MAK | 10 | 81 | 100 |
| MAP3K1 | 44 | 67 | 94 |
| MAP3K15 | 72 | 100 | 98 |
| MAP3K2 | 1 | 84 | 100 |
| MAP3K3 | 0 | 33 | 77 |
| MAP3K4 | 70 | 92 | 90 |
| MAP4K2 | 1 | 98 | 100 |
| MAP4K3 | 25 | 66 | 100 |
| MAP4K4 | 1 | 4 | 99 |
| MAP4K5 | 1 | 12 | 82 |
| MAPKAPK2 | 100 | 81 | 98 |
| MAPKAPK5 | 100 | 100 | 100 |
| MARK1 | 78 | 95 | 100 |
| MARK2 | 73 | 99 | 89 |
| MARK3 | 53 | 94 | 100 |
| MARK4 | 100 | 86 | 97 |
| MAST1 | 81 | 56 | 82 |
| MEK1 | 100 | 100 | 100 |
| MEK2 | 76 | 88 | 97 |
| MEK3 | 81 | 100 | 96 |
| MEK4 | 98 | 100 | 97 |
| MEK5 | 1 | 1 | 21 |
| MEK6 | 86 | 89 | 100 |
| MELK | 9 | 98 | 91 |
| MERTK | 0 | 3 | 100 |
| MET | 18 | 47 | 100 |
| MET (M1250T) | 32 | 28 | 91 |
| MET (Y1235D) | 61 | 59 | 82 |
| MINK | 2 | 44 | 87 |
| MKK7 | 90 | 100 | 99 |
| MKNK1 | 47 | 100 | 100 |
| MKNK2 | 2 | 78 | 100 |
| MLCK | 90 | 91 | 100 |
| MLK1 | 3 | 35 | 100 |
| MLK2 | 29 | 48 | 94 |
| MLK3 | 1 | 14 | 94 |
| MRCKA | 96 | 91 | 100 |
| MRCKB | 99 | 94 | 100 |
| MST1 | 27 | 84 | 100 |
| MST1R | 32 | 87 | 97 |
| MST2 | 5 | 100 | 85 |
| MST3 | 62 | 86 | 100 |
| MST4 | 55 | 91 | 100 |
| MTOR | 77 | 66 | 91 |
| MUSK | 1 | 21 | 63 |
| MYLK | 64 | 100 | 100 |
| MYLK2 | 6 | 40 | 100 |
| MYLK4 | 86 | 92 | 100 |
| MYO3A | 14 | 88 | 100 |
| MYO3B | 35 | 81 | 92 |
| NDR1 | 56 | 98 | 83 |
| NDR2 | 23 | 84 | 98 |
| NEK1 | 52 | 96 | 100 |
| NEK10 | 100 | 100 | 100 |
| NEK11 | 13 | 100 | 100 |
| NEK2 | 80 | 100 | 100 |
| NEK3 | 64 | 86 | 96 |
| NEK4 | 9 | 61 | 100 |
| NEK5 | 2 | 86 | 100 |
| NEK6 | 65 | 88 | 100 |
| NEK7 | 71 | 82 | 100 |
| NEK9 | 6 | 86 | 100 |
| NIK | 91 | 85 | 97 |
| NIM1 | 92 | 100 | 100 |
| NLK | 24 | 15 | 50 |
| OSR1 | 88 | 100 | 100 |
| p38-alpha | 0 | 7 | 14 |
| p38-beta | 0 | 6 | 88 |
| p38-delta | 16 | 78 | 100 |
| p38-gamma | 18 | 55 | 100 |
| PAK1 | 89 | 87 | 100 |
| PAK2 | 64 | 54 | 100 |
| PAK3 | 85 | 95 | 83 |
| PAK4 | 85 | 98 | 100 |
| PAK6 | 66 | 84 | 97 |
| PAK7 | 100 | 100 | 100 |
| PCTK1 | 93 | 100 | 100 |

TABLE 3-continued

| DiscoveRx Gene Symbol (enzyme identification gene) | Example 1 | Example 12 | Example 78 |
|---|---|---|---|
| | Concentration | | |
| | 1 uM | 1 uM | 1 uM |
| | Percent Control (%) | | |
| PCTK2 | 19 | 98 | 100 |
| PCTK3 | 60 | 84 | 100 |
| PDGFRA | 1 | 4 | 29 |
| PDGFRB | 0 | 1 | 0 |
| PDPK1 | 50 | 93 | 92 |
| PFCDPK1 (*P. falciparum*) | 1 | 55 | 97 |
| PFPK5 (*P. falciparum*) | 87 | 100 | 93 |
| PFTAIRE2 | 6 | 75 | 100 |
| PFTK1 | 11 | 87 | 100 |
| PHKG1 | 85 | 84 | 88 |
| PHKG2 | 72 | 89 | 100 |
| PIK3C2B | 100 | 91 | 100 |
| PIK3C2G | 75 | 100 | 100 |
| PIK3CA | 99 | 100 | 100 |
| PIK3CA (C420R) | 97 | 100 | 100 |
| PIK3CA (E542K) | 100 | 100 | 100 |
| PIK3CA (E545A) | 87 | 79 | 100 |
| PIK3CA (E545K) | 81 | 77 | 92 |
| PIK3CA (H1047L) | 100 | 100 | 92 |
| PIK3CA (H1047Y) | 74 | 84 | 100 |
| PIK3CA (I800L) | 80 | 75 | 92 |
| PIK3CA (M1043I) | 90 | 100 | 100 |
| PIK3CA (Q546K) | 83 | 100 | 89 |
| PIK3CB | 92 | 100 | 100 |
| PIK3CD | 89 | 100 | 100 |
| PIK3CG | 100 | 100 | 100 |
| PIK4CB | 88 | 100 | 99 |
| PIKFYVE | 84 | 65 | 91 |
| PIM1 | 82 | 92 | 100 |
| PIM2 | 100 | 91 | 100 |
| PIM3 | 88 | 90 | 100 |
| PIP5K1A | 94 | 84 | 98 |
| PIP5K1C | 88 | 71 | 92 |
| PIP5K2B | 82 | 100 | 79 |
| PIP5K2C | 97 | 73 | 95 |
| PKAC-alpha | 35 | 93 | 100 |
| PKAC-beta | 34 | 87 | 98 |
| PKMYT1 | 93 | 98 | 90 |
| PKN1 | 78 | 82 | 83 |
| PKN2 | 83 | 83 | 89 |
| PKNB (*M. tuberculosis*) | 95 | 100 | 97 |
| PLK1 | 77 | 100 | 100 |
| PLK2 | 84 | 100 | 62 |
| PLK3 | 77 | 100 | 92 |
| PLK4 | 79 | 85 | 100 |
| PRKCD | 61 | 81 | 100 |
| PRKCE | 67 | 71 | 90 |
| PRKCH | 100 | 100 | 100 |
| PRKCI | 51 | 66 | 69 |
| PRKCQ | 53 | 87 | 85 |
| PRKD1 | 54 | 94 | 100 |
| PRKD2 | 41 | 98 | 95 |
| PRKD3 | 43 | 96 | 88 |
| PRKG1 | 94 | 86 | 100 |
| PRKG2 | 75 | 90 | 100 |
| PRKR | 80 | 89 | 100 |
| PRKX | 93 | 97 | 78 |
| PRP4 | 89 | 95 | 100 |
| PYK2 | 4 | 29 | 100 |
| QSK | 89 | 97 | 100 |
| RAF1 | 11 | 42 | 100 |
| RET | 0 | 1 | 97 |
| RET (M918T) | 0 | 0 | 100 |
| RET (V804L) | 0 | 2 | 100 |
| RET (V804M) | 0 | 1 | 100 |
| RIOK1 | 77 | 91 | 100 |
| RIOK2 | 88 | 100 | 100 |
| RIOK3 | 94 | 96 | 95 |
| RIPK1 | 0 | 5 | 19 |
| RIPK2 | 7 | 22 | 99 |
| RIPK4 | 13 | 100 | 100 |
| RIPK5 | 41 | 100 | 79 |
| ROCK1 | 89 | 100 | 100 |
| ROCK2 | 15 | 100 | 100 |
| ROS1 | 39 | 51 | 92 |
| RPS6KA4 (Kin.Dom.1-N-terminal) | 31 | 85 | 94 |
| RPS6KA4 (Kin.Dom.2-C-terminal) | 94 | 100 | 78 |
| RPS6KA5 (Kin.Dom.1-N-terminal) | 38 | 99 | 100 |
| RPS6KA5 (Kin.Dom.2-C-terminal) | 69 | 94 | 100 |
| RSK1 (Kin.Dom.1-N-terminal) | 60 | 79 | 100 |
| RSK1 (Kin.Dom.2-C-terminal) | 64 | 69 | 95 |
| RSK2 (Kin.Dom.1-N-terminal) | 35 | 100 | 99 |
| RSK2 (Kin.Dom.2-C-terminal) | 93 | 94 | 81 |
| RSK3 (Kin.Dom.1-N-terminal) | 29 | 65 | 97 |
| RSK3 (Kin.Dom.2-C-terminal) | 61 | 86 | 100 |
| RSK4 (Kin.Dom.1-N-terminal) | 81 | 93 | 93 |
| RSK4 (Kin.Dom.2-C-terminal) | 59 | 68 | 98 |
| S6K1 | 14 | 100 | 100 |
| SBK1 | 89 | 94 | 100 |
| SGK | 93 | 100 | 96 |
| SgK110 | 95 | 81 | 100 |
| SGK2 | 84 | 100 | 100 |
| SGK3 | 97 | 100 | 78 |
| SIK | 0 | 5 | 25 |
| SIK2 | 44 | 58 | 53 |
| SLK | 0 | 5 | 11 |
| SNARK | 73 | 100 | 68 |
| SNRK | 84 | 100 | 95 |
| SRC | 0 | 1 | 73 |
| SRMS | 8 | 75 | 94 |
| SRPK1 | 3 | 69 | 97 |
| SRPK2 | 97 | 87 | 100 |
| SRPK3 | 82 | 100 | 100 |
| STK16 | 38 | 70 | 99 |
| STK33 | 5 | 40 | 100 |
| STK35 | 33 | 58 | 100 |
| STK36 | 1 | 89 | 100 |
| STK39 | 97 | 87 | 89 |
| SYK | 2 | 12 | 78 |
| TAK1 | 0 | 14 | 76 |
| TAOK1 | 51 | 100 | 89 |
| TAOK2 | 14 | 25 | 100 |
| TAOK3 | 1 | 61 | 99 |
| TBK1 | 68 | 84 | 100 |
| TEC | 0 | 8 | 100 |
| TESK1 | 26 | 81 | 100 |
| TGFBR1 | 85 | 85 | 100 |
| TGFBR2 | 24 | 94 | 100 |
| TIE1 | 2 | 26 | 27 |
| TIE2 | 0 | 0 | 16 |
| TLK1 | 93 | 75 | 96 |
| TLK2 | 86 | 97 | 100 |
| TNIK | 11 | 17 | 88 |
| TNK1 | 0 | 19 | 100 |
| TNK2 | 2 | 28 | 100 |
| TNNI3K | 0 | 25 | 93 |
| TRKA | 0 | 1 | 100 |
| TRKB | 0 | 16 | 89 |
| TRKC | 0 | 3 | 96 |
| TRPM6 | 100 | 87 | 87 |
| TSSK1B | 95 | 61 | 100 |
| TSSK3 | 95 | 100 | 100 |
| TTK | 12 | 70 | 100 |
| TXK | 1 | 3 | 91 |
| TYK2 (JH1domain-catalytic) | 9 | 96 | 97 |
| TYK2 (JH2domain-pseudokinase) | 100 | 100 | 100 |
| TYRO3 | 21 | 42 | 95 |
| ULK1 | 68 | 100 | 100 |
| ULK2 | 62 | 100 | 90 |
| ULK3 | 1 | 91 | 100 |
| VEGFR2 | 5 | 55 | 63 |
| VPS34 | 100 | 96 | 80 |
| VRK2 | 86 | 100 | 100 |
| WEE1 | 92 | 90 | 100 |
| WEE2 | 60 | 80 | 100 |
| WNK1 | 55 | 100 | 92 |

TABLE 3-continued

| DiscoveRx Gene Symbol (enzyme identification gene) | Example 1 | Example 12 | Example 78 |
|---|---|---|---|
| | Concentration | | |
| | 1 uM | 1 uM | 1 uM |
| | Percent Control (%) | | |
| WNK2 | 82 | 100 | 100 |
| WNK3 | 85 | 100 | 100 |
| WNK4 | 96 | 100 | 100 |
| YANK1 | 69 | 98 | 84 |
| YANK2 | 100 | 99 | 100 |
| YANK3 | 74 | 81 | 99 |
| YES | 1 | 2 | 100 |
| YSK1 | 90 | 86 | 100 |
| YSK4 | 2 | 2 | 71 |
| ZAK | 1 | 1 | 19 |
| ZAP70 | 26 | 100 | 96 |

As shown in Table 3, the compounds of Examples 1, 12, and 78 of the present invention were confirmed to have the % control of less than 35 for ABL1 (E255K)-phosphorylated, ABL1 (F317I)-nonphosphorylated, ABL1 (F317I)-phosphorylated, ABL1 (F317L)-nonphosphorylated, ABL1 (F317L)-phosphorylated, ABL1 (H396P)-nonphosphorylated, ABL1 (H396P)-phosphorylated, ABL1 (M351T)-phosphorylated, ABL1 (Q252H)-nonphosphorylated, ABL1 (Q252H)-phosphorylated, ABL1 (T315I)-nonphosphorylated, ABL1 (T315I)-phosphorylated, ABL1 (Y253F)-phosphorylated, ABL1-nonphosphorylated, ABL1-phosphorylated, ABL2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR (E746-A750del), EGFR (G719C), EGFR (G719S), EGFR (L747-E749del, A750P), EGFR (L747-S752del, P753S), EGFR (L747-T751del, Sins), EGFR (L858R), EGFR (L858R,T790M), EGFR (L861Q), EGFR(S752-I759del), EGFR (T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3 (G697C), FGFR4, FGR, FLT1, FLT3, FLT3 (D835H), FLT3 (D835V), FLT3 (D835Y), FLT3 (ITD), FLT3 (ITD,D835V), FLT3 (ITD,F691L), FLT3 (K663Q), FLT3 (N841I), FLT3 (R834Q), FLT4, FRK, FYN, GAK, GCN2 (Kin.Dom.2,S808G), HCK, HIPK4, HPK1, IKK-alpha, IKK-beta, IRAK1, IRAK4, ITK, JAK1 (JH1domain-catalytic), JAK2 (JH1domain-catalytic), JAK3 (JH1domain-catalytic), JNK1, JNK2, JNK3, KIT, KIT (A829P), KIT (D816H), KIT (D816V), KIT (L576P), KIT (V559D), KIT (V559D,T670I), KIT (V559D,V654A), LCK, LIMK1, LIMK2, LOK, LRRK2, LRRK2 (G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1 (*P. falciparum*), PFTAIRE2, PFTK1, PKAC-alpha, PKAC-beta, PYK2, RAF1, RET, RET (M918T), RET (V804L), RET (V804M), RIPK1, RIPK2, RIPK4, ROCK2, RPS6KA4 (Kin.Dom.1-N-terminal), RSK2 (Kin.Dom.1-N-terminal), RSK3 (Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, and ZAP70. This indicates that the compounds of examples of the present invention have an inhibitory activity against the enzymes listed above, suggesting that the compounds can be effectively used for the treatment of the diseases related to the enzymes above.

Since the compounds of the present invention have an excellent selectivity for cancer cell-associated kinases ABL1 (E255K)-phosphorylated, ABL1 (F317I)-nonphosphorylated, ABL1 (F317I)-phosphorylated, ABL1 (F317L)-nonphosphorylated, ABL1 (F317L)-phosphorylated, ABL1 (H396P)-nonphosphorylated, ABL1 (H396P)-phosphorylated, ABL1 (M351T)-phosphorylated, ABL1 (Q252H)-nonphosphorylated, ABL1 (Q252H)-phosphorylated, ABL1 (T315I)-nonphosphorylated, ABL1 (T315I)-phosphorylated, ABL1 (Y253F)-phosphorylated, ABL1-nonphosphorylated, ABL1-phosphorylated, ABL2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR (E746-A750del), EGFR (G719C), EGFR (G719S), EGFR (L747-E749del, A750P), EGFR (L747-S752del, P753S), EGFR (L747-T751del,Sins), EGFR (L858R), EGFR (L858R, T790M), EGFR (L861Q), EGFR(S752-I759del), EGFR (T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3 (G697C), FGFR4, FGR, FLT1, FLT3, FLT3 (D835H), FLT3 (D835V), FLT3 (D835Y), FLT3 (ITD), FLT3 (ITD,D835V), FLT3 (ITD,F691L), FLT3 (K663Q), FLT3 (N841I), FLT3 (R834Q), FLT4, FRK, FYN, GAK, GCN2 (Kin.Dom.2,S808G), HCK, HIPK4, HPK1, IKK-alpha, IKK-beta, IRAK1, IRAK4, ITK, JAK1 (JH1 domain-catalytic), JAK2 (JH1 domain-catalytic), JAK3 (JH1domain-catalytic), JNK1, JNK2, JNK3, KIT, KIT (A829P), KIT (D816H), KIT (D816V), KIT (L576P), KIT (V559D), KIT (V559D,T670I), KIT (V559D,V654A), LCK, LIMK1, LIMK2, LOK, LRRK2, LRRK2 (G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1 (*P. falciparum*), PFTAIRE2, PFTK1, PKAC-alpha, PKAC-beta, PYK2, RAF1, RET, RET (M918T), RET (V804L), RET (V804M), RIPK1, RIPK2, RIPK4, ROCK2, RPS6KA4 (Kin.Dom.1-N-terminal), RSK2 (Kin.Dom.1-N-terminal), RSK3 (Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, and ZAP70 and at the same time have a significant inhibitory activity, the compounds of the invention can be effectively used as an active ingredient of a pharmaceutical composition for the prevention or treatment of the diseases related to the enzymes above and further cancer as well.

In the meantime, the excellent activity to inhibit Src and Fyn, among the enzymes above, indicates that the compounds of the present invention can be efficiently used for the treatment of Src and Fyn related diseases, preferably diabetic nephropathy. Thus, the compounds of the present invention can be effectively used as an active ingredient of a pharmaceutical composition for the prevention or treatment of diabetic nephropathy.

<Experimental Example 2> Evaluation of Cancer Cell Proliferation Inhibition (Cancer Cell Apoptosis) Activity The following experiment was performed to evaluate the cancer cell proliferation inhibition (cancer cell apoptosis) activity of the compound of the present invention.

MTS assay was performed to evaluate the cancer cell proliferation inhibition (cancer cell apoptosis) effect of the compounds of examples of the present invention. Particularly, the assay was performed using the cancer cell lines GIST-T1, GIST-T1/816, GIST-430, GIST-430/654, GIST-R1, GIST-R3, M-NFS-60, RetParental (Ba/F3), Retwt (Ba/F3), RetV804M (Ba/F3), RET (LC2/ad-CDC6), FYN (MCP-1), FYN (FN), MDA-MB-231, Huh7, K562, T315I (Ba/F3), SK-MEL-28 and A375. Cell culture was performed using a medium suitable for each cell line.

More precisely, GIST-T1 (imatinib-sensitive, p.V560_Y578del (exon 11)), GIST-T1/816 (imatinib-resistant, p.V560_Y578del (exon 11), p.D816E (exon 17)), GIST-430 (imatinib-sensitive, p.V560_L576del (exon 11)), GIST-430/654 (imatinib-resistant, p.V560_L576del (exon 11), p.V654A (exon 13)) cell lines were seeded in each well of a 96-well flat bottom plate (SPL Life Sciences) at the density of $2\times10^4/100$ μl, while the GIST patient originated cell lines GIST-R1 (imatinib-resistant, p.W557_K558del (exon 11)) and GIST-R3 (imatinib/sunitinib-resistant, p.558_560KVV>1 (exon 11), p.Y823D (exon 17)) were seeded in each well of a 96-well white plate (Corning) at the density of $2\times10^4/100$ μl. On the next day, the compounds of examples of the present invention were treated thereto at 8 different concentrations. 72 hours later, cell survival rate was measured by using EZ-cytox cell viability kit (DAEIL Lab, Seoul, Korea) or CellTiter-Glo Luminescent cell viability assay (Promega) according to the manufacturer's protocol. Each experiment was performed twice independently. Data were presented as % by the vehicle treated cells and $IC_{50}$ values were calculated by using GraphPad Prism 5.0 software (GraphPad software Inc., San Diego).

M-NFS-60 cell line was cultured in the complete growth medium prepared by adding 10% FBS, 0.05 mM 2-mercaptoethanol and 62 ng of human M-CSF to RPMI. When the confluence reached 80% in T-75 flask, the cells were collected in a 50 ml tube for seeding, followed by centrifugation at 800 rpm for 5 minutes. The cells were suspended in 10 mL of growth medium. The cell number was counted by using a hematocytometer to determine the necessary cell number and the medium volume for seeding. The cells were seeded in a 96-well plate at the density of 20000 cells/well (200 μL/well), followed by stabilization in a 37° C. $CO_2$ incubator, while the compounds of the present invention were prepared. The compounds of the present invention were serially diluted with DMSO at the ratio of 1/3 with setting the maximum concentration at 1968 nM, which were loaded in a new V-bottom 96-well plate, resulting in the preparation of total 11 concentrations including the DMSO control. The cells that had been placed in the incubator were taken out, to which the compounds of the present invention were added (2 μl/well). The plate treated with the compounds was cultured in a 37° C. $CO_2$ incubator for 72 hours.

72 hours later, the plate treated with the compounds was taken out, to which CCK-8 solution was treated (20 μl/well). After well mixing, the plate was further cultured in a 37° C. $CO_2$ incubator for 2 hours. Then, $OD_{450}$ was measured by using a microplate reader. To obtain accurate results, the wells displaying bubbles were eliminated from the measurement.

In the meantime, MDA-MB-231 and A375 cells were seeded in a 96well plate at the density of $2\times10^3/100$ μl/well, which stood for a day for attachment. The culture fluid was eliminated. After removing the culture medium, the medium was replaced with the culture medium containing the compounds of the present invention at 3-times serially diluted 9 concentrations (0.0015-10 μM) and the DMSO control, followed by incubation in a 37° C. $CO_2$ incubator for 72 hours. On the other hand, K-562 and Ba/F3-T315I cells were seeded in a 96-well plate at the density of $1\times10^4/90$ μl/well. The plate containing K-562 cells was added with the culture medium containing the compounds of the present invention at 3-times serially diluted 9 concentrations (0.015-100 μM) and the DMSO control (10 μl/well). The plate containing Ba/F3-T315I cells was added with the culture medium containing the compounds of the present invention at 5-times serially diluted 9 concentrations (0.000256-100 μM) and the DMSO control (10 μl/well). The final concentration was made 0-10 μM and then the cells were cultured in a 37° C. $CO_2$ incubator for 72 hours.

The real time cell proliferation of MDA-MB-231 was measured for 72 hours by using IncuCyte ZOOM® analyzer software and then $IC_{50}$ was calculated using GraphPad Prism 6 software.

A375, K-562 and Ba/F3-T315I cells were added with CCK-8 solution at the concentration of 10 μl/well, followed by orbital shaking for 30 seconds. Then, the cells were cultured in a 37° C. $CO_2$ incubator for 2 hours. $OD_{450}$ was measured by using a microplate reader. The OD value of the well treated with the culture medium and CCK-8 solution alone was subtracted from the OD value measured above, followed by calculation of $IC_{50}$ using GraphPad Prism 6 software.

Other cell lines were seeded in a 96-well plate containing the corresponding medium appropriate for each cell line at the density of 3,000 cells/well, followed by culture in a 5% $CO_2$ and 37° C. incubator for 24 hours. The compounds of examples of the present invention were added to each well at the concentration of from the highest volume of 50 μM to every step of serial dilution. The solvent control, dimethylsulfoxide (DMSO), was treated at the same concentration of 0.05% (v/v) as the volume used for the treatment of the compounds above. Each cell line was cultured for 72 hours. To investigate the cell viability, the MTS and PMS (phenazine methosulfate) mixture provided in CellTiter 96® AQuous Non-Radioactive Cell Proliferation Assay Kit (Promega) was added to each cell culture medium, followed by additional culture at 37° C. for 2 hours. Then, $OD_{450}$ was measured. Based on OD of the solvent control cells not treated with any compounds of the present invention, the cell proliferation inhibition rate was calculated according to the treatment concentration of each compound. At this time, the concentration of each compound that was able to inhibit cancer cell proliferation up to 50% was determined as $IC_{50}$ (uM). $IC_{50}$ of each compound was determined with three data sets and calculated by using Prism softwater (version 6.01, GraphPad).

The results of the experiments on each cell line described above are shown in Tables 4, 5 and 6, respectively.

TABLE 4

| Example | GIST-T1 (nM) | GIST-T1/816 (nM) | GIST430 (nM) | GIST430/654 (nM) | GIST-R1 (nM) | GIST-R3 (nM) | M-NFS-60 (nM) |
|---|---|---|---|---|---|---|---|
| 1 | 1.90 | 35.4 | 36.8 | 332.1 | | | 64.57 |
| 2 | | | | | | | |
| 3 | | | | | | | 8.22 |
| 4 | | | | | | | |
| 5 | | | | | | | |
| 6 | | | | | | | 6.82 |
| 7 | | | | | | | |
| 8 | | | | | | | 34.14 |
| 9 | 3.90 | 265.2 | — | — | | | |
| 10 | | | | | | | 169.80 |
| 11 | 0.80 | 40.7 | 63.6 | 560.0 | | | 30.84 |
| 12 | 12.30 | 307.5 | 56.3 | 563.9 | | | 247.40 |
| 13 | | | | | | | 46.37 |
| 14 | | | | | | | 198.40 |
| 15 | | | | | | | |
| 16 | | | | | | | |
| 17 | | | | | | | |
| 18 | | | | | | | |
| 19 | | | | | | | 240.00 |
| 20 | | | | | | | 1055.00 |
| 21 | | | | | | | |
| 22 | | | | | | | 56.22 |
| 23 | | | | | | | |
| 24 | | | | | | | |
| 25 | | | | | | | |
| 26 | | | | | | | 119.20 |
| 27 | | | | | | | 56.87 |
| 28 | 11.30 | 122.0 | 43.1 | 382.2 | | | 70.79 |
| 29 | | | | | | | |
| 30 | | | | | | | |
| 31 | | | | | | | 63.57 |
| 32 | | | | | | | 64.15 |
| 33 | | | | | | | 32.09 |
| 34 | | | | | | | |
| 35 | | | | | | | |
| 36 | | | | | | | 7.76 |
| 37 | | | | | | | |
| 38 | | | | | | | |
| 39 | | | | | | | |
| 40 | | | | | | | |
| 41 | 0.10 | 45.0 | — | — | | | |
| 42 | | | | | | | |
| 43 | | | | | | | |
| 44 | | | | | | | 38.77 |
| 45 | | | | | | | |
| 46 | | | | | | | |
| 47 | | | | | | | 43.80 |
| 48 | | | | | | | |
| 49 | | | | | | | |
| 50 | | | | | | | 40.32 |
| 51 | | | | | | | 31.07 |
| 52 | | | | | | | |
| 53 | | | | | | | |
| 54 | | | | | | | |
| 55 | | | | | | | |
| 56 | | | | | | | |
| 57 | 0.13 | 23.7 | 22.1 | 86.5 | | | 19.81 |
| 58 | | | | | | | |
| 59 | 17.40 | 86.1 | 67.8 | 420.7 | | | 32.54 |
| 60 | | | | | | | 21.32 |
| 61 | | | | | | | 45.34 |
| 62 | 19.40 | 284.3 | 75.2 | 269.8 | | | 103.20 |
| 63 | | | | | | | 71.05 |
| 64 | | | | | | | 127.40 |
| 65 | | | | | | | |
| 66 | | | | | | | 62.70 |
| 67 | | | | | | | 19.36 |
| 69 | 2.90 | 60.6 | 145.3 | 350.0 | | | |
| 70 | | | | | | | 12.28 |
| 71 | | | | | | | |
| 72 | 1.00 | 58.5 | 69.7 | 534.3 | | | 22.48 |
| 73 | | | | | | | |
| 74 | | | | | | | 21.38 |
| 75 | 16.93 | 360.4 | 120.5 | 2083.0 | | | |
| 76 | 455.5 | 13093 | 558.7 | 6997 | 25411 | 328.4 | |
| 77 | | | | | | | 180.30 |
| 78 | | | | | | | 671.6 |

TABLE 4-continued

| Example | GIST-T1 (nM) | GIST-T1/816 (nM) | GIST430 (nM) | GIST430/654 (nM) | GIST-R1 (nM) | GIST-R3 (nM) | M-NFS-60 (nM) |
|---|---|---|---|---|---|---|---|
| 79 | | | | | | | |
| 80 | | | | | | | 46.05 |
| 81 | | | | | | | |
| 82 | | | | | | | |
| 83 | | | | | | | |
| 84 | | | | | | | 1612.00 |
| 85 | | | | | | | |

TABLE 5

| Example | Ret$^{Parental}$ (Ba/F3) (μM) | Ret$^{wt}$ (Ba/F3) (μM) | Ret$^{V804M}$ (Ba/F3) (μM) | RET (LC2/ad-CDC6) (uM) | FYN (MCP-1) (μM) | FYN (FN) (μM) |
|---|---|---|---|---|---|---|
| 1 | 1.209 | 0.003 | 0.005 | <0.01 | 0.73 | |
| 2 | — | — | — | | | |
| 3 | — | 0.251 | 0.737 | | | |
| 4 | — | 1.913 | — | | | |
| 5 | — | 0.35 | 2.381 | | | |
| 6 | — | 12.84 | — | | | |
| 7 | 7.499 | 0.798 | 1.915 | | | |
| 8 | 1.316 | 0.002 | 0.01 | | <1 | <1 |
| 9 | 3.883 | 0.005 | 0.019 | | 0.73 | <1 |
| 10 | 2.525 | 0.004 | 0.023 | | <0.1 | <0.1 |
| 11 | 2.401 | 0.005 | 0.098 | | <0.1 | <0.1 |
| 12 | — | 0.017 | 0.054 | <0.1 | <0.1 | <0.1 |
| 13 | — | 0.016 | 0.172 | <0.1 | <1 | <1 |
| 14 | 1.834 | 0.009 | 0.022 | <0.1 | <0.1 | <0.1 |
| 15 | 2.159 | 0.006 | 0.018 | >0.01 | <0.1 | <0.1 |
| 16 | — | 0.32 | 13.03 | <1 | <10 | <10 |
| 17 | — | 0.434 | — | | <10 | <10 |
| 18 | — | 19.4 | — | | <10 | <10 |
| 19 | | | | <10 | — | |
| 20 | | | | <0.1 | 1.33 | |
| 21 | | | | <0.1 | — | |
| 22 | | | | <0.01 | 0.32 | |
| 23 | | | | <0.01 | 0.27 | |
| 24 | | | | <1 | — | |
| 25 | | | | <1 | — | |
| 26 | | | | <0.1 | 3.13 | |
| 27 | | | | <1 | 1.50 | |
| 28 | | | | >0.01 | 0.36 | |
| 29 | | | | <0.1 | 3.13 | |
| 30 | | | | 0.1 | 7.79 | |
| 31 | | | | | 0.77 | |
| 32 | | | | | 0.89 | |
| 33 | | | | | 2.04 | |
| 34 | | | | | 9.83 | |
| 35 | | | | | 1.12 | |
| 36 | | | | | | |
| 37 | | | | | | |
| 38 | | | | | | |
| 39 | | | | | | |
| 40 | | | | 0.01 | | |
| 41 | | | | >0.01 | | |
| 42 | | | | >0.01 | | |
| 43 | | | | >0.01 | | |
| 44 | | | | 0.01 | | |
| 45 | | | | >0.01 | | |
| 46 | | | | >0.01 | | |
| 47 | | | | >0.01 | | |
| 48 | | | | >0.01 | | |
| 49 | | | | >0.01 | | |
| 50 | | | | >0.01 | | |
| 51 | | | | >0.01 | | |
| 52 | | | | >0.01 | 9.52 | |
| 53 | | | | >0.01 | | |
| 54 | | | | >0.01 | | |
| 55 | | | | >0.01 | 5.60 | |
| 56 | | | | >0.01 | | |
| 57 | | | | <0.01 | | |
| 58 | | | | | 0.32 | |
| 59 | | | | >0.01 | 0.16 | |
| 60 | | | | >0.01 | 1.47 | |

TABLE 5-continued

| Example | Ret^Parental (Ba/F3) (μM) | Ret^wt (Ba/F3) (μM) | Ret^V804M (Ba/F3) (μM) | RET (LC2/ad-CDC6) (uM) | FYN (MCP-1) (μM) | FYN (FN) (μM) |
|---|---|---|---|---|---|---|
| 61 | | | | >0.01 | 1.17 | |
| 62 | | | | >0.01 | | |
| 63 | | | | >0.01 | | |
| 64 | | | | >0.01 | | |
| 65 | | | | >0.01 | | |
| 66 | | | | | | |
| 67 | | | | | | |
| 69 | | | | | | |
| 70 | | | | | | |
| 71 | | | | | | |
| 72 | | | | | | |
| 73 | | | | | | |
| 74 | | | | | | |
| 75 | | | | | | |
| 76 | | | | | | |
| 77 | | | | >0.01 | 5.08 | |
| 78 | | | | <10 | — | |
| 79 | | | | | | |
| 80 | | | | | 1.87 | |
| 81 | | | | >0.01 | | |
| 82 | | | | <0.1 | 1.52 | |
| 83 | | | | 1 | — | |
| 84 | | | | 1 | — | |
| 85 | | | | >0.01 | | |

TABLE 6

| Example | MDA-MB-231 (μM) | Huh7 (μM) | K562 (μM) | T315I (Ba/F3) (nM) | SK-MEL-28 (μM) | A375 (μM) |
|---|---|---|---|---|---|---|
| 1 | 0.187 | 0.065 | <0.001 | 26 | 0.334 | 0.026 |
| 2 | >10 | >50 | 0.012 | >10,000 | >10 | >10 |
| 3 | >10 | 2.344 | <0.001 | 164 | >10 | >10 |
| 4 | >10 | 6.017 | <0.001 | >10,000 | >10 | >10 |
| 5 | >10 | 6.189 | 0.056 | 1212 | 1.215 | >10 |
| 6 | >10 | 6.261 | 0.004 | 8444 | >10 | >10 |
| 7 | >10 | 4.796 | 0.002 | >10,000 | 6.209 | 6.209 |
| 8 | 0.096 | 0.255 | <0.001 | 32 | 0.586 | 0.052 |
| 9 | 0.332 | 0.075 | <0.001 | 40.7 | 1.091 | 0.312 |
| 10 | 0.288 | 0.127 | <0.001 | 37.1 | 0.792 | 0.259 |
| 11 | 0.679 | 1.224 | <0.001 | 6.34 (138.9) | 1.462 | 1.252 |
| 12 | 1.19 | 0.147 | <0.001 | 6.72 (43.3) | >10 | 0.942 |
| 13 | 1.584 | 0.309 | <0.001 | 7.06 (106.6) | 2.223 | 1.505 |
| 14 | 0.624 | 0.0537 | 0.007 | 135.3 | 1.442 | 0.39 |
| 15 | 0.569 | 0.067 | 0.003 | 47.4 | 1.167 | 0.297 |
| 16 | 1.619 | 9.862 | 0.076 | 54.45 | 1.836 | >10 |
| 17 | 9.485 | 2.856 | 0.085 | 1465 | 1.705 | >10 |
| 18 | 8.377 | 3.064 | 0.097 | >10000 | | >10 |
| 19 | 3.187 | 15.15 | 0.131 | 785 | 3.721 | 4.078 |
| 20 | 1.555 | 1.747 | 0.014 | 234 | 1.45 | 3.363 |
| 21 | 1.648 | 1.85 | 0.015 | 149 | 1.478 | 1.846 |
| 22 | 0.318 | 0.091 | <0.001 | 37.5 | 0.803 | 0.140 |
| 23 | 0.342 | 0.0738 | <0.001 | 39 | 0.917 | 0.142 |
| 24 | 3.605 | 11.3 | 0.045 | 668 | 2.632 | 3.523 |
| 25 | 3.035 | 17.28 | 0.052 | 619 | 2.089 | 3.711 |
| 26 | 1.297 | 0.024 | <0.001 | 158 | 1.923 | 0.830 |
| 27 | 3.058 | 2.02 | <0.001 | 60.2 | >10 | 4.457 |
| 28 | 0.339 | 0.119 | 0.002 | 100 | 0.722 | 0.154 |
| 29 | 0.963 | 0.03 | 0.005 | 102 | 0.717 | 0.292 |
| 30 | 1.384 | 0.017 | <0.001 | 126 | 1.112 | 0.758 |
| 31 | 0.212 | 0.064 | <0.001 | 54.2 | 0.482 | 0.152 |
| 32 | 0.456 | 0.107 | <0.001 | 60.4 | 1.15 | 0.406 |
| 33 | 0.444 | 0.082 | <0.001 | 156 | | 0.452 |
| 34 | 1.008 | 0.07 | <0.001 | 831 | | 0.903 |
| 35 | 1.111 | 0.066 | <0.001 | 247 | | 1.28 |
| 36 | >10 | 0.145 | 0.006 | >10000 | | >10 |
| 37 | >10 | 1.804 | 0.002 | 663 | | >10 |
| 38 | 0.77 | 0.247 | 0.019 | 133 | | 0.668 |
| 39 | 1.46 | 0.457 | 0.043 | 238 | | 1.525 |
| 40 | 0.23 | 0.101 | 0.008 | 33.5 | | 0.097 |
| 41 | 0.51 | 0.067 | 0.010 | 39.8 | | 0.303 |
| 42 | 0.32 | 0.100 | 0.008 | 122 | | 0.163 |

TABLE 6-continued

| Example | MDA-MB-231 (µM) | Huh7 (µM) | K562 (µM) | T315I (Ba/F3) (nM) | SK-MEL-28 (µM) | A375 (µM) |
|---|---|---|---|---|---|---|
| 43 | 0.19 | 0.098 | 0.016 | 59.7 | | 0.341 |
| 44 | 0.24 | 0.165 | 0.012 | 42.2 | | 0.183 |
| 45 | 0.816 | | 0.002 | 145 | | 0.720 |
| 46 | 0.273 | | 0.007 | 6.27 (202) | | 0.250 |
| 47 | 0.168 | | <0.001 | 25 | | 0.152 |
| 48 | 0.382 | | <0.001 | 86.3 | | 0.406 |
| 49 | 0.513 | | 0.005 | 217 | | 1.024 |
| 50 | 0.325 | 0.057 | <0.001 | 28.2 | | 0.224 |
| 51 | 0.3187 | 0.0878 | <0.001 | 28.8 | | 0.249 |
| 52 | >10 | | 0.016 | 195 | | >10 |
| 53 | 0.324 | | <0.001 | 2.67 (143) | | 0.285 |
| 54 | 0.3878 | | <0.001 | 30.9 | | 0.454 |
| 55 | 0.755 | | <0.001 | 97.5 | | 0.791 |
| 56 | >10 | | <0.001 | 1143 | | >10 |
| 57 | 0.074 | 0.011 | <0.001 | 19.8 | | 0.106 |
| 58 | 1.298 | | 0.008 | 32.6 | | 1.388 |
| 59 | 0.431 | | <0.001 | 11.7 | | 0.4042 |
| 60 | 0.289 | | <0.001 | 34.8 | | 0.229 |
| 61 | 0.268 | | <0.001 | 58.6 | | 0.172 |
| 62 | >10 | | 0.004 | 308 | | 3.402 |
| 63 | 1.411 | | <0.001 | 374 | | 1.334 |
| 64 | 0.987 | | 0.003 | 75 | | 0.741 |
| 65 | 0.219 | 0.033 | <0.0015 | | | 0.221 |
| 66 | 0.386 | | <0.0015 | 170 | | |
| 67 | 0.4289 | 0.919 | <0.0015 | 40.1 | | |
| 69 | 0.301 | 0.025 | <0.0015 | 30.4 | 2.90 | 60.6 |
| 70 | 1.155 | 0.848 | <0.0015 | 26.1 | | |
| 71 | 4.731 | 0.955 | 0.006 | 25.2 | | |
| 72 | 1.156 | | <0.0015 | 51.3 | 1.00 | 58.5 |
| 73 | 0.916 | | <0.0015 | 421 | | |
| 74 | 1.124 | | <0.0015 | 93.1 | | |
| 75 | 0.474 | 1.143 | 0.002 | 149 | 16.93 | 360.4 |
| 76 | | | | | | |
| 77 | 0.508 | 0.126 | <0.001 | 84.6 | 1.09 | 0.412 |
| 78 | 8.776 | 5.119 | 1.201 | 3244 | 4.551 | 4.603 |
| 79 | >10 | 5.649 | 0.763 | 5411 | | >10 |
| 80 | 0.32 | 0.089 | <0.001 | 82.4 | | 0.132 |
| 81 | 1.726 | | 0.043 | 190 | | 1.956 |
| 82 | 1.554 | 0.587 | 0.015 | 63 | 1.122 | 1.822 |
| 83 | 5.696 | 2.178 | 0.02 | 627 | 1.439 | 5.161 |
| 84 | >10 | 5.65 | 0.09 | 3066 | 4.457 | 5.044 |
| 85 | >10 | | 0.29 | 3079 | | >10 |

As shown in Tables 4, 5 and 6, the compounds of examples of the present invention demonstrated excellent cancer cell proliferation inhibition (cancer cell apoptosis) effect on the cancer cell lines GIST-T1, GIST-T1/816, GIST-430, GIST-430/654, GIST-R1, GIST-R3, M-NFS-60, Ret-Parental (Ba/F3), Retwt (Ba/F3), RetV804M (Ba/F3), RET (LC2/ad-CDC6), FYN (MCP-1), FYN (FN), MDA-MB-231, Huh7, K562, T315I(Ba/F3), SK-MEL-28 and A375 at the concentrations of micromol or nanomol units.

Therefore, the compounds of the present invention can be effectively used as an active ingredient of a pharmaceutical composition for the prevention or treatment of cancer because the compounds of the present invention demonstrated the cancer cell proliferation inhibition (cancer cell apoptosis) effect at the concentrations of micromol or nanomol units.

<Experimental Example 3> Evaluation of In Vivo Pharmacological Activity

It was confirmed in Experimental Examples 1 and 2 above that the compounds of the present invention were excellent in inhibiting Src/Fyn enzymes related to diabetic nephropathy. Thereafter, in vivo experiments were performed with the disease induced mouse model as follows in order to evaluate the medicinal effect of the compound of the present invention on the disease.

The analysis and index calculation method for the mice used in the following experiments were performed as follows.

Hematological Analysis

Blood was collected with a heparinized syringe before sacrificing the experimental animals. HbA1c was measured by using a DCA2000 HbA1c reagent kit (SIEMENS Healthcare Diagnostics, Inc., Tarrytown, N.Y., USA) and blood sugar was measured by using a glucometer (OneTouch Ultra, Johnson & Johnson co., CA, USA). The blood sample obtained above was centrifuged at 3000 rpm at 4° C. for 15 minutes to obtain serum. Serum cystatin C was measured by using an ELISA kit (R&D Systems, Minneapolis, Minn., USA).

Urine Index Measurement

The urine excreted for 24 hours was collected before sacrificing the experimental animals, and the urine sample was centrifuged at 3000 rpm for 10 minutes to remove the precipitate. Urine albumin and KIM-1 were measured by using ALPCO (Westlake, Ohio, USA) and R&D Systems (Minneapolis, Minn., USA) ELISA Kits, respectively.

Histological and Immunohistochemical (IHC) Observations

The right kidney was fixed in 2% paraformaldehyde-lysin-periodate (pH 7.4). After dehydration and hardening the kidney in paraffin, thin sections were made. Periodic acid-Schiff (PAS) staining was performed and 15 cortical glomeruli were randomly selected and photographed. The mean size of each glomerulus and fractional mesangial area (FAM) were measured. Standardized Masson's Trichrome staining was performed to confirm the collagen matrix deposition in the kidney, and IHC staining was performed using CD68 antibody to measure the chronic inflammatory response.

All the staining photographs were observed with a Zeiss microscope equipped with Axio Cam HRC digital camera and Axio Cam software (Carl Zeiss, Thornwood, N.Y., USA) and quantified using Image-Pro Plus4.5 software (Media Cybernetics).

Real Time Quantitative PCR

RNA was extracted by using TRIzol (Invitrogen, Carlsbad, Calif., USA). The expression of mRNA was quantified with Real-time PCR ABI7300 (Applied Biosystems, Carlsbad, Calif., USA) using cDNA transcripts, primer and SYBR Green PCR Master Mix (Applied Biosystems) mixture (20 μl). The primer sequences are shown in Table 1. The standardization was accomplished by using the house keeping gene 18S.

Table 7 below shows the primer sequences used in real-time quantitative PCR.

FIG. 1 presents graphs illustrating the proteinuria and urinary KIM-1 according to the treatment of three different compounds which were the compound of the present invention, PP2 and DMSO/Tween 20/DW, measured to evaluate renal damage in a UUO induced mouse model.

Figure 2:
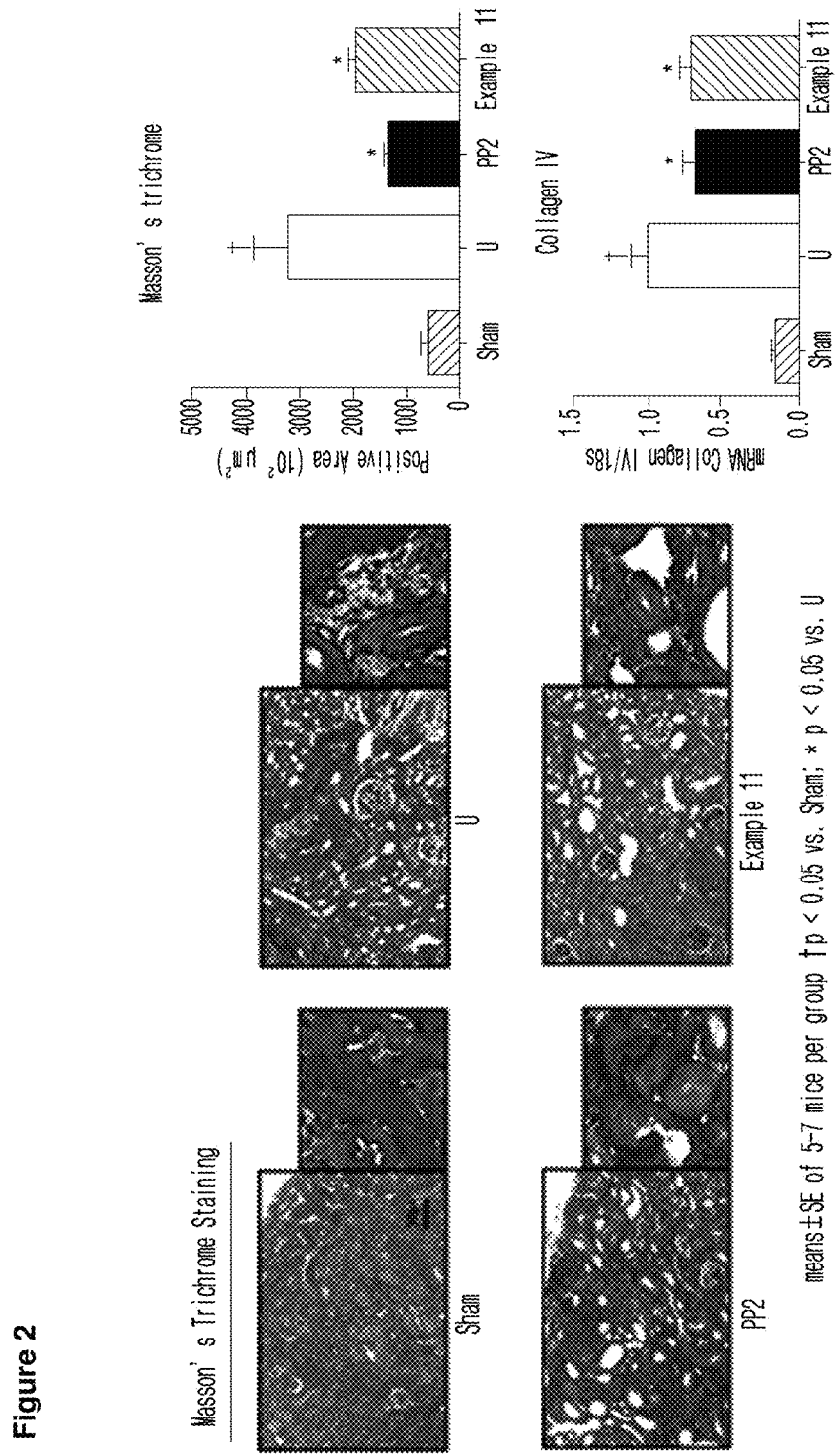
FIG. 2 presents photographs (MAsson's Trichrome Staining, 50 μm scale) and graphs (MAsson's Trichrome) illustrating the collagen accumulation and mRNA expression according to the treatment of four different compounds which were the compound of the present invention, Sham, PP2 and DMSO/Tween 20/DW, measured to evaluate kidney fibrosis in a UUO induced mouse model.

FIG. 2 presents photographs (MAsson's Trichrome Staining, 50 μm scale) and graphs (MAsson's Trichrome) illustrating the collagen accumulation and mRNA expression according to the treatment of four different compounds which were the compound of the present invention, Sham, PP2 and DMSO/Tween 20/DW, measured to evaluate kidney fibrosis in a UUO induced mouse model.

Figure 3:
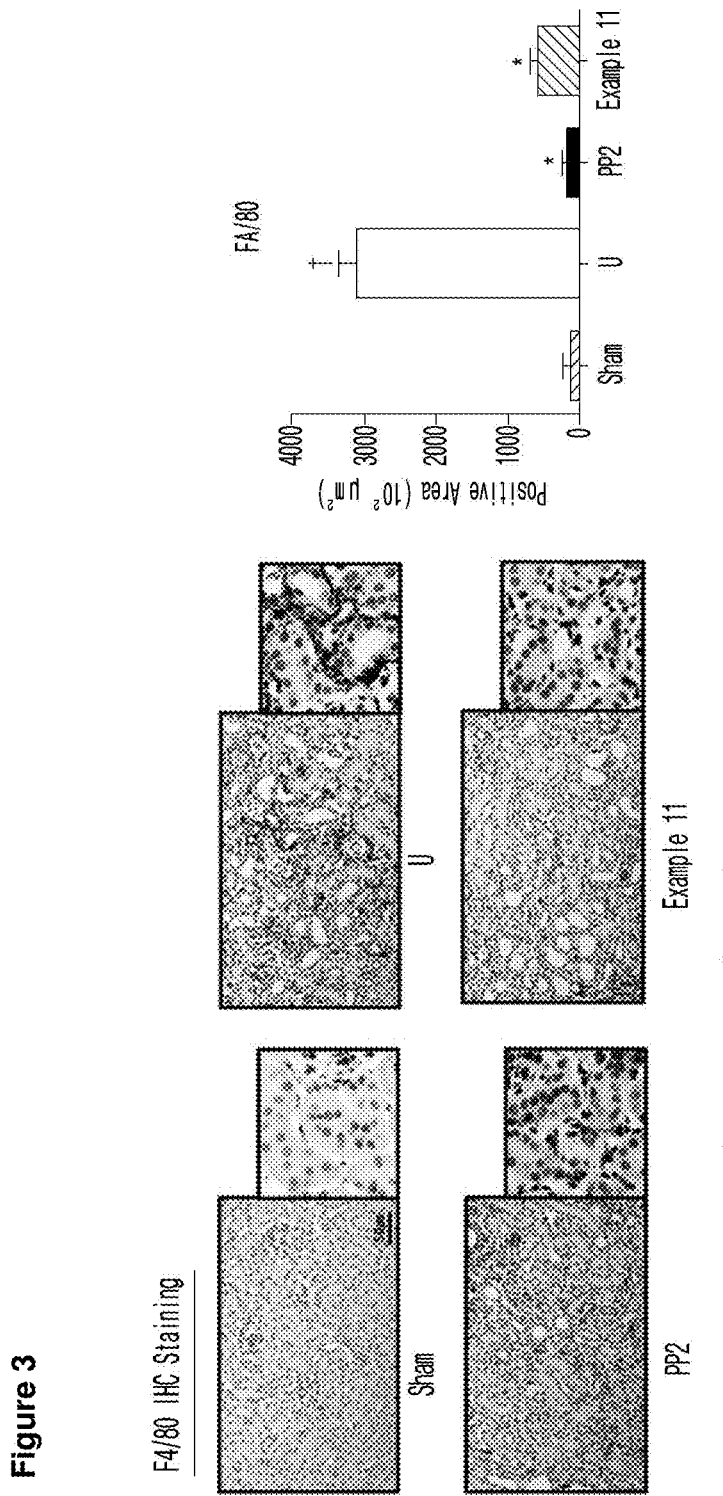
FIG. 3 presents photographs (FA/80 IHC Staining, 50 μm scale) and graphs (FA/80) illustrating the macrophage infiltration according to the treatment of four different compounds which were the compound of the present invention, Sham, PP2 and DMSO/Tween 20/DW, measured to evaluate kidney inflammation reaction in a UUO induced mouse model.

FIG. 3 presents photographs (FA/80 IHC Staining, 50 μm scale) and graphs (FA/80) illustrating the macrophage infiltration according to the treatment of four different compounds which were the compound of the present invention, Sham, PP2 and DMSO/Tween 20/DW, measured to evaluate kidney inflammation reaction in a UUO induced mouse model.

Figure 4:
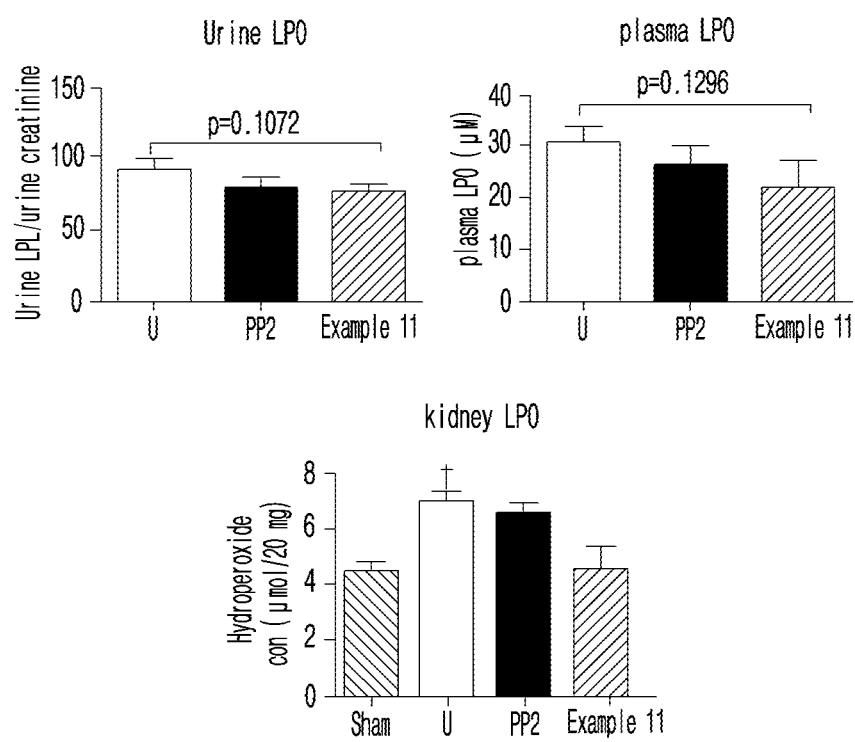
FIG. 4 presents graphs illustrating the lipid peroxidation observed in urine, plasma and kidney according to the treatment of three different compounds which were the compound of the present invention, PP2 and DMSO/Tween 20/DW, measured to evaluate oxidative stress in a UUO induced mouse model.

FIG. 4 presents graphs illustrating the lipid peroxidation observed in urine, plasma and kidney according to the treatment of three different compounds which were the compound of the present invention, PP2 and DMSO/Tween 20/DW, measured to evaluate oxidative stress in a UUO induced mouse model.

TABLE 7

| Gene | Forward | Reverse |
| --- | --- | --- |
| 18s | 5'-AGGAATTGACGGAAGGGCAC-3' (SEQ ID NO: 1) | 5'-GTGCAGCCCCGGACATCTAAG-3 (SEQ ID NO: 2) |
| a-SMA | 5'-GATCACCATCGGGAATGAACGC-3' (SEQ ID NO: 3) | 5'-CTTAGAAGCATTTGCGGTGGA-3' (SEQ ID NO: 4) |
| Collagen-1 | 5'-TCTAAGACATCCCTGGTCAC-3' (SEQ ID NO: 5) | 5'-GTCCTTCCAGAAGAAACCTT-3' (SEQ ID NO: 6) |
| MCP | 5'-CTGTAGCATCCACGTGCTGT-3' (SEQ ID NO: 7) | 5'-CCGACTCATTGGGATCATCT-3' (SEQ ID NO: 8) |

Statistical Analysis

All data are expressed as mean±standard deviation. The mean values obtained in each group were analyzed by ANOVA and Fisher's least significant difference method was used to compare the differences between the two groups. When p<0.05, it was considered statistically significant.

<Experimental Example 3-1> Experiment with One-Way Urethral Obstruction Induced Renal Fibrosis Mice Male C57BL6 mice at 6 weeks of age were purchased (Japan SLC Inc., Hamamatsu, Japan). The test animals were adapted to the animal facility for one week. UUO was performed in the left kidney and the right kidney on the opposite side was used as the control for the comparison. The animals were grouped randomly in three groups, which were treated with the compound of Example 11 (30 mg/kg/day, p.o.), PP2 (2 mg/kg/d, i.p.) or the solvent of the compound of Example 11 DMSO/Tween 20/DW (indicated by U in the figure) at the ratio of 10:5:85 for 7 days.

Particularly, in the USS induced mouse models, the effects of the compounds on renal damage (FIG. 1), renal fibrosis (FIG. 2), renal inflammation response (FIG. 3) and oxidative stress (FIG. 4) were investigated and compared among the three groups above.

As shown in FIGS. 1-4, it was confirmed that the compound of the present invention reduced renal damage significantly, inhibited renal fibrosis, suppressed renal inflammation response and inhibited oxidative lipid peroxidation in the UUO model. Therefore, the compound of the present invention was confirmed to be effectively used as a drug to prevent the kidney deterioration caused by urethral obstruction.

The compound of the present invention was confirmed to have not only an excellent inhibitory effect on Src/Fyn enzyme, but also a medicinal effect on disease including diabetic nephropathy, so that the compound of the present invention is useful as a pharmaceutical composition.

<Experimental Example 3-2> Experiment with Diabetes Induced White Mice

Male SD white mice at 6-7 weeks of age (Japan SLC Inc., Hamamatsu, Japan) were used. Streptozotocin (STZ, 60 mg/kg, intraperitoneally administered) was administered to the experimental animals to induce type I diabetes. The STZ non-treated control group was treated with sodium citrate buffer (sodium citrate 100 mM, citric acid 100 mM, pH 4.5). To investigate the therapeutic effect of the compound of example 11, the compound was orally administered to the experimental animals for 8 weeks from the beginning of diabetes induction. The effect was compared with that of losartan (1 mg/kg/d) that is an angiotensin receptor antagonist being used clinically as a drug to treat diabetic nephropathy. The diabetic control (treated with STZ alone) was administered with the solvent of Example 11, DMSO/Tween 70.DW (10:5:85).

Table 8 below presents the body weight, kidney weight, ratio of kidney to body weight, HbA1C, blood sugar and urine amount (volume) of the mice of each group, which were measured 8 weeks after the treatment of control (non-treated with STZ), STZ, STZ+compound of Example 11 (30 mg/kg) and STZ+losartan (1 mg/kg).

TABLE 8

| | Control | STZ | STZ + Example 11 (30 mg/kg) | STZ+ losartan (1 mg/kg) |
|---|---|---|---|---|
| Weight (g) | 513 ± 13.4 | 242 ± 9.2* | 241 ± 16.0* | 250 ± 12.1* |
| Kidney (g) | 1.6 ± 0.1 | 1.41 ± 0.1 | 1.6 ± 0.1 | 1.3 ± 0.1* |
| kidney/Weight ratio | 0.3 ± 0.01 | 0.6 ± 0.02* | 0.7 ± 0.04*† | 0.5 ± 0.03*† |
| HbA1C (%) | 3.6 ± 0.1 | 6.6 ± 0.2* | 6.7 ± 0.2* | 7.3 ± 0.2* |
| blood sugar (mg/dl) | 163 ± 6 | 416 ± 35* | 392 ± 33* | 384 ± 4* |
| Urine volume | 16.5 ± 0.9 | 80.2 ± 13.2* | 93.0 ± 12.5* | 77.8 ± 12.5* |

Mean ± SE (n = 6-8 mice/group)
*P, 0.05 vs control,
†P < 0.05 vs STZ

Figure 5:
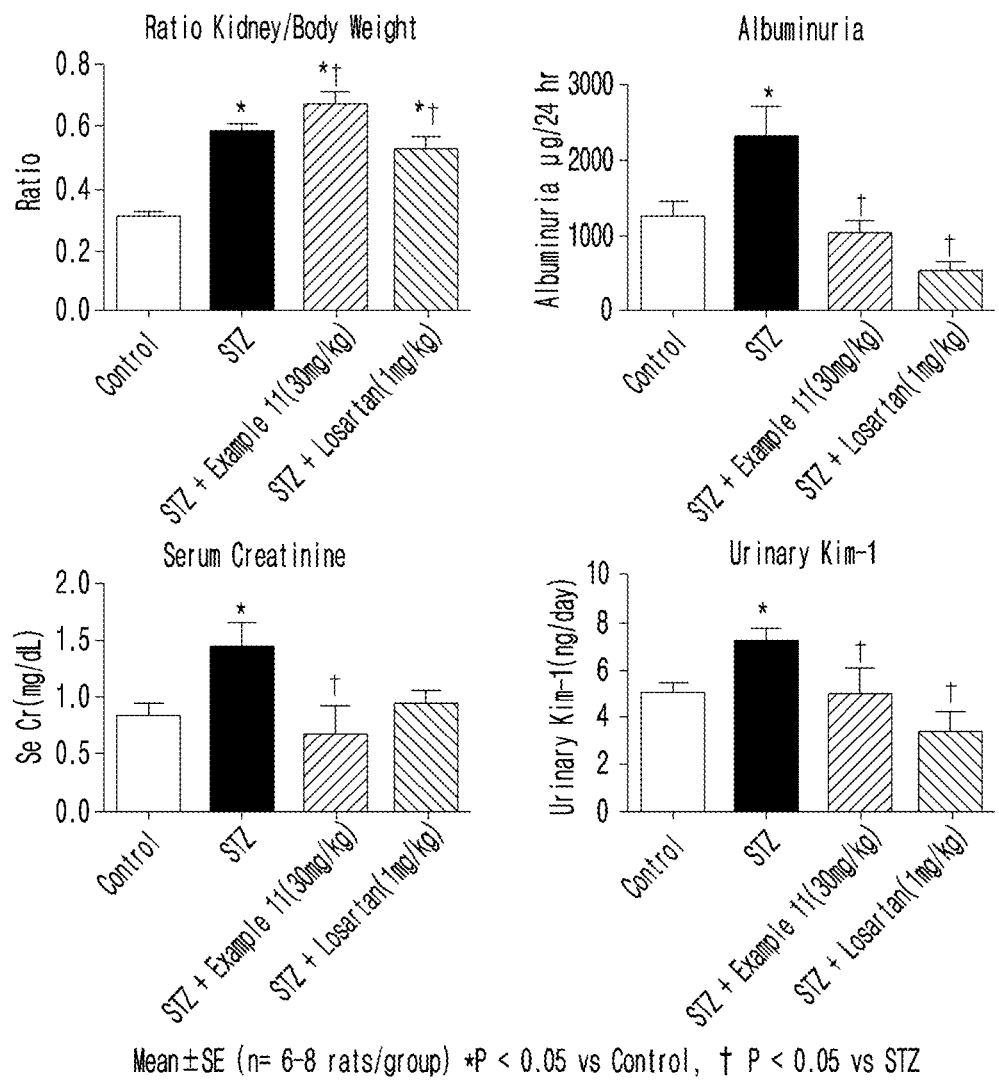
FIG. 5 presents graphs illustrating the effect of the compound of the present invention on renal function investigated by measuring the ratio of body length to body weight, proteinuria, serum creatinine, and urine KIM-1 of the mice of each experimental group 8 weeks after the treatment of the compound of the present invention (Example 11), the control, STZ (streptozotocin), STZ + compound of Example 11 and STZ + losartan.

FIG. 5 presents graphs illustrating the effect of the compound of the present invention on renal function investigated by measuring the ratio of body length to body weight, proteinuria, serum creatinin, and urine KIM-1 of the mice of each experimental group 8 weeks after the treatment of the compound of the present invention (Example 11), the control, STZ (streptozotocin), STZ+compound of Example 11 and STZ+losartan.

Figure 6:
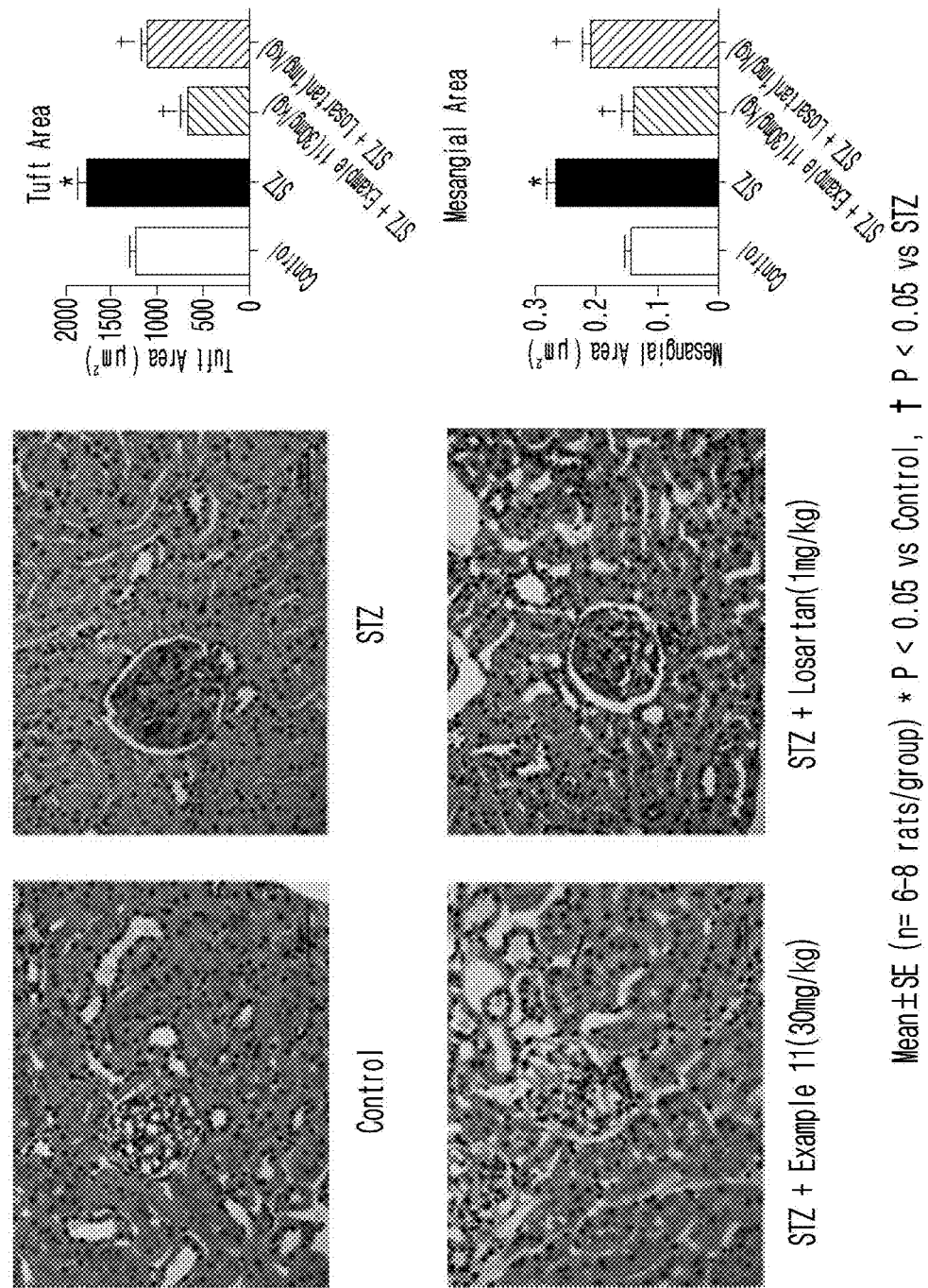
FIG. 6 presents photographs (50 μm scale) illustrating the glomerulus section of each group respectively treated with the compound of the present invention (example 11), the control, STZ (streptozotocin), STZ+compound of example 11 and STZ+losartan compound and graphs illustrating the numeric values of the tuft region and the glomerular mesangium region calculated from the above, measured to evaluate the effect of those compounds on glomerular hypertrophy.

FIG. 6 presents photographs (50 μm scale) illustrating the glomerulus section of each group respectively treated with the compound of the present invention (Example 11), the control, STZ (streptozotocin), STZ+compound of Example 11 and STZ+losartan and graphs illustrating the numeric values of the tuft region and the glomerular mesangium region calculated from the above, measured to evaluate the effect of those compounds on glomerular hypertrophy.

Figure 7:
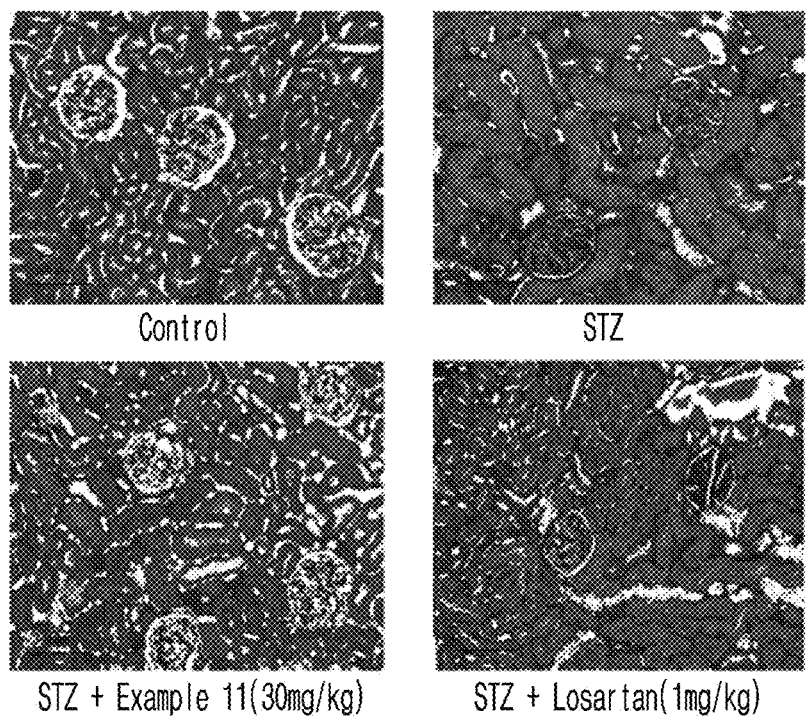
FIG. 7 presents photographs (100 μm scale) illustrating the glomerulus section of each group respectively treated with the compound of the present invention (example 11), the control, STZ (streptozotocin), STZ+compound of example 11 and STZ+losartan compound and stained with trichrome according to Mason's method, investigated to evaluate the effect on collagen deposition.

FIG. 7 presents photographs (100 μm scale) illustrating the glomerulus section of each group respectively treated with the compound of the present invention (example 11), the control, STZ (streptozotocin), STZ+compound of example 11 and STZ+losartan and stained with trichrome according to Mason's method, investigated to evaluate the effect on collagen deposition.

Figure 8:
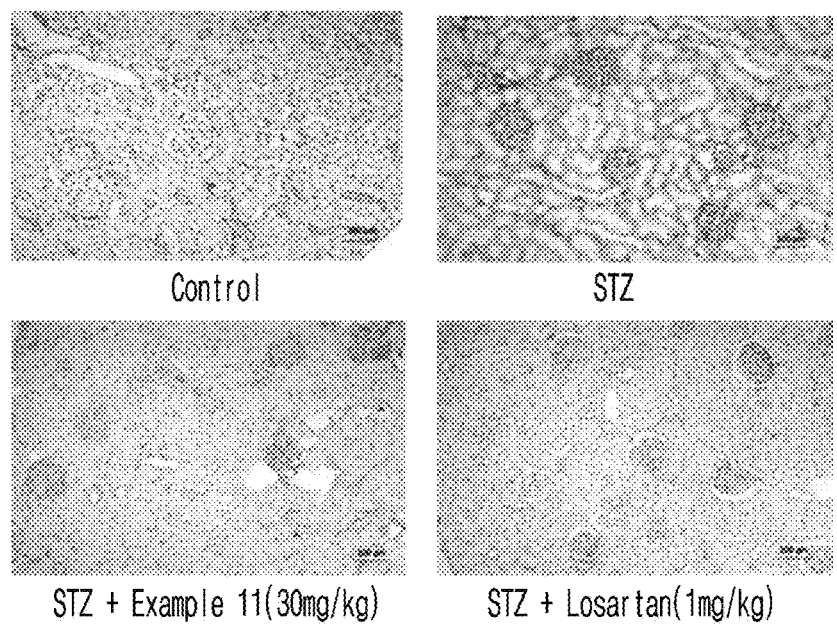
FIG. 8 presents photographs (100 μm scale) illustrating the glomerulus section of each group respectively treated with the compound of the present invention (example 11), the control, STZ (streptozotocin), STZ+compound of example 11 and STZ+losartan compound and stained with IHC, investigated to evaluate the effect on macrophage deposition in kidney.

FIG. 8 presents photographs (100 m scale) illustrating the glomerulus section of each group respectively treated with the compound of the present invention (example 11), the control, STZ (streptozotocin), STZ+compound of example 11 and STZ+losartan and stained with IHC, investigated to evaluate the effect on macrophage deposition in kidney.

Figure 9:
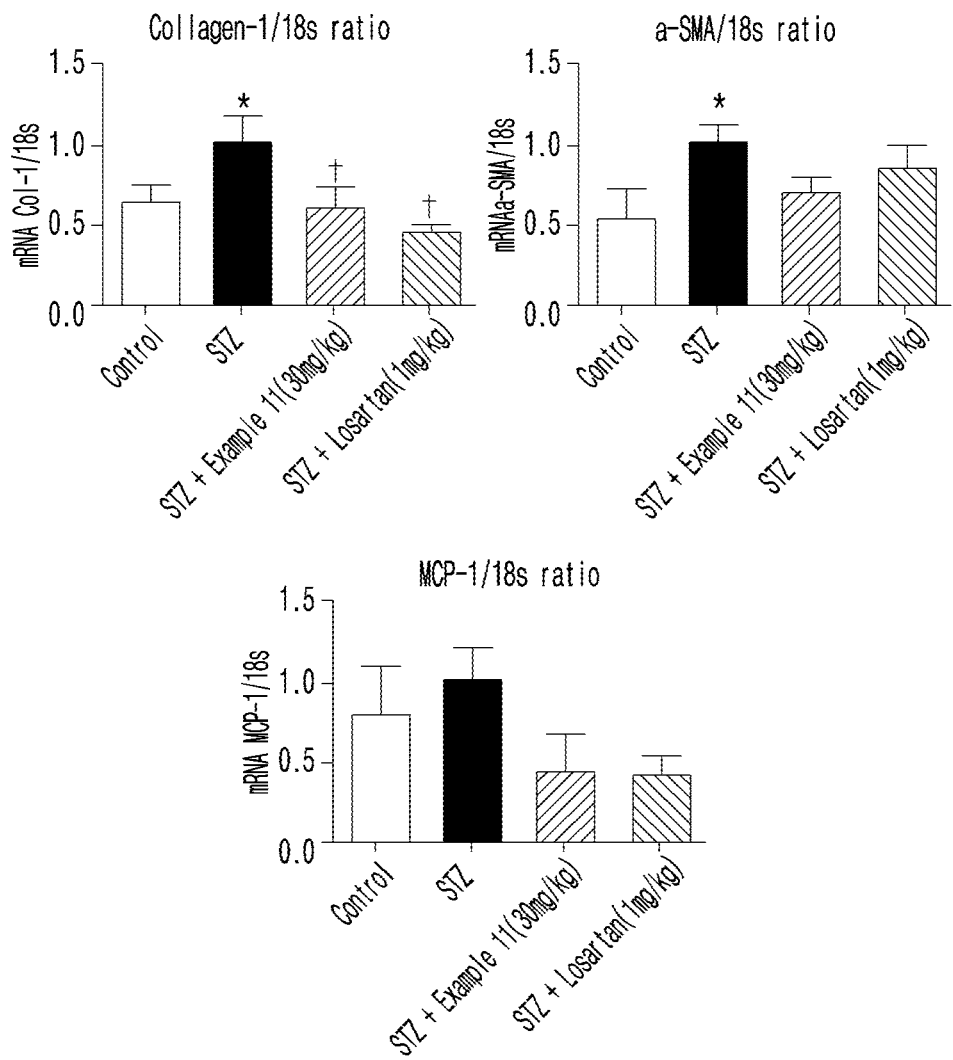
FIG. 9 presents graphs illustrating the ratio of collagen-1/18s, a-SMA/18s and MCP-1/18s according to the treatment of the compound of the present invention (example 11), the control, STZ (streptozotocin), STZ+compound of example 11 and STZ+losartan compound, investigated to evaluate the effect of those compounds on fibrosis and the expression of inflammatory marker protein mRNA.

FIG. 9 presents graphs illustrating the ratio of collagen-1/18s, a-SMA/18s and MCP-1/18s according to the treatment of the compound of the present invention (example 11), the control, STZ (streptozotocin), STZ+compound of example 11 and STZ+losartan, investigated to evaluate the effect of those compounds on fibrosis and the expression of inflammatory marker protein mRNA.

As shown in FIGS. 5-9, it was confirmed that the compound of the present invention normalized renal function, inhibited renal fibrosis, and suppressed renal inflammation response like losartan. Therefore, the compound of the present invention was confirmed to be effectively used as a drug to prevent the kidney deterioration caused by diabetes.

The compound of the present invention was confirmed to have not only an excellent inhibitory effect on Src/Fyn enzyme, but also a medicinal effect on disease including diabetic nephropathy, so that the compound of the present invention is useful as a pharmaceutical composition.

INDUSTRIAL APPLICABILITY

The novel imidazopyridine derivative according to the present invention, a stereoisomer thereof and a pharmaceutically acceptable salt thereof can effectively inhibit cancer-related kinases, are excellent in inhibiting proliferation of cancer cells in a cancer cell line, and effectively inhibit proliferation of cancer cells (cancer cell apoptosis) in a cancer cell heterograft model, and thus can be useful as a pharmaceutical composition containing the same as an active ingredient for preventing or treating cancer.

Also, the novel imidazopyridine derivative according to the present invention, the stereoisomer thereof, and the pharmaceutically acceptable salt thereof can effectively inhibit Src and Fyn, thereby being useful as a pharmaceutical composition for preventing or treating the Src and Fyn related diseases, and in particular, have been confirmed to be useful in diabetic nephropathy in animal model experiments. Therefore, the compound of the present invention can be effective as a pharmaceutical composition containing the same as an active ingredient for preventing or treating diabetic nephropathy.

What is claimed is:
1. A compound represented by formula 1, an optical isomer thereof or a pharmaceutically acceptable salt thereof:

[Formula 1]

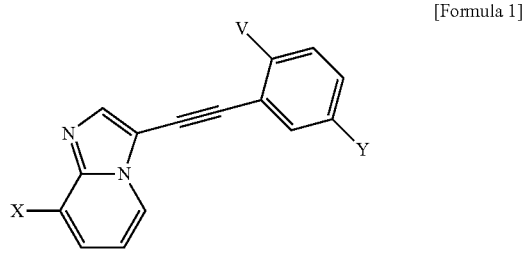

in formula 1,
V is hydrogen, halogen, or methyl;
X is —NHR$^1$;
R$^1$ is nonsubstituted or substituted 5 membered heteroaryl containing one or more heteroatoms selected from the group consisting of N, O and S,
  wherein, the substituted 5 membered heteroaryl can be substituted with nonsubstituted C$_{1-10}$ straight or branched alkyl;
    C$_{1-10}$ straight or branched alkyl substituted with one or more substituents selected from the group consisting of halogen, methoxy and dimethylamino;
    halogen;
    amino; or
    5-6 membered heterocycloalkyl containing one or more heteroatoms selected from the group consisting of N, O and S, or
  the substituted 5 membered heteroaryl is fused with a 5-6 membered ring containing one or more heteroatoms selected from the group consisting of N, O and S to form a fused ring;
Y is —(C═O)NHR$^2$, —NH(C═O)R$^2$, —NH(C═O)NHR$^2$ or

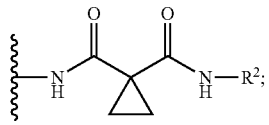

R$^2$ is nonsubstituted or substituted C$_{6-10}$ aryl or nonsubstituted or substituted 5-10 membered heteroaryl containing one or more heteroatoms selected from the group consisting of N, O and S,
  wherein, the substituted C$_{6-10}$ aryl or the substituted 5-10 membered heteroaryl can be substituted with one or more substituents selected from the group consisting of
    halogen;
    —CH$_2$—R$^3$;
    nonsubstituted C$_{1-10}$ straight or branched alkyl or C$_{1-10}$ straight or branched alkyl substituted with halogen;
    nonsubstituted C$_{1-2}$ alkoxy or C$_{1-2}$ alkoxy substituted with halogen;
    nonsubstituted C$_{6-10}$ cycloalkyl or C$_{6-10}$ cycloalkyl substituted with halogen;
    substituted or nonsubstituted 5-10 membered heterocycloalkyl containing one or more heteroatoms selected from the group consisting of N, O and S;
    nonsubstituted or substituted 5-10 membered heteroaryl containing one or more heteroatoms selected from the group consisting of N, O and S; or
    nonsubstituted or substituted amino,
      wherein, the substituted heteroaryl, the substituted heterocycloalkyl, and the substituted amino can be substituted with substituted or nonsubstituted C$_{1-3}$ straight or branched alkyl,
      wherein, the substituted C$_{1-3}$ straight or branched alkyl can be substituted with dimethyl amino; and
R$^3$ is 5-10 membered heterocycloalkyl containing one or more heteroatoms selected from the group consisting of N, O and S,
  wherein, the 5-10 membered heterocycloalkyl can be nonsubstituted 5-10 membered heterocycloalkyl or 5-10 membered heterocycloalkyl substituted with one or more substituents selected from the group consisting of methyl, ethyl, dimethyl amino, and halogen.

2. The compound represented by formula 1, the optical isomer thereof or the pharmaceutically acceptable salt thereof according to claim 1, wherein the R$^1$ is oxazolyl or pyrazolyl.

3. The compound represented by formula 1, the optical isomer thereof or the pharmaceutically acceptable salt thereof according to claim 1, wherein the X is

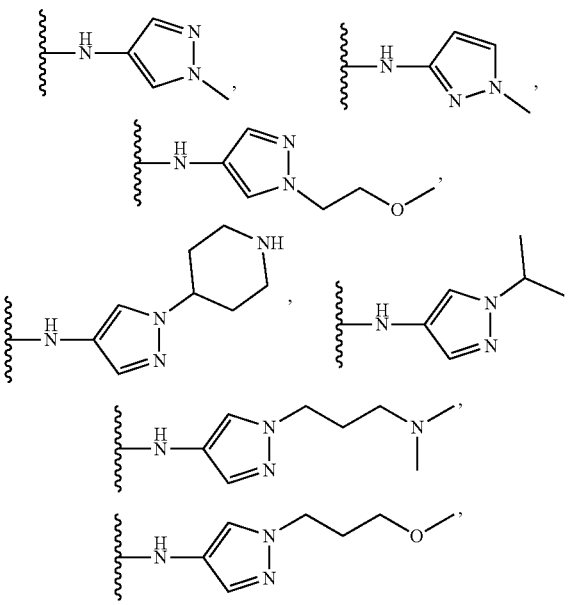

-continued
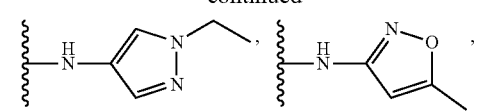
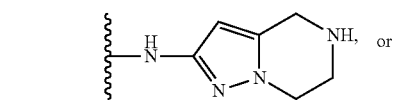
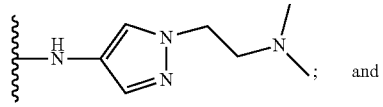
the Y is 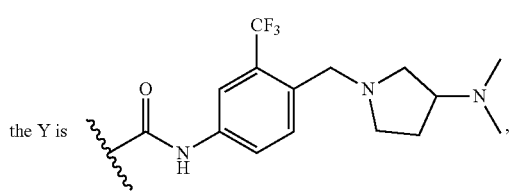
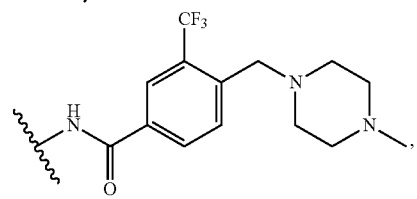
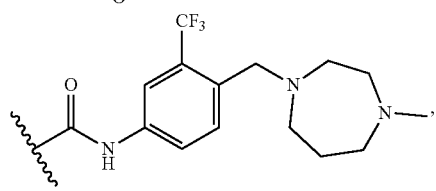
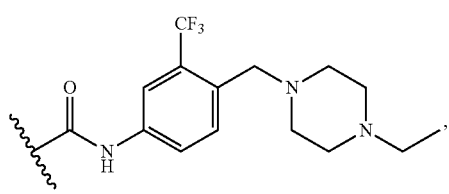
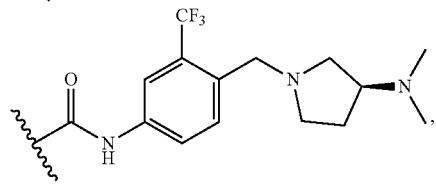
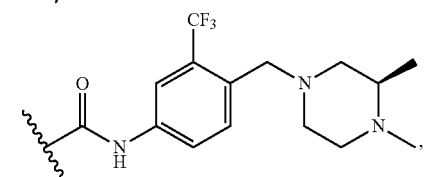
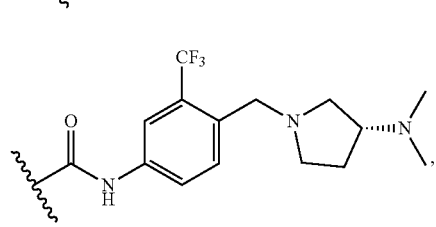
-continued
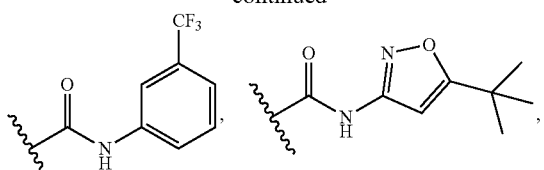
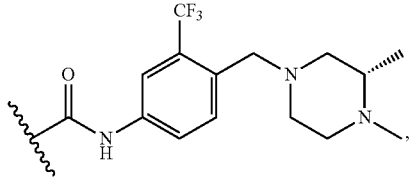
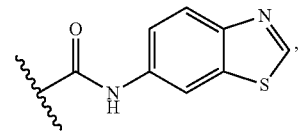
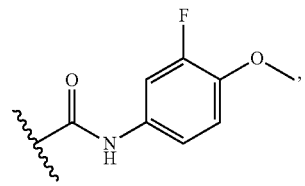
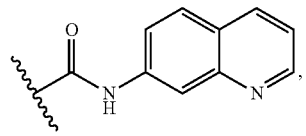
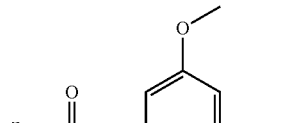
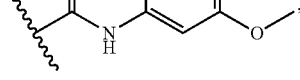
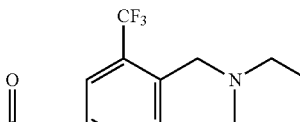
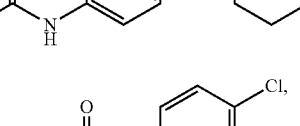
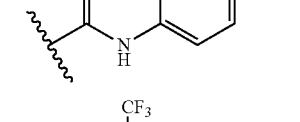
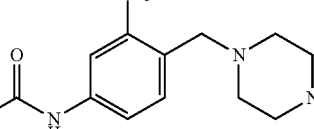
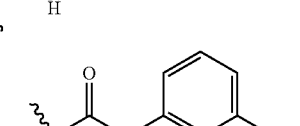

4. A compound, the optical isomer thereof, or the pharmaceutically acceptable salt thereof, wherein the compound is selected from the group consisting of:

(1) 4-methyl-3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;

(2) N-(2-fluorophenyl)-4-methyl-3-((8-((1-methyl-1H-pyrazol-4-yl)amino)imidazo[1,2-a]pyridin-3-yl)ethynyl)benzamide;

(3) N-(3,5-dimethoxyphenyl)-4-methyl-3-((8-((1-methyl-1H-pyrazol-4-yl)amino)imidazo[1,2-a]pyridin-3-yl)ethynyl)benzamide;

(4) N-(3-fluoro-4-methoxyphenyl)-4-methyl-3-((8-((1-methyl-1H-pyrazol-4-yl)amino)imidazo[1,2-a]pyridin-3-yl)ethynyl)benzamide;

(6) N-(3-fluorophenyl)-4-methyl-3-((8-((1-methyl-1H-pyrazol-4-yl)amino)imidazo[1,2-a]pyridin-3-yl)ethynyl)benzamide;

(7) N-(4-chlorophenyl)-4-methyl-3-((8-((1-methyl-1H-pyrazol-4-yl)amino)imidazo[1,2-a]pyridin-3-yl)ethynyl)benzamide;

(8) N-(4-((4-ethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(9) 4-methyl-3-((8-((1-methyl-1H-pyrazol-3-yl)amino)imidazo[1,2-a]pyridin-3-yl)ethynyl)-N-(4-((4-methylpiperazin-1-yl)methyl)-3-(trifluoromethyl)phenyl)benzamide;

(10) N-(4-((4-ethylpiperazin-1-yl)methyl)-3-(trifluoromethyl)phenyl)-4-methyl-3-((8-((1-methyl-1H-pyrazol-3-yl)amino)imidazo[1,2-a]pyridin-3-yl)ethynyl)benzamide;

(11) 4-methyl-3-((8-((1-(piperidin-4-yl)-1H-pyrazol-4-yl)amino)imidazo[1,2-a]pyridin-3-yl)ethynyl)-N-(3-(trifluoromethyl)phenyl)benzamide;

(12) 4-methyl-N-(3-(4-methyl-1H-imidazol-1-yl)-5-(trifluoromethyl)phenyl)-3-((8-((1-methyl-1H-pyrazol-4-yl)amino)imidazo[1,2-a]pyridin-3-yl)ethynyl)benzamide;

(13) 4-methyl-3-((8-((1-methyl-1H-pyrazol-4-yl)amino)imidazo[1,2-a]pyridin-3-yl)ethynyl)-N-(3-(trifluoromethyl)phenyl)benzamide;

(14) 3-((8-((1-isopropyl-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;

(22) 3-((8-((1-ethyl-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;

(23) 3-((8-((1-ethyl-1H-pyrazol-4-yl)amino)imidazo[1,2-a]pyridin-3-yl)ethynyl)-N-(4-((4-ethylpiperazin-1-yl)methyl)-3-(trifluoromethyl)phenyl)-4-methylbenzamide;

(26) 3-((8-((1-(3-(dimethylamino)propyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;

(27) 3-((8-((1-(3-(dimethylamino)propyl)-1H-pyrazol-4-yl)amino)imidazo[1,2-a]pyridin-3-yl)ethynyl)-4-methyl-N-(3-(trifluoromethyl)phenyl)benzamide;

(28) 4-methyl-3-((8-((5-methylisoxazol-3-yl)amino)imidazo[1,2-a]pyridin-3-yl)ethynyl)-N-(4-((4-methylpiperazin-1-yl)methyl)-3-(trifluoromethyl)phenyl)benzamide;

(29) (R)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;

(30) N-(4-((3-(dimethylamino)pyrrolidin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;

(31) (R)—N-(4-((3,4-dimethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(32) N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(33) 3-((8-((1-(3-(dimethylamino)propyl)-1H-pyrazol-4-yl)amino)imidazo[1,2-a]pyridin-3-yl)ethynyl)-N-(4-((4-ethylpiperazin-1-yl)methyl)-3-(trifluoromethyl)phenyl)-4-methylbenzamide;

(34) (R)-3-((8-((1-(3-(dimethylamino)propyl)-1H-pyrazol-4-yl)amino)imidazo[1,2-a]pyridin-3-yl)ethynyl)-N-(4-((3,4-dimethylpiperazin-1-yl)methyl)-3-(trifluoromethyl)phenyl)-4-methylbenzamide;

(35) 3-((8-((1-(3-(dimethylamino)propyl)-1H-pyrazol-4-yl)amino)imidazo[1,2-a]pyridin-3-yl)ethynyl)-N-(4-((3-(dimethylamino)pyrrolidin-1-yl)methyl)-3-(trifluoromethyl)phenyl)-4-methylbenzamide;

(36) 3-((8-((1-(3-(dimethylamino)propyl)-1H-pyrazol-4-yl)amino)imidazo[1,2-a]pyridin-3-yl)ethynyl)-N-(4-((3-(dimethylamino)pyrrolidin-1-yl)methyl)-3-(trifluoromethyl)phenyl)-4-methylbenzamide;

(37) N-(benzo[d]thiazol-6-yl)-4-methyl-3-((8-((1-methyl-1H-pyrazol-4-yl)amino)imidazo[1,2-a]pyridin-3-yl)ethynyl)benzamide;

(38) 3-((8-((1-isopropyl-1H-pyrazol-4-yl)amino)imidazo[1,2-a]pyridin-3-yl)ethynyl)-4-methyl-N-(4-((4-methyl-1,4-diazepin-1-yl)methyl)-3-(trifluoromethyl)phenyl)benzamide;

(39) 3-((8-((1-(3-(dimethylamino)propyl)-1H-pyrazol-4-yl)amino)imidazo[1,2-a]pyridin-3-yl)ethynyl)-4-methyl-N-(4-((4-methyl-1,4-diazepin-1-yl)methyl)-3-(trifluoromethyl)phenyl)benzamide;

(40) (R)—N-(4-((3,4-dimethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;

(41) N-(4-((3-(dimethylamino)pyrrolidin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;

(42) (R)—N-(4-((3,4-dimethylpiperazin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide;

(43) N-(4-((3-(dimethylamino)pyrrolidin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide;

(44) (S)—N-(4-((3,4-dimethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;

(45) N-(4-((3-(dimethylamino)pyrrolidin-1-yl)methyl)-3-(trifluoromethyl)phenyl)-4-methyl-3-((8-(((5-methylisoxazol-3-yl)amino)imidazo[1,2-a]pyridin-3-yl)ethynyl)benzamide;

(46) (S)—N-(4-((3,4-dimethylpiperazin-1-yl)methyl)-3-(trifluoromethyl)phenyl)-3-((8-((1-(3-methoxypropyl)-1H-pyrazol-4-yl)amino)imidazo[1,2-a]pyridin-3-yl)ethynyl)-4-methylbenzamide;

(47) (S)—N-(4-((3,4-dimethylpiperazin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(48) (S)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;

(49) (S)-3-((8-((1-(3-(dimethylamino)propyl)-1H-pyrazol-4-yl)amino)imidazo[1,2-a]pyridin-3-yl)ethynyl)-N-(4-((3,4-dimethylpiperazin-1-yl)methyl)-3-(trifluoromethyl)phenyl)-4-methylbenzamide;

(50) (R)—N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(51) (S)—N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(52) N-(4-((4,4-difluoropiperidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(53) (R)—N-(4-((3-(dimethylamino)pyrrolidin-1-yl)methyl)-3-(trifluoromethyl)phenyl)-3-((8-((1-ethyl-1H-pyrazol-4-yl)amino)imidazo[1,2-a]pyridin-3-yl)ethynyl)-4-methylbenzamide;

(54) (S)—N-(4-((3-(dimethylamino)pyrrolidin-1-yl)methyl)-3-(trifluoromethyl)phenyl)-3-((8-((1-ethyl-1H-pyrazol-4-yl)amino)imidazo[1,2-a]pyridin-3-yl)ethynyl)-4-methylbenzamide;

(55) N-(4-((3-(dimethylamino)pyrrolidin-1-yl)methyl)-3-(trifluoromethyl)phenyl)-4-methyl-3-((8-((1-methyl-1H-pyrazol-4-yl)amino)imidazo[1,2-a]pyridin-3-yl)ethynyl)benzamide;

(56) 3-((8-((1-ethyl-1H-pyrazol-4-yl)amino)imidazo[1,2-a]pyridin-3-yl)ethynyl)-N-(3-fluoro-4-morpholinophenyl)-4-methylbenzamide;

(57) 3-((8-((1-(2-methoxyethyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;

(58) 3-((8-((1-(2-methoxyethyl)-1H-pyrazol-4-yl)amino)imidazo[1,2-a]pyridin-3-yl)ethynyl)-4-methyl-N-(5-(1,1,1-trifluoro-2-methylpropan-2-yl)isoxazol-3-yl)benzamide;

(59) N-(5-(tert-butyl)isoxazol-3-yl)-3-((8-((1-(2-methoxyethyl)-1H-pyrazol-4-yl)amino)imidazo[1,2-a]pyridin-3-yl)ethynyl)-4-methylbenzamide;

(60) 3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;

(61) 4-fluoro-3-((8-((1-methyl-1H-pyrazol-4-yl)amino)imidazo[1,2-a]pyridin-3-yl)ethynyl)-N-(4-((4-methylpiperazin-1-yl)methyl)-3-(trifluoromethyl)phenyl)benzamide;

(62) N-(4-chloro-3-(trifluoromethyl)phenyl)-4-methyl-3-((8-((1-methyl-1H-pyrazol-4-yl)amino)imidazo[1,2-a]ethynyl)benzamide;

(63) N-(4-chloro-3-(trifluoromethyl)phenyl)-4-methyl-3-((8-((1-(piperidin-4-yl)-1H-pyrazol-4-yl)amino)imidazo[1,2-a]pyridin-3-yl)ethynyl)benzamide;
(65) 3-((8-(1-(3-methoxypropyl)-1H-pyrazol-4-yl)amino)imidazo[1,2-a]pyridin-3-yl)ethynyl)-4-methyl-N-(4-((4-methylpiperazin-1-yl)methyl)-3-(trifluoromethyl)phenyl)benzamide;
(66) 4-methyl-N-(4-((4-methylpiperazin-1-yl)methyl)-3-(trifluoromethyl)phenyl)-3-((8-((4,5,6,7-tetrahydropyrazolo[1,5-a]pyrazin-2-yl)amino)imidazo[1,2-a]pyridin-3-yl)ethynyl)benzamide;
(67) 4-methyl-3-((8-((4,5,6,7-tetrahydropyrazolo[1, 5-a]pyrazin-2-yl)amino)imidazo[1,2-a]pyridin-3-yl)ethynyl)-N-(3-(trifluoromethyl)phenyl)benzamide;
(68) N-(5-(tert-butyl)isoxazol-3-yl)-4-methyl-3-((8-((4,5,6,7-tetrahydropyrazolo[1,5-a]pyrazin-2-yl)amino)imidazo[1,2-a]pyridin-3-yl)ethynyl)benzamide;
(69) N-(4-((4-ethylpiperazin-1-yl)methyl)-3-(trifluoromethyl)phenyl)-3-((8-((1-(2-methoxyethyl)-1H-pyrazol-4-yl)amino)imidazo[1,2-a]pyridin-3-yl)ethynyl)-4-methylbenzamide;
(70) 3-((8-(1-(2-methoxyethyl)-1H-pyrazol-4-yl)amino)imidazo[1,2-a]pyridin-3-yl)ethynyl)-4-methyl-N-((trifluoromethyl)phenyl)benzamide;
(71) 3-((8-(1-(2-methoxyethyl)-1H-pyrazol-4-yl)amino)imidazo[1,2-a]pyridin-3-yl)ethynyl)-4-methyl-N-((4-methyl-1H-imidazol-1-yl)-5-(trifluoromethyl)phenyl)benzamide;
(72) 4-methyl-3-((8-((1-(1-methylpiperidin-4-yl)-1H-pyrazol-4-yl)amino)imidazo[1,2-a]pyridin-3-yl)-N-(3-(trifluoromethyl)phenyl)benzamide;
(73) 3-((8-(2-(dimethylamino)ethyl)-1H-pyrazol-4-yl)amino)imidazo[1,2-a]pyridin-3-yl)-ethynyl)-N-((4-ethylpiperazin-1-yl)methyl)-3-(trifluoromethyl)phenyl)-4-methylbenzamide;
(74) 3-((8-(2-(dimethylamino)ethyl)-1H-pyrazol-4-yl)amino)imidazo[1,2-a]pyridin-3-yl) N-(3-(trifluoromethyl)phenyl)benzamide;
(75) 3-((8-(2-(dimethylamino)ethyl)-1H-pyrazol-4-yl)amino)imidazo[1,2-a]pyridin-3-yl) N-(3-(4-methyl-1H-imidazol-1-yl)-5-(trifluoromethyl)phenyl)benzamide;
(76) (3-(4-methyl-1H-imidazol-1-yl)-5-(trifluoromethyl)phenyl)-3-((8-((1-(1-methylpiperidin-4-yl)-1H-pyrazol-4-yl)amino)imidazo[1,2-a]pyridin-3-yl)ethynyl)benzamide;
(77) N-(3-((8-((1-isopropyl-1H-pyrazol-4-yl)amino)imidazo[1,2-a]pyridin-3-yl)ethynyl)-4-methylphenyl)-4-((4-methylpiperazin-1-yl)methyl)-3-(trifluoromethyl)benzamide;
(78) N-(4-fluorophenyl)-N-(3-((8-((1-isopropyl-1H-pyrazol-4-yl)amino)imidazo[1,2-a]pyridin-3-yl)ethynyl)-4-methylphenyl)cyclopropan-1,1-dicarboxamide;
(79) N-(4-fluorophenyl)-N-(4-methyl-3-((8-((1-methyl-1H-pyrazol-4-yl)amino)imidazo[1,2-a]pyridin-3-yl)ethynyl)phenyl)cyclopropan-1,1-dicarboxamide;
(80) N-(4-methyl-3-((8-((1-methyl-1H-pyrazol-4-yl)amino)imidazo[1,2-a]pyridin-3-yl)ethynyl)phenyl)-4-((4-methylpiperazin-1-yl)methyl)-3-(trifluoromethyl)benzamide;
(81) (R)—N-(4-((3,4-dimethylpiperazin-1-yl)methyl)-3-(trifluoromethyl)phenyl)-3-((8-((1-isopropyl-1H-pyrazol-4-yl)amino)imidazo[1,2-a]pyridin-3-yl)ethynyl)-4-methylbenzamide;
(82) 1-(3-((8-((1-isopropyl-1H-pyrazol-4-yl)amino)imidazo[1,2-a]pyridin-3-yl)ethynyl)-4-methylphenyl)-3-(4-((4-methylpiperazin-1-yl)methyl)-3-(trifluoromethyl)phenyl)urea;
(83) 1-(3-((8-((1-isopropyl-1H-pyrazol-4-yl)amino)imidazo[1,2-a]pyridin-3-yl)ethynyl)-4-methylphenyl)-3-(3-(trifluoromethyl)phenyl)urea;
(84) 1-(5-(tert-butyl)isoxazol-3-yl)-3-(3-((8-((1-isopropyl-1H-pyrazol-4-yl)amino)imidazo[1,2-a]pyridin-3-yl)ethynyl)-4-methylphenyl)urea; and
(85) 1-(3-((8-((1-isopropyl-1H-pyrazol-4-yl)amino)imidazo[1,2-a]pyridin-3-yl)ethynyl)-4-methylphenyl)-3-(5-(1,1,1-trifluoro-2-methylpropan-2-yl)isoxazol-3-yl)urea.

5. A preparation method of the compound represented by formula 1 of claim 1 comprising, as shown in reaction formula 1 below:

preparing the compound represented by formula 4 by reacting the compound represented by formula 2 with the compound represented by formula 3 (step 1);

preparing the compound represented by formula 6 by reacting the compound represented by formula 4 prepared in step 1 above with the compound represented by formula 5 (step 2);

preparing the compound represented by formula 7 from the compound represented by formula 6 prepared in step 2 above (step 3); and preparing the compound represented by formula 1 by reacting the compound represented by formula 7 prepared in step 3 above with the compound represented by formula 8 (step 4);

[Reaction Formula 1]

STEP 1

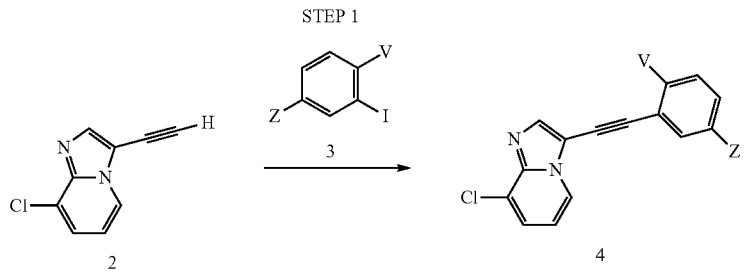

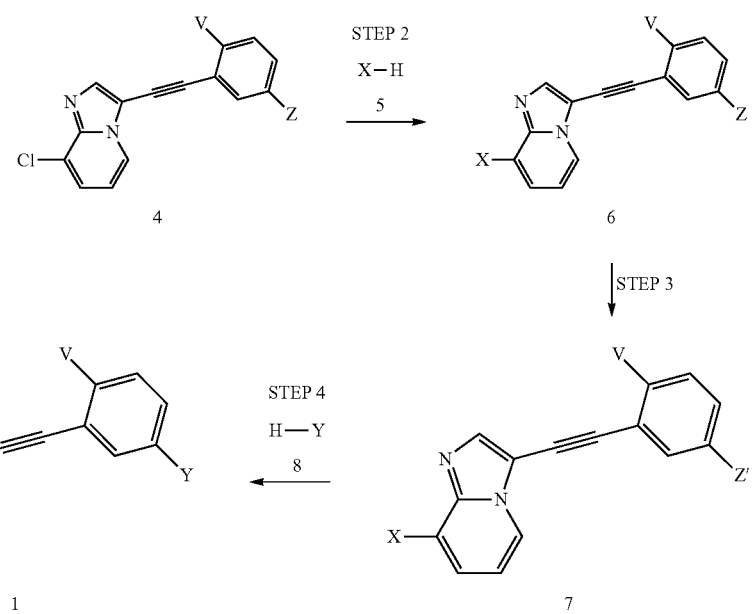

wherein
V, X and Y are as defined in formula 1 of claim 1; and
Z' is —NH² when Z is —NO₂ and Z' is

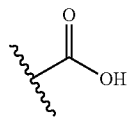 [SMILES: *C(=O)O]

when Z is

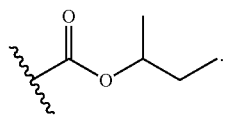 [SMILES: *C(=O)OC(C)CC]

6. A pharmaceutical composition comprising the compound represented by formula 1 of claim 1, the optical isomer thereof or the pharmaceutically acceptable salt thereof as an active ingredient for the prevention or treatment of cancer.

7. The pharmaceutical composition according to claim 6, wherein the compound inhibits Rearranged during transfection (Ret), ABL1(E255K)-phosphorylated, ABL1(F317I)-nonphosphorylated, ABL1(F317I)-phosphorylated, ABL1(F317L)-nonphosphorylated, ABL1(F317L)-phosphorylated, ABL1(H396P)-nonphosphorylated, ABL1(H396P)-phosphorylated, ABL1(M351T)-phosphorylated, ABL1(Q252H)-nonphosphorylated, ABL1(Q252H)-phosphorylated, ABL1(T315I)-nonphosphorylated, ABL1(T315I)-phosphorylated, ABL1(Y253F)-phosphorylated, ABL1-nonphosphorylated, ABL1-phosphorylated, ABL2, ALK(L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDCl2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR(E746-A750del), EGFR(G719C), EGFR (G719S), EGFR(L747-E749del, A750P), EGFR(L747-S752del, P753S), EGFR(L747-T751del,Sins), EGFR (L858R), EGFR(L858R,T790M), EGFR(L861Q), EGFR (S752-I759del), EGFR(T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3(G697C), FGFR4, FGR, FLT1, FLT3, FLT3(D835H), FLT3(D835V), FLT3(D835Y), FLT3(ITD), FLT3(ITD,D835V), FLT3(ITD, F691L), FLT3(K663Q), FLT3(N841I), FLT3(R834Q), FLT4, FRK, FYN, GAK, GCN2(Kin.Dom.2,S808G), HCK, HIPK4, HPK1, IKK-alpha, IKK-beta, IRAK1, IRAK4, ITK, JAK1(JH1domain-catalytic), JAK2(JH1domain-catalytic), JAK3(JH1domain-catalytic), JNK1, JNK2, JNK3, KIT, KIT (A829P), KIT(D816H), KIT(D816V), KIT(L576P), KIT (V559D), KIT(V559D,T670I), KIT(V559D,V654A), LCK, LIMK1, LIMK2, LOK, LRRK2, LRRK2(G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1(P.falciparum), PFTAIRE2, PFTK1, PKAC-alpha, PKAC-beta, PYK2, RAF1, RET, RET(M918T), RET(V804L), RET(V804M), RIPK1, RIPK2, RIPK4, ROCK2, RPS6KA4(Kin.Dom.1-N-terminal), RSK2(Kin.Dom.1-N-terminal), RSK3(Kin.DoN-terminal), S6K1, SIK, SLK, SRC, SRMS, SRPK1, STK33, STK35, STK36, SYK, TAK1, TAOK2, TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, ZAP70 or fibroblast growth factor receptor (FGFR) to prevent or treat cancer.

8. The pharmaceutical composition according to claim 6, wherein the cancer is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblastic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamos cell carcinoma of lung, skin cancer, anal cancer, rhabdomyosarcoma, laryngeal cancer, pleural cancer, and thymus cancer.

9. A health functional food composition comprising the compound represented by formula 1 of claim 1, the optical isomer thereof or the pharmaceutically acceptable salt thereof as an active ingredient for preventing or ameliorating cancer.

10. A pharmaceutical composition comprising the compound represented by formula 1 of claim 1, the optical isomer thereof or the pharmaceutically acceptable salt thereof as an active ingredient for the prevention or treatment of diabetic nephropathy.

11. The pharmaceutical composition according to claim 10, wherein the compound inhibits SRC or Fyn to prevent or treat diabetic nephropathy.

12. The pharmaceutical composition according to claim 10, wherein the compound of the pharmaceutical composition is used for the prevention and/or treatment of diabetic microalbuminuria characterized by decreasing albuminuria in the early microalbuminuria stage of diabetic nephropathy and reducing the ratio of albumin-creatinine.

13. A health functional food composition comprising the compound represented by formula 1 of claim 1, the optical isomer thereof or the pharmaceutically acceptable salt thereof as an active ingredient for preventing or ameliorating diabetic nephropathy.

14. A pharmaceutical composition comprising the compound of claim 4, the optical isomer thereof or the pharmaceutically acceptable salt thereof as an active ingredient for the prevention or treatment of cancer.

15. The pharmaceutical composition according to claim 14, wherein the compound inhibits Rearranged during transfection (Ret), ABL1 (E255K)-phosphorylated, ABL1 (F317I)-nonphosphorylated, ABL1 (F317I)-phosphorylated, ABL1 (F317L)-nonphosphorylated, ABL1 (F317L)-phosphorylated, ABL1 (H396P)-nonphosphorylated, ABL1 (H396P)-phosphorylated, ABL1 (M351T)-phosphorylated, ABL1 (Q252H)-nonphosphorylated, ABL1 (Q252H)-phosphorylated, ABL1 (T315I)-nonphosphorylated, ABL1 (T315I)-phosphorylated, ABL1 (Y253F)-phosphorylated, ABL1-nonphosphorylated, ABL1-phosphorylated, ABL2, ALK (L1196M), AMPK-alpha1, AMPK-alpha2, ANKK1, AURKB, AURKC, AXL, BLK, BMX, BRAF, BRAF (V600E), BRK, BTK, CAMK1, CAMKK1, CAMKK2, CDC2L1, CDC2L2, CDC2L5, CDK11, CDK2, CDK5, CDK7, CDK8, CDKL1, CDKL2, CDKL3, CHEK2, CIT, CLK1, CLK4, CSF1R, CSK, CTK, DDR1, DDR2, DLK, EGFR, EGFR (E746-A750del), EGFR (G719C), EGFR (G719S), EGFR (L747-E749del, A750P), EGFR (L747-S752del, P753S), EGFR (L747-T751del, Sins), EGFR (L858R), EGFR (L858R,T790M), EGFR (L861Q), EGFR (S752-I759del), EGFR (T790M), EPHA1, EPHA2, EPHA3, EPHA4, EPHA5, EPHA6, EPHA7, EPHA8, EPHB1, EPHB2, EPHB4, EPHB6, ERBB2, ERBB4, ERK8, FAK, FER, FES, FGFR1, FGFR2, FGFR3, FGFR3 (G697C), FGFR4, FGR, FLT1, FLT3, FLT3 (D835H), FLT3 (D835V), FLT3 (D835Y), FLT3 (ITD), FLT3 (ITD,D835V), FLT3 (ITD,F691L), FLT3 (K663Q), FLT3 (N841I), FLT3 (R834Q), FLT4, FRK, FYN, GAK, GCN2 (Kin.Dom.2, S808G), HCK, HIPK4, HPK1, IKK-alpha, IKK-beta, IRAK1, IRAK4, ITK, JAK1 (JH1domain-catalytic), JAK2 (JH1domain-catalytic), JAK3 (JH1domain-catalytic), JNK1, JNK2, JNK3, KIT, KIT (A829P), KIT (D816H), KIT (D816V), KIT (L576P), KIT (V559D), KIT (V559D,T670I), KIT (V559D,V654A), LCK, LIMK1, LIMK2, LOK, LRRK2, LRRK2 (G2019S), LTK, LYN, MAK, MAP3K2, MAP3K3, MAP4K2, MAP4K3, MAP4K4, MAP4K5, MEK5, MELK, MERTK, MET, MET (M1250T), MINK, MKNK2, MLK1, MLK2, MLK3, MST1, MST1R, MST2, MUSK, MYLK2, MYO3A, MYO3B, NDR2, NEK1, NEK11, NEK4, NEK5, NEK9, NLK, p38-alpha, p38-beta, p38-delta, p38-gamma, PCTK2, PDGFRA, PDGFRB, PFCDPK1 (*P. falciparum*), PFTAIRE2, PFTK1, PKAC-alpha, PKAC-beta, PYK2, RAF1, RET, RET (M918T), RET (V804L), RET (V804M), RIPK1, RIPK2, RIPK4, ROCK2, RPS6KA4 (Kin.Dom.1-N-terminal), RSK2 (Kin.Dom.1-N-terminal), RSK3 (Kin.DoN-terminal), S6K1, SIK, SLK, SRC, SRMS, SRPK1, STK33, STK35, STK36, SYK, TAK1, TAOK2, GG:cms 06/22/20 {{2018FPO-12-003/US}}TAOK3, TEC, TESK1, TGFBR2, TIE1, TIE2, TNIK, TNK1, TNK2, TNNI3K, TRKA, TRKB, TRKC, TTK, TXK, TYK2 (JH1domain-catalytic), TYRO3, ULK3, VEGFR2, YES, YSK4, ZAK, and ZAP70 or fibroblast growth factor receptor (FGFR) to prevent or treat cancer.

16. The pharmaceutical composition according to claim 14, wherein the cancer is at least one selected from the group consisting of pseudomyxoma, intrahepatic cholangiocarcinoma, hepatoblastoma, liver cancer, thyroid cancer, colon cancer, testicular cancer, myelodysplastic syndrome, glioblastoma, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, retinoblastoma, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, astrocytoma, small cell lung cancer, pediatric brain cancer, pediatric lymphoma, childhood leukemia, small bowel cancer, meningioma, esophagus cancer, glioma, neuroblastoma, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblatic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, vestibular schwannoma, pancreatic cancer, salivary gland cancer, Kaposi's sarcoma, Paget's disease, tonsil cancer, squamous cell carcinoma, adenocarcinoma of lung, lung cancer, squamos cell carcinoma of lung, skin cancer, anal cancer, rhabdomyosarcoma, laryngeal cancer, pleural cancer, and thymus cancer.

17. A health functional food composition comprising the compound of claim 4, the optical isomer thereof or the pharmaceutically acceptable salt thereof as an active ingredient for preventing or ameliorating cancer.

18. A pharmaceutical composition comprising the compound of claim 4, the optical isomer thereof or the pharmaceutically acceptable salt thereof as an active ingredient for the prevention or treatment of diabetic nephropathy.

19. The pharmaceutical composition according to claim 18, wherein the compound inhibits SRC or Fyn to prevent or treat diabetic nephropathy.

20. The pharmaceutical composition according to claim 18, wherein the compound of the pharmaceutical composition is used for the prevention and/or treatment of diabetic microalbuminuria characterized by decreasing albuminuria in the early microalbuminuria stage of diabetic, nephropathy and reducing the ratio of albumin-creatinine.

21. A health functional food composition comprising the compound of claim 4, the optical isomer thereof or the pharmaceutically acceptable salt thereof as an active ingredient for preventing or ameliorating diabetic nephropathy.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 1
aggaattgac ggaagggcac                                        20
```

-continued

```
<210> SEQ ID NO 2
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 2
gtgcagcccc ggacatctaa g                                         21

<210> SEQ ID NO 3
<211> LENGTH: 22
<212> TYPE: DNA
<213> ORGANISM: Artificial sequence
<220> FEATURE:
<223> OTHER INFORMATION: Synthetic nucleic acid

<400> SEQUENCE: 3
gatcaccatc gggaatgaac gc                                        22

<210> SEQ ID NO 4
<211> LENGTH: 21
<212> TYPE: DNA
<213> ORGANISM: Artificial sequence
<220> FEATURE:
<223> OTHER INFORMATION: Synthetic nucleic acid

<400> SEQUENCE: 4
cttagaagca tttgcggtgg a                                         21

<210> SEQ ID NO 5
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 5
tctaagacat ccctggtcac                                           20

<210> SEQ ID NO 6
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 6
gtccttccag aagaaacctt                                           20

<210> SEQ ID NO 7
<211> LENGTH: 20
<212> TYPE: DNA
<213> ORGANISM: Artificial sequence
<220> FEATURE:
<223> OTHER INFORMATION: Synthetic nucleic acid

<400> SEQUENCE: 7
ctgtagcatc cacgtgctgt                                           20

<210> SEQ ID NO 8
<211> LENGTH: 20
<212> TYPE: DNA
<213> ORGANISM: Artificial sequence
<220> FEATURE:
<223> OTHER INFORMATION: Synthetic nucleic acid
```

```
<400> SEQUENCE: 8
ccgactcatt gggatcatct                                          20
```